US008030023B2

(12) United States Patent
Adams et al.

(10) Patent No.: US 8,030,023 B2
(45) Date of Patent: Oct. 4, 2011

(54) NUCLEIC ACID ENCODING DR5 ANTIBODIES AND USES THEREOF

(75) Inventors: Camellia W. Adams, San Jose, CA (US); Avi J. Ashkenazi, San Mateo, CA (US)

(73) Assignee: Genentech, Inc., South San Francisco, CA (US)

( * ) Notice: Subject to any disclaimer, the term of this patent is extended or adjusted under 35 U.S.C. 154(b) by 197 days.

(21) Appl. No.: 11/546,133

(22) Filed: Oct. 10, 2006

(65) Prior Publication Data
US 2007/0031414 A1    Feb. 8, 2007

Related U.S. Application Data

(62) Division of application No. 11/344,564, filed on Jan. 30, 2006.

(60) Provisional application No. 60/649,550, filed on Feb. 2, 2005.

(51) Int. Cl.
C12P 21/08      (2006.01)
C12N 5/10       (2006.01)
C07K 16/18      (2006.01)
C07K 16/28      (2006.01)

(52) U.S. Cl. .... 435/69.1; 435/326; 435/334; 435/252.3; 435/320.1; 530/387.1; 530/388.1; 530/388.22; 536/23.1

(58) Field of Classification Search .......... None
See application file for complete search history.

(56) References Cited

U.S. PATENT DOCUMENTS

| | | | |
|---|---|---|---|
| 4,342,566 A | 8/1982 | Theofilopoulos et al. |
| 4,419,446 A | 12/1983 | Howley et al. |
| 4,485,045 A | 11/1984 | Regen et al. |
| 4,544,545 A | 10/1985 | Ryan et al. |
| 4,560,655 A | 12/1985 | Baker et al. |
| 4,601,978 A | 7/1986 | Karin et al. |
| 4,657,866 A | 4/1987 | Kumar et al. |
| 4,676,980 A | 6/1987 | Segal et al. |
| 4,736,866 A | 4/1988 | Leder et al. |
| 4,767,704 A | 8/1988 | Cleveland et al. |
| 4,816,567 A | 3/1989 | Cabilly et al. |
| 4,873,191 A | 10/1989 | Wagner et al. |
| 4,927,762 A | 5/1990 | Darfler et al. |
| 4,975,278 A | 12/1990 | Senter et al. |
| 5,013,556 A | 5/1991 | Woodle et al. |
| 5,047,335 A | 9/1991 | Paulson et al. |
| 5,122,469 A | 6/1992 | Mather et al. |
| 5,278,299 A | 1/1994 | Wong et al. |
| 5,500,362 A | 3/1996 | Robinson et al. |
| 5,510,261 A | 4/1996 | Goochee et al. |
| 5,545,806 A | 8/1996 | Lonberg et al. |
| 5,545,807 A | 8/1996 | Surani et al. |
| 5,569,825 A | 10/1996 | Lonberg et al. |
| 5,625,126 A | 4/1997 | Lonberg et al. |
| 5,633,425 A | 5/1997 | Lonberg et al. |
| 5,661,016 A | 8/1997 | Lonberg et al. |
| 5,739,277 A | 4/1998 | Presta et al. |
| 5,750,373 A | 5/1998 | Garrard et al. |
| 5,763,223 A | 6/1998 | Wiley et al. |
| 5,807,715 A | 9/1998 | Morrison et al. |
| 5,821,333 A | 10/1998 | Carter et al. |
| 5,821,337 A | 10/1998 | Carter et al. |
| 6,030,945 A | 2/2000 | Ashkenazi et al. |
| 6,072,047 A | 6/2000 | Rauch et al. |
| 6,113,898 A | 9/2000 | Anderson et al. |
| 6,252,050 B1 | 6/2001 | Ashkenazi et al. |
| 6,284,236 B1 | 9/2001 | Wiley et al. |
| 6,313,269 B1 | 11/2001 | Deen et al. |
| 6,342,369 B1 | 1/2002 | Ashkenazi et al. |
| 6,342,383 B1 | 1/2002 | Perron et al. |
| 6,433,147 B1 | 8/2002 | Ni et al. |
| 6,461,823 B1 | 10/2002 | Ni et al. |
| 6,468,532 B1 | 10/2002 | Hsei et al. |
| 6,569,642 B1 | 5/2003 | Rauch et al. |
| 6,642,358 B1 | 11/2003 | Rauch et al. |
| 6,743,625 B2 | 6/2004 | Ni et al. |
| 6,746,668 B2 | 6/2004 | Ashkenazi et al. |
| 7,115,717 B2 | 10/2006 | Mori et al. |
| 7,244,429 B2 | 7/2007 | Zhou et al. |
| 7,279,160 B2 | 10/2007 | Zhou et al. |
| 2001/0010924 A1 | 8/2001 | Deew et al. |
| 2001/0023691 A1 | 9/2001 | Sekiya |
| 2002/0048785 A1 | 4/2002 | Holtzman |
| 2002/0072091 A1 | 6/2002 | Ni et al. |
| 2002/0098550 A1 | 7/2002 | Ni et al. |
| 2002/0160446 A1 | 10/2002 | Holtzman et al. |

(Continued)

FOREIGN PATENT DOCUMENTS

EP     0003089 B1     8/1981

(Continued)

OTHER PUBLICATIONS

Wells, J.A. (1990). Additivity of mutational effects in proteins. Biochemistry. 29(37):8509-8517.*
Ngo et al. (1994). Computational complexity, protein structure prediction, and the Levinthal paradox. In Merz and Le Grand (Eds.) The Protein Folding Problem and Tertiary Structure Prediction. Birkhauser:Boston, pp. 491-495.*
Skolnick et al. (2000). From genes to protein structure and function: novel applications of computational approaches in the genomic era. Trends in Biotechnology. 18:34-39.*
Wang et al. (1999). Rapid analysis of gene expression (RAGE) facilitates universal expression profiling. Nucleic Acds Research. 27(23):4609-4618.*

(Continued)

Primary Examiner — Christine J Saoud
Assistant Examiner — Jon M Lockard
(74) Attorney, Agent, or Firm — Arnold & Porter LLP; Diane Marschang; Ginger R. Dreger

(57) ABSTRACT

The invention concerns anti-DR5 antibodies with improved properties, compositions comprising such antibodies, methods and means for making such antibodies, and their therapeutic use, in particular in the treatment of cancer.

8 Claims, 46 Drawing Sheets

U.S. PATENT DOCUMENTS

| | | | |
|---|---|---|---|
| 2003/0125554 | A1 | 7/2003 | Bernard et al. |
| 2005/0249729 | A1 | 11/2005 | Mori et al. |

FOREIGN PATENT DOCUMENTS

| | | | |
|---|---|---|---|
| EP | 417563 | B1 | 8/1990 |
| EP | 870827 | A2 | 10/1998 |
| EP | 1 396 500 | A1 | 10/2004 |
| WO | WO 81/01145 | A1 | 4/1981 |
| WO | WO 87/00195 | A1 | 1/1987 |
| WO | WO 88/07378 | A1 | 10/1988 |
| WO | WO 90/03430 | A1 | 4/1990 |
| WO | WO 91/00360 | A1 | 1/1991 |
| WO | WO 93/06213 | A1 | 4/1993 |
| WO | WO 93/08829 | A1 | 5/1993 |
| WO | WO 94/11026 | A2 | 5/1994 |
| WO | WO 94/04690 | A1 | 6/1994 |
| WO | WO 94/29348 | A2 | 12/1994 |
| WO | WO 97/01633 | A1 | 1/1997 |
| WO | WO 97/25428 | A1 | 7/1997 |
| WO | WO 98/18921 | A1 | 5/1998 |
| WO | WO 98/25986 | A1 | 6/1998 |
| WO | WO 98/28426 | A3 | 7/1998 |
| WO | WO 98/32856 | A1 | 7/1998 |
| WO | WO 98/41629 | A2 | 9/1998 |
| WO | WO 98/46643 | A1 | 10/1998 |
| WO | WO 98/46751 | A1 | 10/1998 |
| WO | WO 98/51793 | A1 | 11/1998 |
| WO | WO 99/02653 | A1 | 1/1999 |
| WO | WO 99/09165 | A1 | 2/1999 |
| WO | WO 99/11791 | A2 | 3/1999 |
| WO | WO 99/36535 | A1 | 7/1999 |
| WO | WO 99/37684 | A1 | 7/1999 |
| WO | WO 99/64461 | A2 | 12/1999 |
| WO | WO 00/73349 | | 12/2000 |
| WO | WO 00/75191 | A2 | 12/2000 |
| WO | WO 01/00832 | A1 | 1/2001 |
| WO | WO 02/09755 | A2 | 2/2002 |
| WO | WO 02/097033 | | 12/2002 |
| WO | WO 03/037913 | A2 | 5/2003 |
| WO | WO 03/042367 | A2 | 5/2003 |
| WO | WO 03/066661 | A2 | 8/2003 |
| WO | WO 2005/100399 | A2 | 10/2005 |
| WO | WO 2007/027713 | | 3/2007 |
| WO | WO 2007/128231 | | 11/2007 |
| WO | WO 2008/066854 | | 6/2008 |

OTHER PUBLICATIONS

Kaufman et al. (1999). Transgenic analysis of a 100-kb human B-globulin cluster-containing DNA fragment propagated as a bacterial artificial chromosome. Blood. 94(9):3178-3184.*
Rudikoff et al. (1982). Single amino acid substitution altering antigen-binding specificity. Proc. Natl. Acad. Sci. USA. 79:1979-1983.*
Agnew *Chem Intl. Ed. Engl.* 33:183-186 (1994).
Anderson et al., *Nature*, 390:175-179 (1997).
Armitage et al. Nature, 357:80-82 (1992).
Ashkenazi and Dixit, *Curr. Opin. Cell Biol.*, *11*:255-260 (2000.
Ashkenazi and Dixit, *Science*, *281*:1305-1308 (1998).
Ashkenazi et al., J. Clin. Invest., 104:155-162 (1999).
Ashkenazi, *Nature Reviews*, 2:420-430 (2002).
Bodmer et al., *Nature Cell Biol.*, 2:241-243 (2000).
Boerner et al., *J. Immunol.*, 147 (1):86-95 (1991.
Boyd et al., *Mol. Immunol.* 32:1311-1318 [1996].
Bradley, in *Teratocarcinomas and Embryonic Stem Cells: A Practical Approach*, E. J. Robertson, ed. (IRL, Oxford, 1987), pp. 113-152.
Brennan et al., *Science* 229:81 (1985).
Brodeur et al., *Monoclonal Antibody Production Techniques and Applications*, Marcel Dekker, Inc., New York, (1987) pp. 51-63.
Browning et al., Cell, 72:847-856 (1993).
Buchsbaum Donald J, et al., "Antitumor efficacy of TRA-8 Anti-DR5 Monoclonal Antibody alone or in combination with Chemotherapy and/or Radiation Therapy in a Human Breast Cancer Model", Clinical Cancer Research: An Official Journal of the American Association for Cancer Research, Sep. 1, 2003, pp. 3731-3741.
Burton, *Molec. Immunol.* 22:161-206 (1985).
Capel et al., *Immunomethods*, 4:25-34 (1994).
Carter et al., *Bio/Technology* 10:163-167 (1992).
Cha et al., Immunity, 11:253-261 (1999).
Chicheportiche et al., *J. Biol. Chem.*, 272:32401-32410 (1997.
Chothia et al., *J. Mol. Biol.*, *186*:651-663 (1985).
Clackson et al., *Nature* 352, 624-628 (1991).
Clynes et al. *PNAS (USA)*, 95:652-656 (1998).
Cole et al., *Monoclonal Antibodies and Cancer Therapy*, Alan R. Liss, p. 77 (1985).
Cunningham and Wells *Science*, 244:1081-1085 (1989).
Daëron, *Annu. Rev. Immunol.*, 15:203-234 (1997).
David et al., *Biochemistry*, *13*:1014-1021 (1974).
Dealtry et al., Eur. J. Immunol., 17:689 (1987).
Degli-Esposti et al., *Immunity*, 7:813-820 (1997).
FcRs are reviewed in Ravetch and Kinet, *Annu. Rev. Immunol.*, 9:457-92 (1991).
Fishwild et al., *Nature Biotechnology*, 14: 845-51 (1996.
Gazitt, Leukemia, 13:1817-1824 (1999.
Gazzano-Santoro et al., *J. Immunol. Methods*, 202:163 (1996).
Goding, *Monoclonal Antibodies: Principles and Practice*, Academic Press, (1986) pp. 59-103.
Gorman et al., DNA Prot. Eng Tech 2: 3-10, 1990.
Graham et al., *J. Gen. Virol.*, 36:59-74, (1977).
Griffith et al., J. Exp. Med., 189:1343-1353 (1999).
Griffith T.S., et al., "Functional Analysis of Trail Receptors Using Monoclonal Antibodies", Journal of Immunology, vol. 162, Mar. 1, 1999, pp. 2597-2605.
Guss et al., *EMBO J.* 5:1567-1575 (1986).
Guyer et al., *J. Immunol.*, 117:587 (1976).
Haas et al, J. Lab. Clin. Med., 126: 330-341, 1995.
*Handbook of Monoclonal Antibodies*, Ferrone et al., eds., Noges Publications, Park Ridge, N.J., (1985) ch. 22 and pp. 303-357.
Hawkins et al, *J. Mol. Biol.*, 226:889-896 (1992).
Hoogenboom and Winter, *J. Mol. Biol.*, 227:381 (1991).
Hunter et al., Nature vol. 144:945, 1962.
Hwang et al., *Proc. Natl Acad. Sci. USA* 77:4030 (1980).
Hylander et al., Journal of Immunotherapy, 25(6): S1-S7, 2002.
Hymowitz et al., Biochemistry, 39:633-644 (2000).
Hymowitz et al., *Molecular Cell*, 4:563-571 (1999).
Issekutz, A. C. et al., *Immunology*, 88:569-576, 1996.
Jackson et al., *J. Immunol.*, 154(7):3310-9 (1995).
Jakobovits et al., *Nature* 362, 255-258 (1993).
Jefferis and Lund, *Chem. Immunol.* 65:111-128 [1997].
Jo et al., Nature Med., 6:564-567 (2000).
Johnsen et al., Cytokine, 11:664-672 (1999).
Johnson, K.S. et al., Current Opinion in Structural Biology 3:564-571, 1993.
Johnson Ron et al., "Human Agonistic Anti-Trail Receptor Antibodies, HGS-ETRI and HGS-ETR2, induce Apoptosis in Diverse Hematological Tumor Lines", Blood, vol. 102, Nov. 16, 2003, p. 891a, & 45th Annual Meeting of the American Society of Hematology; San Diego, CA USa; Dec. 6-9, 2003, abstract.
Jones et al., *Nature*, *321*:522-525 (1986).
Keane et al., Cancer Research, 59:734-741 (1999.
Kevin S. and Chiswell, David J., *Current Opinion in Structural Biology 3*, 564-571 (1993).
Kim et al., *J. Immunol.*, 24:249 (1994).
Kischkel et al., *Immunity*, *12*:611-620 (2000.
Kohler and Milstein, *Nature*, 256:495 (1975).
Kortt et al., *Protein Engineering*, *10*:423-433 (1997).
Kozbor, *J. Immunol.* *133*, 3001 (1984).
Lasko et al., *Proc. Natl. Acad. Sci. USA*, 89, 6232-636 (1992).
Lavitrano et al., *Cell*, *57*, 717-73 [1989].
Lawrence et al., Nature Med., Letter to the Editor, 7:383-385 (2001).
Lewis et al., *Proc. Natl. Acad. Sci.*, 88:2830-2834 (1991).
Li et al., *Cell*, *69*:915 (1992).
Lindmark et al., *J. Immunol. Meth.* 62:1-13 (1983)).
Liu W.M. et al., "Trail R2 (DR5) is a Novel, Selective Therapeutic Target for Rheumatoid Arthritis" abstract, & Faseb Journal, vol. 16, Mar. 22, 2002, p. A1047, Annual Meeting of Professional Research Scientists on Experimental biology; New Orleans, Louisiana, USA; Apr. 20-24, 2002.
Lo, *Mol. Cel. Biol.*, 3, 1803-1814 [1983].
Locksley et al., *Cell*, 104:487-501 (2001).

Loetscher et al., *Cell, 61*:351 (1990).
Lonberg et al., Intern. Rev. Immunol., 13:65-93, 1995.
Lonberg et al., *Nature*, 368: 856-859 (1994).
Mage et al., in *Monoclonal Antibody Production Techniques and Applications*, pp. 79-97 (Marcel Dekker, Inc.: New York, 1987.
Malhotra et al., *Nature Med. 1*:237-243 [1995].
Mallett et al., *EMBO J., 9*:1063-1068 (1990).
Marks et al., *Bio/Technol. 10*, 779-783 [1992].
Marks et al., *J. Mol. Biol. 222*, 581-597 (1991).
Marsters et al., Curr. Biol., 8:525-528 (1998).
Massey, *Nature* 328: 457-458 (1987.
McCafferty et al., *Nature 348*, 552-553 [1990].
Mendez et al. (*Nature Genetics* 15: 146-156 [1997].
Millstein and Cuello, *Nature 305*, 537-539 (1983).
Mongkolsapaya et al., Nature Structural Biology, 6:1048 (1999).
Moore et al., Science, 285:260-263 (1999).
Morimoto et al., *J. Biochem. Biophys. Methods* 24:107-117 (1992).
Morl E. et al., "An Anti-Tumor Trail Receptor 2 Human Antibody without Hepatocyte Toxicity", Proceedings of the Annual Meeting of the American Association for Cancer Research, New York, NY, US, vol. 44, Jul. 11, 2003, p. 1285.
Morrison, et al., *Proc. Nat. Acad. Sci. 81*, 6851 (1984).
Morrison, Nature 368:812-813, 1994.
Munson P.J. et al., "Ligand: A Versatile Computerized Approach for Characterization of Ligand-Binding Systems", Analytical Biochemistry 107:220-239, 1980.
Murakami et al, "Cell cycle regulation, oncogenes, and antineoplastic drugs" p. 13, 1995.
Nagata, Cell, 88:355-365 (1998).
Nagata, Nature Med., 6:502-503 (2000).
Neuberger et al., *Nature*, 312: 604-608 (1984).
Neuberger, *Nature Biotechnology*, 14: 826 (1996).
Nickoloff, B. J. et al., *Am. J. Path.*, (1995) 146:580.
Nygren, *J. Histochem. and Cytochem., 30*:407-412 (1982).
Pain et al., *J. Immunol. Meth., 40*:219-230 (1981).
Pan et al., *Science, 276*:111 (1997).
Pan et al., *Science, 277*:815-818 (1997).
Pitti et al., J. Biol. Chem., 271:12687-12690 (1996).
Qin et al., Nature Med., Letter to the Editor, 7:385-386 (2001).
Ravetch, J.V. et al, "Fc Receptors", Annual Rev Immunol vol. 9, 457-492, (1991).
Sachs, D. H., *Fundamental Immunology*, 2nd ed., W. E. Paul ed., Raven Press, NY, 1989, 889-992.
Salvesen et al., *Cell*, 91:443-446 (1997).
Schall et al., *Cell, 61*:361 (1990).
Schier et al. *Gene*, 169:147-155 (1995).
Schon M.P. et al., "Murine Psoriasis-Like Disorder Induced by Naïve CD4 T Cells", vol. 3, 183-188, 1997.
Screaton et al., *Curr. Biol., 7*:693-696 (1997).
Shalaby et al., J. Exp. Med. 175:217-225 (1992).
Sheets et al. *PNAS, (USA)* 95:6157-6162 (1998)).
Sheridan et al., *Science*, 277:818-821 (1997).
Sidhu et al., Curr. Opin. Biotechnol. 11:610-616 (2002).

Smith et al., *Antibodies in Human Diagnosis and Therapy*, Haber et al., eds., Raven Press, New York (1977) pp. 365-389.
Smith et al., *Science, 248*:1019-1023 (1990).
Song et al., J. Exp. Med., 191:1095-1103 (2000).
Sprick et al., *Immunity, 12*:599-609 (2000).
Stella et al., "Prodrugs: A Chemical Approach to Targeted Drug Delivery," *Directed Drug Delivery*, Borchardt et al., (ed.), pp. 247-267.
Suresh et al., *Methods in Enzymology 121*, 210 (1986).
Tanabe, M. et al., *Transplantation*, (1994) 58:23.
Thomas and Capecchi, *Cell, 51*:503 (1987).
Thornberry and Lazebnik, *Science* 281:1312-6 (1998).
Tinubu, S. A. et al., *J. Immunol.*, (1994) 4330-4338.
Traunecker et al., *EMBO 10*, 3655-3659 (1991).
Tsuda et al., *BBRC*, 234:137-142 (1997).
Umana et al., *Mature Biotech. 17*:176-180 [1999].
Vajdos et al., J. Mol. Biol. 320:415-428 (2002).
Van der Putten et al., *Proc. Natl. Acad. Sci. USA, 82*, 6148-615 [1985].
Vaughan et al. *Nature Biotechnology*, 14:309-314 (1996).
Verhoeyen et al., Science 239:1534-1536, 1988.
vonBulow et al., *Science*, 278:138-141 (1997).
Walczak et al., *EMBO J., 16*:5386-5387 (1997).
Walczak et al., Nature Med., 5:157-163 (1999).
Wallach, *Cytokine Reference*, Academic Press, 2000, pp. 377-411.
Wiley et al., Immunity, 3:673-682 (1995).
Wilman, "Prodrugs in Cancer Chemotherapy" *Biochemical Society Transactions*, 14, pp. 375-382.
Wittwer and Howard, *Biochem. 29*:4175-4180 [1990].
Wright and Morrison, *TibTECH 15*:26-32 [1997].
Wu et al., *Nature Genetics, 17*:141-143 (1997).
Yelton et al. *J. Immunol.*, 155:1994-2004 (1995).
Zola, *Monoclonal Antibodies: A Manual of Techniques*, CRC Press, Inc., pp. 147-158, 1987.
Buchsbaum, et al., "Antitumor efficacy of TRA-8 anti-DR5 monoclonal antibody alone or in combination with chemotherapy and/or radiation therapy in a human breast cancer model". Clinical Cancer Research, vol. 9, pp. 3731-3741, (2003).
Guo, et al., "A novel anti-human DR5 monoclonal antibody with tumoricidal activity induces caspase-dependent cell death", The journal of biological chemistry, vol. 280, No. 5, pp. 41940-41952, (2005).
Ichikawa, et al., "Trail-R2 (DR5) mediates apoptosis of synovial fibroblasts in rheumatoid arthritis". The Journal of Immunology, 171: 1061-1069, (2003).
Kaliberov, et al., "Enhanced apoptosis following treatment with TRA-8 anti-human DR5 monoclonal antibody and overexpression of exogenous Bax in human glioma cells", Gene Therapy, 11: 658-667, (2004).
Ma, et al., "Analysis of TRAIL receptor expression using anti-TRAIL, death receptor-5 monoclonal antibodies", Chinese Medical journal, 116(6): 947-950, (2003).

\* cited by examiner

```
  1 TTTCCTCACTGACTATAAAGAATAGAGAAGGAAGGGCTTCAGTGACCGGCTGCCTGGCTGACTTACAGCAGTCTGACAGGATC

91 ATGGCTATGATGGAGGTTCCAGGGGGGACCCAGCTGGGACAGACCTGCGTGCTGATCGTGATCTTCACAGTGCTCCTCTGT
  1 MetAlaMetMetGluValGlnGlyProSerLeuGlyGlnThrCysValLeuIleValIlePheThrValLeuLeuSerLeuCys

181 GTGGCTGTAACTTACGTGTACTTTACCAACGAGCTGAAGCAGATGCAGGACAAGTACTCCAAAAGTGGCATTGCTGTTTCTTAAAAGAA
 31 ValAlaValThrTyrValTyrPheThrAsnGluLeuLysGlnMetGlnAspLysTyrSerGlyIleAlaCysPheLeuLysGlu

271 GATGACAGTTATTGGGACCCAATGACGAA AGAGTATGAACAGCCCCTGCTGGCAAGTGGCAACTCCGTCAGCTCGTTAGAAAG
 61 AspAspSerTyrTrpAspProMetThrAsnSerMetGluGluGlnProLeuLeuAlaSerGlyAsnSerValSerSerLeuArgLys

361 ATGATTTTGAGAACCTCTGAGGAAACCATTGTCTACAGTTCTCAAGAAAAAGCAACAAATATTCTCCCCTAGTGAGAGAAGGTCNCAG
 91 MetIleLeuArgThrSerGluGluThrIleSerThrValGlnLysGlnAsnIleSerProLeuValArgGlyArgGlyProGln

451 AGAGTAGCAGCTCACATAACTGGGACCAGAGGAA GAAGCAACACATTGTCTTCCAAACTCCAAGAATGAAAGGCTCTGGGCCGCAAA
121 ArgValAlaAlaHisIleThrGlyThrArgGlyArgSerAsnThrLeuSerProAsnSerLysGluArgLeuGlyAlaLeuArgLys

541 ATAAACTCCTGGGAATCATCAAGGAGTGGGCATTCATTCCTGAGCAACTTGAGCACTTGCTCATTCATCCATGAAAAGG
151 IleAsnSerTrpGluSerSerArgSerGlyHisSerPheLeuSerAsnLeuHisLeuValIleHisGluLysGly

631 ATAAACTCCTGGGAATCATCAAGGAGTGGGCATTCATTCCTGAGCAACTTGAGCACTTGCTCATTCATCCATGAAAAAGG
181 PheTyrTyrIleTyrSerGlnThrTyrPheArgPheGlnGlyLysSerValLysThrLysAsnAspLysAsnMetValGlnTyrIle

721 TACAAATACACACAAGTTATCCTGACCCTATATTGTTGATGAAAATGAATGCTAGAAAAGTGCTAGAAATGATGAGCACTTGATAGAACATGGACCAT
211 TyrLysTyrThrSerTyrProAspProIleLeuLeuMetLysSerAlaArgAsnSerCysTrpSerLysAsnGluHisLeuIleLeuAspHis

811 TCCATCTATCAAGGGGAATATTTGAGCTTAAGGACGAATTTTGTTTCTGTAACAAATGAGCACTTGACTACTATTCAGTTTTCAGGAT
241 SerIleTyrGlnGlyGlyIleLeuPheGlyAlaPheLeuValGlyStp

901 GAAGCCAGTTTTTTCGGGGCCTTTTAGTGGCTAACTGACCTGAAAAGAAAAAGCAATAACCTCAAAGTGACTATTCAGTTTTCAGGAT
271 GluAlaSerPhePheGlyAlaPheLeuValGlyStp

991 GATACACTATGAAGATGTTTCAAAAAATCTGACCAAAAACAAACAGAAA
```

FIG. 1

```
                10                      30                      50
TTCGGGCACGAGGGCAGGATGGCGCCACCACCAGCTAGAGTACATCTAGGTGCGTTCCTG
                  M  A  P  P  P  A  R  V  H  L  G  A  F  L
                70                      90                     110
GCAGTGACTCCGAATCCCGGGAGCGCAGCGAGTGGGACAGAGGCAGCCGCGGCCACACCC
 A  V  T  P  N  P  G  S  A  A  S  G  T  E  A  A  A  A  T  P
               130                     150                     170
AGCAAAGTGTGGGGCTCTTCCGCGGGGAGGATTGAACCACGAGGCGGGGGCCGAGGAGCG
 S  K  V  W  G  S  S  A  G  R  I  E  P  R  G  G  G  R  G  A
               190                     210                     230
CTCCCTACCTCCATGGGACAGCACGGACCCAGTGCCCGGGCCCGGGCAGGGCGCGCCCCA
 L  P  T  S  M  G  Q  H  G  P  S  A  R  A  R  A  G  R  A  P
               250                     270                     290
GGACCCAGGCCGGCGCGGGAAGCCAGCCCTCGGCTCCGGGTCCACAAGACCTTCAAGTTT
 G  P  R  P  A  R  E  A  S  P  R  L  R  V  H  K  T  F  K  F
               310                     330                     350
GTCGTCGTCGGGGTCCTGCTGCAGGTCGTACCTAGCTCAGCTGCAACCATCAAACTTCAT
 V  V  V  G  V  L  L  Q  V  V  P  S  S  A  A  T  I  K  L  H
               370                     390                     410
GATCAATCAATTGGCACACAGCAATGGGAACATAGCCCTTTGGGAGAGTTGTGTCCACCA
 D  Q  S  I  G  T  Q  Q  W  E  H  S  P  L  G  E  L  C  P  P
               430                     450                     470
GGATCTCATAGATCAGAACGTCCTGGAGCCTGTAACCGGTGCACAGAGGGTGTGGGTTAC
 G  S  H  R  S  E  R  P  G  A  C  N  R  C  T  E  G  V  G  Y
               490                     510                     530
ACCAATGCTTCCAACAATTTGTTTGCTTGCCTCCCATGTACAGCTTGTAAATCAGATGAA
 T  N  A  S  N  N  L  F  A  C  L  P  C  T  A  C  K  S  D  E
               550                     570                     590
GAAGAGAGAAGTCCCTGCACCACGACCAGGAACACAGCATGTCAGTGCAAACCAGGAACT
 E  E  R  S  P  C  T  T  T  R  N  T  A  C  Q  C  K  P  G  T
               610                     630                     650
TTCCGGAATGACAATTCTGCTGAGATGTGCCGGAAGTGCAGCACAGGGTGCCCCAGAGGG
 F  R  N  D  N  S  A  E  M  C  R  K  C  S  T  G  C  P  R  G
               670                     690                     710
ATGGTCAAGGTCAAGGATTGTACGCCCTGGAGTGACATCGAGTGTGTCCACAAAGAATCA
 M  V  K  V  K  D  C  T  P  W  S  D  I  E  C  V  H  K  E  S
               730                     750                     770
GGCAATGGACATAATATATGGGTGATTTTGGTTGTGACTTTGGTTGTTCCGTTGCTGTTG
 G  N  G  H  N  I  W  V  I  L  V  V  T  L  V  V  P  L  L  L
**************************************************************
               790                     810                     830
GTGGCTGTGCTGATTGTCTGTTGTTGCATCGGCTCAGGTTGTGGAGGGGACCCCAAGTGC
 V  A  V  L  I  V  C  C  C  I  G  S  G  C  G  G  D  P  K  C
***************************************************
```

FIG. 2A

```
              850                 870                 890
ATGGACAGGGTGTGTTTCTGGCGCTTGGGTCTCCTACGAGGGCCTGGGGCTGAGGACAAT
 M  D  R  V  C  F  W  R  L  G  L  L  R  G  P  A  E  D  N
              910                 930                 950
GCTCACAACGAGATTCTGAGCAACGCAGACTCGCTGTCCACTTTCGTCTCTGAGCAGCAA
 A  H  N  E  I  L  S  N  A  D  S  L  S  T  F  V  S  E  Q  Q
              970                 990                1010
ATGGAAAGCCAGGAGCCGGCAGATTTGACAGGTGTCACTGTACAGTCCCCAGGGGAGGCA
 M  E  S  Q  E  P  A  D  L  T  G  V  T  V  Q  S  P  G  E  A
             1030                1050                1070
CAGTGTCTGCTGGGACCGGCAGAAGCTGAAGGGTCTCAGAGGAGGAGGCTGCTGGTTCCA
 Q  C  L  L  G  P  A  E  A  E  G  S  Q  R  R  R  L  L  V  P
             1090                1110                1130
GCAAATGGTGCTGACCCCACTGAGACTCTGATGCTGTTCTTTGACAAGTTTGCAAACATC
 A  N  G  A  D  P  T  E  T  L  M  L  F  F  D  K  F  A  N  I
             1150                1170                1190
GTGCCCTTTGACTCCTGGGACCAGCTCATGAGGCAGCTGGACCTCACGAAAAATGAGATC
 V  P  F  D  S  W  D  Q  L  M  R  Q  L  D  L  T  K  N  E  I
             1210                1230                1250
GATGTGGTCAGAGCTGGTACAGCAGGCCCAGGGGATGCCTTGTATGCAATGCTGATGAAA
 D  V  V  R  A  G  T  A  G  P  G  D  A  L  Y  A  M  L  M  K
             1270                1290                1310
TGGGTCAACAAAACTGGACGGAACGCCTCGATCCACACCCTGCTGGATGCCTTGGAGAGG
 W  V  N  K  T  G  R  N  A  S  I  H  T  L  L  D  A  L  E  R
             1330                1350                1370
ATGGAAGAGAGACATGCAAAAGAGAAGATTCAGGACCTCTTGGTGGACTCTGGAAAGTTC
 M  E  E  R  H  A  K  E  K  I  Q  D  L  L  V  D  S  G  K  F
             1390                1410                1430
ATCTACTTAGAAGATGGCACAGGCTCTGCCGTGTCCTTGGAGTGAAAGACTCTTTTTACC
 I  Y  L  E  D  G  T  F  S  A  V  S  L  E
             1450                1470                1490
AGAGGTTTCCTCTTAGGTGTTAGGAGTTAATACATATTAGGTTTTTTTTTTTTTTAACAT
             1510                1530                1550
GTATACAAAGTAAATTCTTAGCCACGTGTATTGGCTCCTGCCTGTAATCCCATCACTTTG
             1570                1590                1610
GGAGGCTGACGCCGGTGGATCCACTTGAGGTCCGAAGTTCCAAGACCAGCCCTGAACCAA
             1630                1650                1670
CATCGTGGAAATGCCCGTCTTTTACAAAAAAATACCAAAAATTCAACTGGAATGTGCATG
```

FIG. 2B

```
      1690                1710                1730
GTGTGTGCCATCATTTCCTCGGCTAACTACGGGAGGTCTGAGGCCAGGAGAATCCACTTG
      1750                1770                1790
AACCCCACGAAGGACAGTGTAGACTGCAGATTGCACCACTGCACTCCCAGCCTGGGAACA
      1810                1830                1850
CAGAGCAAGACTCTGTCTCAAGATAAAATAAAATAAACTTGAAAGAATTATTGCCCGACT
      1870                1890                1910
GAGGCTCACATGCCAAAGGAAAATCTGGTTCTCCCCTGAGCTGGCCTCCGTGTGTTTCCT
      1930                1950                1970
TATCATGGTGGTCAATTGGAGGTGTTAATTTGAATGGATTAAGGAACACCTAGAACACTG
      1990                2010                2030
GTAAGGCATTATTTCTGGGACATTATTTCTGGGCATGTCTTCGAGGGTGTTTCCAGAGGG
      2050                2070                2090
GATTGGCATGCGATCGGGTGGACTGAGTGGAAAAGACCTACCCTTAATTTGGGGGGGCAC
      2110                2130                2150
CGTCCGACAGACTGGGGAGCAAGATAGAAGAAAACAAAAAAAAAAAAAAAAA
```

```
1601 GTCTGGATCA TTCCGTTTGT GCGTACTTTG AGATTGGTT TGGGATGTCA TTGTTTTCAC AGCACTTTTT TATCCTAATG TAAATGCTTT ATTTATTTAT
     CAGACCTAGT AAGGCAAACA CGCATGAAAC TCTAAACCAA ACCCTACAGT AACAAAAGTG TCGTGAAAAA ATAGGATTAC ATTTACGAAA TAAATAAATA

1701 TTGGGCTACA TTGTAAGATC CATCTACAAA AAAAAAAAAA AAAAAAAAAG GGCGGCCGCG ACTCTAGAGT CGACCTGCAG AAGCTTGGCC GCCATGGCC
     AACCCGATGT AACATTCTAG GTAGATGTTT TTTTTTTTTT TTTTTTTTTC CCGCCGGCGC TGAGATCTCA GCTGGACGTC TTCGAACCGG CGGTACCGG
```

FIG. 3C

```
ATG GAA CAA CGG GGA CAG AAC GCC CCG GCC GCT TCG GGG GCC CGG AAA    48
Met Glu Gln Arg Gly Gln Asn Ala Pro Ala Ala Ser Gly Ala Arg Lys
 1            5                  10                  15

AGG CAC GGC CCA GGA CCC AGG GAG GCG CGG GGA GCC AGG CCT GGG CCC    96
Arg His Gly Pro Gly Pro Arg Glu Ala Arg Gly Ala Arg Pro Gly Pro
                20                  25                  30

CGG GTC CCC AAG ACC CTT GTG CTC GTT GTC GCC GCG GTC CTG CTG TTG   144
Arg Val Pro Lys Thr Leu Val Leu Val Val Ala Ala Val Leu Leu Leu
             35                  40                  45

GTC TCA GCT GAG TCT GCT CTG ATC ACC CAA CAA GAC CTA GCT CCC CAG   192
Val Ser Ala Glu Ser Ala Leu Ile Thr Gln Gln Asp Leu Ala Pro Gln
         50                  55                  60

CAG AGA GCG GCC CCA CAA CAA AAG AGG TCC AGC CCC TCA GAG GGA TTG   240
Gln Arg Ala Ala Pro Gln Gln Lys Arg Ser Ser Pro Ser Glu Gly Leu
65                  70                  75                  80

TGT CCA CCT GGA CAC CAT ATC TCA GAA GAC GGT AGA GAT TGC ATC TCC   288
Cys Pro Pro Gly His His Ile Ser Glu Asp Gly Arg Asp Cys Ile Ser
                85                  90                  95

TGC AAA TAT GGA CAG GAC TAT AGC ACT CAC TGG AAT GAC CTC CTT TTC   336
Cys Lys Tyr Gly Gln Asp Tyr Ser Thr His Trp Asn Asp Leu Leu Phe
            100                 105                 110
```

FIG. 4A

```
TGC TTG CGC TGC ACC AGG TGT GAT TCA GGT GAA GTG GAG CTA AGT CCG    384
Cys Leu Arg Cys Thr Arg Cys Asp Ser Gly Glu Val Glu Leu Ser Pro
    115             120                 125

TGC ACC ACG ACC AGA AAC ACA GTG TGT CAG TGC GAA GAA GGC ACC TTC    432
Cys Thr Thr Thr Arg Asn Thr Val Cys Gln Cys Glu Glu Gly Thr Phe
130             135                 140

CGG GAA GAA GAT TCT CCT GAG ATG TGC CGG AAG TGC CGC ACA GGG TGT    480
Arg Glu Glu Asp Ser Pro Glu Met Cys Arg Lys Cys Arg Thr Gly Cys
145             150                 155                 160

CCC AGA GGG ATG GTC AAG GTC GGT GAT TGT ACA CCC TGG AGT GAC ATC    528
Pro Arg Gly Met Val Lys Val Gly Asp Cys Thr Pro Trp Ser Asp Ile
                165             170                 175

GAA TGT GTC CAC AAA GAA TCA GGT ACA AAG CAC AGT GGG GAA GCC CCA    576
Glu Cys Val His Lys Glu Ser Gly Thr Lys His Ser Gly Glu Ala Pro
            180             185                 190

GCT GTG GAG GAG ACG GTG ACC TCC AGC CCA GGG ACT CCT GCC TCT CCC    624
Ala Val Glu Glu Thr Val Thr Ser Ser Pro Gly Thr Pro Ala Ser Pro
        195             200                 205

TGT TCT CTC TCA GGC ATC ATC ATA GGA GTC ACA GTT GCA GCC GTA GTC    672
Cys Ser Leu Ser Gly Ile Ile Ile Gly Val Thr Val Ala Ala Val Val
    210             215                 220

TTG ATT GTG GCT GTG TTT GTT TGC AAG TCT TTA CTG TGG AAG AAA GTC    720
Leu Ile Val Ala Val Phe Val Cys Lys Ser Leu Leu Trp Lys Lys Val
225             230                 235                 240

CTT CCT TAC CTG AAA GGC ATC TGC TCA GGT GGT GGT GGG GAC CCT GAG    768
Leu Pro Tyr Leu Lys Gly Ile Cys Ser Gly Gly Gly Gly Asp Pro Glu
            245             250                 255

CGT GTG GAC AGA AGC TCA CAA CGA CCT GGG GCT GAG GAC AAT GTC CTC    816
Arg Val Asp Arg Ser Ser Gln Arg Pro Gly Ala Glu Asp Asn Val Leu
        260             265                 270

AAT GAG ATC GTG AGT ATC TTG CAG CCC ACC CAG GTC CCT GAG CAG GAA    864
Asn Glu Ile Val Ser Ile Leu Gln Pro Thr Gln Val Pro Glu Gln Glu
    275             280                 285

ATG GAA GTC CAG GAG CCA GCA GAG CCA ACA GGT GTC AAC ATG TTG TCC    912
Met Glu Val Gln Glu Pro Ala Glu Pro Thr Gly Val Asn Met Leu Ser
290             295                 300

CCC GGG GAG TCA GAG CAT CTG CTG GAA CCG GCA GAA GCT GAA AGG TCT    960
Pro Gly Glu Ser Glu His Leu Leu Glu Pro Ala Glu Ala Glu Arg Ser
305             310                 315                 320

CAG AGG AGG AGG CTG CTG GTT CCA GCA AAT GAA GGT GAT CCC ACT GAG    1008
Gln Arg Arg Arg Leu Leu Val Pro Ala Asn Glu Gly Asp Pro Thr Glu
            325             330                 335

ACT CTG AGA CAG TGC TTC GAT GAC TTT GCA GAC TTG GTG CCC TTT GAC    1056
Thr Leu Arg Gln Cys Phe Asp Asp Phe Ala Asp Leu Val Pro Phe Asp
        340             345                 350
```

FIG. 4B

```
TCC TGG GAG CCG CTC ATG AGG AAG TTG GGC CTC ATG GAC AAT GAG ATA   1104
Ser Trp Glu Pro Leu Met Arg Lys Leu Gly Leu Met Asp Asn Glu Ile
        355                 360                 365

AAG GTG GCT AAA GCT GAG GCA GCG GGC CAC AGG GAC ACC TTG TAC ACG   1152
Lys Val Ala Lys Ala Glu Ala Ala Gly His Arg Asp Thr Leu Tyr Thr
        370                 375                 380

ATG CTG ATA AAG TGG GTC AAC AAA ACC GGG CGA GAT GCC TCT GTC CAC   1200
Met Leu Ile Lys Trp Val Asn Lys Thr Gly Arg Asp Ala Ser Val His
385                 390                 395                 400

ACC CTG CTG GAT GCC TTG GAG ACG CTG GGA GAG AGA CTT GCC AAG CAG   1248
Thr Leu Leu Asp Ala Leu Glu Thr Leu Gly Glu Arg Leu Ala Lys Gln
                405                 410                 415

AAG ATT GAG GAC CAC TTG TTG AGC TCT GGA AAG TTC ATG TAT CTA GAA   1296
Lys Ile Glu Asp His Leu Leu Ser Ser Gly Lys Phe Met Tyr Leu Glu
                    420                 425                 430

GGT AAT GCA GAC TCT GCC ATG TCC TAA                               1323
Gly Asn Ala Asp Ser Ala Met Ser  *
                435                 440
```

FIG. 4C

```
ATGACCATGA TTACGCCAAG CTTTGGAGCC TTTTTTTTGG AGATTTTCAA  50
CGTGAAAAAA TTATTATTCG CAATTCCTTT AGTTGTTCCT TTCTATGCGG 100
CCCAGCCGGC CATGGCCGAG GTGCAGCTGG TGCAGTCTGG GGGAGGTGTG 150
GAACGGCCGG GGGGGTCCCT GAGACTCTCC TGTGCAGCCT CTGGATTCAC 200
CTTTGATGAT TATGGCATGA GCTGGGTCCG CCAAGCTCCA GGGAAGGGGC 250
TGGAGTGGGT CTCTGGTATT AATTGGAATG GTGGTAGCAC AGGATATGCA 300
GACTCTGTGA AGGGCCGAGT CACCATCTCC AGAGACAACG CCAAGAACTC 350
CCTGTATCTG CAAATGAACA GCCTGAGAGC CGAGGACACG GCCGTATATT 400
ACTGTGCGAA AATCCTGGGT GCCGGACGGG CTGGTACTT CGATCTCTGG 450
GGGAAGGGGA CCACGGTCAC CGTCTCGAGT GGTGGAGGCG GTTCAGGCGG 500
AGGTGGCAGC GGCGGTGGCG GATCGTCTGA GCTGACTCAG GACCCTGCTG 550
TGTCTGTGGC CTTGGGACAG ACAGTCAGGA TCACATGCCA AGGAGACAGC 600
CTCAGAAGCT ATTATGCAAG CTGGTACCAG CAGAAGCCAG GACAGGCCCC 650
TGTACTTGTC ATCTATGGTA AAAACAACCG GCCCTCAGGG ATCCCAGACC 700
GATTCTCTGG CTCCAGCTCA GGAAACACAG CTTCCTTGAC CATCACTGGG 750
GCTCAGGCGG AAGATGAGGC TGACTATTAC TGTAACTCCC GGGACAGCAG 800
TGGTAACCAT GTGGTATTCG GCGGAGGGAC CAAGCTGACC GTCCTAGGTG 850
CGGCCGCACA TCATCATCAC CATCACGGGG CCGCAGAACA AAAACTCATC 900
TCAGAAGAGG ATCTGAATGG GGCCGCATAG                       930
```

FIG. 5

```
                              signal                                    Heavy chain
Apo-2.16E2.his    1 MTMITPSFGAFFLEIFNVKKLLFAIPLVVPFYAAQPAMAEVQLVQSGGGV CDR1                    CDR2
Apo-2.16E2.his   51 ERPGGSLRLSCAASGFTFDDYGMSWVRQAPGKGLEWVSGINWNGGSTGYA CDR3
Apo-2.16E2.his  101 DSVKGRVTISRDNAKNSLYLQMNSLRAEDTAVYYCAKIL----GAGRGWY Light chain
Apo-2.16E2.his  147 F-DLWGKGTTVTVSSGGGGSGGGGSGGGGS-SELTQDPAVSVALGQTVRI CDR1                        CDR2
Apo-2.16E2.his  195 TCQGDSLR---SYYASWYQQKPGQAPVLVIYGKNNRPSGIPDRFSGSSSG CDR3
Apo-2.16E2.his  242 NTASLTITGAQAEDEADYYCNSRDSSGNHVVFGGGTKLTVLGAAAHHHHH Apo-2.16E2.his  292 HGAAEQKLISEEDLNGAA
```

FIG. 6

EVQLVQSGGGVERPGGSLRLSCAASGFTFDDYGMSWVRQAPGKGLEWVSGINWNGGSTGY
ADSVKGRVTISRDNAKNSLYLQMNSLRAEDTAVYYCAKILGAGRGWYFDLWGKGTTVTVS
SASTKGPSVFPLAPSSKSTSGGTAALGCLVKDYFPEPVTVSWNSGALTSGVHTFPAVLQS
SGLYSLSSVVTVPSSSLGTQTYICNVNHKPSNTKVDKKVEPKSCDKTHTCPPCPAPELLG
GPSVFLFPPKPKDTLMISRTPEVTCVVVDVSHEDPEVKFNWYVDGVEVHNAKTKPREEQY
NSTYRVVSVLTVLHQDWLNGKEYKCKVSNKALPAPIEKTISKAKGQPREPQVYTLPPSRE
EMTKNQVSLTCLVKGFYPSDIAVEWESNGQPENNYKTTPPVLDSDGSFFLYSKLTVDKSR
WQQGNVFSCSVMHEALHNHYTQKSLSLSPGK

<451 residues, 0 stop; molecular weight: 49089.42

FIG. 7 ss.16E2.Heavy.txt

GAAGTTCAGCTGGTGCAGTCTGGGGGAGGTGTGGCCAAGCGGCCGGGGGGTCCCTGAGACTCTCCTGTGCAGCCTCTGGATTCACC
TTTGATGATTATGGCATGAGCTGGATCCGCCAGGCTCCAGGGAAGGGCCTGGAGTGGGTCTCTGGTATTAATTGGAATGGTGGT
AGCACAGGATATGCAGACTCTGTGAAGGGCCGAGTCACCATCTCCAGAGACAACGCCAAGAACTCCCTGTATCTGCAAATGAAC
AGCCTGAGAGCCGAGGACACGGCCGTGTACTACTGTGCAAGGGACTACTTCGATCTCTGGGGG
AAGGGGACCACGGTCACCGTCTCGGGCTGCCTCGGCTGTGTCCTGGTCCTGGTCGTGTCAGCGCCCCTGACC
GGGGGCAGCAGGCGTGCACACCTTCCCGGCTGTCCTACAGTCCTCAGGACTCAGTGACTGTGCCCTCTAGCAGC
TTGGGCACCCAGACCTACATCTGCAACGTGAATCACAAGCCCAGCAACACCAAGGTGGACAAGAAAGTTGAGCCCAAATCTTGT
GACAAAACTCACACATGCCCACCGTGCCCAGCACCTGAACTCCTGGGGGGACCGTCAGTCTTCCTCTTCCCCCCAAAACCCAAG
GACACCCTCATGATCTCCCGGACCCCTGAGGTCACATGCGTGGTGGTGGACGTGAGCCACGAAGACCCTGAGGTCAAGTTCAAC
TGGTACGTGGACGGCGTGGAGGTGCATAATGCCAAGACAAAGCCGCGGGAGGAGCAGTACAACAGCACGTACCGTGTGGTCAGC
GTCCTCACCGTCCTGCACCAGGACTGGCTGAATGGCAAGGAGTACAAGTGCAAGGTCTCCAACAAAI

AGCCCCTCCCCAGCCCCCATCGAGAAAACCATCTCCAAAGCCAAAGGGCAGCCCCGAGAACCACAGGTGTACACCCTGCCCCATC
CCGGGAGGAGATGACCAAGAACCAGGTCAGCCTGACCTGCCTGGTCAAAGGCTTCTATCCCAGCGACATCGCCGTGGAGTGGGA
GAGCAATGGGCAGCCGGAGAACAACTACAAGACCACGCCTCCCGTGCTGGACTCCGACGGCTCCTTCTTCCTACAGCAAGCT
CACCGTGGACAAGAGCAGGTGGCAGCAGGGGAACGTCTTCTCATGCTCCGTGATGCATGAGGCTCTGCACAACCACTACACGCA
GAAGAGCCTCTCCCTGTCTCCGGGTAAA

FIG. 8

SELTQDPAVSVALGQTVRITCQGDSLRSYYASWYQQKPGQAPVLVIYGKNNRPSGIPDRF
SGSSSGNTASLTITGAQAEDEADYYCNSRDSSGNHVVFGGGTKLTVLGQPKAAPSVTLFP
PSSEELQANKATLVCLISDFYPGAVTVAWKADSSPVKAGVETTTPSKQSNNKYAASSYLS
LTPEQWKSHKSYSCQVTHEGSTVEKTVAPTECS

<213 residues, 0 stop; molecular weight: 22583.95

FIG. 9 ss.16E2.light.txt

TCTGAGCTGACTCAGGACCCTGCTGTGTCTGTGGCCCTTGGGACAGAGTCAGGATCACATGCCAAGGAGACAGCCTCAGAAGC
TATTATGCAAGCTGGTACCAGCAGAAGCCAGGACAGGCCCCTGTACTTGTCATCTATGGTAAAAACAACCGGCCCTCAGGGATC
CCAGACCGATTCTCTGGCTCCAGCTCAGTAGACACAGCTTCCTTGACCATCACTGGGGCTCAGGCGGAAGATGAGGCTGACTAT
TACTGTAACTCTGTAACTCTCCCGGGACAGCAGCCTCTTCCCGCCATCTTCTGAGGAGTTGCAAGCTGACCAAGCTGGACCTAAGGCT
GCACCATCTGTCACCCTGTCACCCTGTCACAGTAGGCGTGGAAGGCGGATAGCGTCGCTGAAGACGACTACCCCTTCGAAGCAG
TATCCCGGAGCGGTCACAGTAGGCGTGGAAGGCGGATAGCGTCGCTGAAGACGACTACCCCTTCGAAGCAG
AGCAACAAATACGCCGCCAGCAGTCCCCTGACCCCAGAACAGTGAAAGAGCCACAAAAGCTACTCCTGCCAAGTC
ACCCATGAGGGCTCGACCGTCGAAAGACCGTCGCCCCGACAGAGTGTTCT

FIG. 10

TTCGAGCTCGCCCGACATTGATTATTGACTAGTTATTAATAGTAATCAATTACGGGGTCA
TTAGTTCATAGCCCATATATGGAGTTCCGCGTTACATAACTTACGGTAAATGGCCCGCCT
GGCTGACCGCCCAACGACCCCCGCCCATTGACGTCAATAATGACGTATGTTCCCATAGTA
ACGCCAATAGGGACTTTCCATTGACGTCAATGGGTGGAGTATTTACGGTAAACTGCCCAC
TTGGCAGTACATCAAGTGTATCATATGCCAAGTACGCCCCCTATTGACGTCAATGACGGT
AAATGGCCCGCCTGGCATTATGCCCAGTACATGACCTTATGGGACTTTCCTACTTGGCAG
TACATCTACGTATTAGTCATCGCTATTACCATGGTGATGCGGTTTTGGCAGTACATCAAT
GGGCGTGGATAGCGGTTTGACTCACGGGGATTTCCAAGTCTCCACCCCATTGACGTCAAT
GGGAGTTTGTTTTGGCACCAAAATCAACGGGACTTTCCAAAATGTCGTAACAACTCCGCC
CCATTGACGCAAATGGGCGGTAGGCGTGTACGGTGGGAGGTCTATATAAGCAGAGCTCGT
TTAGTGAACCGTCAGATCGCCTGGAGACGCCATCCACGCTGTTTTGACCTCCATAGAAGA
CACCGGGACCGATCCAGCCTCCGCGGCCGGGAACGGTGCATTGGAACGCGGATTCCCCGT
GCCAAGAGTGACGTAAGTACCGCCTATAGAGTCTATAGGCCCACCCCCTTGGCTTCGTTA
GAACGCGGCTACAATTAATACATAACCTTATGTATCATACACATACGATTTAGGTGACAC
TATAGAATAACATCCACTTTGCCTTTCTCTCCACAGGTGTCCACTCCCAGGTCCAACTGC
ACCTCGGTTCTATCGATTGAATTCCACC<u>ATG</u>GGATGGTCATGTATCATCCTTTTTCTAGT
AGCAACTGCAACTGGAGTACATTCAGATATCCAGATGACCCAGTCCCCGAGCTCCCTGTC
CGCCTCTGTGGGCGATAGGGTCACCATCACCTGCCGTGCCAGTCAGGACATCCGTAATTA
TTTGAACTGGTATCAACAGAAACCAGGAAAAGCTCCGAAACTACTGATTTACTATACCTC
CCGCCTGGAGTCTGGAGTCCCTTCTCGCTTCTCTGGTTCTGGTTCTGGGACGGATTACAC
TCTGACCATCAGTAGTCTGCAACCGGAGGACTTCGCAACTTATTACTGTCAGCAAGGTAA
TACTCTGCCGTGGACGTTCGGACAGGGCACCAAGGTGGAGATCAAACGAACTGTGGCTGC
ACCATCTGTCTTCATCTTCCCGCCATCTGATGAGCAGTTGAAATCTGGAACTGCCTCTGT
TGTGTGCCTGCTGAATAACTTCTATCCCAGAGAGGCCAAAGTACAGTGGAAGGTGGATAA
CGCCCTCCAATCGGGTAACTCCCAGGAGAGTGTCACAGAGCAGGACAGCAAGGACAGCAC
CTACAGCCTCAGCAGCACCCTGACGCTGAGCAAAGCAGACTACGAGAAACACAAAGTCTA
CGCCTGCGAAGTCACCCATCAGGGCCTGAGCTCGCCCGTCACAAAGAGCTTCAACAGGGG
AGAGTGT<u>TAA</u>GCTTGGCCGCCATGGCCCAACTTGTTTATTGCAGCTTATAATGGTTACAA
ATAAAGCAATAGCATCACAAATTTCACAAATAAAGCATTTTTTCACTGCATTCTAGTTG
TGGTTTGTCCAAACTCATCAATGTATCTTATCATGTCTGGATCGATCGGGAATTAATTCG
GCGCAGCACCATGGCCTGAAATAACCTCTGAAAGAGGAACTTGGTTAGGTACCTTCTGAG
GCGGAAAGAACCAGCTGTGGAATGTGTGTCAGTTAGGGTGTGGAAAGTCCCCAGGCTCCC
CAGCAGGCAGAAGTATGCAAAGCATGCATCTCAATTAGTCAGCAACCAGGTGTGGAAAGT
CCCCAGGCTCCCCAGCAGGCAGAAGTATGCAAAGCATGCATCTCAATTAGTCAGCAACCA
TAGTCCCGCCCCTAACTCCGCCCATCCCGCCCCTAACTCCGCCCAGTTCCGCCCATTCTC
CGCCCCATGGCTGACTAATTTTTTTTATTTATGCAGAGGCCGAGGCCGCCTCGGCCTCTG
AGCTATTCCAGAAGTAGTGAGGAGGCTTTTTTGGAGGCCTAGGCTTTTGCAAAAAGCTGT
TAACAGCTTGGCACTGGCCGTCGTTTTACAACGTCGTGACTGGGAAAACCCTGGCGTTAC
CCAACTTAATCGCCTTGCAGCACATCCCCCTTCGCCAGCTGGCGTAATAGCGAAGAGGC
CCGCACCGATCGCCCTTCCCAACAGTTGCGTAGCCTGAATGGCGAATGGCGCCTGATGCG
GTATTTTCTCCTTACGCATCTGTGCGGTATTTCACACCGCATACGTCAAAGCAACCATAG
TACGCGCCCTGTAGCGGCGCATTAAGCGCGGCGGGTGTGGTGGTTACGCGCAGCGTGACC
GCTACACTTGCCAGCGCCCTAGCGCCCGCTCCTTTCGCTTTCTTCCCTTCCTTTCTCGCC
ACGTTCGCCGGCTTTCCCCGTCAAGCTCTAAATCGGGGGCTCCCTTTAGGGTTCCGATTT
AGTGCTTTACGGCACCTCGACCCCAAAAAACTTGATTTGGGTGATGGTTCACGTAGTGGG
CCATCGCCCTGATAGACGGTTTTTCGCCCTTTGACGTTGGAGTCCACGTTCTTTAATAGT
GGACTCTTGTTCCAAACTGGAACAACACTCAACCCTATCTCGGGCTATTCTTTTGATTTA
TAAGGGATTTTGCCGATTTCGGCCTATTGGTTAAAAAATGAGCTGATTTAACAAAAATTT
AACGCGAATTTTAACAAAATATTAACGTTTACAATTTTATGGTGCACTCTCAGTACAATC
TGCTCTGATGCCGCATAGTTAAGCCAACTCCGCTATCGCTACGTGACTGGGTCATGGCTG
CGCCCCGACACCCGCCAACACCCGCTGACGCGCCCTGACGGGCTTGTCTGCTCCCGGCAT
CCGCTTACAGACAAGCTGTGACCGTCTCCGGGAGCTGCATGTGTCAGAGGTTTTCACCGT
CATCACCGAAACGCGCGAGGCAGTATTCTTGAAGACGAAAGGGCCTCGTGATACGCCTAT
```

FIG. 11A

```
TTTTATAGGTTAATGTCATGATAATAATGGTTTCTTAGACGTCAGGTGGCACTTTTCGGG
GAAATGTGCGCGGAACCCCTATTTGTTTATTTTTCTAAATACATTCAAATATGTATCCGC
TCATGAGACAATAACCCTGATAAATGCTTCAATAATATTGAAAAAGGAAGAGTATGAGTA
TTCAACATTTCCGTGTCGCCCTTATTCCCTTTTTGCGGCATTTTGCCTTCCTGTTTTTG
CTCACCCAGAAACGCTGGTGAAAGTAAAAGATGCTGAAGATCAGTTGGGTGCACGAGTGG
GTTACATCGAACTGGATCTCAACAGCGGTAAGATCCTTGAGAGTTTTCGCCCCGAAGAAC
GTTTTCCAATGATGAGCACTTTTAAAGTTCTGCTATGTGGCGCGGTATTATCCCGTGATG
ACGCCGGGCAAGAGCAACTCGGTCGCCGCATACACTATTCTCAGAATGACTTGGTTGAGT
ACTCACCAGTCACAGAAAAGCATCTTACGGATGGCATGACAGTAAGAGAATTATGCAGTG
CTGCCATAACCATGAGTGATAACACTGCGGCCAACTTACTTCTGACAACGATCGGAGGAC
CGAAGGAGCTAACCGCTTTTTTGCACAACATGGGGGATCATGTAACTCGCCTTGATCGTT
GGGAACCGGAGCTGAATGAAGCCATACCAAACGACGAGCGTGACACCACGATGCCAGCAG
CAATGGCAACAACGTTGCGCAAACTATTAACTGGCGAACTACTTACTCTAGCTTCCCGGC
AACAATTAATAGACTGGATGGAGGCGGATAAAGTTGCAGGACCACTTCTGCGCTCGGCCC
TTCCGGCTGGCTGGTTTATTGCTGATAAATCTGGAGCCGGTGAGCGTGGGTCTCGCGGTA
TCATTGCAGCACTGGGGCCAGATGGTAAGCCCTCCCGTATCGTAGTTATCTACACGACGG
GGAGTCAGGCAACTATGGATGAACGAAATAGACAGATCGCTGAGATAGGTGCCTCACTGA
TTAAGCATTGGTAACTGTCAGACCAAGTTTACTCATATATACTTTAGATTGATTTAAAAC
TTCATTTTTAATTTAAAAGGATCTAGGTGAAGATCCTTTTTGATAATCTCATGACCAAAA
TCCCTTAACGTGAGTTTTCGTTCCACTGAGCGTCAGACCCCGTAGAAAAGATCAAAGGAT
CTTCTTGAGATCCTTTTTTTCTGCGCGTAATCTGCTGCTTGCAAACAAAAAAACCACCGC
TACCAGCGGTGGTTTGTTTGCCGGATCAAGAGCTACCAACTCTTTTTCCGAAGGTAACTG
GCTTCAGCAGAGCGCAGATACCAAATACTGTCCTTCTAGTGTAGCCGTAGTTAGGCCACC
ACTTCAAGAACTCTGTAGCACCGCCTACATACCTCGCTCTGCTAATCCTGTTACCAGTGG
CTGCTGCCAGTGGCGATAAGTCGTGTCTTACCGGGTTGGACTCAAGACGATAGTTACCGG
ATAAGGCGCAGCGGTCGGGCTGAACGGGGGGTTCGTGCACACAGCCCAGCTTGGAGCGAA
CGACCTACACCGAACTGAGATACCTACAGCGTGAGCATTGAGAAAGCGCCACGCTTCCCG
AAGGGAGAAAGGCGGACAGGTATCCGGTAAGCGGCAGGGTCGGAACAGGAGAGCGCACGA
GGGAGCTTCCAGGGGGAAACGCCTGGTATCTTTATAGTCCTGTCGGGTTTCGCCACCTCT
GACTTGAGCGTCGATTTTTGTGATGCTCGTCAGGGGGCGGAGCCTATGGAAAAACGCCA
GCAACGCGGCCTTTTACGGTTCCTGGCCTTTTGCTGGCCTTTTGCTCACATGTTCTTTC
CTGCGTTATCCCCTGATTCTGTGGATAACCGTATTACCGCCTTTGAGTGAGCTGATACCG
CTCGCCGCAGCCGAACGACCGAGCGCAGCGAGTCAGTGAGCGAGGAAGCGGAAGAGCGCC
CAATACGCAAACCGCCTCTCCCCGCGCGTTGGCCGATTCATTAATCCAGCTGGCACGACA
GGTTTCCCGACTGGAAAGCGGGCAGTGAGCGCAACGCAATTAATGTGAGTTACCTCACTC
ATTAGGCACCCCAGGCTTTACACTTTATGCTTCCGGCTCGTATGTTGTGTGGAATTGTGA
GCGGATAACAATTTCACACAGGAAACAGCTATGACCATGATTACGAATTAA
```

FIG. 11B

```
ATTCGAGCTCGCCCGACATTGATTATTGACTAGTTATTAATAGTAATCAATTACGGGGTC
ATTAGTTCATAGCCCATATATGGAGTTCCGCGTTACATAACTTACGGTAAATGGCCCGCC
TGGCTGACCGCCCAACGACCCCGCCCATTGACGTCAATAATGACGTATGTTCCCATAGT
AACGCCAATAGGGACTTTCCATTGACGTCAATGGGTGGAGTATTTACGGTAAACTGCCCA
CTTGGCAGTACATCAAGTGTATCATATGCCAAGTACGCCCCCTATTGACGTCAATGACGG
TAAATGGCCCGCCTGGCATTATGCCCAGTACATGACCTTATGGGACTTTCCTACTTGGCA
GTACATCTACGTATTAGTCATCGCTATTACCATGGTGATGCGGTTTTGGCAGTACATCAA
TGGGCGTGGATAGCGGTTTGACTCACGGGGATTTCCAAGTCTCCACCCCATTGACGTCAA
TGGGAGTTTGTTTTGGCACCAAAATCAACGGGACTTTCCAAAATGTCGTAACAACTCCGC
CCCATTGACGCAAATGGGCGGTAGGCGTGTACGGTGGGAGGTCTATATAAGCAGAGCTCG
TTTAGTGAACCGTCAGATCGCCTGGAGACGCCATCCACGCTGTTTTGACCTCCATAGAAG
ACACCGGGACCGATCCAGCCTCCGCGGCCGGGAACGGTGCATTGGAACGCGGATTCCCCG
TGCCAAGAGTGACGTAAGTACCGCCTATAGAGTCTATAGGCCCACCCCCTTGGCTTCGTT
AGAACGCGGCTACAATTAATACATAACCTTATGTATCATACACATACGATTTAGGTGACA
CTATAGAATAACATCCACTTTGCCTTTCTCTCCACAGGTGTCCACTCCCAGGTCCAACTG
CACCTCGGTTCTATCGATTGAATTCCACCATGGGATGGTCATGTATCATCCTTTTTCTAG
TAGCAACTGCAACTGGAGTACATTCAGAAGTTCAGCTGGTGGAGTCTGGCGGTGGCCTGG
TGCAGCCAGGGGGCTCACTCCGTTTGTCCTGTGCAGCTTCTGGCTACTCCTTTACCGGCT
ACACTATGAACTGGGTGCGTCAGGCCCCAGGTAAGGGCCTGGAATGGGTTGCACTGATTA
ATCCTTATAAGGTGTTACTACCTATGCCGATAGCGTCAAGGGCCGTTTCACTATAAGCG
TAGATAAATCCAAAAACACAGCCTACCTGCAAATGAACAGCCTGCGTGCTGAGGACACTG
CCGTCTATTATTGTGCTAGAAGCGGATACTACGGCGATAGCGACTGGTATTTTGACGTCT
GGGGTCAAGGAACCCTGGTCACCGTCTCCTCGGCCTCCACCAAGGGCCCATCGGTCTTCC
CCCTGGCACCCTCCTCCAAGAGCACCTCTGGGGGCACAGCGGCCCTGGGCTGCCTGGTCA
AGGACTACTTCCCCGAACCGGTGACGGTGTCGTGGAACTCAGGCGCCCTGACCAGCGGCG
TGCACACCTTCCCGGCTGTCCTACAGTCCTCAGGACTCTACTCCCTCAGCAGCGTGGTGA
CTGTGCCCTCTAGCAGCTTGGGCACCCAGACCTACATCTGCAACGTGAATCACAAGCCCA
GCAACACCAAGGTGGACAAGAAAGTTGAGCCCAAATCTTGTGACAAAACTCACACATGCC
CACCGTGCCCAGCACCTGAACTCCTGGGGGGACCGTCAGTCTTCCTCTTCCCCCCAAAAC
CCAAGGACACCCTCATGATCTCCCGGACCCCTGAGGTCACATGCGTGGTGGTGGACGTGA
GCCACGAAGACCCTGAGGTCAAGTTCAACTGGTACGTGGACGGCGTGGAGGTGCATAATG
CCAAGACAAAGCCGCGGGAGGAGCAGTACAACAGCACGTACCGTGTGGTCAGCGTCCTCA
CCGTCCTGCACCAGGACTGGCTGAATGGCAAGGAGTACAAGTGCAAGGTCTCCAACAAAG
CCCTCCCAGCCCCCATCGAGAAAACCATCTCCAAAGCCAAAGGGCAGCCCCGAGAACCAC
AGGTGTACACCCTGCCCCCATCCCGGGAAGAGATGACCAAGAACCAGGTCAGCCTGACCT
GCCTGGTCAAAGGCTTCTATCCCAGCGACATCGCCGTGGAGTGGGAGAGCAATGGGCAGC
CGGAGAACAACTACAAGACCACGCCTCCCGTGCTGGACTCCGACGGCTCCTTCTTCCTCT
ACAGCAAGCTCACCGTGGACAAGAGCAGGTGGCAGCAGGGGAACGTCTTCTCATGCTCCG
TGATGCATGAGGCTCTGCACAACCACTACACGCAGAAGAGCCTCTCCCTGTCTCCGGGTA
AATGAGTGCGACGGCCCTAGAGTCGACCTGCAGAAGCTTGGCCGCCATGGCCCAACTTGT
TTATTGCAGCTTATAATGGTTACAAATAAAGCAATAGCATCACAAATTTCACAAATAAAG
CATTTTTTTCACTGCATTCTAGTTGTGGTTTGTCCAAACTCATCAATGTATCTTATCATG
TCTGGATCGATCGGGAATTAATTCGGCGCAGCACCATGGCCTGAAATAACCTCTGAAAGA
GGAACTTGGTTAGGTACCTTCTGAGGCGGAAAGAACCATCTGTGGAATGTGTGTCAGTTA
GGGTGTGGAAAGTCCCCAGGCTCCCCAGCAGGCAGAAGTATGCAAAGCATGCATCTCAAT
TAGTCAGCAACCAGGTGTGGAAAGTCCCCAGGCTCCCCAGCAGGCAGAAGTATGCAAAGC
ATGCATCTCAATTAGTCAGCAACCATAGTCCCGCCCCTAACTCCGCCCATCCCGCCCTA
ACTCCGCCCAGTTCCGCCCATTCTCCGCCCCATGGCTGACTAATTTTTTTATTTATGCA
GAGGCCGAGGCCGCCTCGGCCTCTGAGCTATTCCAGAAGTAGTGAGGAGGCTTTTTGGA
GGCCTAGGCTTTTGCAAAAAGCTGTTAACAGCTTGGCACTGGCCGTCGTTTTACAACGTC
GTGACTGGGAAAACCCTGGCGTTACCCAACTTAATCGCCTTGCAGCACATCCCCCCTTCG
CCAGTTGGCGTAATAGCGAAGAGGCCCGCACCGATCGCCCTTCCCAACAGTTGCGTAGCC
TGAATGGCGAATGGCGCCTGATGCGGTATTTTCTCCTTACGCATCTGTGCGGTATTTCAC
ACCGCATACGTCAAAGCAACCATAGTACGCGCCCTGTAGCGGCGCATTAAGCGCGGCGGG
```

FIG. 12A

```
TGTGGTGGTTACGCGCAGCGTGACCGCTACACTTGCCAGCGCCCTAGCGCCCGCTCCTTT
CGCTTTCTTCCCTTCCTTTCTCGCCACGTTCGCCGGCTTTCCCCGTCAAGCTCTAAATCG
GGGGCTCCCTTTAGGGTTCCGATTTAGTGCTTTACGGCACCTCGACCCCAAAAAACTTGA
TTTGGGTGATGGTTCACGTAGTGGGCCATCGCCCTGATAGACGGTTTTTCGCCCTTTGAC
GTTGGAGTCCACGTTCTTTAATAGTGGACTCTTGTTCCAAACTGGAACAACACTCAACCC
TATCTCGGGCTATTCTTTTGATTTATAAGGGATTTTGCCGATTTCGGCCTATTGGTTAAA
AAATGAGCTGATTTAACAAAAATTTAACGCGAATTTTAACAAAATATTAACGTTTACAAT
TTTATGGTGCACTCTCAGTACAATCTGCTCTGATGCCGCATAGTTAAGCCAACTCCGCTA
TCGCTACGTGACTGGGTCATGGCTGCGCCCGACACCCGCCAACACCCGCTGACGCGCCC
TGACGGGCTTGTCTGCTCCCGGCATCCGCTTACAGACAAGCTGTGACCGTCTCCGGGAGC
TGCATGTGTCAGAGGTTTTCACCGTCATCACCGAAACGCGCGAGGCAGTATTCTTGAAGA
CGAAAGGGCCTCGTGATACGCCTATTTTTATAGGTTAATGTCATGATAATAATGGTTTCT
TAGACGTCAGGTGGCACTTTTCGGGGAAATGTGCGCGGAACCCCTATTTGTTTATTTTTC
TAAATACATTCAAATATGTATCCGCTCATGAGACAATAACCCTGATAAATGCTTCAATAA
TATTGAAAAAGGAAGAGTATGAGTATTCAACATTTCCGTGTCGCCCTTATTCCCTTTTTT
GCGGCATTTTGCCTTCCTGTTTTGCTCACCCAGAAACGCTGGTGAAAGTAAAAGATGCT
GAAGATCAGTTGGGTGCACGAGTGGGTTACATCGAACTGGATCTCAACAGCGGTAAGATC
CTTGAGAGTTTTCGCCCCGAAGAACGTTTTCCAATGATGAGCACTTTTAAAGTTCTGCTA
TGTGGCGCGGTATTATCCCGTGATGACGCCGGGCAAGAGCAACTCGGTCGCCGCATACAC
TATTCTCAGAATGACTTGGTTGAGTACTCACCAGTCACAGAAAAGCATCTTACGGATGGC
ATGACAGTAAGAGAATTATGCAGTGCTGCCATAACCATGAGTGATAACACTGCGGCCAAC
TTACTTCTGACAACGATCGGAGGACCGAAGGAGCTAACCGCTTTTTTGCACAACATGGGG
GATCATGTAACTCGCCTTGATCGTTGGGAACCGGAGCTGAATGAAGCCATACCAAACGAC
GAGCGTGACACCACGATGCCAGCAGCAATGGCAACAACGTTGCGCAAACTATTAACTGGC
GAACTACTTACTCTAGCTTCCCGGCAACAATTAATAGACTGGATGGAGGCGGATAAAGTT
GCAGGACCACTTCTGCGCTCGGCCCTTCCGGCTGGCTGGTTTATTGCTGATAAATCTGGA
GCCGGTGAGCGTGGGTCTCGCGGTATCATTGCAGCACTGGGGCCAGATGGTAAGCCCTCC
CGTATCGTAGTTATCTACACGACGGGGAGTCAGGCAACTATGGATGAACGAAATAGACAG
ATCGCTGAGATAGGTGCCTCACTGATTAAGCATTGGTAACTGTCAGACCAAGTTTACTCA
TATATACTTTAGATTGATTTAAAACTTCATTTTTAATTTAAAAGGATCTAGGTGAAGATC
CTTTTTGATAATCTCATGACCAAAATCCCTTAACGTGAGTTTTCGTTCCACTGAGCGTCA
GACCCCGTAGAAAAGATCAAAGGATCTTCTTGAGATCCTTTTTTTCTGCGCGTAATCTGC
TGCTTGCAAACAAAAAAACCACCGCTACCAGCGGTGGTTTGTTTGCCGGATCAAGAGCTA
CCAACTCTTTTTCCGAAGGTAACTGGCTTCAGCAGAGCGCAGATACCAAATACTGTCCTT
CTAGTGTAGCCGTAGTTAGGCCACCACTTCAAGAACTCTGTAGCACCGCCTACATACCTC
GCTCTGCTAATCCTGTTACCAGTGGCTGCTGCCAGTGGCGATAAGTCGTGTCTTACCGGG
TTGGACTCAAGACGATAGTTACCGGATAAGGCGCAGCGGTCGGGCTGAACGGGGGGTTCG
TGCACACAGCCCAGCTTGGAGCGAACGACCTACACCGAACTGAGATACCTACAGCGTGAG
CATTGAGAAAGCGCCACGCTTCCCGAAGGGAGAAAGGCGGACAGGTATCCGGTAAGCGGC
AGGGTCGGAACAGGAGAGCGCACGAGGGAGCTTCCAGGGGGAAACGCCTGGTATCTTTAT
AGTCCTGTCGGGTTTCGCCACCTCTGACTTGAGCGTCGATTTTTGTGATGCTCGTCAGGG
GGGCGGAGCCTATGGAAAAACGCCAGCAACGCGGCCTTTTTACGGTTCCTGGCCTTTTGC
TGGCCTTTTGCTCACATGTTCTTTCCTGCGTTATCCCCTGATTCTGTGGATAACCGTATT
ACCGCCTTTGAGTGAGCTGATACCGCTCGCCGCAGCCGAACGACCGAGCGCAGCGAGTCA
GTGAGCGAGGAAGCGGAAGAGCGCCCAATACGCAAACCGCCTCTCCCCGCGCGTTGGCCG
ATTCATTAATCCAACTGGCACGACAGGTTTCCCGACTGGAAAGCGGGCAGTGAGCGCAAC
GCAATTAATGTGAGTTACCTCACTCATTAGGCACCCCAGGCTTTACACTTTATGCTTCCG
GCTCGTATGTTGTGTGGAATTGTGAGCGGATAACAATTTCACACAGGAAACAGCTATGAC
CATGATTACGAATTA
```

FIG. 12B ss.Apomab7.3.heavy.txt

GAAGTTCAGCTGGTGCAGTCTGGGGGAGGCTTGGTACAGCCTGGGGGGTCCCTGAGACTCTCCTGTGCAGCCTCTGGATTCACC
TTTGATGATTATGCCATGAGCTGGGTCCGCCAAGCTCCAGGGAAGGGGCTGGAGTGGGTCTCTGGTATCAATTGGCAGGGTGGT
AGCACAGGATATGCAGACTCTGTGAAGGGCCGAGTCACCATCTCCAGAGACAACGCCAAGAACTCCCTGTATCTGCAAATGAAC
AGCCTGAGAGCCGAGGACACGGTCTCGGTCGCCGTATATTACTGTGCGAAGGGCTGGTACTTCGATTACTGGGGG
AAGGGGACCACGGTCACCGTCTGCCGCTCAGTGCCTCCACCAAGGGCCCATCGGTCTTCCCCCTGGCACCCTCCTCCAAGAGCACCTCT
GGGGCACAGCGGCCCTGGGCTGCCTGGTCAAGGACTACTTCCCCGAACCGGTGACGGTGTCGTGGAACTCAGGCGCCCTGACC
AGCGGCGTGCACACCTTCCCGGCTGTCCTACAGTCCTCAGGACTCTACTCCCTCAGCAGCGTGGTGACCGTGCCCTCTAGCAGC
TTGGGCACCCAGACCTACATCTGCAACGTGAATCACAAGCCCAGCAACACCAAGGTGGACAAGAAAGTTGAGCCCAAATCTTGT
GACAAAACTCACACATGCCCACCGTGCCCAGCACCTGAACTCCTGGGGGGACCGTCAGTCTTCCTCTTCCCCCCAAAACCCAAGG
ACACCCTCATGATCTCCCGGACCCCTGAGGTCACATGCGTGGTGGTGGACGTGAGCCACGAAGACCCTGAGGTCAAGTTCAAC
TGGTACGTGGACGGCGTGGAGGTGCATAATGCCAAGACAAAGCCGCGGGAGGAGCAGTACAACAGCACGTACCGTGTGGTCAGC
GTCCTCACCGTCCTGCACCAGGACTGGCTGAATGGCAAGGAGTACAAGTGCAAGGTCTCCAACAAA

AGCCCCTCCCAGCCCCCATCGAGAAAACCATCTCCAAAGCCAAAGGGCAGCCCCGAGAACCACAGGTGTACACCCTGCCCCCATC
CCGGGAAGATGACCAAGAACCAGGTCAGCCTGACCTGCCTGGTCAAAGGCTTCTATCCCAGCGACATCGCCGTGGAGTGGGA
GAGCAATGGGCAGCCGGAGAACAACTACAAGACCACGCCTCCCGTGCTGGACTCCGACGGCTCCTTCTTCCTCTACAGCAAGCT
CACCGTGGACAAGAGCAGGTGGCAGCAGGGGAACGTCTTCTCATGCTCCGTGATGCATGAGGCTCTGCACAACCACTACACGCA
GAAGAGCCTCTCCCTGTCTCCGGGTAAA

FIG. 13

EVQLVQSGGGVERPGGSLRLSCAASGFTFDDYAMSWVRQAPGKGLEWVSGINWQGGSTGY
ADSVKGRVTISRDNAKNSLYLQMNSLRAEDTAVYYCAKILGAGRGWYFDYWGKGTTVTVS
SASTKGPSVFPLAPSSKSTSGGTAALGCLVKDYFPEPVTVSWNSGALTSGVHTFPAVLQS
SGLYSLSSVVTVPSSSLGTQTYICNVNHKPSNTKVDKKVEPKSCDKTHTCPPCPAPELLG
GPSVFLFPPKPKDTLMISRTPEVTCVVVDVSHEDPEVKFNWYVDGVEVHNAKTKPREEQY
NSTYRVVSVLTVLHQDWLNGKEYKCKVSNKALPAPIEKTISKAKGQPREPQVYTLPPSRE
EMTKNQVSLTCLVKGFYPSDIAVEWESNGQPENNYKTTPPVLDSDGSFFLYSKLTVDKSR
WQQGNVFSCSVMHEALHNHYTQKSLSLSPGK

<451 residues, 0 stop; molecular weight: 49167.50

FIG. 14 ss.Apomab7.3.light.txt

TCTGAGCTGACTCAGGACCCTGCTGTGTCTGTGGCCCTGGGACAGACAGTCAGGATCACATGCTCAGGAGACAGCCTCAGAAGC
TATTATGCAAGCTGGTACCAGCAGAAGCCAGGACAGGCCCCTGTACTTGTCATCTATGGTCAAACACAGGCCTTCAGGGATC
CCAGACCGATTCTCTGGCTCCAGCTCAGGAAACACAGCTTCCTTGACCATCACTGGGGCTCAGGCGGAAGATGAGGCTGACTAT
TACTGTAACTCCGTAACCATGTGTATTCGGCGGAGGACCAAGCTGACCGTCCTTGGCCAACTGAGTCAGTGACTTC
GCACCATCTGTCACCCTCTTCCCGCCATCTCTGAGGAGTTGCAAGCTAACAAAGCCACTCTGTGTGCCTGATCAGTGACTTC
TATCCCGGAGCGGTCACAGTAGCGTGGAAGGCGATAGCCAGCAGTCCCCGTAAACAGTGGAAGAGCCACAAAAGCTACTCCTGCCAAGTC
AGCAACAACAAATACGCCAGCAGCTCGTGTCGCTGACCCGAGAACAGTGGAAGAGCCACAAAAGCTACTCCTGCCAAGTC
ACCCATGAGGGCTGAAAAGACCGTCGCCCCGACAGAGTGTCT

FIG. 15

```
SELTQDPAVSVALGQTVRITCSGDSLRSYYASWYQQKPGQAPVLVIYGANNRPSGIPDRF
SGSSSGNTASLTITGAQAEDEADYYCNSADSSGNHVVFGGGTKLTVLGQPKAAPSVTLFP
PSSEELQANKATLVCLISDFYPGAVTVAWKADSSPVKAGVETTTPSKQSNNKYAASSYLS
LTPEQWKSHKSYSCQVTHEGSTVEKTVAPTECS
```

<213 residues, 0 stop; molecular weight: 22400.70

FIG. 16

Alignment, 16E5 and Apomab 7.3 Heavy chains

```
16E2       1 EVQLVQSGGGVERPGGSLRLSCAASGFTFDDYGMSW
Apomab7.3  1 EVQLVQSGGGVERPGGSLRLSCAASGFTFDDYAMSW
                                             *

16E2      37 VRQAPGKGLEWVSGINWNGGSTGYADSVKGRVTISRDNAKNSLYLQMNSL
Apomab7.3 37 VRQAPGKGLEWVSGINWQGGSTGYADSVKGRVTISRDNAKNSLYLQMNSL
                             *

16E2      87 RAEDTAVYYCAKILGAGRGWYFDLWGKGTTVTVSSASTKGPSVFPLAPSS
Apomab7.3 87 RAEDTAVYYCAKILGAGRGWYFDYWGKGTTVTVSSASTKGPSVFPLAPSS
                                   *

16E2     137 KSTSGGTAALGCLVKDYFPEPVTVSWNSGALTSGVHTFPAVLQSSGLYSL
Apomab7.3 137 KSTSGGTAALGCLVKDYFPEPVTVSWNSGALTSGVHTFPAVLQSSGLYSL 16E2     187 SSVVTVPSSSLGTQTYICNVNHKPSNTKVDKKVEPKSCDKTHTCPPCPAP
Apomab7.3 187 SSVVTVPSSSLGTQTYICNVNHKPSNTKVDKKVEPKSCDKTHTCPPCPAP 16E2     237 ELLGGPSVFLFPPKPKDTLMISRTPEVTCVVVDVSHEDPEVKFNWYVDGV
Apomab7.3 237 ELLGGPSVFLFPPKPKDTLMISRTPEVTCVVVDVSHEDPEVKFNWYVDGV 16E2     287 EVHNAKTKPREEQYNSTYRVVSVLTVLHQDWLNGKEYKCKVSNKALPAPI
Apomab7.3 287 EVHNAKTKPREEQYNSTYRVVSVLTVLHQDWLNGKEYKCKVSNKALPAPI
```

FIG. 17A

| | | |
|---|---|---|
| 16E2 | 337 | EKTISKAKGQPREPQVYTLPPSREEMTKNQVSLTCLVKGFYPSDIAVEWE |
| Apomab7.3 | 337 | EKTISKAKGQPREPQVYTLPPSREEMTKNQVSLTCLVKGFYPSDIAVEWE |
| 16E2 | 387 | SNGQPENNYKTTPPVLDSDGSFFLYSKLTVDKSRWQQGNVFSCSVMHEAL |
| Apomab7.3 | 387 | SNGQPENNYKTTPPVLDSDGSFFLYSKLTVDKSRWQQGNVFSCSVMHEAL |
| 16E2.huIgG1 | 437 | HNHYTQKSLSLSPGK |
| Apomab7.3 | 437 | HNHYTQKSLSLSPGK |

FIG. 17B

Alignment, 16E2 and Apomab 7.3 Light chains

```
16E2       1  SELTQDPAVSVALGQTVRITCQGDSLRSYYASWYQQKPGQAPVLVIYGKN
Apomab7.3  1  SELTQDPAVSVALGQTVRITCSGDSLRSYYASWYQQKPGQAPVLVIYGAN
                                   *                              *

16E2      51  NRPSGIPDRFSGSSSGNTASLTITGAQAEDEADYYCNSRDSSGNHVVFGG
Apomab7.3 51  NRPSGIPDRFSGSSSGNTASLTITGAQAEDEADYYCNSADSSGNHVVFGG
                                                      *

16E2     101  GTKLTVLGQPKAAPSVTLFPPSSEELQANKATLVCLISDFYPGAVTVAWK
Apomab7.3 101 GTKLTVLGQPKAAPSVTLFPPSSEELQANKATLVCLISDFYPGAVTVAWK 16E2     151  ADSSPVKAGVETTTPSKQSNNKYAASSYLSLTPEQWKSHKSYSCQVTHEG
Apomab7.3 151 ADSSPVKAGVETTTPSKQSNNKYAASSYLSLTPEQWKSHKSYSCQVTHEG 16E2     201  STVEKTVAPTECS
Apomab7.3 201 STVEKTVAPTECS
```

FIG. 18

Heavy Chain Variants

Light Chain Libraries

Single IP Dose of Apomab 5.3, 6.3 & 8.3 compared to 16E2 version 1 in the COLO205 Xenograft Athymic Nude Mouse Model Single IP Dose of Apomabs 5.2, 6.2, 5.3, 7.2 & 7.3 compared to 16E21 version 1 in the COLO205 Xenograft Athymic Nude Mouse Model Single IP Dose of Apomabs 5.2, 7.3 & 8.3 compared to 16E2 version 1 in the COLO205 Xenograft Athymic Nude Mouse Model Apomab 7.3 Derived from a Stable Cell vs. a Transient Cell Line in the COLO205 Xenograft in Nude Mice Apomab 7.3 (10mg/kg) Alone & in Combination with CPT-11 (80mg/kg) vs. HCT15 Xenograft Apomab 7.3 (10mg/kg) alone & in Combination with CPT-11 (80mg/kg) vs. LS180 Xenograft Apomab 7.3 (10 mg/kg; q1wk.) alone & in Combination with Rituxan (4 mg/kg; q1wk.) vs. BJAB Xenograft CB17 ICR SCID Mouse Model Apomab 7.3 (10 mg/kg; IV) alone & in combination with
Gemcitabine (160 mg/kg; IP) vs. BxPC3 Xenograft in Athymic Nude Mice Apomab 7.3 (10 mg/kg; q1wk.) alone and
in combination with Carboplatin (100 mg/kg; 1x) & Taxol (6.25 mg/kg; 5x/wk.)
in the H2122 xenograft model Dose Response of Apomab 7.3 vs. H2122

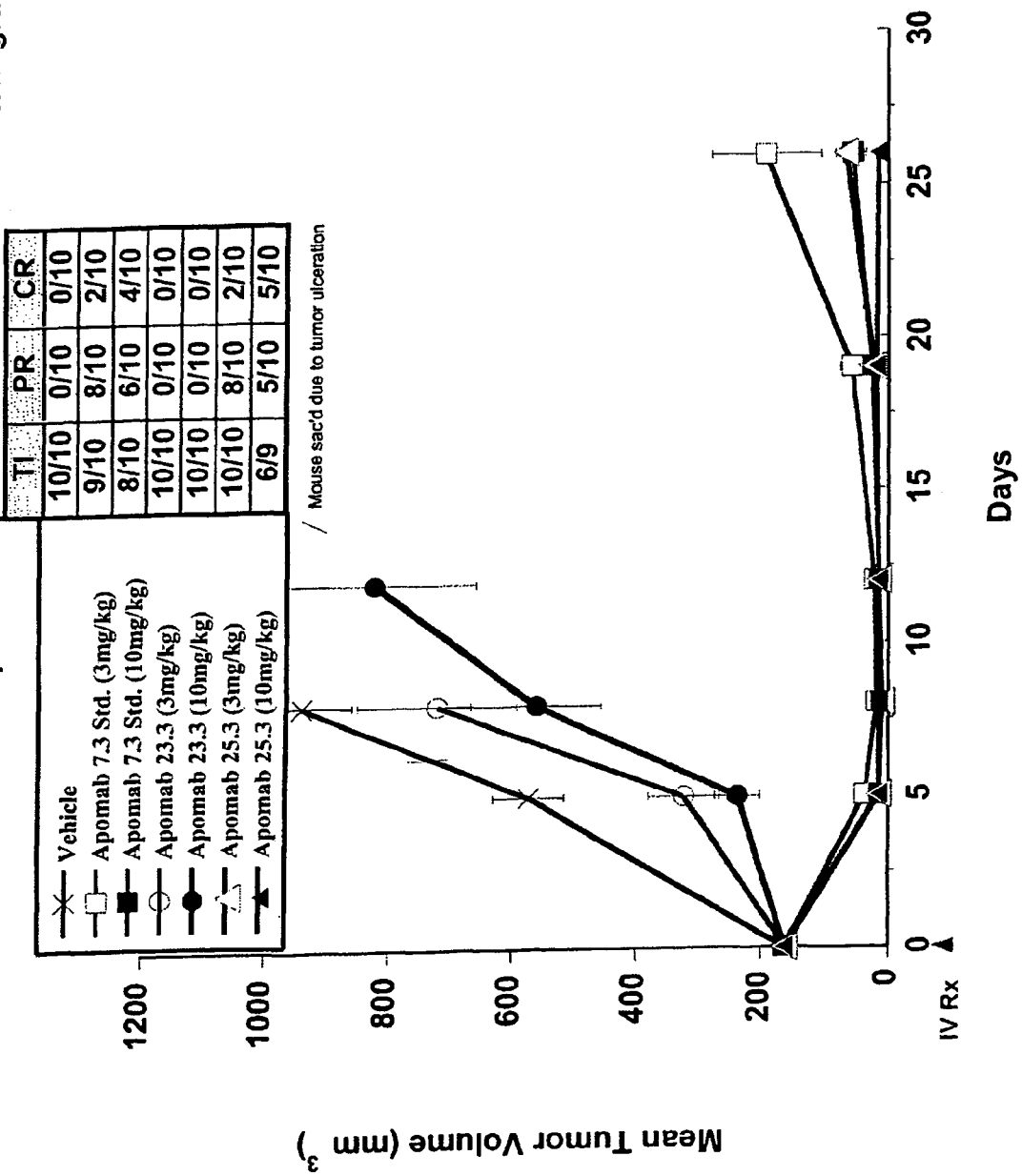

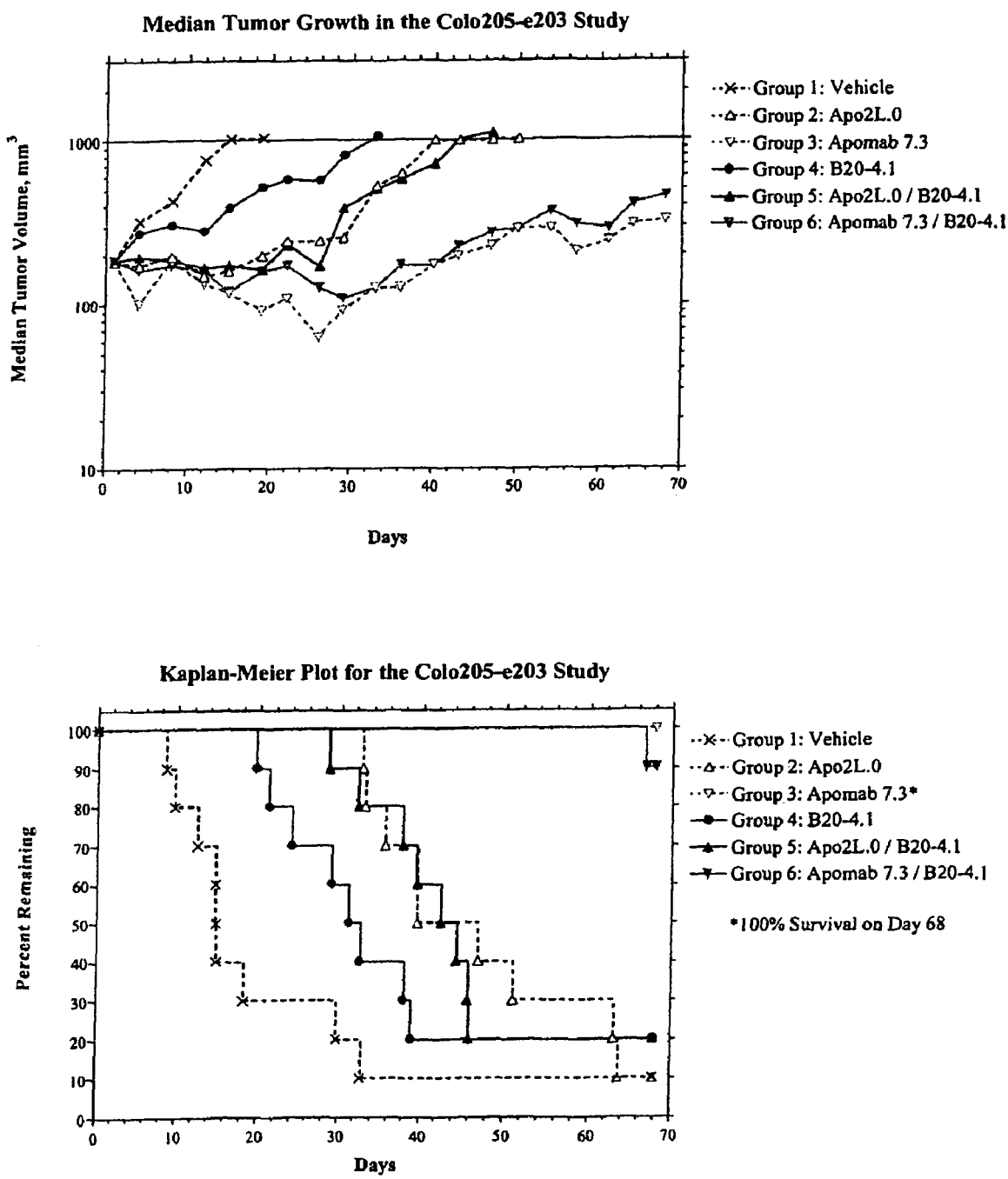
Figure 34 Median Tumor Growth and Kaplan-Meier Plot for Groups in the Colo205-e203 Study Figure 35. Group Median Tumor Growth and Kaplan-Meier Plot for Groups Treated with Apo2L.0 as Monotherapy or in Combination with Carboplatin and Paclitaxel the SKMES-e209 Study
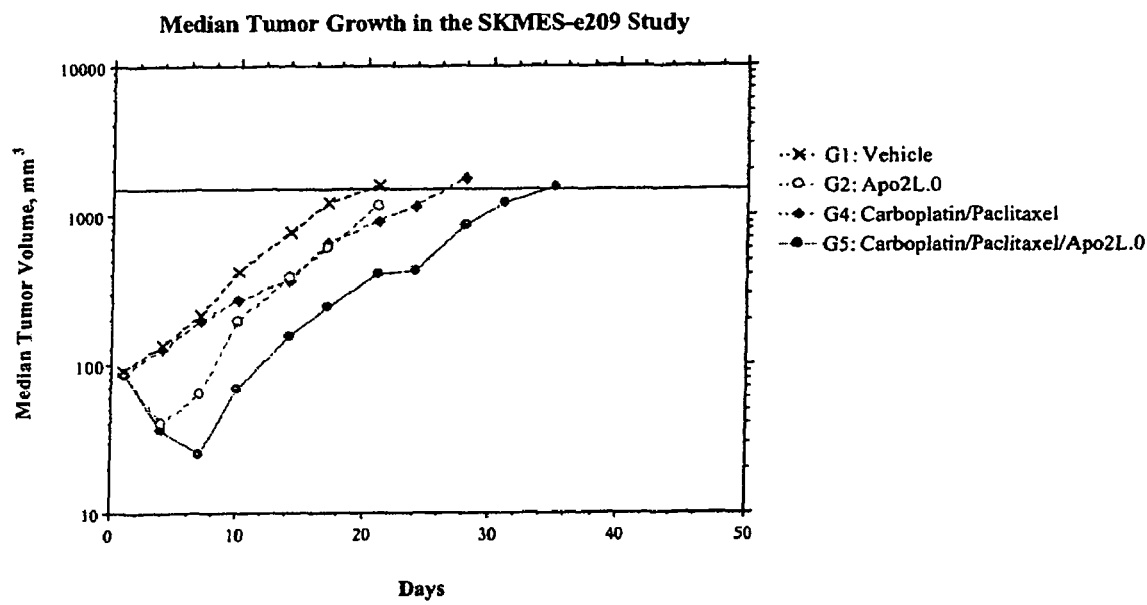
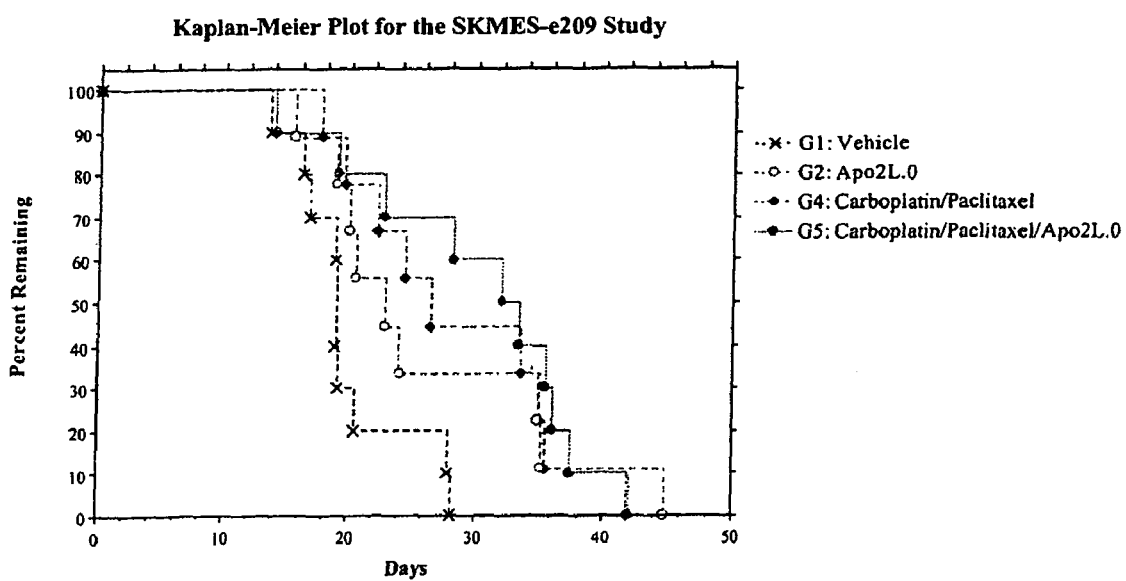

Figure 36. Group Median Tumor Growth and Kaplan-Meier Plot for Groups Treated with Apomab 7.3 as Monotherapy or in Combination with Carboplatin and Paclitaxel the SKMES-e209 Study
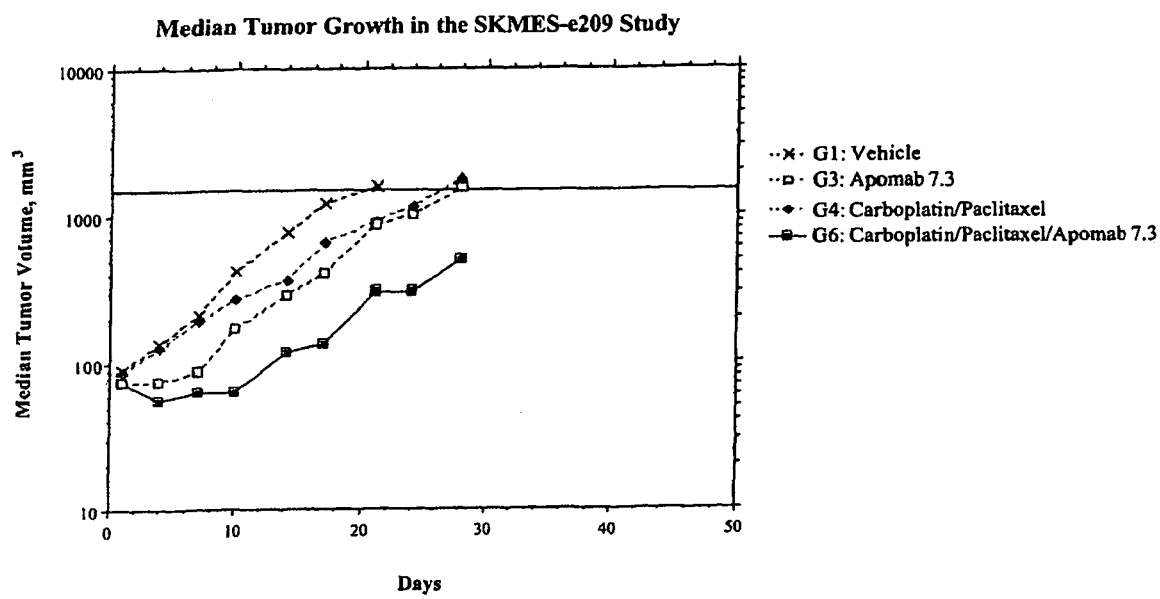
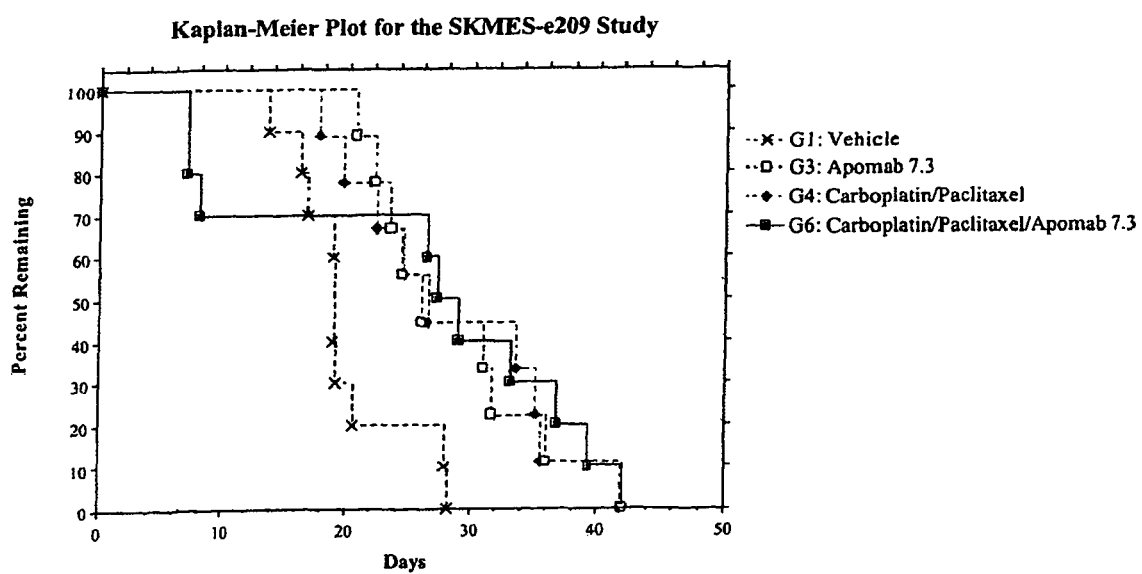

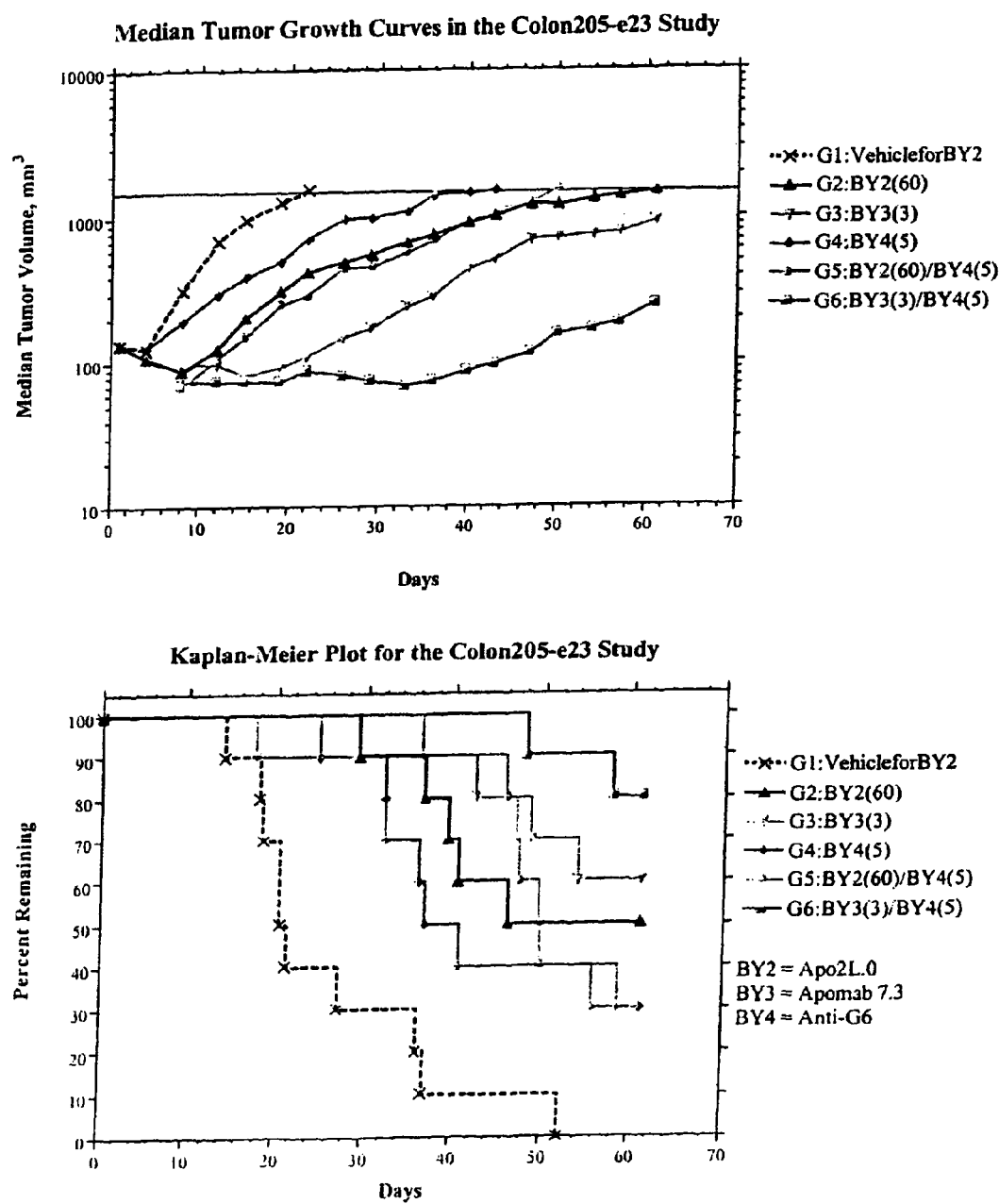
Figure 37. Group Median Tumor Growth Curves and Kaplan-Meier Plot for Mice Treated with BY2, BY3, or BY4 in the Colon205-e23 Study

NUCLEIC ACID ENCODING DR5 ANTIBODIES AND USES THEREOF

CROSS-REFERENCE TO RELATED APPLICATIONS

This application is a divisional application and claims the benefit under 35 U.S.C. §120 of copending U.S. patent application Ser. No. 11/344,564, filed on Jan. 30, 2006, which claims the benefit under 35 U.S.C. §119, of U.S. Provisional Patent Application Ser. No. 60/649,550 filed Feb. 2, 2005. The entire disclosures of both applications are hereby expressly incorporated by reference.

FIELD OF THE INVENTION

The present invention relates generally to DR5 antibodies, including agonistic antibodies, and to methods of using such DR5 antibodies.

BACKGROUND OF THE INVENTION

Various ligands and receptors belonging to the tumor necrosis factor (TNF) superfamily have been identified in the art. Included among such ligands are tumor necrosis factor-alpha ("TNF-alpha"), tumor necrosis factor-beta ("TNF-beta" or "lymphotoxin-alpha"), lymphotoxin-beta ("LT-beta"), CD30 ligand, CD27 ligand, CD40 ligand, OX-40 ligand, 4-1BB ligand, LIGHT, Apo-1 ligand (also referred to as Fas ligand or CD95 ligand), Apo-2 ligand (also referred to as Apo2L or TRAIL), Apo-3 ligand (also referred to as TWEAK), APRIL, OPG ligand (also referred to as RANK ligand, ODF, or TRANCE), and TALL-1 (also referred to as BlyS, BAFF or THANK) (See, e.g., Ashkenazi, *Nature Review*, 2:420-430 (2002); Ashkenazi and Dixit, *Science*, 281:1305-1308 (1998); Ashkenazi and Dixit, *Curr. Opin. Cell Biol.*, 11:255-260 (2000); Golstein, *Curr. Biol.*, 7:750-753 (1997) Wallach, *Cytokine Reference*, Academic Press, 2000, pages 377-411; Locksley et al., *Cell*, 104:487-501 (2001); Gruss and Dower, *Blood*, 85:3378-3404 (1995); Schmid et al., Proc. Natl. Acad. Sci., 83:1881 (1986); Dealtry et al., Eur. J. Immunol., 17:689 (1987); Pitti et al., J. Biol. Chem., 271:12687-12690 (1996); Wiley et al., Immunity, 3:673-682 (1995); Browning et al., Cell, 72:847-856 (1993); Armitage et al. Nature, 357:80-82 (1992), WO 97/01633 published Jan. 16, 1997; WO 97/25428 published Jul. 17, 1997; Marsters et al., Curr. Biol., 8:525-528 (1998); Chicheportiche et al., Biol. Chem., 272:32401-32410 (1997); Hahne et al., J. Exp. Med., 188:1185-1190 (1998); WO98/28426 published Jul. 2, 1998; WO98/46751 published Oct. 22, 1998; WO/98/18921 published May 7, 1998; Moore et al., Science, 285:260-263 (1999); Shu et al., J. Leukocyte Biol., 65:680 (1999); Schneider et al., J. Exp. Med., 189:1747-1756 (1999); Mukhopadhyay et al., J. Biol. Chem., 274:15978-15981 (1999)).

Induction of various cellular responses mediated by such TNF family ligands is typically initiated by their binding to specific cell receptors. Some, but not all, TNF family ligands bind to, and induce various biological activity through, cell surface "death receptors" to activate caspases, or enzymes that carry out the cell death or apoptosis pathway (Salvesen et al., *Cell*, 91:443-446 (1997). Included among the members of the TNF receptor superfamily identified to date are TNFR1, TNFR2, TACI, GITR, CD27, OX-40, CD30, CD40, HVEM, Fas (also referred to as Apo-1 or CD95), DR4 (also referred to as TRAIL-R1), DR5 (also referred to as Apo-2 or TRAIL-R2), DCR1, DcR2, osteoprotegerin (OPG), RANK and Apo-3 (also referred to as DR3 or TRAMP) (see, e.g., Ashkenazi, *Nature Reviews*, 2:420-430 (2002); Ashkenazi and Dixit, *Science*, 281:1305-1308 (1998); Ashkenazi and Dixit, *Curr. Opin. Cell Biol.*, 11:255-260 (2000); Golstein, *Curr. Biol.*, 7:750-753 (1997) Wallach, *Cytokine Reference*, Academic Press, 2000, pages 377411; Locksley et al., *Cell*, 104:487-501 (2001); Gruss and Dower, Blood, 85:3378-3404 (1995); Hohman et al., *J. Biol. Chem.*, 264:14927-14934 (1989); Brockhaus et al., *Proc. Natl. Acad. Sci.* 87:3127-3131 (1990); EP 417,563, published Mar. 20, 1991; Loetscher et al., *Cell*, 61:351 (1990); Schall et al., *Cell*, 61:361 (1990); Smith et al., *Science*, 248:1019-1023 (1990); Lewis et al., *Proc. Natl. Acad. Sci.*, 88:2830-2834 (1991); Goodwin et al., *Mol. Cell. Biol.*, 11:3020-3026 (1991); Stamenkovic et al., *EMBO J.*, 8:1403-1410 (1989); Mallett et al., *EMBO J.*, 9:1063-1068 (1990); Anderson et al., *Nature*, 390:175-179 (1997); Chicheportiche et al., *J. Biol. Chem.*, 272:32401-32410 (1997); Pan et al., *Science.* 276:111-113 (1997); Pan et al., *Science*, 277:815-818 (1997); Sheridan et al., *Science*, 277:818-821 (1997); Degli-Esposti et al., *J. Exp. Med.*, 186:1165-1170 (1997); Marsters et al., *Curr. Biol.*, 7:1003-1006 (1997); Tsuda et al., *BBRC*, 234:137-142 (1997); Nocentini et al., *Proc. Natl. Acad. Sci.*, 94:6216-6221 (1997); vonBulow et al., *Science*, 278:138-141 (1997)).

Most of these TNF receptor family members share the typical structure of cell surface receptors including extracellular, transmembrane and intracellular regions, while others are found naturally as soluble proteins lacking a transmembrane and intracellular domain. The extracellular portion of typical TNFRs contains a repetitive amino acid sequence pattern of multiple cysteine-rich domains (CRDs), starting from the $NH_2$-terminus.

The ligand referred to as Apo-2L or TRAIL was identified several years ago as a member of the TNF family of cytokines. (See, e.g., Wiley et al., Immunity, 3:673-682 (1995); Pitti et al., J. Biol. Chem., 271:12697-12690 (1996); WO 97/01633; WO 97/25428; U.S. Pat. No. 5,763,223 issued Jun. 9, 1998; U.S. Pat. No. 6,284,236 issued Sep. 4, 2001). The full-length native sequence human Apo2L/TRAIL polypeptide is a 281 amino acid long, Type II transmembrane protein. Some cells can produce a natural soluble form of the polypeptide, through enzymatic cleavage of the polypeptide's extracellular region (Mariani et al., J. Cell. Biol., 137:221-229 (1997)). Crystallographic studies of soluble forms of Apo2L/TRAIL reveal a homotrimeric structure similar to the structures of TNF and other related proteins (Hymowitz et al., Molec. Cell, 4:563-571 (1999); Cha et al., Immunity, 11:253-261 (1999); Mongkolsapaya et al., Nature Structural Biology, 6:1048 (1999); Hymowitz et al., Biochemistry, 39:633-644 (2000)). Apo2L/TRAIL, unlike other TNF family members however, was found to have a unique structural feature in that three cysteine residues (at position 230 of each subunit in the homotrimer) together coordinate a zinc atom, and that the zinc binding is important for trimer stability and biological activity. (Hymowitz et al., supra; Bodmer et al., J. Biol. Chem., 275:20632-20637 (2000)).

It has been reported in the literature that Apo2L/TRAIL may play a role in immune system modulation, including autoimmune diseases such as rheumatoid arthritis [see, e.g., Thomas et al., J. Immunol., 161:2195-2200 (1998); Johnsen et al., Cytokine, 11:664-672 (1999); Griffith et al., J. Exp. Med., 189:1343-1353 (1999); Song et al., J. Exp. Med., 191:1095-1103 (2000)].

Soluble forms of Apo2L/TRAIL have also been reported to induce apoptosis in a variety of cancer cells, including colon, lung, breast, prostate, bladder, kidney, ovarian and brain tumors, as well as melanoma, leukemia, and multiple myeloma (see, e.g., Wiley et al., supra; Pitti et al., supra; U.S. Pat. No. 6,030,945 issued Feb. 29, 2000; U.S. Pat. No. 6,746,668 issued Jun. 8, 2004; Rieger et al., FEBS Letters, 427:124-128 (1998); Ashkenazi et al., J. Clin. Invest., 104:155-162 (1999); Walczak et al., Nature Med., 5:157-163 (1999); Keane et al., Cancer Research, 59:734-741 (1999); Mizutani et al., Clin. Cancer Res., 5:2605-2612 (1999); Gazitt, Leukemia, 13:1817-1824 (1999); Yu et al., Cancer Res., 60:2384-2389 (2000); Chinnaiyan et al., Proc. Natl. Acad. Sci., 97:1754-1759 (2000)). In vivo studies in murine tumor models further suggest that Apo2L/TRAIL, alone or in combination with chemotherapy or radiation therapy, can exert substantial anti-tumor effects (see, e.g., Ashkenazi et al., supra; Walzcak et al., supra; Gliniak et al., Cancer Res., 59:6153-6158 (1999); Chinnaiyan et al., supra; Roth et al., Biochem. Biophys. Res. Comm., 265:1999 (1999); PCT Application US/00/15512; PCT Application US/01/23691). In contrast to many types of cancer cells, most normal human cell types appear to be resistant to apoptosis induction by certain recombinant forms of Apo2L/TRAIL (Ashkenazi et al., supra; Walzcak et al., supra). Jo et al. has reported that a polyhistidine-tagged soluble form of Apo2L/TRAIL induced apoptosis in vitro in normal isolated human, but not non-human, hepatocytes (Jo et al., Nature Med., 6:564-567 (2000); see also, Nagata, Nature Med., 6:502-503 (2000)). It is believed that certain recombinant Apo2L/TRAIL preparations may vary in terms of biochemical properties and biological activities on diseased versus normal cells, depending, for example, on the presence or absence of a tag molecule, zinc content, and % trimer content (See, Lawrence et al., Nature Med., Letter to the Editor, 7:383-385 (2001); Qin et al., Nature Med., Letter to the Editor, 7:385-386 (2001)).

Apo2L/TRAIL has been found to bind at least five different receptors. At least two of the receptors which bind Apo2L/TRAIL contain a functional, cytoplasmic death domain. One such receptor has been referred to as "DR4" (and alternatively as TR4 or TRAIL-R1) (Pan et al., Science, 276:111-113 (1997); see also WO98/32856 published Jul. 30, 1998; WO99/37684 published Jul. 29, 1999; WO 00/73349 published Dec. 7, 2000; U.S. Pat. No. 6,433,147 issued Aug. 13, 2002; U.S. Pat. No. 6,461,823 issued Oct. 8, 2002, and U.S. Pat. No. 6,342,383 issued Jan. 29, 2002).

Another such receptor for Apo2L/TRAIL has been referred to as DR5 (it has also been alternatively referred to as Apo-2; TRAIL-R or TRAIL-R, TR6, Tango-63, hAPO8, TRICK2 or KILLER) (see, e.g., Sheridan et al., Science, 277:818-821 (1997), Pan et al., Science, 277:815-818 (1997), WO98/51793 published Nov. 19, 1998; WO98/41629 published Sep. 24, 1998; Screaton et al., Curr. Biol., 7:693-696 (1997); Walczak et al., EMBO J., 16:5386-5387 (1997); Wu et al., Nature Genetics, 17:141-143 (1997); WO98/35986 published Aug. 20, 1998; EP870,827 published Oct. 14, 1998; WO98/46643 published Oct. 22, 1998; WO99/02653 published Jan. 21, 1999; WO99/09165 published Feb. 25, 1999; WO99/11791 published Mar. 11, 1999; US 2002/0072091 published Aug. 13, 2002; US 2002/0098550 published Dec. 7, 2001; U.S. Pat. No. 6,313,269 issued Dec. 6, 2001; US 2001/0010924 published Aug. 2, 2001; US 2003/01255540 published Jul. 3, 2003; US 2002/0160446 published Oct. 31, 2002, US 2002/0048785 published Apr. 25, 2002; U.S. Pat. No. 6,342,369 issued February, 2002; U.S. Pat. No. 6,569,642 issued May 27, 2003, U.S. Pat. No. 6,072,047 issued Jun. 6, 2000, U.S. Pat. No. 6,642,358 issued Nov. 4, 2003; IS 6,743,625 issued Jun. 1, 2004). Like DR4, DR5 is reported to contain three cysteine-rich domains in its extracellular portion and a single cytoplasmic death domain and be capable of signaling apoptosis upon ligand binding (or upon binding a molecule, such as an agonist antibody, which mimics the activity of the ligand). The crystal structure of the complex formed between Apo-2L/TRAIL and DR5 is described in Hymowitz et al., Molecular Cell, 4:563-571 (1999).

Upon ligand binding, both DR4 and DR5 can trigger apoptosis independently by recruiting and activating the apoptosis initiator, caspase-8, through the death-domain-containing adaptor molecule referred to as FADD/Mort1 [Kischkel et al., Immunity, 12:611-620 (2000); Sprick et al., Immunity, 12:599-609 (2000); Bodmer et al., Nature Cell Biol., 2:241-243 (2000)]. In particular, DR5 signals apoptosis through the "cell-extrinsic" pathway, which is independent of the p53 tumor suppressor gene (Ashkenazi and Dixit, Science 281: 1305-8 (1998); Ashkenazi, Nat Rev Cancer 2:420-30 (2002)). Activation of this pathway involves raid formation of a death-inducing signaling complex (DISC) at the activated receptor's cytoplasmic death domain. First, the adaptor molecule FADD binds to DR5 through homophilic death domain interaction (Kischkel et al., supra, Sprick et al., supra, Bodmer et al., supra). Subsequently, FADD recruits the apoptosis-initiating proteases caspase-8 and caspase-10, mediating their activation by induced proximity Caspase-9 and caspase-10 undergo self-processing, releasing soluble active caspase subunits into the cytoplasm, where they assemble and cleave effector caspases, such as caspase-3 and caspase-7. Cleavage results in activation of the effector caspases, which carry out the apoprotix cell program (Thornberry and Lazebnik, Science 281:1312-6 (1998)).

Apo2L/TRAIL has been reported to also bind those receptors referred to as DcR1, DcR2 and OPG, which believed to function as inhibitors, rather than transducers of signaling (see., e.g., DCR1 (also referred to as TRID, LIT or TRAIL-R3) [Pan et al., Science, 276:111-113 (1997); Sheridan et al., Science 277:818-821 (1997); McFarlane et al., J. Biol. Chem., 272:25417-25420 (1997); Schneider et al., FEBS Letters, 416:329-334 (1997); Degli-Esposti et al., J. Exp. Med., 186: 1165-1170 (1997); and Mongkolsapaya et al., J. Immunol., 160:3-6 (1998); DCR2 (also called TRUNDD or TRAIL-R4) [Marsters et al., Curr. Biol., 7:1003-1006 (1997); Pan et al., FEBS Letters, 424:41-45 (1998); Degli-Esposti et al., Immunity, 7:813-820 (1997)], and OPG [Simonet et al., supra]. In contrast to DR4 and DR5, the DcR1 and DcR2 receptors do not signal apoptosis.

Certain antibodies which bind to the DR4 and/or DR5 receptors have been reported in the literature. For example, anti-DR4 antibodies directed to the DR4 receptor and having agonistic or apoptotic activity in certain mammalian cells are described in, e.g., WO 99/37684 published Jul. 29, 1999; WO 00/73349 published Jul. 12, 2000; WO 03/066661 published Aug. 14, 2003. See, also, e.g., Griffith et al., J. Immunol., 162:2597-2605 (1999); Chuntharapai et al., J. Immunol., 166: 4891-4898 (2001); WO 02/097033 published Dec. 2, 2002; WO 03/042367 published May 22, 2003; WO 03/038043 published May 8, 2003; WO 03/037913 published May 8, 2003. Certain anti-DR5 antibodies have likewise been described, see, e.g., WO 98/51793 published Nov. 8, 1998; Griffith et al., J. Immunol., 162:2597-2605 (1999); Ichikawa et al., Nature Med., 7:954-960 (2001); Hylander et al., "An Antibody to DR5 (TRAIL-Receptor 2) Suppresses the Growth of Patient Derived Gastrointestinal Tumors Grown in SCID mice", Abstract, 2d International Congress on Monoclonal Antibodies in Cancers, Aug. 29-Sep. 1, 2002, Banff, Alberta, Canada; WO 03/038043 published May 8, 2003; WO 03/037913 published May 8, 2003. In addition, certain antibodies having cross-reactivity to both DR4 and DR5 receptors have been described (see, e.g., U.S. Pat. No. 6,252,050 issued Jun. 26, 2001).

SUMMARY OF THE INVENTION

The invention provides DR5 antibodies which are capable of specifically binding to human DR5 and/or are capable of modulating biological activities associated with DR5 and/or its ligand(s), in particular, apoptosis, and thus are useful in the treatment of various diseases and pathological conditions, including cancer or immune related diseases.

In one aspect, the invention concerns an anti-DR5 antibody comprising at least one mutation in the heavy and/or light chain of full-length antibody 16E2 (SEQ ID NOS: 11 and 13, respectively), or a fragment thereof, wherein the antibody, or antibody fragment, shows at least the same affinity for DR5, and/or exhibits at least the same biological activity and/or potency as antibody 16E2. In a particular embodiment, the antibody or antibody fragment will bind essentially to the same epitope as full-length antibody 16E2. In another embodiment, the anti-DR5 antibody will exhibit higher affinity for DR5 than full-length antibody 16E2 and/or shows increased biological activity and/or increased potency relative to full-length antibody 16E2. In yet another embodiment, the anti-DR5 antibodies and antibody fragments of the present invention show at least the same affinity for DR5 and/or exhibit at least the same biological activity and/or potency as the single-chain Fc anti-DR5 antibody 16E2 described in WO 98/51793.

In one embodiment, the anti-DR5 antibody comprises a heavy and/or light chain having at least one substitution listed in any of Tables 1 through 7, and 9-12, or a fragment thereof.

In another embodiment, the anti-DR5 antibody comprises one or more mutations in the framework of the 16E2 antibody heavy chain variable domain.

In yet another embodiment, the anti-DR5 antibody comprises a framework mutation selected from the group consisting of Q6E, V11L, E12V, R13Q, and K105Q.

In a further embodiment, the anti-DR5 antibody comprises all of the framework mutations Q6E, V11L, E12V, R13Q, and K105Q.

In a still further embodiment, the anti-DR5 antibody comprises at least one mutation in the heavy chain (SEQ ID NO: 11) of full-length antibody 16E2, or a fragment thereof.

In a different embodiment, the anti-DR5 antibody comprises at least one mutation selected from the group consisting of T28A, G33A, M34L, M34A, M34I, M34S, N53Q, N53Y, and L102Y, in the amino acid sequence of SEQ ID NO: 11, or a fragment thereof.

In another embodiment, the anti-DR5 antibody comprises at least one of the mutations G99A and R100A in the amino acid sequence of SEQ ID NO: 11, or a fragment thereof.

In yet another embodiment, the anti-DR5 antibody comprises a set of mutations selected from the group consisting of (i) N53Q, L102Y; (ii) M34L, N53Q, L102Y; (iii) N53Y, L102Y; (iv) M34L, N53Y, L102Y; (v) G33A, N53Q, L102Y; (vi) M34L, N53Y, L102Y; (vii) G33A, N53Q, L102Y; (viii) G33A, N53Y, L102Y; (ix) T28A, N53Q, L102Y; and (x) T28A, N53Y, L102Y in the amino acid sequence of SEQ ID NO: 11, or a fragment thereof.

In a further embodiment, the anti-DR5 antibody comprises at least one mutation in the light chain (SEQ ID NO: 13) of the full-length 16E2 antibody, or a fragment thereof.

In a particular embodiment, the light chain is a lambda chain.

In another particular embodiment, the light chain mutation is in CDR L1.

In a further embodiment, the light chain mutation is selected from the group consisting of Q24A, Q24S, G25A, D26E, S27A, L28A, R29A, S30A, Y31A, Y31K, Y32H, A33G, S34A, and S34Y in the amino acid sequence of SEQ ID NO: 13.

In a still further embodiment, the light chain mutation is selected from the group consisting of (i) Q24S, D26E, Y31K, S34Y; and (ii) D26E, Y31K in the amino acid sequence of SEQ ID NO: 13.

In a different embodiment, the light chain mutation is in CDR L2.

Thus, for example, the mutation can be selected from the group consisting of G50A, G50K, G50S, K51D, N52A, N52S, N52L, N52Q, N53A, N53E, N53Q, N53S, P55A, and S56A in the amino acid sequence of SEQ ID NO: 13.

In another embodiment, the antibody may contain a set of mutations selected from the group consisting of (i) G50K, K52S, N53E; (ii) G50S, K51D, N52S, N53E; (ii) N52S, N53E; and (iv) N52Q, N53S, in the amino acid sequence of SEQ ID NO: 13.

In a further embodiment, the light chain mutation is in CDR L3.

In a still further embodiment, the antibody comprises at least one mutation selected from the group consisting of, N89A, N89L, N89Q, R91A, S93A, N95aA, N95aT, N95aQ, H95bA, N95bY, V96A, V97A in SEQ ID NO: 13.

Alternatively, the anti-DR5 antibody may comprise a set of mutations selected from the group consisting of (i) N89L, R91A, N95aT, H95bY; and (ii) N95aT, H95bY in the sequence of SEQ ID NO: 13.

In a further embodiment, the anti-DR5 antibody comprises a set of light chain mutations selected from the group consisting of (i) Q24S, G50K, K51D, H95bY; (ii) Q24S, K51A, D92S, S93Y; and (iii) Q24S, K51A, R91A in the amino acid sequence of SEQ ID NO: 13, and may additionally comprise a set of heavy chain mutations selected from the group consisting of (ii) M34L, N53Q, L102Y; (ii) M34L, N53Y, L102Y; (iii) G33A, N53Q, L102Y; (iv) G33A, N53Y, L102Y; (v) M34L, N53Q, L102Y; (vi) M34L, N53Y, L103Y; (vii) G33A, N53Q, L102Y; (viii) G33A, N53Y, L102Y; and (ix) T28A, N53Q, L102Y in the amino acid sequence of SEQ ID NO: 11, and optionally a set of framework mutations listed in Table 5.

In a particular embodiment, the anti-DR5 antibody comprises the following mutations: G33A, N53Q, L102Y in the sequence of SEQ ID NO: 11, and Q24S, K51A, R91A in the sequence of SEQ ID NO: 13, and may additionally comprise at least one framework mutation, which may, for example, be at least one of residues 6, 11, 12, 13, and 105 of SEQ ID NO: 11.

In a specific embodiment, the anti-DR5 antibody is selected from the group consisting of Apomabs 1.1, 2.1, 3.1, 4.1, 5.1, 6.1, 7.1, 8.1, 9.1, 1.2, 2.2, 3.2, 4.2, 5.2, 6.2, 7.2, 8.2, 9.2, 1.3, 2.2, 3.3, 4.3, 5.3, 6.3, 7.3, 8.3, and 9.3.

In a particular embodiment, the anti-DR5 antibody is selected from the group consisting of Apomabs 5.2, 5.3, 6.2, 6.3, 7.2, 7.3, 8.3 and 25.3.

In yet another particular embodiment, the anti-DR5 antibody is Apomab 7.3 or Apomab 8.3, especially Apomab 7.3.

In a still further embodiment, the anti-DR5 antibody is an antibody fragment, which may be selected from the group consisting of Fab, Fab', F(ab')2, and Fv fragments, diabodies, single chain antibody molecules, and multispecific antibodies formed from antibody fragments.

In other embodiments, the antibody can be a single-chain antibody.

The anti-DR5 antibodies can, for example, have anti-cancer activity, such as, for example, they can possess the ability to activate or stimulate apoptosis in cancer cells.

The cancer includes, for example, carcinoma, lymphoma, blastoma, sarcoma and leukemia.

More specific examples of cancer include squamous cell cancer, small-cell lung cancer, non-small cell lung cancer (NSCLC), non-Hodgkin's lymphoma, blastoma, gastrointestinal cancer, renal cancer, ovarian cancer, liver cancer, stomach cancer, bladder cancer, hepatoma, breast cancer, colon cancer, colorectal cancer, pancreatic cancer, endometrial carcinoma, salivary gland carcinoma, kidney cancer, liver cancer, prostate cancer, vulval cancer, thyroid cancer, hepatic carcinoma, and head and neck cancer.

Particular groups of cancer include lung cancer (e.g., non-small cell lung carcinoma—NSCLC); or adenocarcinoma, which can, for example, be colorectal, pancreatic, or metastatic adenocarcinoma. Hematological cancers are also included.

Chimeric, humanized and human antibodies are within the scope herein, as are antibodies which mediate antibody-dependent cellular cytotoxicity (ADCC).

In a preferred embodiment, the anti-DR5 antibody comprises Apomab 7.3, or Apomab 8.3, or a fragment thereof.

The antibodies may be in a dimeric form and/or in a form cross-linked, for example, with an anti-human IgG Fc region.

In other embodiments, the anti-DR5 antibodies herein are fused to an epitope tag sequence.

In another aspect, the invention concerns a chimeric molecule comprising an anti-DR5 antibody or antibody fragment herein, fused to a heterologous amino acid sequence, where the heterologous amino acid sequence may, for example, comprise an immunoglobulin sequence, such as an anti-human IgG Fc region.

In yet another aspect, the invention concerns isolated nucleic acid molecules encoding the anti-DR5 antibodies or antibody fragments herein, vectors comprising such nucleic acid molecules, host cells comprising such nucleic acid molecules, and methods for producing antibodies and antibody fragment herein.

The invention further relates to a composition comprising an anti-DR5 antibody as herein above defined, and a carrier.

The carrier may be a pharmaceutically acceptable carrier, and the composition may further comprise an additional anti-cancer agent, and/or an additional anti-DR5 antibody.

In a further aspect, the invention concerns a method of inducing apoptosis comprising exposing mammalian cancer cells to an anti-DR5 antibody as hereinabove defined.

In a still further aspect, the invention concerns a method for the treatment of cancer comprising administering to a mammalian subject an effective amount of an anti-DR5 antibody as defined above.

In all aspects, the subject can be a human patient, and the cancer can be any cancer, including the cancers listed above In an additional aspect, the invention concerns an article of manufacture comprising a container and compositions contained within said container, wherein the composition includes an anti-DR5 antibody of the present invention. The article of manufacture may further comprise instructions for using the anti-DR5 antibody in vitro or in vivo. In a preferred embodiment, the instructions concern the treatment of cancer.

BRIEF DESCRIPTION OF THE DRAWINGS

FIG. 1 shows the nucleotide sequence of human Apo-2 ligand cDNA (SEQ ID NO:2) and its derived amino acid sequence (SEQ ID NO:1). The "N" at nucleotide position 447 (in SEQ ID NO:2) is used to indicate that the nucleotide base may be a "T" or "G".

FIGS. 2A-2C show the nucleotide sequence of a cDNA (SEQ ID NO:4) for full-length human DR4 receptor and its derived amino acid sequence (SEQ ID NO:3). The respective nucleotide and amino acid sequences for human DR4 receptor are also reported in Pan et al., *Science*, 276:111 (1997).

FIGS. 3A-3C show the 411 amino acid sequence of human DR5 receptor (SEQ ID NO:5) as published in WO 98/51793 on Nov. 19, 1998, and the encoding nucleotide sequence (SEQ ID NO: 6).

FIGS. 4A-4C show the 440 amino acid sequence of human DR5 (SEQ ID NO:7) and the encoding nucleotide sequence (SEQ ID NO:8), as also published in WO 98/35986 on Aug. 20, 1998.

FIG. 5 shows the nucleotide sequence of single-chain anti-DR5 antibody 16E2 (16E2 scFv) (SEQ ID NO: 9).

FIG. 6 shows the amino acid sequence of single-chain anti-DR5 antibody 16E2 (16E2 scFv) (SEQ ID NO: 10), where the signal sequence and the heavy and light chain CDRs are shown.

FIG. 7 shows the amino acid sequence of full-length 16E2 antibody heavy chain (SEQ ID NO: 11).

FIG. 8 shows the nucleotide sequence of full-length 16E2 antibody heavy chain (SEQ ID NO: 12).

FIG. 9 shows the amino acid sequence of full-length 16E2 antibody light chain (SEQ ID NO: 13).

FIG. 10 shows the nucleotide sequence of full-length 6E2 antibody light chain (SEQ ID NO: 14).

FIGS. 11A and B show the sequence of plasmid pDR1 (SEQ ID NO: 15, 5391 bp) for expression of immunoglobulin light chains. pDR1 contains sequences encoding an irrelevant antibody, the light chain of a humanized anti-CD3 antibody (Shalaby et al., J. Exp. Med. 175:217-225 (1992)), the start and stop codons for which are indicated in bold and underlined.

FIGS. 12 A and B show the sequence of plasmid pDR2 (SEQ ID NO: 16) for expression of immunoglobulin heavy chains. pDR2 contains sequences encoding an irrelevant antibody, the heavy chain of a humanized anti-CD3 antibody (Shalaby et al., supra), the start and stop codons for which are indicated in bold and underlined.

FIG. 13 shows the Apomab 7.3 heavy chain nucleotide sequence (SEQ ID NO: 17).

FIG. 14 shows the Apomab 7.3 heavy chain amino acid sequence (SEQ ID NO: 18).

FIG. 15 shows the Apomab 7.3 light chain nucleotide sequence (SEQ ID NO: 19).

FIG. 16 shows the Apomab 7.3 light chain amino acid sequence (SEQ ID NO: 20).

FIGS. 17A and B show the alignment of 16E2 and Apomab 7.3 heavy chains.

FIG. 18 shows the alignment of 16E2 and Apomab 7.3 light chains.

(Version 1) antibody in the Colo 205 xenograft athymic nude mouse model of human colon cancer.

Figure 24:
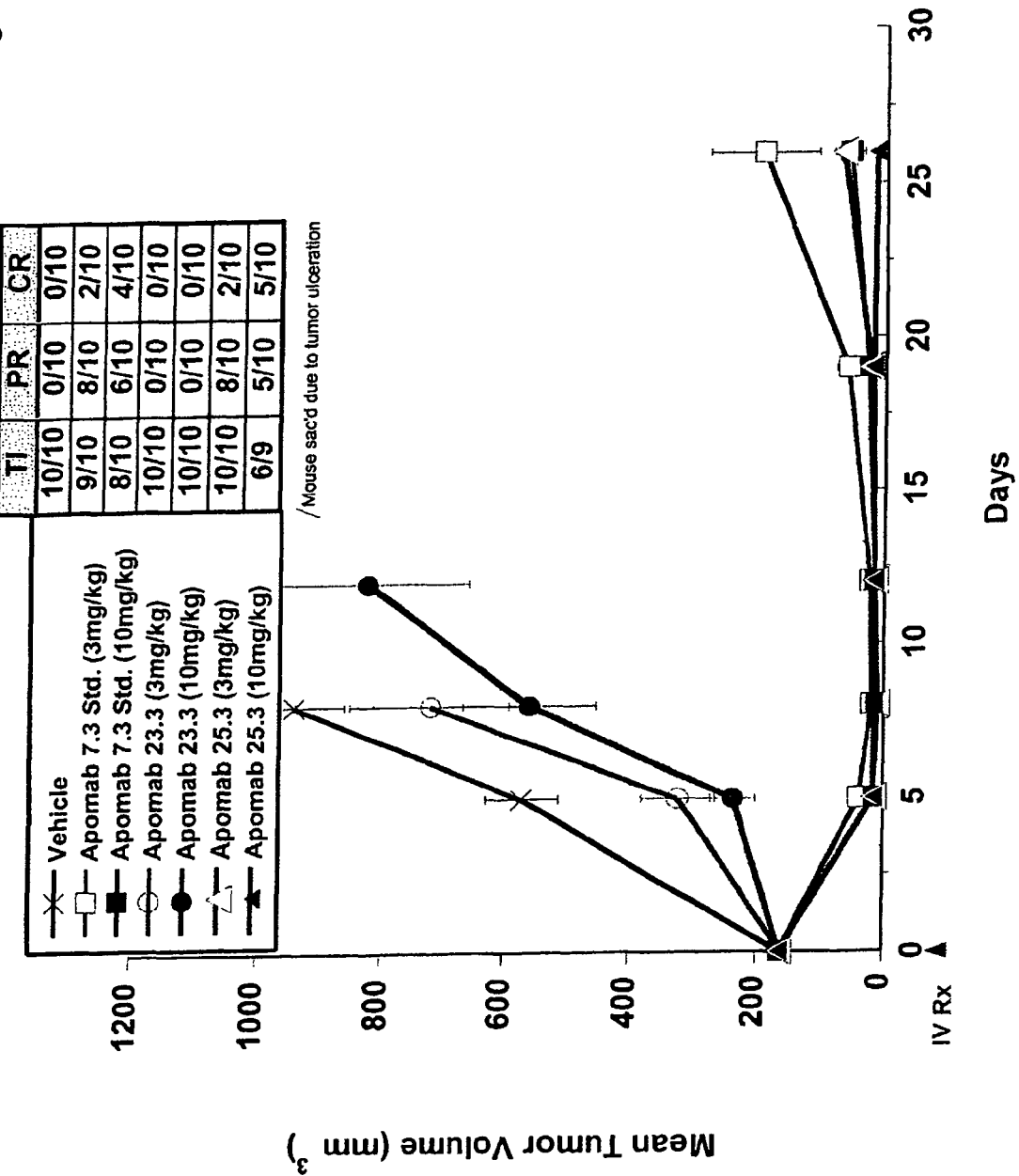

FIG. 24 shows the anticancer activity of Apomabs 23.3 and 25.3 compared to Apomab 7.3 in the Colo 205 xenograft athymic nude mouse model of human colon cancer.

Figure 25:
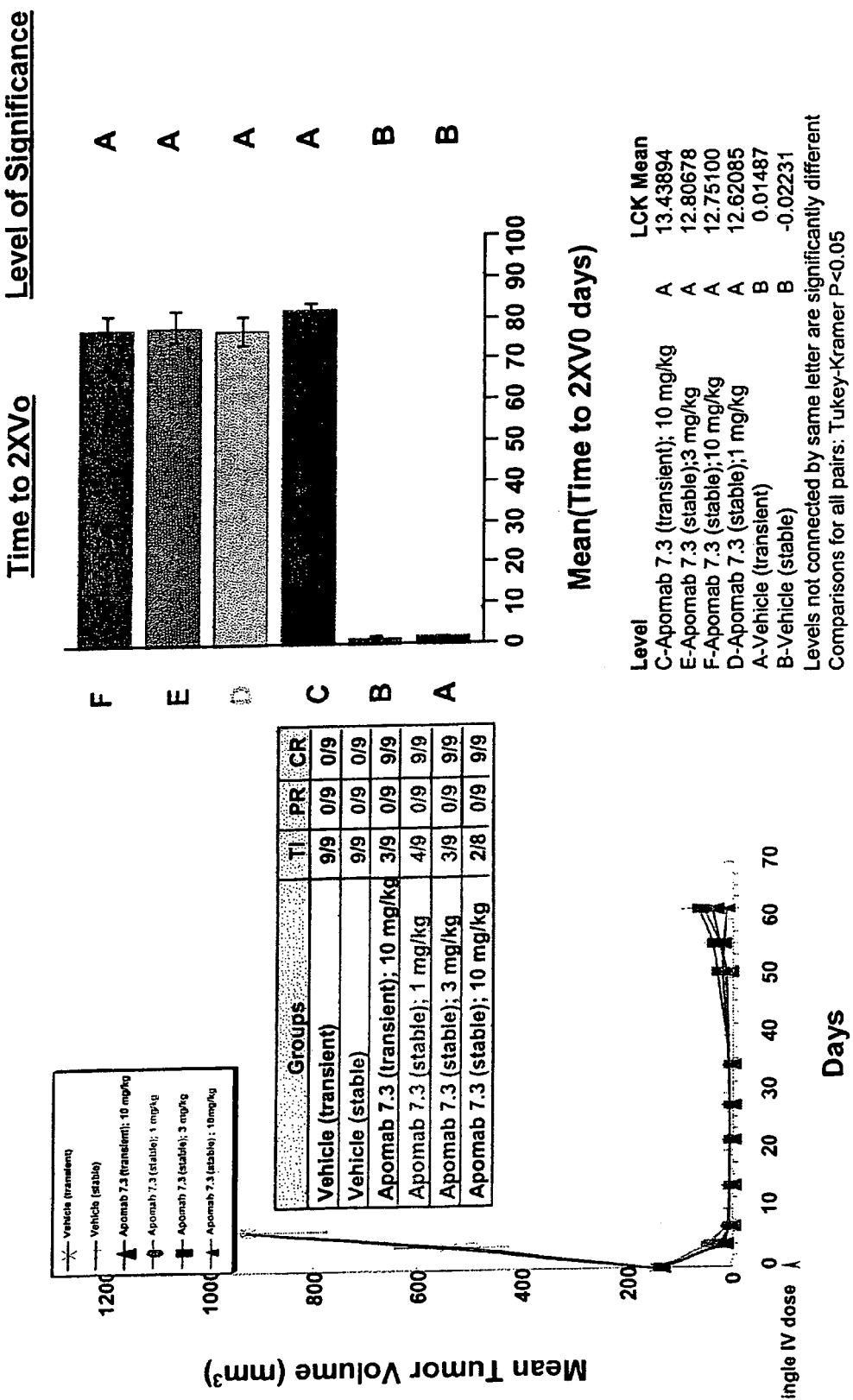

FIG. 25 shows the anticancer activity of Apomab 7.3 derived from a stable cell line versus a transient cell line in the Colo 205 xenograft athymic nude mouse model of human colon cancer.

Figure 26:
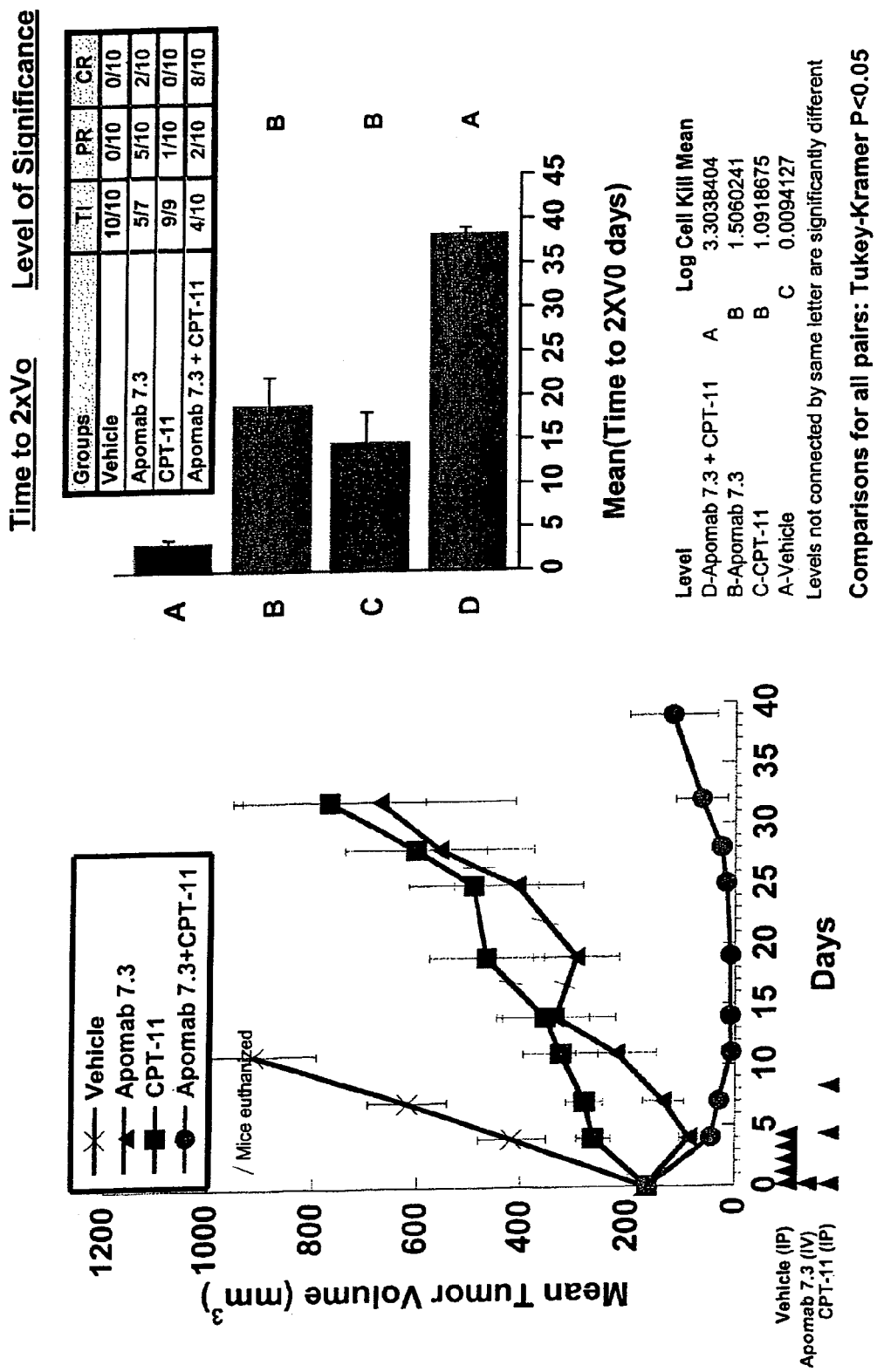

FIG. 26 shows the anticancer activity of Apomab 7.3 alone and in combination with CPT-11 in a HCT15 xenograft model of lung cancer.

Figure 27:
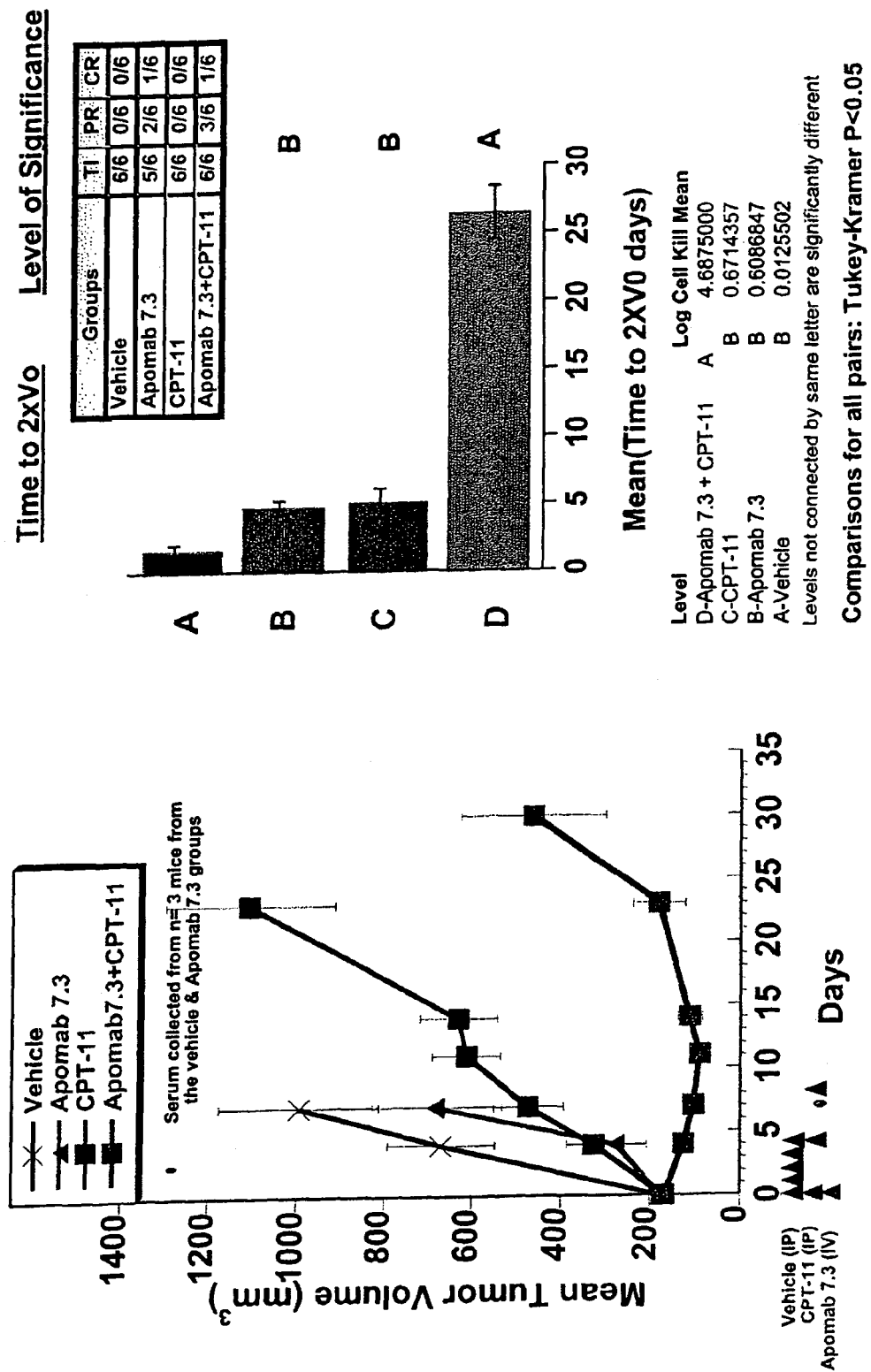

FIG. 27 shows the anticancer activity of Apomab 7.3 alone and in combination with CPT-11 in a LS180 xenograft model of human sarcoma.

Figure 28:
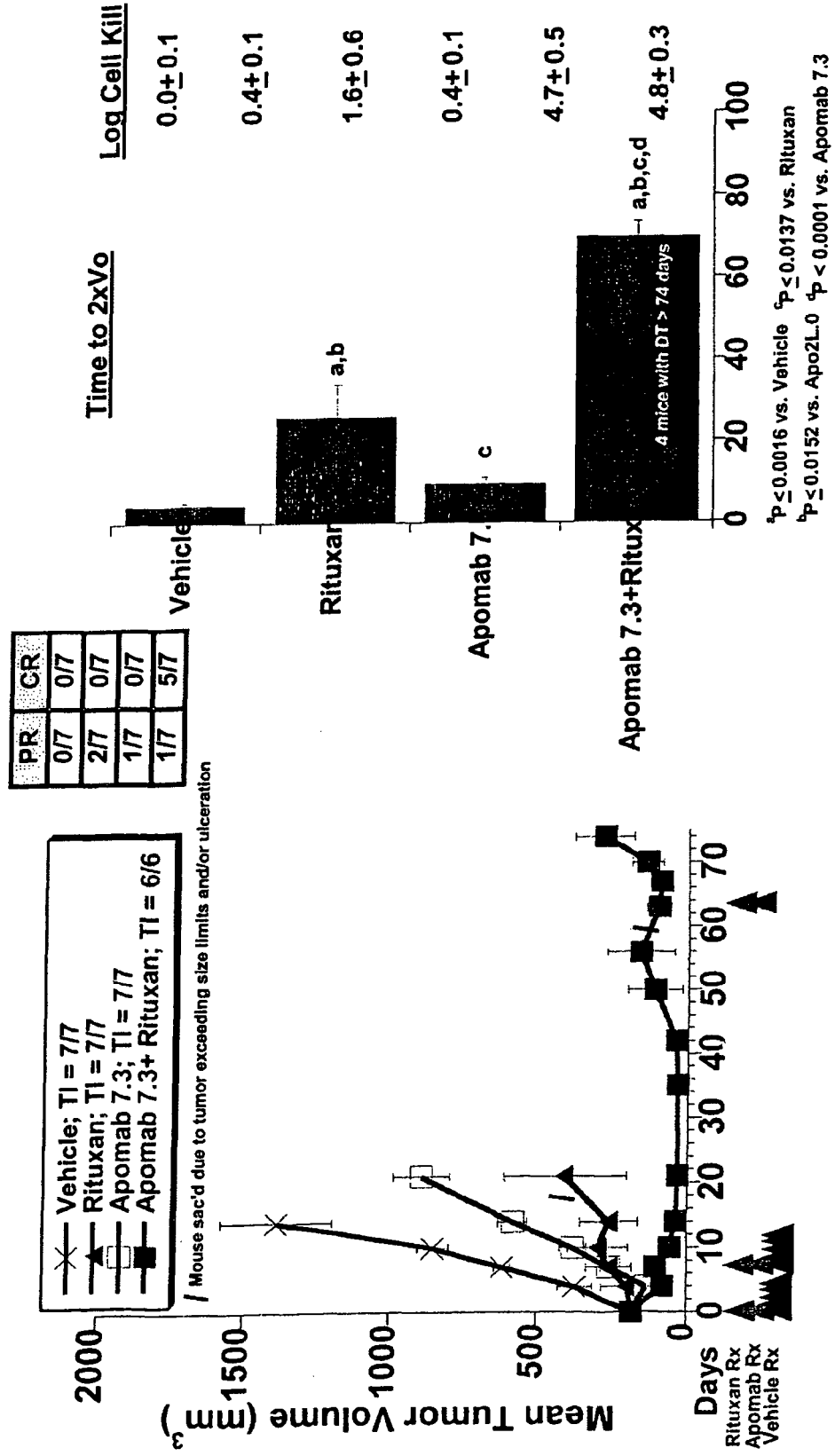

FIG. 28 shows the anticancer activity of Apomab 7.3 alone and in combination with RITUXAN® (rituximab) in a BJAB xenograft CB17 ICR SCID mouse model of non-Hodgkin's lymphoma.

Figure 29:
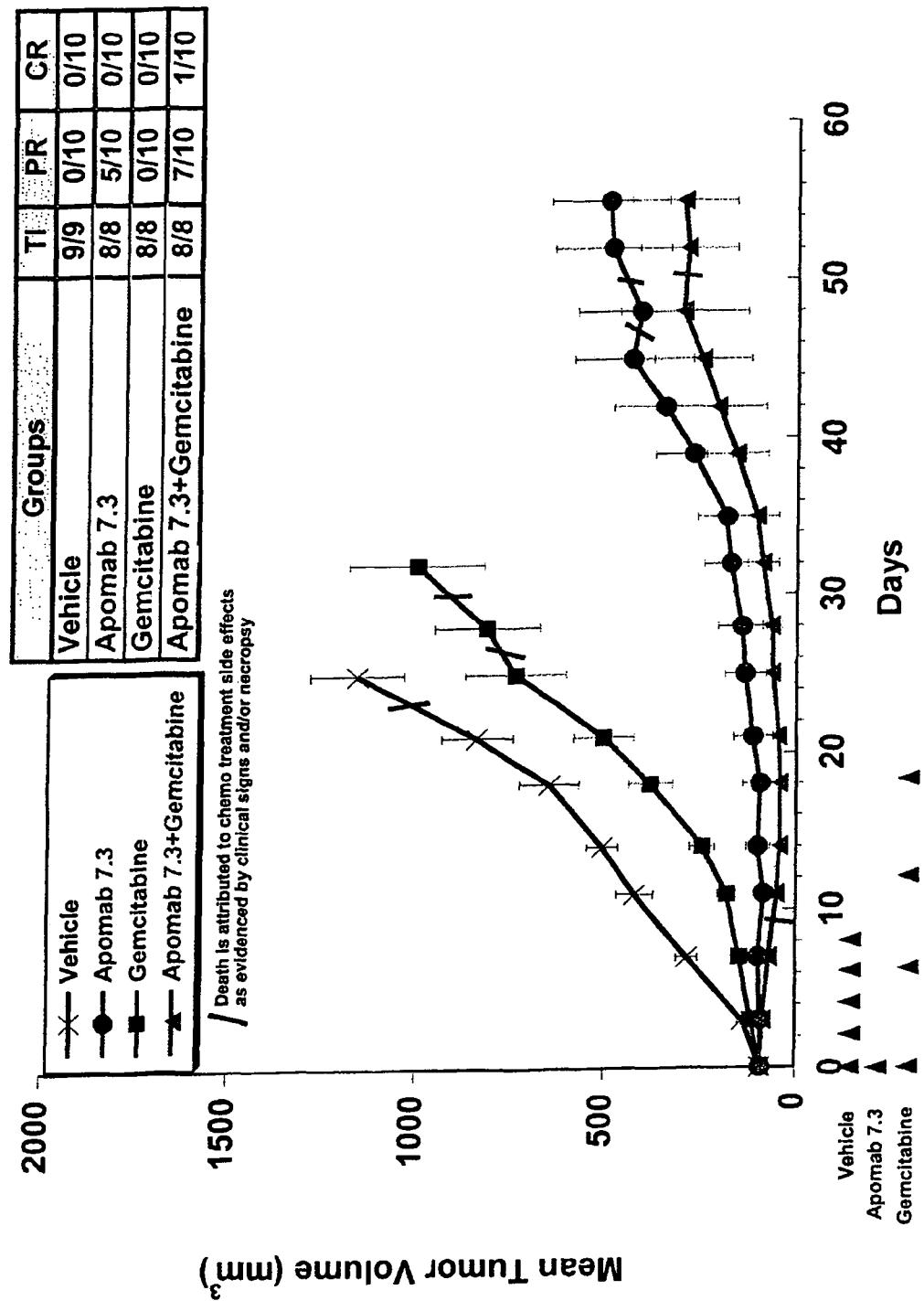

FIG. 29 shows the anticancer activity of Apomab 7.3 alone and in combination with gemcitabine in a BxPC3 xenograft athymic nude mouse model of human pancreatic adenocarcinoma.

Figure 30:
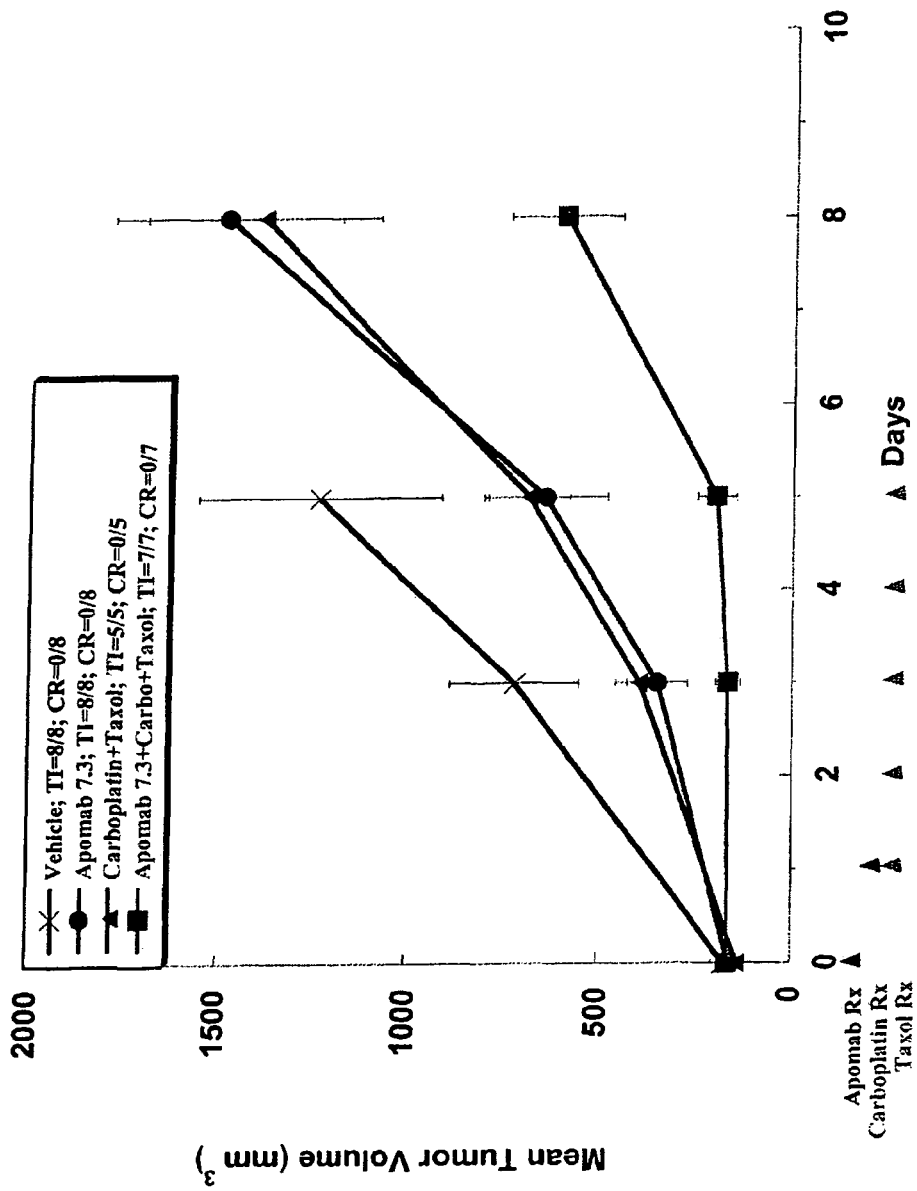

FIG. 30 shows the anticancer activity of Apomab 7.3 alone and in combination with carboplatin and taxol in a H460 xenograft model of human lung cancer.

Figure 31:
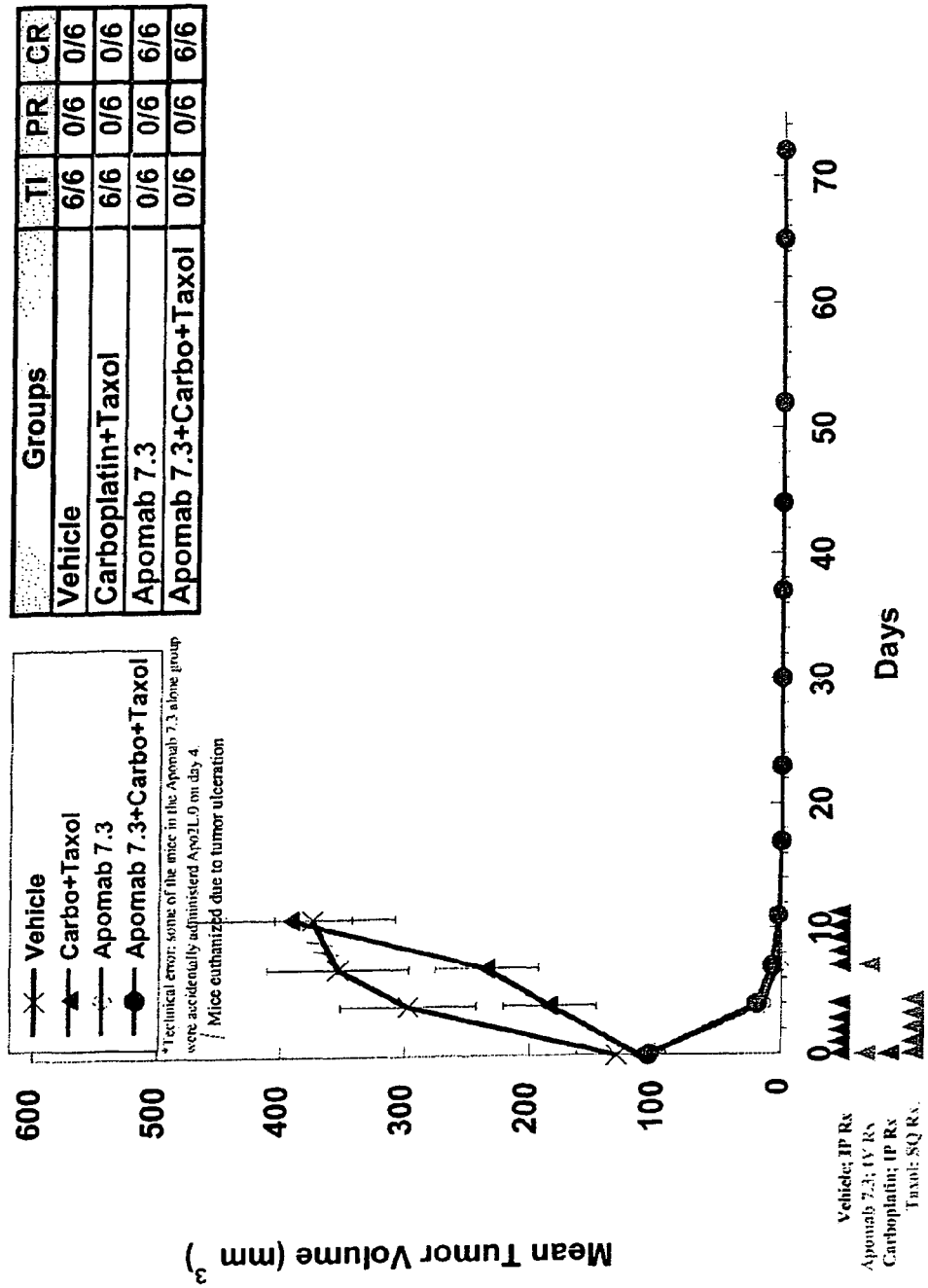

FIG. 31 shows the anticancer activity of Apomab 7.3 alone and in combination with carboplatin and taxol in the H2122 xenograft model of human lung cancer.

Figure 32:
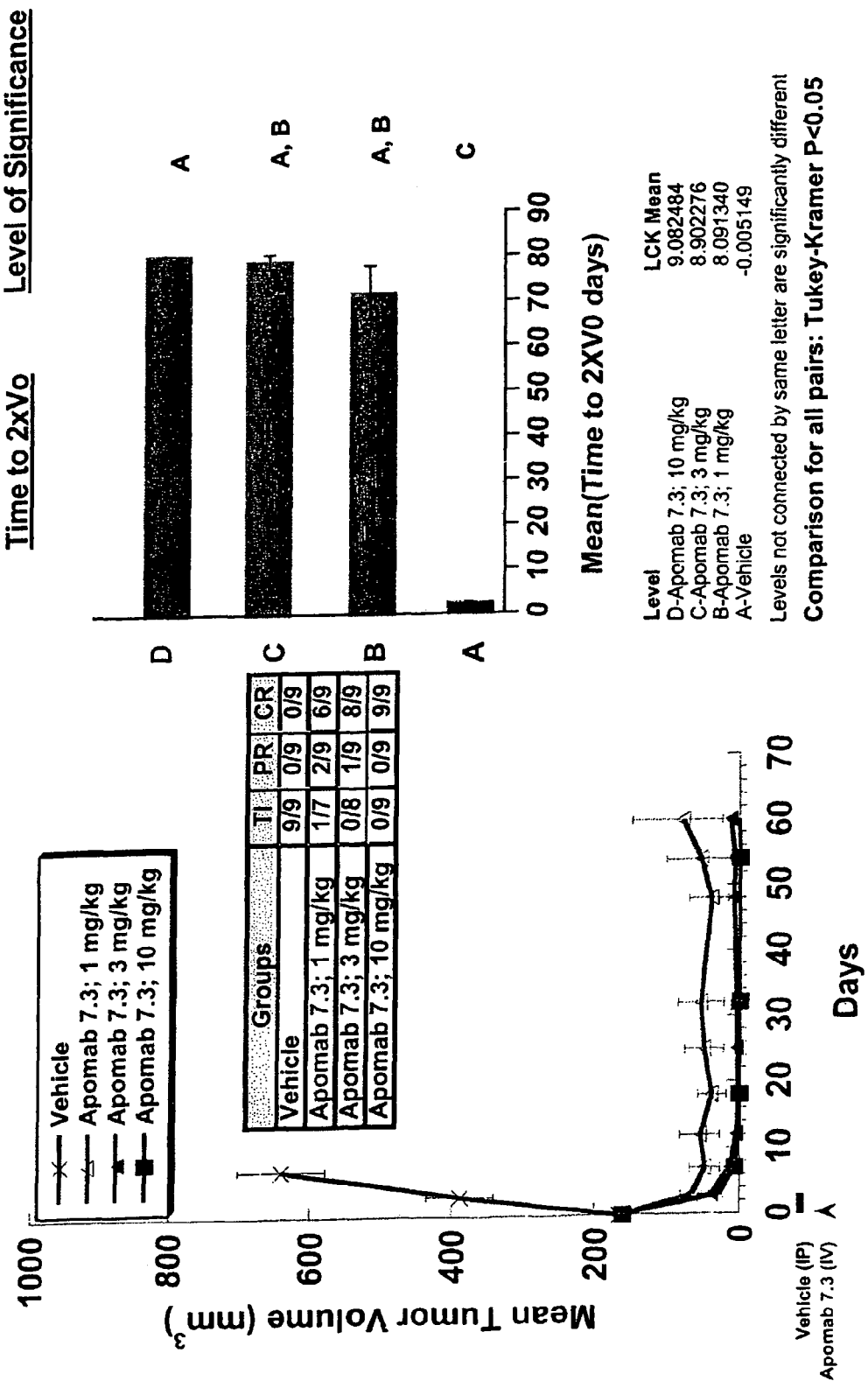

FIG. 32 shows the dose-response curve of Apomab 7.3 in the H2122 xenograft model of human lung cancer.

FIG. 33 shows the anticancer activity of Apomabs 23.3 and 25.3 compared to Apomab 7.3 in the Colo 205 xenograft model of human colon cancer.

FIG. 34 shows the median tumor growth and Kaplan-Meier plot for Apo2L.0 alone, Apomab 7.3 alone, and in various combinations, against Colo 205 human colon carcinoma xenografts in nude mice.

FIGS. 35 and 36 show the median tumor growth and Kaplan-Meier plots for Apo2L.0 alone, Apomab 7.3 alone, and in various combinations, against SKMES-1 human non-small cell lung carcinoma (NSCLC) cells in an athymic nude mouse xenograft model.

FIG. 37 shows the median tumor growth and Kaplan-Meier plot for Apo2L.0 alone, Apomab 7.3 alone, and in various combinations, in the human Colo 205 colon carcinoma xenograft model.

DETAILED DESCRIPTION OF THE PREFERRED EMBODIMENTS

I. Definitions

The terms "Apo-2 ligand", "Apo-2L", "Apo2L", Apo-2 ligand/TRAIL" and "TRAIL" are used herein interchangeably to refer to a polypeptide sequence which includes amino acid residues 114-281, inclusive, 95-281, inclusive, residues 92-281, inclusive, residues 91-281, inclusive, residues 41-281, inclusive, residues 39-281, inclusive, residues 15-281, inclusive, or residues 1-281, inclusive, of the amino acid sequence shown in FIG. 1 (SEQ ID NO:1), as well as biologically active fragments, deletional, insertional, and/or substitutional variants of the above sequences. In one embodiment, the polypeptide sequence comprises residues 114-281 of FIG. 1 (SEQ ID NO:1). Optionally, the polypeptide sequence comprises residues 92-281 or residues 91-281 of FIG. 1 (SEQ ID NO:1). The Apo-2L polypeptides may be encoded by the native nucleotide sequence shown in FIG. 1 (SEQ ID NO:2). Optionally, the codon that encodes residue Pro119 (FIG. 1; SEQ ID NO:2) may be "CCT" or "CCG". Optionally, the fragments or variants are biologically active and have at least about 80% amino acid sequence identity, or at least about 90% sequence identity, or at least 95%, 96%, 97%, 98%, or 99% sequence identity with any one of the above sequences. The definition encompasses substitutional variants of Apo-2 ligand in which at least one of its native amino acids are substituted by another amino acid such as an alanine residue. The definition also encompasses a native sequence Apo-2 ligand isolated from an Apo-2 ligand source or prepared by recombinant and/or synthetic methods. The Apo-2 ligand of the invention includes the polypeptides referred to as Apo-2 ligand or TRAIL disclosed in WO97/01633 published Jan. 16, 1997, WO97/25428 published Jul. 17, 1997, WO99/36535 published Jul. 22, 1999, WO 01/00832 published Jan. 4, 2001, WO02/09755 published Feb. 7, 2002, WO 00/75191 published Dec. 14, 2000, and U.S. Pat. No. 6,030,945 issued Feb. 29, 2000. The terms are used to refer generally to forms of the Apo-2 ligand, which include monomer, dimer, trimer, hexamer or higher oligomer forms of the polypeptide. All numbering of amino acid residues referred to in the Apo-2L sequence use the numbering according to FIG. 1 (SEQ ID NO:1), unless specifically stated otherwise.

"Apo-2 ligand receptor" includes the receptors referred to in the art as "DR4" and "DR5" whose polynucleotide and polypeptide sequences are shown in FIGS. 2A-2C (SEQ ID NOS 4 and 3) and 3A-3C (SEQ ID NOS: 6 and 5), respectively. Pan et al. have described the TNF receptor family member referred to as "DR4" (Pan et al., *Science,* 276:111-113 (1997); see also WO98/32856 published Jul. 30, 1998; WO 99/37684 published Jul. 29, 1999; WO 00/73349 published Dec. 7, 2000; U.S. Pat. No. 6,433,147 issued Aug. 13, 2002; U.S. Pat. No. 6,461,823 issued Oct. 8, 2002, and U.S. Pat. No. 6,342,383 issued Jan. 29, 2002). Sheridan et al., *Science,* 277:818-821 (1997) and Pan et al., *Science,* 277: 815-818 (1997) described another receptor for Apo2L/ TRAIL (see also, WO98/51793 published Nov. 19, 1998; WO98/41629 published Sep. 24, 1998). This receptor is referred to as DR5 (the receptor has also been alternatively referred to as Apo-2; TRAIL-R, TR6, Tango-63, hAPO8, TRICK2 or KILLER; Screaton et al., *Curr. Biol.,* 7:693-696 (1997); Walczak et al., *EMBO J.,* 16:5386-5387 (1997); Wu et al., *Nature Genetics,* 17:141-143 (1997); WO98/35986 published Aug. 20, 1998; EP870,827 published Oct. 14, 1998; WO98/46643 published Oct. 22, 1998; WO99/02653 published Jan. 21, 1999; WO99/09165 published Feb. 25, 1999; WO99/11791 published Mar. 11, 1999; US 2002/0072091 published Aug. 13, 2002; US 2002/0098550 published Dec. 7, 2001; U.S. Pat. No. 6,313,269 issued Dec. 6, 2001; US 2001/0010924 published Aug. 2, 2001; US 2003/01255540 published Jul. 3, 2003; US 2002/0160446 published Oct. 31, 2002, US 2002/0048785 published Apr. 25, 2002; U.S. Pat. No. 6,569,642 issued May 27, 2003, U.S. Pat. No. 6,072,047 issued Jun. 6, 2000, U.S. Pat. No. 6,642,358 issued Nov. 4, 2003). As described above, other receptors for Apo-2L include DcR1, DcR2, and OPG (see, Sheridan et al., supra; Marsters et al., supra; and Simonet et al., supra). The term "Apo-2L receptor" when used herein encompasses native sequence receptor and receptor variants. These terms encompass Apo-2L receptor expressed in a variety of mammals, including humans. Apo-2L receptor may be endogenously expressed as occurs naturally in a variety of human tissue lineages, or may be expressed by recombinant or synthetic methods. A "native sequence Apo-2L receptor" comprises a polypeptide having the same amino acid sequence as an Apo-2L receptor derived from nature. Thus, a native sequence Apo-2L receptor can have the amino acid sequence of naturally occurring Apo-2L receptor from any mammal, including humans. Such native sequence Apo-2L receptor can be isolated from nature or can be produced by recombinant or synthetic means. The term "native sequence Apo-2L receptor" specifically encompasses naturally occurring truncated or secreted forms of the receptor (e.g., a soluble form containing, for instance, an extracellular domain sequence), naturally occurring variant forms (e.g., alternatively spliced forms) and naturally occurring allelic variants. Receptor variants may include fragments or deletion mutants of the native sequence Apo-2L receptor. FIGS. 3A-3C show the 411 amino acid sequence of human DR5 as published in WO 98/51793 on Nov. 19, 1998. A transcriptional splice variant of human DR5 is known in the art. This DR5 splice variant encodes the 440 amino acid sequence of human DR5 as shown in FIGS. 4A-4C, along with its nucleotide sequence (SEQ ID NOS: 7 and 8), and as published in WO 98/35986 on Aug. 20, 1998.

"Death receptor antibody" is used herein to refer generally to antibody or antibodies directed to a receptor in the tumor necrosis factor receptor superfamily and containing a death domain capable of signaling apoptosis, and such antibodies include DR5 antibody and DR4 antibody.

"DR5 receptor antibody", "DR5 antibody", or "anti-DR5 antibody" is used in a broad sense to refer to antibodies that bind to at least one form of a DR5 receptor or extracellular domain thereof. Optionally the DR5 antibody is fused or linked to a heterologous sequence or molecule. Preferably the heterologous sequence allows or assists the antibody to form higher order or oligomeric complexes. Optionally, the DR5 antibody binds to DR5 receptor but does not bind or cross-react with any additional Apo-2L receptor (e.g. DR4, DcR1, or DcR2). Optionally the antibody is an agonist of DR5 signaling activity. The term "anti-DR5 antibody" and is grammatical equivalents specifically encompass the antibodies described in the examples, including but not limited to the "Apomab" antibodies listed in Tables 11 and 12, such as, for example, Apomabs 1.1, 2.1, 3.1, 4.1, 5.1, 6.1, 7.1, 8.1, 9.1, 1.2, 2.2, 3.2, 4.2, 5.2, 6.2, 7.2, 8.2, 9.2, 1.3, 2.2, 3.3, 4.3, 5.3, 6.3, 7.3, 8.3, and 9.3, preferably Apomab 7.3.

Optionally, the DR5 antibody of the invention binds to a DR5 receptor at a concentration range of about 0.11 nM to about 20 mM as measured in a BIAcore binding assay. Optionally, the DR5 antibodies of the invention exhibit an Ic 50 value of about 0.6 nM to about 18 mM as measured in a BIAcore binding assay.

"DR4 receptor antibody", "DR4 antibody", or "anti-DR4 antibody" is used in a broad sense to refer to antibodies that bind to at least one form of a DR4 receptor or extracellular domain thereof. Optionally the DR4 antibody is fused or linked to a heterologous sequence or molecule. Preferably the heterologous sequence allows or assists the antibody to form higher order or oligomeric complexes. Optionally, the DR4 antibody binds to DR4 receptor but does not bind or cross-react with any additional Apo-2L receptor (e.g. DR5, DcR1, or DcR2). Optionally the antibody is an agonist of DR4 signaling activity.

Optionally, the DR4 antibody binds to a DR4 receptor at a concentration range of about 0.11 nM to about 20 mM as measured in a BIAcore binding assay. Optionally, the DR5 antibodies of the invention exhibit an Ic 50 value of about 0.6 nM to about 18 mM as measured in a BIAcore binding assay.

The term "agonist" is used in the broadest sense, and includes any molecule that partially or fully enhances, stimulates or activates one or more biological activities of Apo2L/TRAIL, DR4 or DR5, in vitro, in situ, or in vivo. Examples of such biological activities binding of Apo2L/TRAIL to DR4 or DR5, include apoptosis as well as those further reported in the literature. An agonist may function in a direct or indirect manner. For instance, the agonist may function to partially or fully enhance, stimulate or activate one or more biological activities of DR4 or DR5, in vitro, in situ, or in vivo as a result of its direct binding to DR4 or DR5, which causes receptor activation or signal transduction. The agonist may also function indirectly to partially or fully enhance, stimulate or activate one or more biological activities of DR4 or DR5, in vitro, in situ, or in vivo as a result of, e.g., stimulating another effector molecule which then causes DR4 or DR5 activation or signal transduction. It is contemplated that an agonist may act as an enhancer molecule which functions indirectly to enhance or increase DR4 or DR5 activation or activity. For instance, the agonist may enhance activity of endogenous Apo-2L in a mammal. This could be accomplished, for example, by pre-complexing DR4 or DR5 or by stabilizing complexes of the respective ligand with the DR4 or DR5 receptor (such as stabilizing native complex formed between Apo-2L and DR4 or DR5).

The term "extracellular domain" or "ECD" refers to a form of ligand or receptor, which is essentially free of transmembrane and cytoplasmic domains. Ordinarily, the soluble ECD will have less than 1% of such transmembrane and cytoplasmic domains, and preferably, will have less than 0.5% of such domains.

The term "epitope tagged" when used herein refers to a chimeric polypeptide comprising a protein such as Apo-2 ligand or DR5 receptor, or a portion thereof or an antibody which binds such ligand or receptor, fused to a "tag polypeptide". The tag polypeptide has enough residues to provide an epitope against which an antibody can be made, yet is short enough such that it does not interfere with activity of the ligand or receptor. The tag polypeptide preferably also is fairly unique so that the antibody does not substantially cross-react with other epitopes. Suitable tag polypeptides generally have at least six amino acid residues and usually between about 8 to about 50 amino acid residues (preferably, between about 10 to about 20 residues).

"Isolated," when used to describe the various proteins disclosed herein, means protein that has been identified and separated and/or recovered from a component of its natural environment. Contaminant components of its natural environment are materials that would typically interfere with diagnostic or therapeutic uses for the protein, and may include enzymes, hormones, and other proteinaceous or non-proteinaceous solutes. In preferred embodiments, the protein will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Isolated protein includes protein in situ within recombinant cells, since at least one component of the Apo-2 ligand natural environment will not be present. Ordinarily, however, isolated protein will be prepared by at least one purification step.

"Percent (%) amino acid sequence identity" with respect to the sequences identified herein is defined as the percentage of amino acid residues in a candidate sequence that are identical with the amino acid residues in the compared ligand, receptor, or antibody sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art can determine appropriate parameters for measuring alignment, including assigning algorithms needed to achieve maximal alignment over the full-length sequences being compared. For purposes herein, percent amino acid identity values can be obtained using the sequence comparison computer program, ALIGN-2, which was authored by Genentech, Inc. and the source code of which has been filed with user documentation in the US Copyright Office, Washington, D.C., 20559, registered under the US Copyright Registration No. TXU510087. The ALIGN-2 program is publicly available through Genentech, Inc., South San Francisco, Calif. All sequence comparison parameters are set by the ALIGN-2 program and do not vary. Percent amino acid sequence identity is then calculated relative to the longer sequence. Accordingly, even if the shorter sequence is fully included in the longer sequence, the sequence identity will be less than 100%.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

The term "polyol" when used herein refers broadly to polyhydric alcohol compounds. Polyols can be any water-soluble poly(alkylene oxide) polymer for example, and can have a linear or branched chain. Preferred polyols include those substituted at one or more hydroxyl positions with a chemical group, such as an alkyl group having between one and four carbons. Typically, the polyol is a poly(alkylene glycol), preferably poly(ethylene glycol) (PEG). However, those skilled in the art recognize that other polyols, such as, for example, poly(propylene glycol) and polyethylene-polypropylene glycol copolymers, can be employed using the techniques for conjugation described herein for PEG. The polyols include those well known in the art and those publicly available, such as from commercially available sources such as Nektar® Corporation.

The term "conjugate" is used herein according to its broadest definition to mean joined or linked together. Molecules are "conjugated" when they act or operate as if joined.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to re-anneal when complementary strands are present in an environment below their melting temperature. The higher the degree of desired identity between the probe and hybridizable sequence, the higher the relative temperature, which can be used. As a result, it follows that higher relative temperatures would tend to make the reaction conditions more stringent, while lower temperatures less so. For additional details and explanation of stringency of hybridization reactions, see Ausubel et al., *Current Protocols in Molecular Biology*, Wiley Interscience Publishers, (1995).

"Stringent conditions" or "high stringency conditions", as defined herein, are identified by those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C.

"Moderately stringent conditions" are identified as described by Sambrook et al., *Molecular Cloning: A Laboratory Manual*, New York: Cold Spring Harbor Press, 1989, and include the use of washing solution and hybridization conditions (e.g., temperature, ionic strength and % SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/ml denatured sheared salmon sperm DNA, followed by washing the filters in 1×SSC at about 37-50° C. The skilled artisan will recognize how to adjust the temperature, ionic strength, etc. as necessary to accommodate factors such as probe length and the like.

The terms "amino acid" and "amino acids" refer to all naturally occurring L-alpha-amino acids. This definition is meant to include norleucine, ornithine, and homocysteine. The amino acids are identified by either the single-letter or three-letter designations:

| Asp | D | aspartic acid | Ile | I | isoleucine |
|-----|---|---------------|-----|---|------------|
| Thr | T | threonine | Leu | L | leucine |
| Ser | S | serine | Tyr | Y | tyrosine |
| Glu | E | glutamic acid | Phe | F | phenylalanine |
| Pro | P | proline | His | H | histidine |
| Gly | G | glycine | Lys | K | lysine |
| Ala | A | alanine | Arg | R | arginine |
| Cys | C | cysteine | Trp | W | tryptophan |
| Val | V | valine | Gln | Q | glutamine |
| Met | M | methionine | Asn | N | asparagine |

In the Figures, certain other single-letter or three-letter designations may be employed to refer to and identify two or more amino acids or nucleotides at a given position in the sequence.

The term "antibody" is used in the broadest sense and specifically covers single anti-DR5 monoclonal antibodies (including agonist, antagonist, and neutralizing or blocking antibodies) and anti-DR5 antibody compositions with polyepitopic specificity. "Antibody" as used herein includes intact immunoglobulin or antibody molecules, polyclonal antibodies, multispecific antibodies (i.e., bispecific antibodies formed from at least two intact antibodies) and immunoglobulin fragments (such as Fab, F(ab')$_2$, or Fv), so long as they exhibit any of the desired agonistic or antagonistic properties described herein.

Antibodies are typically proteins or polypeptides which exhibit binding specificity to a specific antigen. Native antibodies are usually heterotetrameric glycoproteins, composed of two identical light (L) chains and two identical heavy (H) chains. Typically, each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light and heavy chain variable domains [Chothia et al., *J. Mol. Biol.,* 186:651-663 (1985); Novotny and Haber, *Proc. Natl. Acad. Sci. USA,* 82:4592-4596 (1985)]. The light chains of antibodies from any vertebrate species can be assigned to one of two clearly distinct types, called kappa and lambda, based on the amino acid sequences of their constant domains. Depending on the amino acid sequence of the constant domain of their heavy chains, immunoglobulins can be assigned to different classes. There are five major classes of immunoglobulins: IgA, IgD, IgE, IgG and IgM, and several of these may be further divided into subclasses (isotypes), e.g., IgG-1, IgG-2, IgG-3, and IgG-4; IgA-1 and IgA-2. The heavy chain constant domains that correspond to the different classes of immunoglobulins are called alpha, delta, epsilon, gamma, and mu, respectively.

"Antibody fragments" comprise a portion of an intact antibody, generally the antigen binding or variable region of the intact antibody. Examples of antibody fragments include Fab, Fab', F(ab')2, and Fv fragments, diabodies, single chain antibody molecules, and multispecific antibodies formed from antibody fragments.

The term "variable" is used herein to describe certain portions of the variable domains, which differ in sequence among antibodies and are used in the binding and specificity of each particular antibody for its particular antigen. However, the variability is not usually evenly distributed through the variable domains of antibodies. It is typically concentrated in three segments called complementarity determining regions (CDRs) or hypervariable regions both in the light chain and the heavy chain variable domains. The more highly conserved portions of the variable domains are called the framework (FR). The variable domains of native heavy and light chains each comprise four FR regions, largely adopting a β-sheet configuration, connected by three CDRs, which form loops connecting, and in some cases forming part of, the β-sheet structure. The CDRs in each chain are held together in close proximity by the FR regions and, with the CDRs from the other chain, contribute to the formation of the antigen binding site of antibodies [see Kabat, E. A. et al., *Sequences of Proteins of Immunological Interest*, National Institutes of Health, Bethesda, Md. (1987)]. The constant domains are not involved directly in binding an antibody to an antigen, but exhibit various effector functions, such as participation of the antibody in antibody-dependent cellular toxicity.

The term "monoclonal antibody" as used herein refers to an antibody obtained from a population of substantially homogeneous antibodies, i.e., the individual antibodies comprising the population are identical except for possible naturally-occurring mutations that may be present in minor amounts. Monoclonal antibodies are highly specific, being directed against a single antigenic site. Furthermore, in contrast to conventional (polyclonal) antibody preparations, which typically include different antibodies directed against different determinants (epitopes), each monoclonal antibody is directed against a single determinant on the antigen.

The monoclonal antibodies herein include chimeric, hybrid and recombinant antibodies produced by splicing a variable (including hypervariable) domain of an anti-DR5 antibody with a constant domain (e.g. "humanized" antibodies), or a light chain with a heavy chain, or a chain from one species with a chain from another species, or fusions with heterologous proteins, regardless of species of origin or immunoglobulin class or subclass designation, as well as antibody fragments (e.g., Fab, F(ab')$_2$, and Fv), so long as they exhibit the desired biological activity or properties. See, e.g. U.S. Pat. No. 4,816,567 and Mage et al., in *Monoclonal Antibody Production Techniques and Applications*, pp. 79-97 (Marcel Dekker, Inc.: New York, 1987).

Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler and Milstein, *Nature,* 256:495 (1975), or may be made by recombinant DNA methods such as described in U.S. Pat. No. 4,816,567. The "monoclonal antibodies" may also be isolated from phage libraries generated using the techniques described in McCafferty et al., *Nature,* 348:552-554 (1990), for example.

"Humanized" forms of non-human (e.g. murine) antibodies are specific chimeric immunoglobulins, immunoglobulin chains, or fragments thereof (such as Fv, Fab, Fab', F(ab')$_2$ or other antigen-binding subsequences of antibodies) which contain minimal sequence derived from non-human immunoglobulin. For the most part, humanized antibodies are human immunoglobulins (recipient antibody) in which residues from a complementary determining region (CDR) of the recipient are replaced by residues from a CDR of a non-human species (donor antibody) such as mouse, rat, or rabbit having the desired specificity, affinity, and capacity. In some instances, Fv framework region (FR) residues of the human immunoglobulin are replaced by corresponding non-human residues. Furthermore, the humanized antibody may comprise residues, which are found neither in the recipient antibody nor in the imported CDR or framework sequences. These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region or domain (Fc), typically that of a human immunoglobulin.

A "human antibody" is one which possesses an amino acid sequence which corresponds to that of an antibody produced by a human and/or has been made using any of the techniques for making human antibodies known in the art or as disclosed herein. This definition of a human antibody includes antibodies comprising at least one human heavy chain polypeptide or at least one human light chain polypeptide, for example an antibody comprising murine light chain and human heavy chain polypeptides. Human antibodies can be produced using various techniques known in the art. In one embodiment, the human antibody is selected from a phage library, where that phage library expresses human antibodies (Vaughan et al. *Nature Biotechnology*, 14:309-314 (1996): Sheets et al. *PNAS, (USA)* 95:6157-6162 (1998)); Hoogenboom and Winter, *J. Mol. Biol.*, 227:381 (1991); Marks et al., *J. Mol. Biol.*, 222:581 (1991)); Human antibodies can also be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., *Bio/Technology*, 10: 779-783 (1992); Lonberg et al., *Nature*, 368: 856-859 (1994); Morrison, *Nature*, 368:812-13 (1994); Fishwild et al., *Nature Biotechnology*, 14: 845-51 (1996); Neuberger, *Nature Biotechnology*, 14: 826 (1996); Lonberg and Huszar, *Intern. Rev. Immunol.*, 13:65-93 (1995). Alternatively, the human antibody may be prepared via immortalization of human B lymphocytes producing an antibody directed against a target antigen (such B lymphocytes may be recovered from an individual or may have been immunized in vitro). See, e.g., Cole et al., *Monoclonal Antibodies and Cancer Therapy*, Alan R. Liss, p. 77 (1985); Boerner et al., *J. Immunol.*, 147 (1):86-95 (1991); and U.S. Pat. No. 5,750,373.

The term "Fc region" is used to define the C-terminal region of an immunoglobulin heavy chain, which may be generated by papain digestion of an intact antibody. The Fc region may be a native sequence Fc region or a variant Fc region. Although the boundaries of the Fc region of an immunoglobulin heavy chain might vary, the human IgG heavy chain Fc region is usually defined to stretch from an amino acid residue at about position Cys226, or from about position Pro230, to the carboxyl-terminus of the Fc region (using herein the numbering system according to Kabat et al., supra). The Fc region of an immunoglobulin generally comprises two constant domains, a CH2 domain and a CH3 domain, and optionally comprises a CH4 domain.

By "Fc region chain" herein is meant one of the two polypeptide chains of an Fc region.

The "CH2 domain" of a human IgG Fc region (also referred to as "Cγ2" domain) usually extends from an amino acid residue at about position 231 to an amino acid residue at about position 340. The CH2 domain is unique in that it is not closely paired with another domain. Rather, two N-linked branched carbohydrate chains are interposed between the two CH2 domains of an intact native IgG molecule. It has been speculated that the carbohydrate may provide a substitute for the domain-domain pairing and help stabilize the CH2 domain. Burton, *Molec. Immunol.* 22:161-206 (1985). The CH2 domain herein may be a native sequence CH2 domain or variant CH2 domain.

The "CH3 domain" comprises the stretch of residues C-terminal to a CH2 domain in an Fc region (i.e. from an amino acid residue at about position 341 to an amino acid residue at about position 447 of an IgG). The CH3 region herein may be a native sequence CH3 domain or a variant CH3 domain (e.g. a CH3 domain with an introduced "protroberance" in one chain thereof and a corresponding introduced "cavity" in the other chain thereof; see U.S. Pat. No. 5,821,333). Such variant CH3 domains may be used to make multispecific (e.g. bispecific) antibodies as herein described.

"Hinge region" is generally defined as stretching from about Glu216, or about Cys226, to about Pro230 of human IgG1 (Burton, *Molec. Immunol.* 22:161-206 (1985)). Hinge regions of other IgG isotypes may be aligned with the IgG1 sequence by placing the first and last cysteine residues forming inter-heavy chain S—S bonds in the same positions. The hinge region herein may be a native sequence hinge region or a variant hinge region. The two polypeptide chains of a variant hinge region generally retain at least one cysteine residue per polypeptide chain, so that the two polypeptide chains of the variant hinge region can form a disulfide bond between the two chains. The preferred hinge region herein is a native sequence human hinge region, e.g. a native sequence human IgG1 hinge region.

A "functional Fc region" possesses at least one "effector function" of a native sequence Fc region. Exemplary "effector functions" include C1q binding; complement dependent cytotoxicity (CDC); Fc receptor binding; antibody-dependent cell-mediated cytotoxicity (ADCC); phagocytosis; down regulation of cell surface receptors (e.g. B cell receptor; BCR), etc. Such effector functions generally require the Fc region to be combined with a binding domain (e.g. an antibody variable domain) and can be assessed using various assays known in the art for evaluating such antibody effector functions.

A "native sequence Fc region" comprises an amino acid sequence identical to the amino acid sequence of an Fc region found in nature. A "variant Fc region" comprises an amino acid sequence, which differs from that of a native sequence Fc region by virtue of at least one amino acid modification. Preferably, the variant Fc region has at least one amino acid substitution compared to a native sequence Fc region or to the Fc region of a parent polypeptide, e.g. from about one to about ten amino acid substitutions, and preferably from about one to about five amino acid substitutions in a native sequence Fc region or in the Fc region of the parent polypeptide. The variant Fc region herein will preferably possess at least about 80% sequence identity with a native sequence Fc region and/or with an Fc region of a parent polypeptide, and most preferably at least about 90% sequence identity therewith, more preferably at least about 95% sequence identity therewith.

"Antibody-dependent cell-mediated cytotoxicity" and "ADCC" refer to a cell-mediated reaction in which nonspecific cytotoxic cells that express Fc receptors (FcRs) (e.g. Natural Killer (NK) cells, neutrophils, and macrophages) recognize bound antibody on a target cell and subsequently cause lysis of the target cell. The primary cells for mediating ADCC, NK cells, express Fc(RIII only, whereas monocytes express Fc(RI, Fc(RII and Fc(RIII. FcR expression on hematopoietic cells is summarized in Table 3 on page 464 of Ravetch and Kinet, *Annu. Rev. Immunol.*, 9:457-92 (1991). To assess ADCC activity of a molecule of interest, an in vitro ADCC assay, such as that described in U.S. Pat. No. 5,500, 362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *PNAS (USA)* 95:652-656 (1998).

"Human effector cells" are leukocytes which express one or more FcRs and perform effector functions. Preferably, the cells express at least Fc(RIII and perform ADCC effector function. Examples of human leukocytes which mediate ADCC include peripheral blood mononuclear cells (PBMC), natural killer (NK) cells, monocytes, cytotoxic T cells and neutrophils; with PBMCs and NK cells being preferred. The effector cells may be isolated from a native source thereof, e.g. from blood or PBMCs as described herein.

The terms "Fc receptor" and "FcR" are used to describe a receptor that binds to the Fc region of an antibody. The preferred FcR is a native sequence human FcR. Moreover, a preferred FcR is one which binds an IgG antibody (a gamma receptor) and includes receptors of the Fc(RI, Fc(RII, and Fc(RIII subclasses, including allelic variants and alternatively spliced forms of these receptors. Fc(RII receptors include Fc(RIIA (an "activating receptor") and Fc(RIIB (an "inhibiting receptor"), which have similar amino acid sequences that differ primarily in the cytoplasmic domains thereof. Activating receptor Fc(RIIA contains an immunoreceptor tyrosine-based activation motif (ITAM) in its cytoplasmic domain. Inhibiting receptor Fc(RIIB contains an immunoreceptor tyrosine-based inhibition motif (ITIM) in its cytoplasmic domain (reviewed in Daëron, *Annu. Rev. Immunol.*, 15:203-234 (1997)). FcRs are reviewed in Ravetch and Kinet, *Annu. Rev. Immunol.*, 9:457-92 (1991); Capel et al., *Immunomethods*, 4:25-34 (1994); and de Haas et al., *J. Lab. Clin. Med.*, 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., *J. Immunol.*, 117:587 (1976); and Kim et al., *J. Immunol.*, 24:249 (1994)).

"Complement dependent cytotoxicity" and "CDC" refer to the lysing of a target in the presence of complement. The complement activation pathway is initiated by the binding of the first component of the complement system (C1q) to a molecule (e.g. an antibody) complexed with a cognate antigen. To assess complement activation, a CDC assay, e.g. as described in Gazzano-Santoro et al., *J. Immunol. Methods*, 202:163 (1996), may be performed.

An "affinity matured" antibody is one with one or more alterations in one or more CDRs thereof which result an improvement in the affinity of the antibody for antigen, compared to a parent antibody which does not possess those alteration(s). Preferred affinity matured antibodies will have nanomolar or even picomolar affinities for the target antigen. Affinity matured antibodies are produced by procedures known in the art. Marks et al. *Bio/Technology*, 10:779-783 (1992) describes affinity maturation by VH and VL domain shuffling. Random mutagenesis of CDR and/or framework residues is described by: Barbas et al. *Proc Nat. Acad. Sci, USA* 91:3809-3813 (1994); Schier et al. *Gene*, 169:147-155 (1995); Yelton et al. *J. Immunol.*, 155:1994-2004 (1995); Jackson et al., *J. Immunol.*, 154(7):3310-9 (1995); and Hawkins et al, *J. Mol. Biol.*, 226:889-896 (1992).

The term "immunospecific" as used in "immunospecific binding of antibodies" for example, refers to the antigen specific binding interaction that occurs between the antigen-combining site of an antibody and the specific antigen recognized by that antibody.

"Biologically active" and "desired biological activity" for the purposes herein mean having the ability to modulate DR5 activity or DR5 activation, including, by way of example, apoptosis (either in an agonistic or stimulating manner or in an antagonistic or blocking manner) in at least one type of mammalian cell in vivo or ex vivo, binding to Apo-2 ligand (TRAIL), or modulating activation of one or more molecules in the intracellular signaling pathway such as caspase 3, caspase 8, caspase 10 or FADD. Assays for determining activation of such intracellular molecules are known in the art, see, e.g., Boldin et al., *J. Biol. Chem.*, 270:7795-7798 (1995); Peter, *Cell Death Differ.*, 7:759-760 (2000); Nagata, *Cell*, 88:355-365 (1998); Ashkenazi et al., *Science*, 281:1305-1308 (1999).

The terms "agonist" and "agonistic" when used herein refer to or describe a molecule which is capable of, directly or indirectly, substantially inducing, promoting or enhancing DR5 biological activity or activation. Optionally, an "agonist DR5 antibody" is an antibody which has activity comparable to the ligand for DR5, known as Apo-2 ligand (TRAIL), or is capable of activating DR5 receptor which results in an activation of one or more intracellular signaling pathways which may include activation of caspase 3, caspase 8, caspase 10 or FADD.

The terms "antagonist" and "antagonistic" when used herein refer to or describe a molecule which is capable of, directly or indirectly, substantially counteracting, reducing or inhibiting DR5 biological activity or DR5 activation. Optionally, an antagonist is a molecule which neutralizes the biological activity resulting from DR5 activation or formation of a complex between DR5 and its ligand, such as Apo-2 ligand.

The terms "apoptosis" and "apoptotic activity" are used in a broad sense and refer to the orderly or controlled form of cell death in mammals that is typically accompanied by one or more characteristic cell changes, including condensation of cytoplasm, loss of plasma membrane microvilli, segmentation of the nucleus, degradation of chromosomal DNA or loss of mitochondrial function. This activity can be determined and measured, for instance, by cell viability assays, annexin V binding assays, PARP assays, FACS analysis or DNA electrophoresis, all of which are known in the art Optionally, apoptotic activity will be determined by way of an annexin V or PARP assay.

The terms "cancer," "cancerous," and "malignant" refer to or describe the physiological condition in mammals that is typically characterized by unregulated cell growth. Examples of cancer include but are not limited to, carcinoma, including adenocarcinoma, lymphoma, blastoma, melanoma, glioma, sarcoma, myeloma (such as multiple myeloma) and leukemia. More particular examples of such cancers include squamous cell cancer, small-cell lung cancer, non-small cell lung cancer, lung adenocarcinoma, lung squamous cell carcinoma, gastrointestinal cancer, Hodgkin's and non-Hodgkin's lymphoma, pancreatic cancer, glioblastoma, cervical cancer, glioma, ovarian cancer, liver cancer such as hepatic carcinoma and hepatoma, bladder cancer, breast cancer, colon cancer, colorectal cancer, endometrial or uterine carcinoma, salivary gland carcinoma, kidney cancer such as renal cell carcinoma and Wilms' tumors, basal cell carcinoma, melanoma, prostate cancer, vulval cancer, thyroid cancer, testicular cancer, esophageal cancer, and various types of head and neck cancer.

The term "immune related disease" means a disease in which a component of the immune system of a mammal causes, mediates or otherwise contributes to a morbidity in the mammal. Also included are diseases in which stimulation or intervention of the immune response has an ameliorative effect on progression of the disease. Included within this term are autoimmune diseases, immune-mediated inflammatory diseases, non-immune-mediated inflammatory diseases, infectious diseases, and immunodeficiency diseases. Examples of immune-related and inflammatory diseases, some of which are immune or T cell mediated, which can be treated according to the invention include systemic lupus erythematosis, rheumatoid arthritis, juvenile chronic arthritis, spondyloarthropathies, systemic sclerosis (scleroderma), idiopathic inflammatory myopathies (dermatomyositis, polymyositis), Sjogren's syndrome, systemic vasculitis, sarcoidosis, autoimmune hemolytic anemia (immune pancytopenia, paroxysmal nocturnal hemoglobinuria), autoimmune thrombocytopenia (idiopathic thrombocytopenic purpura, immune-mediated thrombocytopenia), thyroiditis (Grave's disease, Hashimoto's thyroiditis, juvenile lymphocytic thyroiditis, atrophic thyroiditis), diabetes mellitus, immune-mediated renal disease (glomerulonephritis, tubulointerstitial nephritis), demyelinating diseases of the central and peripheral nervous systems such as multiple sclerosis, idiopathic demyelinating polyneuropathy or Guillain-Barré syndrome, and chronic inflammatory demyelinating polyneuropathy, hepatobiliary diseases such as infectious hepatitis (hepatitis A, B, C, D, E and other non-hepatotropic viruses), autoimmune chronic active hepatitis, primary biliary cirrhosis, granulomatous hepatitis, and sclerosing cholangitis, inflammatory and fibrotic lung diseases such as inflammatory bowel disease (ulcerative colitis: Crohn's disease), gluten-sensitive enteropathy, and Whipple's disease, autoimmune or immune-mediated skin diseases including bullous skin diseases, erythema multiforme and contact dermatitis, psoriasis, allergic diseases such as asthma, allergic rhinitis, atopic dermatitis, food hypersensitivity and urticaria, immunologic diseases of the lung such as eosinophilic pneumonias, idiopathic pulmonary fibrosis and hypersensitivity pneumonitis, transplantation associated diseases including graft rejection and graft-versus-host-disease. Infectious diseases include AIDS (HIV infection), hepatitis A, B, C, D, and E, bacterial infections, fungal infections, protozoal infections and parasitic infections.

"Autoimmune disease" is used herein in a broad, general sense to refer to disorders or conditions in mammals in which destruction of normal or healthy tissue arises from humoral or cellular immune responses of the individual mammal to his or her own tissue constituents. Examples include, but are not limited to, lupus erythematous, thyroiditis, rheumatoid arthritis, psoriasis, multiple sclerosis, autoimmune diabetes, and inflammatory bowel disease (IBD).

A "growth inhibitory agent" when used herein refers to a compound or composition which inhibits growth of a cell in vitro and/or in vivo. Thus, the growth inhibitory agent may be one which significantly reduces the percentage of cells in S phase. Examples of growth inhibitory agents include agents that block cell cycle progression (at a place other than S phase), such as agents that induce G1 arrest and M-phase arrest. Classical M-phase blockers include the vincas (vincristine and vinblastine), TAXOL®, and topo II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in *The Molecular Basis of Cancer*, Mendelsohn and Israel, eds., Chapter 1, entitled "Cell cycle regulation, oncogenes, and antineoplastic drugs" by Murakami et al. (WB Saunders: Philadelphia, 1995), especially p. 13.

The term "prodrug" as used in this application refers to a precursor or derivative form of a pharmaceutically active substance that is less cytotoxic to cancer cells compared to the parent drug and is capable of being enzymatically activated or converted into the more active parent form. See, e.g., Wilman, "Prodrugs in Cancer Chemotherapy" *Biochemical Society Transactions*, 14, pp. 375-382, 615th Meeting Belfast (1986) and Stella et al., "Prodrugs: A Chemical Approach to Targeted Drug Delivery," *Directed Drug Delivery*, Borchardt et al., (ed.), pp. 247-267, Humana Press (1985). The prodrugs of this invention include, but are not limited to, phosphate-containing prodrugs, thiophosphate-containing prodrugs, sulfate-containing prodrugs, peptide-containing prodrugs, D-amino acid-modified prodrugs, glycosylated prodrugs, beta-lactam-containing prodrugs, optionally substituted phenoxyacetamide-containing prodrugs or optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use in this invention include, but are not limited to, those chemotherapeutic agents described below.

The term "cytotoxic agent" as used herein refers to a substance that inhibits or prevents the function of cells and/or causes destruction of cells. The term is intended to include radioactive isotopes (e.g. $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu), chemotherapeutic agents, and toxins such as small molecule toxins or enzymatically active toxins of bacterial, fungal, plant or animal origin, including fragments and/or variants thereof.

A "chemotherapeutic agent" is a chemical compound useful in the treatment of conditions like cancer. Examples of chemotherapeutic agents include alkylating agents such as thiotepa and cyclosphosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CBI-TMI); eleutherobin; pancratistatin; a sarcodictyin; spongistatin; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as the enediyne antibiotics (e.g. calicheamicin, especially calicheamicin $\gamma_1^I$ and calicheamicin $2^I_1$, see, e.g., Agnew *Chem Intl. Ed. Engl.* 33:183-186 (1994); dynemicin, including dynemicin A; an esperamicin; as well as neocarzinostatin chromophore and related chromoprotein enediyne antibiotic chromophores), aclacinomysins, actinomycin, authramycin, azaserine, bleomycins, cactinomycin, carabicin, carminomycin, carzinophilin, chromomycins, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidamine; maytansinoids such as maytansine and ansamitocins; mitoguazone; mitoxantrone; mopidamol; nitracrine; pentostatin; phenamet; pirarubicin; podophyllinic acid; 2-ethylhydrazide; procarbazine; PSK®; razoxane; rhizoxin; sizofuran; spirogermanium; tenuazonic acid; triaziquone; 2,2',2''-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel (TAXOL®, Bristol-Myers Squibb Oncology, Princeton, N.J.) and doxetaxel (TAXOTERE®, Rhône-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylornithine (DMFO); retinoic acid; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above.

The term "cytokine" is a generic term for proteins released by one cell population which act on another cell as intercellular mediators. Examples of such cytokines are lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-alpha and -beta; mullerian-inhibiting substance; mouse gonadotropin-associated peptide; inhibin; activin; vascular endothelial growth factor; integrin; thrombopoietin (TPO); nerve growth factors such as NGF-alpha; platelet-growth factor; transforming growth factors (TGFs) such as TGF-alpha and TGF-beta; insulin-like growth factor-I and -II; erythropoietin (EPO); osteoinductive factors; interferons such as interferon-alpha, -beta and -gamma colony stimulating factors (CSFS) such as macrophage-CSF (M-CSF); granulocyte-macrophage-CSF (GM-CSF); and granulocyte-CSF (G-CSF); interleukins (ILs) such as IL-1, IL-1 alpha, IL-2, IL-3, IL-4, IL-5, IL-6, IL-7, IL-8, IL-9, IL-10, IL-11, IL-12; a tumor necrosis factor such as TNF-alpha or TNF-beta; and other polypeptide factors including LIF and kit ligand (KL). As used herein, the term cytokine includes proteins from natural sources or from recombinant cell culture and biologically active equivalents of the native sequence cytokines.

The terms "treating," "treatment," and "therapy" as used herein refer to curative therapy, prophylactic therapy, and preventative therapy.

The term "therapeutically effective amount" refers to an amount of a drug effective to treat a disease or disorder in a mammal. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the disorder. To the extent the drug may prevent growth and/or kill existing cancer cells, it may be cytostatic and/or cytotoxic. For cancer therapy, efficacy in vivo can, for example, be measured by assessing tumor burden or volume, the time to disease progression (TTP) and/or determining the response rates (RR).

The term "mammal" as used herein refers to any mammal classified as a mammal, including humans, higher primates, cows, horses, dogs and cats. In a preferred embodiment of the invention, the mammal is a human.

The term "objective response" is defined as a complete or partial response to treatment of a subject, as determined using the Response Evaluation Criteria in Solid Tumors (RECIST) (J. Nat. Cancer Inst. 92(3):205-216 (2000)).

The term "duration of response" is used herein to refer to the time from an initial complete or partial response to the time of disease progression or death.

The term "progression-free survival" is used herein to refer to the time from the first day of treatment to disease progression or death, whichever occurs first.

The term "complete regression (CR)" is used to indicate that the tumor volume is $\leq 13.5$ mm$^3$ for three consecutive measurements.

The term "partial regression (PR)" indicates that the tumor volume is $\leq 50\%$ of its Day 1 volume, for three consecutive measurements, and $\leq 13.5$ mm$^3$ for one or more of these measurements.

II. Compositions and Methods of the Invention

A. DR5 Antibodies

In one embodiment of the invention, DR5 antibodies are provided. Exemplary antibodies include polyclonal, monoclonal, humanized, bispecific, and heteroconjugate antibodies. These antibodies may be agonists, antagonists or blocking antibodies.

1. Polyclonal Antibodies

The antibodies of the invention may comprise polyclonal antibodies. Methods of preparing polyclonal antibodies are known to the skilled artisan. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. The immunizing agent may include the DR5 polypeptide (or a DR5 ECD) or a fusion protein thereof. It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation. The mammal can then be bled, and the serum assayed for DR5 antibody titer. If desired, the mammal can be boosted until the antibody titer increases or plateaus.

2. Monoclonal Antibodies

The antibodies of the invention may, alternatively, be monoclonal antibodies. Monoclonal antibodies may be prepared using hybridoma methods, such as those described by Kohler and Milstein, *Nature*, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro.

The immunizing agent will typically include the DR5 polypeptide (or a DR5 ECD) or a fusion protein thereof, such as a DR5 ECD-IgG fusion protein. The immunizing agent may alternatively comprise a fragment or portion of DR5 having one or more amino acids that participate in the binding of Apo-2L to DR5. In a preferred embodiment, the immunizing agent comprises an extracellular domain sequence of DR5 fused to an IgG sequence.

Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell [Goding, *Monoclonal Antibodies: Principles and Practice*, Academic Press, (1986) pp. 59-103]. Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. An example of such a murine myeloma cell line is P3X63Ag8U.1, (ATCC CRL 1580). Human myeloma and mouse-human heteromyeloma cell lines also have been described for the production of human monoclonal antibodies [Kozbor, *J. Immunol.*, 133:3001 (1984); Brodeur et al., *Monoclonal Antibody Production Techniques and Applications*, Marcel Dekker, Inc., New York, (1987) pp. 51-63].

The culture medium in which the hybridoma cells are cultured can then be assayed for the presence of monoclonal antibodies directed against DR5. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, *Anal. Biochem.*, 107:220 (1980).

After the desired hybridoma cells are identified, the clones may be subcloned by limiting dilution procedures and grown by standard methods [Goding, supra]. Suitable culture media for this purpose include, for example, Dulbecco's Modified Eagle's Medium or RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies is readily isolated and sequenced using conventional procedures (e.g., by using oligonucleotide probes that are capable of binding specifically to genes encoding the heavy and light chains of the monoclonal antibodies). The hybridoma cells serve as a preferred source of such DNA. Once isolated, the DNA may be placed into expression vectors, which are then transfected into host cells such as *E. coli* cells, simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences, Morrison, et al., *Proc. Nat. Acad. Sci.* 81, 6851 (1984), or by covalently joining to the immunoglobulin coding sequence all or part of the coding sequence for a non-immunoglobulin polypeptide. In that manner, "chimeric" or "hybrid" antibodies are prepared that have the binding specificity of an anti-DR5 monoclonal antibody herein.

Typically such non-immunoglobulin polypeptides are substituted for the constant domains of an antibody of the invention, or they are substituted for the variable domains of one antigen-combining site of an antibody of the invention to create a chimeric bivalent antibody comprising one antigen-combining site having specificity for DR5 and another antigen-combining site having specificity for a different antigen.

Chimeric or hybrid antibodies also may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate.

Single chain Fv fragments may also be produced, such as described in Iliades et al., *FEBS Letters*, 409:437-441 (1997). Coupling of such single chain fragments using various linkers is described in Kortt et al., *Protein Engineering*, 10:423-433 (1997). A variety of techniques for the recombinant production and manipulation of antibodies are well known in the art. Illustrative examples of such techniques that are typically utilized by skilled artisans are described in greater detail below.

(i) Humanized Antibodies

Generally, a humanized antibody has one or more amino acid residues introduced into it from a non-human source. These non-human amino acid residues are often referred to as "import" residues, which are typically taken from an "import" variable domain. Humanization can be essentially performed following the method of Winter and co-workers [Jones et al., *Nature*, 321:522-525 (1986); Riechmann et al., *Nature*, 332:323-327 (1988); Verhoeyen et al., *Science*, 239: 1534-1536 (1988)], by substituting rodent CDRs or CDR sequences for the corresponding sequences of a human antibody.

Accordingly, such "humanized" antibodies are chimeric antibodies wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

It is important that antibodies be humanized with retention of high affinity for the antigen and other favorable biological properties. To achieve this goal, according to a preferred method, humanized antibodies are prepared by a process of analysis of the parental sequences and various conceptual humanized products using three dimensional models of the parental and humanized sequences. Three dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e. the analysis of residues that influence the ability of the candidate immunoglobulin to bind its antigen. In this way, FR residues can be selected and combined from the consensus and import sequence so that the desired antibody characteristic, such as increased affinity for the target antigen(s), is achieved. In general, the CDR residues are directly and most substantially involved in influencing antigen binding.

(ii) Human Antibodies

Human monoclonal antibodies can be made by the hybridoma method. Human myeloma and mouse-human heteromyeloma cell lines for the production of human monoclonal antibodies have been described, for example, by Kozbor, *J. Immunol.* 133, 3001 (1984), and Brodeur, et al., *Monoclonal Antibody Production Techniques and Applications*, pp. 51-63 (Marcel Dekker, Inc., New York, 1987).

It is now possible to produce transgenic animals (e.g. mice) that are capable, upon immunization, of producing a repertoire of human antibodies in the absence of endogenous immunoglobulin production. For example, it has been described that the homozygous deletion of the antibody heavy chain joining region ($J_H$) gene in chimeric and germline mutant mice results in complete inhibition of endogenous antibody production. Transfer of the human germ-line immunoglobulin gene array in such germ-line mutant mice will result in the production of human antibodies upon antigen challenge. See, e.g. Jakobovits et al., *Proc. Natl. Acad. Sci. USA* 90, 2551-255 (1993); Jakobovits et al., *Nature* 362, 255-258 (1993).

Mendez et al. (*Nature Genetics* 15: 146-156 [1997]) have further improved the technology and have generated a line of transgenic mice designated as "Xenomouse II" that, when challenged with an antigen, generates high affinity fully human antibodies. This was achieved by germ-line integration of megabase human heavy chain and light chain loci into mice with deletion into endogenous $J_H$ segment as described above. The Xenomouse II harbors 1,020 kb of human heavy chain locus containing approximately 66 $V_H$ genes, complete $D_H$ and $J_H$ regions and three different constant regions (μ, δ and χ), and also harbors 800 kb of human κ locus containing 32 Vκ genes, Jκ segments and Cκ genes. The antibodies produced in these mice closely resemble that seen in humans in all respects, including gene rearrangement, assembly, and repertoire. The human antibodies are preferentially expressed over endogenous antibodies due to deletion in endogenous $J_H$ segment that prevents gene rearrangement in the murine locus.

Alternatively, the phage display technology (McCafferty et al., *Nature* 348, 552-553 [1990]) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats; for their review see, e.g. Johnson, Kevin S. and Chiswell, David J., *Current Opinion in Structural Biology* 3, 564-571 (1993). Several sources of V-gene segments can be used for phage display. Clackson et al., *Nature* 352, 624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al, *J. Mol. Biol.* 222, 581-597 (1991), or Griffith et al., *EMBO J.* 12, 725-734 (1993). In a natural immune response, antibody genes accumulate mutations at a high rate (somatic hypermutation). Some of the changes introduced will confer higher affinity, and B cells displaying high-affinity surface immunoglobulin are preferentially replicated and differentiated during subsequent antigen challenge. This natural process can be mimicked by employing the technique known as "chain shuffling" (Marks et al., *Bio/Technol.* 10, 779-783 [1992]). In this method, the affinity of "primary" human antibodies obtained by phage display can be improved by sequentially replacing the heavy and light chain V region genes with repertoires of naturally occurring variants (repertoires) of V domain genes obtained from unimmunized donors. This technique allows the production of antibodies and antibody fragments with affinities in the nM range. A strategy for making very large phage antibody repertoires (also known as "the mother-of-all libraries") has been described by Waterhouse et al., *Nucl. Acids Res.* 21, 2265-2266 (1993). Gene shuffling can also be used to derive human antibodies from rodent antibodies, where the human antibody has similar affinities and specificities to the starting rodent antibody. According to this method, which is also referred to as "epitope imprinting", the heavy or light chain V domain gene of rodent antibodies obtained by phage display technique is replaced with a repertoire of human V domain genes, creating rodent-human chimeras. Selection on antigen results in isolation of human variable capable of restoring a functional antigen-binding site, i.e. the epitope governs (imprints) the choice of partner. When the process is repeated in order to replace the remaining rodent V domain, a human antibody is obtained (see PCT patent application WO 93/06213, published 1 Apr. 1993). Unlike traditional humanization of rodent antibodies by CDR grafting, this technique provides completely human antibodies, which have no framework or CDR residues of rodent origin.

As discussed in detail below, the antibodies of the invention may optionally comprise monomeric, antibodies, dimeric antibodies, as well as multivalent forms of antibodies. Those skilled in the art may construct such dimers or multivalent forms by techniques known in the art and using the DR5 antibodies herein. Methods for preparing monovalent antibodies are also well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking.

(iii) Bispecific Antibodies

Bispecific antibodies are monoclonal, preferably human or humanized, antibodies that have binding specificities for at least two different antigens. In the present case, one of the binding specificities is for the DR5 receptor, the other one is for any other antigen, and preferably for another receptor or receptor subunit. For example, bispecific antibodies specifically binding a DR5 receptor and another apoptosis/signaling receptor are within the scope of the present invention.

Methods for making bispecific antibodies are known in the art. Traditionally, the recombinant production of bispecific antibodies is based on the coexpression of two immunoglobulin heavy chain-light chain pairs, where the two heavy chains have different specificities (Millstein and Cuello, *Nature* 305, 537-539 (1983)). Because of the random assortment of immunoglobulin heavy and light chains, these hybridomas (quadromas) produce a potential mixture of 10 different antibody molecules, of which only one has the correct bispecific structure. The purification of the correct molecule, which is usually done by affinity chromatography steps, is rather cumbersome, and the product yields are low. Similar procedures are disclosed in PCT application publication No. WO 93/08829 (published 13 May 1993), and in Traunecker et al., *EMBO* 10, 3655-3659 (1991).

According to a different and more preferred approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2 and CH3 regions. It is preferred to have the first heavy chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are cotransfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance. In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in PCT Publication No. WO 94/04690, published on Mar. 3, 1994.

For further details of generating bispecific antibodies see, for example, Suresh et al., *Methods in Enzymology* 121, 210 (1986).

(iv) Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells (U.S. Pat. No. 4,676,980), and for treatment of HIV infection (PCT application publication Nos. WO 91/00360 and WO 92/200373; EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

(v) Antibody Fragments

In certain embodiments, the anti-DR5 antibody (including murine, human and humanized antibodies, and antibody variants) is an antibody fragment. Various techniques have been developed for the production of antibody fragments. Traditionally, these fragments were derived via proteolytic digestion of intact antibodies (see, e.g., Morimoto et al., *J. Biochem. Biophys. Methods* 24:107-117 (1992) and Brennan et al., *Science* 229:81 (1985)). However, these fragments can now be produced directly by recombinant host cells. For example, Fab'-SH fragments can be directly recovered from *E. coli* and chemically coupled to form $F(ab')_2$ fragments (Carter et al., *Bio/Technology* 10:163-167 (1992)). In another embodiment, the $F(ab')_2$ is formed using the leucine zipper GCN4 to promote assembly of the $F(ab')_2$ molecule. According to another approach, Fv, Fab or $F(ab')_2$ fragments can be isolated directly from recombinant host cell culture. A variety of techniques for the production of antibody fragments will be apparent to the skilled practitioner. For instance, digestion can be performed using papain. Examples of papain digestion are described in WO 94/29348 published Dec. 22, 1994 and U.S. Pat. No. 4,342,566. Papain digestion of antibodies typically produces two identical antigen binding fragments, called Fab fragments, each with a single antigen binding site, and a residual Fc fragment. Pepsin treatment yields an $F(ab')_2$ fragment that has two antigen combining sites and is still capable of cross-linking antigen.

The Fab fragments produced in the antibody digestion also contain the constant domains of the light chain and the first constant domain ($CH_1$) of the heavy chain. Fab' fragments differ from Fab fragments by the addition of a few residues at the carboxy terminus of the heavy chain $CH_1$ domain including one or more cysteines from the antibody hinge region. Fab'-SH is the designation herein for Fab' in which the cysteine residue(s) of the constant domains bear a free thiol group. $F(ab')_2$ antibody fragments originally were produced as pairs of Fab' fragments which have hinge cysteines between them. Other chemical couplings of antibody fragments are also known.

(vi) Amino Acid Sequence Variants of Antibodies

Amino acid sequence variants of the anti-DR5 antibodies are prepared by introducing appropriate nucleotide changes into the anti-DR5 antibody DNA, or by peptide synthesis. Such variants include, for example, deletions from, and/or insertions into and/or substitutions of, residues within the amino acid sequences of the anti-DR5 antibodies of the examples herein. Any combination of deletion, insertion, and substitution is made to arrive at the final construct, provided that the final construct possesses the desired characteristics. The amino acid changes also may alter post-translational processes of the humanized or variant anti-DR5 antibody, such as changing the number or position of glycosylation sites.

A useful method for identification of certain residues or regions of the anti-DR5 antibody that are preferred locations for mutagenesis is called "alanine scanning mutagenesis," as described by Cunningham and Wells *Science*, 244:1081-1085 (1989). Here, a residue or group of target residues are identified (e.g., charged residues such as arg, asp, his, lys, and glu) and replaced by a neutral or negatively charged amino acid (most preferably alanine or polyalanine) to affect the interaction of the amino acids with DR5 antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed anti-DR5 antibody variants are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an anti-DR5 antibody with an N-terminal methionyl residue or the antibody fused to an epitope tag. Other insertional variants of the anti-DR5 antibody molecule include the fusion to the N- or C-terminus of the anti-DR5 antibody of an enzyme or a polypeptide or polyol which increases the serum half-life of the antibody.

Another type of variant is an amino acid substitution variant. These variants have at least one amino acid residue in the anti-DR5 antibody molecule removed and a different residue inserted in its place. The sites of greatest interest for substitutional mutagenesis include the hypervariable regions, but FR alterations are also contemplated. Conservative substitutions are shown in Table 1 under the heading of "preferred substitutions". If such substitutions result in a change in biological activity, then more substantial changes, denominated "exemplary substitutions" in Table 1, or as further described below in reference to amino acid classes, may be introduced and the products screened.

TABLE 1

| Original Residue | Exemplary Substitutions | Preferred Substitutions |
| --- | --- | --- |
| Ala (A) | val; leu; ile | Val |
| Arg (R) | lys; gln; asn | Lys |
| Asn (N) | gln; his; asp, lys; arg | Gln |
| Asp (D) | glu; asn | Glu |
| Cys (C) | ser; ala | Ser |
| Gln (Q) | asn; glu | Asn |
| Glu (E) | asp; gln | Asp |
| Gly (G) | Ala | Ala |
| His (H) | asn; gln; lys; arg | Arg |
| Ile (I) | leu; val; met; ala; phe; norleucine | Leu |
| Leu (L) | Norleucine; ile; val; met; ala; phe | Ile |
| Lys (K) | arg; gln; asn | Arg |
| Met (M) | leu; phe; ile | Leu |
| Phe (F) | leu; val; ile; ala; tyr | Tyr |
| Pro (P) | Ala | Ala |
| Ser (S) | Thr | Thr |
| Thr (T) | Ser | Ser |
| Trp (W) | tyr; phe | Tyr |
| Tyr (Y) | trp; phe; thr; ser | Phe |
| Val (V) | ile; leu; met; phe; ala; norleucine | Leu |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:
   (1) hydrophobic: norleucine, met, ala, val, leu, ile;
   (2) neutral hydrophilic: cys, ser, thr;
   (3) acidic: asp, glu;
   (4) basic: asn, gln, his, lys, arg;
   (5) residues that influence chain orientation: gly, pro; and
   (6) aromatic: trp, tyr, phe.

Non-conservative substitutions will entail exchanging a member of one of these classes for another class.

Any cysteine residue not involved in maintaining the proper conformation of the humanized or variant anti-DR5 antibody also may be substituted, generally with serine, to improve the oxidative stability of the molecule and prevent aberrant crosslinking. Conversely, cysteine bond(s) may be added to the antibody to improve its stability (particularly where the antibody is an antibody fragment such as an Fv fragment).

A particularly preferred type of substitutional variant involves substituting one or more hypervariable region residues of a parent antibody (e.g. a humanized or human antibody). Generally, the resulting variant(s) selected for further development will have improved biological properties relative to the parent antibody from which they are generated. A convenient way for generating such substitutional variants is affinity maturation using phage display. Briefly, several hypervariable region sites (e.g. 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g. binding affinity) as herein disclosed. In order to identify candidate hypervariable region sites for modification, alanine scanning mutagenesis can be performed to identify hypervariable region residues contributing significantly to antigen binding. Alternatively, or in addition, it may be beneficial to analyze a crystal structure of the antigen-antibody complex to identify contact points between the antibody and human DR5. Such contact residues and neighboring residues are candidates for substitution according to the techniques elaborated herein. Once such variants are generated, the panel of variants is subjected to screening as described herein and antibodies with superior properties in one or more relevant assays may be selected for further development.

(vii) Glycosylation Variants of Antibodies

Antibodies are glycosylated at conserved positions in their constant regions (Jefferis and Lund, *Chem. Immunol.* 65:111-128 [1997]; Wright and Morrison, *TibTECH* 15:26-32 [1997]). The oligosaccharide side chains of the immunoglobulins affect the protein's function (Boyd et al., *Mol. Immunol.* 32:1311-1318 [1996]; Wittwe and Howard, *Biochem.* 29:4175-4180 [1990]), and the intramolecular interaction between portions of the glycoprotein which can affect the conformation and presented three-dimensional surface of the glycoprotein (Hefferis and Lund, supra; Wyss and Wagner, *Current Opin. Biotech.* 7:409-416 [1996]). Oligosaccharides may also serve to target a given glycoprotein to certain molecules based upon specific recognition structures. For example, it has been reported that in a galactosylated IgG, the oligosaccharide moiety 'flips' out of the inter-CH2 space and terminal N-acetylglucosamine residues become available to bind mannose binding protein (Malhotra et al., *Nature Med.* 1:237-243

Removal by glycopeptidase of the oligosaccharides from CAMPATH-1H (a recombinant humanized murine monoclonal IgG1 antibody which recognizes the CDw52 antigen of human lymphocytes) produced in Chinese Hamster Ovary (CHO) cells resulted in a complete reduction in complement mediated lysis (CMCL) (Boyd et al., *Mol. Immunol.* 32:1311-1318 [1996]), while selective removal of sialic acid residues using neuraminidase resulted in no loss of DMCL. Glycosylation of antibodies has also been reported to affect antibody-dependent cellular cytotoxicity (ADCC). In particular, CHO cells with tetracycline-regulated expression of β(1,4)-N-acetylglucosaminyltransferase III (GnTIII), a glycosyltransferase catalyzing formation of bisecting GlcNAc, was reported to have improved ADCC activity (Umana et al., *Mature Biotech.* 17:176-180 [1999]).

Glycosylation variants of antibodies are variants in which the glycosylation pattern of an antibody is altered. By altering is meant deleting one or more carbohydrate moieties found in the antibody, adding one or more carbohydrate moieties to the antibody, changing the composition of glycosylation (glycosylation pattern), the extent of glycosylation, etc. Glycosylation variants may, for example, be prepared by removing, changing and/or adding one or more glycosylation sites in the nucleic acid sequence encoding the antibody.

Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Nucleic acid molecules encoding amino acid sequence variants of the anti-DR5 antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the anti-DR5 antibody.

The glycosylation (including glycosylation pattern) of antibodies may also be altered without altering the underlying nucleotide sequence. Glycosylation largely depends on the host cell used to express the antibody. Since the cell type used for expression of recombinant glycoproteins, e.g. antibodies, as potential therapeutics is rarely the native cell, significant variations in the glycosylation pattern of the antibodies can be expected (see, e.g. Hse et al., *J. Biol. Chem.* 272:9062-9070 [1997]). In addition to the choice of host cells, factors which affect glycosylation during recombinant production of antibodies include growth mode, media formulation, culture density, oxygenation, pH, purification schemes and the like. Various methods have been proposed to alter the glycosylation pattern achieved in a particular host organism including introducing or overexpressing certain enzymes involved in oligosaccharide production (U.S. Pat. Nos. 5,047,335; 5,510,261 and 5,278,299). Glycosylation, or certain types of glycosylation, can be enzymatically removed from the glycoprotein, for example using endoglycosidase H (Endo H). In addition, the recombinant host cell can be genetically engineered, e.g. make defective in processing certain types of polysaccharides. These and similar techniques are well known in the art.

The glycosylation structure of antibodies can be readily analyzed by conventional techniques of carbohydrate analysis, including lectin chromatography, NMR, Mass spectrometry, HPLC, GPC, monosaccharide compositional analysis, sequential enzymatic digestion, and HPAEC-PAD, which uses high pH anion exchange chromatography to separate oligosaccharides based on charge. Methods for releasing oligosaccharides for analytical purposes are also known, and include, without limitation, enzymatic treatment (commonly performed using peptide-N-glycosidase F/endo-β-galactosidase), elimination using harsh alkaline environment to release mainly O-linked structures, and chemical methods using anhydrous hydrazine to release both N- and O-linked oligosaccharides.

(viii) Exemplary Antibodies

The invention disclosed herein has a number of exemplary embodiments. A variety of the typical embodiments of the invention are described below. The following embodiments are offered for illustrative purposes only, and are not intended to limit the scope of the present invention in any way.

As described in the Examples below, a number of anti-DR5 monoclonal antibodies have been identified. In one embodiment, the DR5 antibodies of the invention will have the same biological characteristics as any of the anti-DR5 antibodies specifically disclosed herein.

The term "biological characteristics" is used to refer to the in vitro and/or in vivo activities or properties of the monoclonal antibody, such as the ability to specifically bind to DR5 or to block, induce or enhance DR5 activation (or DR5-related activities). The properties and activities of the DR5 antibodies are further described in the Examples below.

Optionally, the monoclonal antibodies of the present invention will have the same biological characteristics as antibody 16E2 or any of the antibodies listed in Tables 11-13, and/or bind to the same epitope(s) as antibody 16E2, or any of the antibodies listed in Tables 11-13, in particular Apomab 7.3 or Apomab 8.3. This can be determined by conducting various assays, such as described herein and in the Examples. For instance, to determine whether a monoclonal antibody has the same specificity as the DR5 antibodies specifically referred to herein, one can compare its activity in competitive binding assays or apoptosis induction assays, such as those described in the Examples below. In addition, an epitope to which a particular anti-DR5 antibody binds can be determined by crystallography study of the complex between DR5 and the antibody in question.

Thus, an X-ray crystallography study of the complex between the Fab fragment of Apomab 7.3 and the extracellular domain of DR5 showed that Apomab 7.3 binds to a DR5 epitope that overlaps with, yet differs from, the binding site of Apo2L/TRAIL on the DR5 receptor.

Human, chimeric, hybrid or recombinant anti-DR5 antibodies (as well as, for instance, diabodies or triabodies described herein) may comprise an antibody having full length heavy and light chains or fragments thereof, such as a Fab, Fab', F(ab')$_2$ or Fv fragment, a monomer or dimer of such light chain or heavy chain, a single chain Fv in which such heavy or light chain(s) are joined by a linker molecule, or having variable domains (or hypervariable domains) of such light or heavy chain(s) combined with still other types of antibody domains.

The DR5 antibodies, as described herein, will optionally possess one or more desired biological activities or properties. Such DR5 antibodies may include but are not limited to chimeric, humanized, human, and affinity matured antibodies. As described above, the DR5 antibodies may be constructed or engineered using various techniques to achieve these desired activities or properties. In one embodiment, the DR5 antibody will have a DR5 receptor binding affinity of at least $10^5$ M$^{-1}$, preferably at least in the range of $10^6$ M$^{-1}$ to $10^7$ M$^{-1}$, more preferably, at least in the range of $10^8$ M$^{-1}$ to $10^{12}$ M$^{-1}$ and even more preferably, at least in the range of $10^9$ M$^{-1}$ to $10^{12}$ M$^{-1}$. The binding affinity of the DR5 antibody can be determined without undue experimentation by testing the DR5 antibody in accordance with techniques known in the art, including Scatchard analysis (see Munson et al., supra).

In another embodiment, the DR5 antibody of the invention may bind the same epitope on DR5 to which Apo-2L binds, or bind an epitope on DR5 which coincides or overlaps with the epitope on DR5 to which Apo-2L binds, as, for example, the antibody designated Apomab 7.3. The DR5 antibody may also interact in such a way to create a steric conformation which prevents Apo-2 ligand binding to DR5. As noted above, the epitope binding property of a DR5 antibody of the present invention may be determined using techniques known in the art. For instance, the DR5 antibody may be tested in an in vitro assay, such as a competitive inhibition assay, to determine the ability of the DR5 antibody to block or inhibit binding of Apo-2L to DR5. Optionally, the DR5 antibody may be tested in a competitive inhibition assay to determine the ability of the DR5 antibody to inhibit binding of an Apo-2L polypeptide to a DR5-IgG construct or to a cell expressing DR5. Optionally, the DR5 antibody will be capable of blocking or inhibiting binding of Apo-2L to DR5 by at least 50%, preferably by at least 75% and even more preferably by at least 90%, which may be determined, by way of example, in an in vitro competitive inhibition assay using a soluble form of Apo-2 ligand (TRAIL) (such as the 114-281 extracellular domain sequence described in Pitti et al., J. Biol. Chem., supra, also referred to as Apo2L.0) and a DR5 ECD-IgG. The epitope binding property of a DR5 antibody may also be determined using in vitro assays to test the ability of the DR5 antibody to block Apo-2L induced apoptosis, or by crystallography studies.

In a further embodiment, the DR5 antibody will comprise an agonist antibody having activity comparable to Apo-2 ligand (TRAIL). Preferably, such an agonist DR5 antibody will induce apoptosis in at least one type of cancer or tumor cell line or primary tumor. The apoptotic activity of an agonist DR5 antibody may be determined using known in vitro or in vivo assays. Examples of a variety of such in vitro and in vivo assays are well known in the art. In vitro, apoptotic activity can be determined using known techniques such as Annexin V binding. In vivo, apoptotic activity may be determined, e.g., by measuring reduction in tumor burden or volume.

As noted above, the antibodies disclosed herein have a number of properties including the ability to modulate certain physiological interactions and/or processes. As shown in the examples below, antibodies disclosed herein are able to induce DR5 mediated apoptosis, and show potent anti-tumor properties in various murine xenograft models of cancer. In a specific embodiment of the invention, the agonistic activity of the antibody is enhanced by crosslinking the antibodies with anti-human IgG Fc. In a preferred embodiment of the invention, this enhanced apoptosis is comparable to the apoptotic activity of Apo-2L.

Additional embodiments of the invention include an anti-DR5 receptor antibody disclosed herein which is linked to one or more non-proteinaceous polymers selected from the group consisting of polyethylene glycol, polypropylene glycol, and polyoxyalkylene. In an alternative embodiment, an anti-DR5 receptor antibody disclosed herein is linked to a cytotoxic agent or enzyme. In yet another embodiment, an anti-DR5 receptor antibody disclosed herein is linked to a radioisotope, a fluorescent compound or a chemiluminescent compound. Optionally, an anti-DR5 receptor antibody disclosed herein is glycosylated or alternatively, unglycosylated.

As discussed in detail below, the antibodies of the invention can be used in a variety of methods of modulating physiological processes. One such embodiment of the invention includes a method of inducing apoptosis in mammalian cells comprising exposing mammalian cells expressing DR5 receptor to a therapeutically effective amount of an isolated anti-DR5 receptor monoclonal antibody, comprising an antibody which binds to a DR5 receptor shown in FIGS. 3A-3C (411 amino acids) or FIGS. 4A-4C (440 amino acids), especially the extracellular domain thereof. In such methods the mammalian cells are typically cancer cells. In preferred embodiments, the anti-DR5 receptor antibody used in these methods is an Apomab antibody described in the Examples below, such as an Apomab 7.3 or Apomab 8.3 antibody.

Yet another embodiment of the invention is a method of inducing apoptosis in mammalian cells comprising exposing mammalian cells expressing DR5 receptor to a therapeutically effective amount of an isolated anti-DR5 receptor monoclonal antibody, comprising an antibody which binds to DR5 receptor as hereinabove defined, or the extracellular domain thereof.

3. Triabodies

Triabodies are also within the scope of the invention. Such antibodies are described for instance in Iliades et al., supra and Kortt et al., supra.

4. Other Modifications

Other modifications of the DR5 antibodies are contemplated herein. The antibodies of the present invention may be modified by conjugating the antibody to a cytotoxic agent (like a toxin molecule) or a prodrug-activating enzyme which converts a prodrug (e.g. a peptidyl chemotherapeutic agent, see WO81/01145) to an active anti-cancer drug. See, for example, WO 88/07378 and U.S. Pat. No. 4,975,278. This technology is also referred to as "Antibody Dependent Enzyme Mediated Prodrug Therapy" (ADEPT).

The enzyme component of the immunoconjugate useful for ADEPT includes any enzyme capable of acting on a prodrug in such a way so as to covert it into its more active, cytotoxic form. Enzymes that are useful in the method of this invention include, but are not limited to, alkaline phosphatase useful for converting phosphate-containing prodrugs into free drugs; arylsulfatase useful for converting sulfate-containing prodrugs into free drugs; cytosine deaminase useful for converting non-toxic 5-fluorocytosine into the anti-cancer drug, 5-fluorouracil; proteases, such as serratia protease, thermolysin, subtilisin, carboxypeptidases and cathepsins (such as cathepsins B and L), that are useful for converting peptide-containing prodrugs into free drugs; caspases such as caspase-3; D-alanylcarboxypeptidases, useful for converting prodrugs that contain D-amino acid substituents; carbohydrate-cleaving enzymes such as beta-galactosidase and neuraminidase useful for converting glycosylated prodrugs into free drugs; beta-lactamase useful for converting drugs derivatized with beta-lactams into free drugs; and penicillin amidases, such as penicillin V amidase or penicillin G amidase, useful for converting drugs derivatized at their amine nitrogens with phenoxyacetyl or phenylacetyl groups, respectively, into free drugs. Alternatively, antibodies with enzymatic activity, also known in the art as "abzymes", can be used to convert the prodrugs of the invention into free active drugs (see, e.g., Massey, Nature 328: 457-458 (1987)). Antibody-enzyme conjugates can be prepared as described herein for delivery of the abzyme to a tumor cell population.

The enzymes can be covalently bound to the antibodies by techniques well known in the art such as the use of heterobifunctional crosslinking reagents. Alternatively, fusion proteins comprising at least the antigen binding region of an antibody of the invention linked to at least a functionally active portion of an enzyme of the invention can be constructed using recombinant DNA techniques well known in the art (see, e.g., Neuberger et al., Nature, 312: 604-608 (1984).

Further antibody modifications are contemplated. For example, the antibody may be linked to one of a variety of nonproteinaceous polymers, e.g., polyethylene glycol, polypropylene glycol, polyoxyalkylenes, or copolymers of polyethylene glycol and polypropylene glycol. The antibody also may be entrapped in microcapsules prepared, for example, by coacervation techniques or by interfacial polymerization (for example, hydroxymethylcellulose or gelatin-microcapsules and poly-(methylmethacylate) microcapsules, respectively), in colloidal drug delivery systems (for example, liposomes, albumin microspheres, microemulsions, nano-particles and nanocapsules), or in macroemulsions. Such techniques are disclosed in *Remington's Pharmaceutical Sciences*, 16th edition, Oslo, A., Ed., (1980). To increase the serum half life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., $IgG_1$, $IgG_2$, $IgG_3$, or $IgG_4$) that is responsible for increasing the in vivo serum half-life of the IgG molecule.

The anti-DR5 antibodies disclosed herein may also be formulated as immunoliposomes. Liposomes containing the antibody are prepared by methods known in the art, such as described in Epstein et al., Proc. Natl. Acad. Sci. USA 82:3688 (1985); Hwang et al., Proc. Natl Acad. Sci. USA 77:4030 (1980); and U.S. Pat. Nos. 4,485,045 and 4,544,545. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., J. Biol. Chem. 257:286-288 (1982) via a disulfide interchange reaction. A chemotherapeutic agent (such as Doxorubicin) is optionally contained within the liposome. See Gabizon et al., J. National Cancer Inst. 81(19):1484 (1989).

The antibodies of the invention include "cross-linked" DR5 antibodies. The term "cross-linked" as used herein refers to binding of at least two IgG molecules together to form one (or single) molecule. The DR5 antibodies may be cross-linked using various linker molecules, preferably the DR5 antibodies are cross-linked using an anti-IgG molecule, complement, chemical modification or molecular engineering. It is appreciated by those skilled in the art that complement has a relatively high affinity to antibody molecules once the antibodies bind to cell surface membrane. Accordingly, it is believed that complement may be used as a cross-linking molecule to link two or more anti-DR5 antibodies bound to cell surface membrane.

5. Recombinant Methods

The invention also provides isolated nucleic acids encoding DR5 antibodies as disclosed herein, vectors and host cells comprising the nucleic acid, and recombinant techniques for the production of the antibody.

For recombinant production of the antibody, the nucleic acid encoding it is isolated and inserted into a replicable vector for further cloning (amplification of the DNA) or for expression. DNA encoding the antibody is readily isolated and sequenced using conventional procedures (e.g., by using oligonucleotide probes that are capable of binding specifically to genes encoding the antibody). Many vectors are available. The vector components generally include, but are not limited to, one or more of the following: a signal sequence, an origin of replication, one or more marker genes, an enhancer element, a promoter, and a transcription termination sequence.

The methods herein include methods for the production of chimeric or recombinant anti-DR5 antibodies which comprise the steps of providing a vector comprising a DNA sequence encoding an anti-DR5 antibody light chain or heavy chain (or both a light chain and a heavy chain), transfecting or transforming a host cell with the vector, and culturing the host cell(s) under conditions sufficient to produce the recombinant anti-DR5 antibody product.

(i) Signal Sequence Component

The anti-DR5 antibody of this invention may be produced recombinantly not only directly, but also as a fusion polypeptide with a heterologous polypeptide, which is preferably a signal sequence or other polypeptide having a specific cleavage site at the N-terminus of the mature protein or polypeptide. The heterologous signal sequence selected preferably is one that is recognized and processed (i.e., cleaved by a signal peptidase) by the host cell. For prokaryotic host cells that do not recognize and process the native antibody signal sequence, the signal sequence is substituted by a prokaryotic signal sequence selected, for example, from the group of the alkaline phosphatase, penicillinase, lpp, or heat-stable enterotoxin II leaders. For yeast secretion the native signal sequence may be substituted by, e.g., the yeast invertase leader, α factor leader (including *Saccharomyces* and *Kluyveromyces* α-factor leaders), or acid phosphatase leader, the *C. albicans* glucoamylase leader, or the signal described in WO 90/13646. In mammalian cell expression, mammalian signal sequences as well as viral secretory leaders, for example, the herpes simplex gD signal, are available.

The DNA for such precursor region is ligated in reading frame to DNA encoding the antibody.

(ii) Origin of Replication Component

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2μ plasmid origin is suitable for yeast, and various viral origins (SV40, polyoma, adenovirus, VSV or BPV) are useful for cloning vectors in mammalian cells. Generally, the origin of replication component is not needed for mammalian expression vectors (the SV40 origin may typically be used only because it contains the early promoter).

(iii) Selection Gene Component

Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid and hygromycin.

Another example of suitable selectable markers for mammalian cells are those that enable the identification of cells competent to take up the antibody nucleic acid, such as DHFR, thymidine kinase, metallothionein-I and -II, preferably primate metallothionein genes, adenosine deaminase, ornithine decarboxylase, etc.

For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity.

Alternatively, host cells (particularly wild-type hosts that contain endogenous DHFR) transformed or co-transformed with DNA sequences encoding the anti-DR5 antibody, wild-type DHFR protein, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

A suitable selection gene for use in yeast is the trp1 gene present in the yeast plasmid YRp7 (Stinchcomb et al., *Nature*, 282:39 (1979)). The trp1 gene provides a selection marker for a mutant strain of yeast lacking the ability to grow in tryptophan, for example, ATCC No. 44076 or PEP4-1. Jones, *Genetics*, 85:12 (1977). The presence of the trp1 lesion in the yeast host cell genome then provides an effective environment for detecting transformation by growth in the absence of tryptophan. Similarly, Leu2-deficient yeast strains (ATCC 20,622 or 38,626) are complemented by known plasmids bearing the Leu2 gene.

In addition, vectors derived from the 1.6 µm circular plasmid pKD1 can be used for transformation of *Kluyveromyces* yeasts. Alternatively, an expression system for large-scale production of recombinant calf chymosin was reported for *K. lactis*. Van den Berg, *Bio/Technology*, 8:135 (1990). Stable multi-copy expression vectors for secretion of mature recombinant human serum albumin by industrial strains of *Kluyveromyces* have also been disclosed. Fleer et al., *Bio/Technology*, 9:968-975 (1991).

(iv) Promoter Component

Expression and cloning vectors usually contain a promoter that is recognized by the host organism and is operably linked to the antibody nucleic acid. Promoters suitable for use with prokaryotic hosts include the phoA promoter, β-lactamase and lactose promoter systems, alkaline phosphatase, a tryptophan (trp) promoter system, and hybrid promoters such as the tac promoter. However, other known bacterial promoters are suitable. Promoters for use in bacterial systems also will contain a Shine-Dalgarno (S.D.) sequence operably linked to the DNA encoding the anti-DR5 antibody.

Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Examples of suitable promoting sequences for use with yeast hosts include the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657. Yeast enhancers also are advantageously used with yeast promoters.

Anti-DR5 antibody transcription from vectors in mammalian host cells is controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and most preferably Simian Virus 40 (SV40), from heterologous mammalian promoters, e.g., the actin promoter or an immunoglobulin promoter, from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419,446. A modification of this system is described in U.S. Pat. No. 4,601,978. See also Reyes et al., *Nature* 297:598-601 (1982) on expression of human β-interferon cDNA in mouse cells under the control of a thymidine kinase promoter from herpes simplex virus. Alternatively, the Rous sarcoma virus long terminal repeat can be used as the promoter. (v)

Enhancer Element Component

Transcription of a DNA encoding the anti-DR5 antibody of this invention by higher eukaryotes is often increased by inserting an enhancer sequence into the vector. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv, *Nature* 297:17-18 (1982) on enhancing elements for activation of eukaryotic promoters. The enhancer may be spliced into the vector at a position 5' or 3' to the antibody-encoding sequence, but is preferably located at a site 5' from the promoter.

(vi) Transcription Termination Component

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding the multivalent antibody. One useful transcription termination component is the bovine growth hormone polyadenylation region. See WO94/11026 and the expression vector disclosed therein.

(vii) Selection and Transformation of Host Cells

Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as *Escherichia*, e.g., *E. coli*, *Enterobacter*, *Erwinia*, *Klebsiella*, *Proteus*, *Salmonella*, e.g., *Salmonella typhimurium*, *Serratia*, e.g., *Serratia marcescans*, and *Shigella*, as well as Bacilli such as *B. subtilis* and *B. licheniformis* (e.g., *B. licheniformis* 41P disclosed in DD 266,710 published 12 Apr. 1989), *Pseudomonas* such as *P. aeruginosa*, and *Streptomyces*. One preferred *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting.

In addition to prokaryotes, eukaryotic microbes such as filamentous fungi or yeast are suitable cloning or expression hosts for DR5 antibody-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe*; *Kluyveromyces* hosts such as, e.g., *K. lactis*, *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus*; *yarrowia* (EP 402,226); *Pichia pastoris* (EP 183, 070); *Candida*; *Trichoderma reesia* (EP 244,234); *Neurospora crassa*; *Schwanniomyces* such as *Schwanniomyces occidentalis*; and filamentous fungi such as, e.g., *Neurospora*, *Penicillium*, *Tolypocladium*, and *Aspergillus* hosts such as *A. nidulans* and *A. niger*.

Suitable host cells for the expression of glycosylated antibody are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells.

Plant cell cultures of cotton, corn, potato, soybean, petunia, tomato, and tobacco can also be utilized as hosts.

However, interest has been greatest in vertebrate cells, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., *J. Gen Virol.* 36:59 (1977)); baby hamster kidney cells (BHK, ATCC CCL 10); Chinese hamster ovary cells/-DHFR (CHO, Urlaub et al., *Proc. Natl. Acad. Sci. USA* 77:4216 (1980)); mouse sertoli cells (TM4, Mather, *Biol. Reprod.* 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TR1 cells (Mather et al., *Annals N.Y. Acad. Sci.* 383:44-68 (1982)); MRC 5 cells; FS4 cells; a human hepatoma line (Hep G2); and myeloma or lymphoma cells (e.g. Y0, J558L, P3 and NS0 cells) (see U.S. Pat. No. 5,807, 715).

Host cells are transformed with the above-described expression or cloning vectors for antibody production and cultured in conventional nutrient media modified as appropriate for inducing promoters, selecting transformants, or amplifying the genes encoding the desired sequences.

(viii) Culturing the Host Cells

The host cells used to produce the antibody of this invention may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., *Meth. Enz.* 58:44 (1979), Barnes et al., *Anal. Biochem.* 102:255 (1980), U.S. Pat. No. 4,767,704; 4,657,866; 4,927,762; 4,560,655; or 5,122,469; WO 90/03430; WO 87/00195; or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

(ix) Purification

When using recombinant techniques, the antibody can be produced intracellularly, in the periplasmic space, or directly secreted into the medium. If the antibody is produced intracellularly, as a first step, the particulate debris, either host cells or lysed fragments, is removed, for example, by centrifugation or ultrafiltration. Carter et al., *Bio/Technology* 10:163-167 (1992) describe a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc region that is present in the antibody. Protein A can be used to purify antibodies that are based on human γ1, γ2, or γ4 heavy chains (Lindmark et al., *J. Immunol. Meth.* 62:1-13 (1983)). Protein G is recommended for all mouse isotypes and for human γ3 (Guss et al., *EMBO J.* 5:1567-1575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $C_H3$ domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

B. Uses for DR5 Antibodies

The DR5 antibodies of the invention have various utilities.

DR5 is known to mediate apoptosis signaling. Although several types of normal cells express DR5, apoptosis signaling through this receptor appears to be restricted primarily to tumor cells, which become more susceptible to death receptor-mediated apoptosis in the context of their transformation by oncogenes such as MYC or RAS (Wang et al., *Cancer Cell* 5:501-12 (2004); Nesterov et al., *Cancer Res.* 64:3922-7 (2004)). DR5 is frequently expressed by human cancer cell lines as well as primary tumors. Thus, anti-DR5 antibodies find utility in the diagnosis and treatment of cancer. For example, DR5 agonistic antibodies may be used in methods for treating cancer in mammals, including humans. In these methods, the DR5 antibody, preferably an agonistic antibody, is administered to a mammal, alone or in combination with still other therapeutic agents or techniques. The cancer can be any type of DR5-expressing cancer, including solid tumors, in particular advanced or metastatic solid tumors that have progressed on prior therapy or for which there is no effective known therapy. Special types of cancer include, without limitation, colorectal cancer, non-small cell lung cancer (NSCLC), pancreatic cancer, ovarian cancer, breast cancer, non-Hodgkin's lymphoma (NHL), glioblastoma, or melanoma, preferably colorectal cancer, NSCLC, or NHL.

In addition, DR5 antibodies are useful in the diagnosis and treatment of other DR5-associated pathological conditions, such as immune-related diseases in mammals, including humans.

Diagnosis in mammals of the various pathological conditions described herein can be made by the skilled practitioner. Diagnostic techniques are available in the art which allow, e.g., for the diagnosis or detection of cancer or immune related disease in a mammal. For instance, cancers may be identified through techniques, including but not limited to, palpation, blood analysis, x-ray, NMR and the like.

Immune related diseases can also be readily identified.

In systemic lupus erythematosus, the central mediator of disease is the production of auto-reactive antibodies to self proteins/tissues and the subsequent generation of immune-mediated inflammation. Multiple organs and systems are affected clinically including kidney, lung, musculoskeletal system, mucocutaneous, eye, central nervous system, cardiovascular system, gastrointestinal tract, bone marrow and blood.

Rheumatoid arthritis (RA) is a chronic systemic autoimmune inflammatory disease that mainly involves the synovial membrane of multiple joints with resultant injury to the articular cartilage. The pathogenesis is T lymphocyte dependent and is associated with the production of rheumatoid factors, auto-antibodies directed against self IgG, with the resultant formation of immune complexes that attain high levels in joint fluid and blood. These complexes in the joint may induce the marked infiltrate of lymphocytes and monocytes into the synovium and subsequent marked synovial changes; the joint space/fluid if infiltrated by similar cells with the addition of numerous neutrophils. Tissues affected are primarily the joints, often in symmetrical pattern. However, extra-articular disease also occurs in two major forms. One form is the development of extra-articular lesions with ongoing progressive joint disease and typical lesions of pulmonary fibrosis, vasculitis, and cutaneous ulcers. The second form of extra-articular disease is the so called Felty's syndrome which occurs late in the RA disease course, sometimes after joint disease has become quiescent, and involves the presence of neutropenia, thrombocytopenia and splenomegaly. This can be accompanied by vasculitis in multiple organs with formations of infarcts, skin ulcers and gangrene. Patients often also develop rheumatoid nodules in the subcutis tissue overlying affected joints; the nodules late stage have necrotic centers surrounded by a mixed inflammatory cell infiltrate. Other manifestations which can occur in RA include: pericarditis, pleuritis, coronary arteritis, interstitial pneumonitis with pulmonary fibrosis, keratoconjunctivitis sicca, and rheumatoid nodules.

Juvenile chronic arthritis is a chronic idiopathic inflammatory disease which begins often at less than 16 years of age. Its phenotype has some similarities to RA; some patients which are rheumatoid factor positive are classified as juvenile rheumatoid arthritis. The disease is sub-classified into three major categories: pauciarticular, polyarticular, and systemic. The arthritis can be severe and is typically destructive and leads to joint ankylosis and retarded growth. Other manifestations can include chronic anterior uveitis and systemic amyloidosis.

Spondyloarthropathies are a group of disorders with some common clinical features and the common association with the expression of HLA-B27 gene product. The disorders include: ankylosing sponylitis, Reiter's syndrome (reactive arthritis), arthritis associated with inflammatory bowel disease, spondylitis associated with psoriasis, juvenile onset spondyloarthropathy and undifferentiated spondyloarthropathy. Distinguishing features include sacroileitis with or without spondylitis; inflammatory asymmetric arthritis; association with HLA-B27 (a serologically defined allele of the HLA-B locus of class I MHC); ocular inflammation, and absence of autoantibodies associated with other rheumatoid disease. The cell most implicated as key to induction of the disease is the CD8+ T lymphocyte, a cell which targets antigen presented by class I MHC molecules. CD8+ T cells may react against the class I MHC allele HLA-B27 as if it were a foreign peptide expressed by MHC class I molecules. It has been hypothesized that an epitope of HLA-B27 may mimic a bacterial or other microbial antigenic epitope and thus induce a CD8+ T cells response.

Systemic sclerosis (scleroderma) has an unknown etiology. A hallmark of the disease is induration of the skin; likely this is induced by an active inflammatory process. Scleroderma can be localized or systemic; vascular lesions are common and endothelial cell injury in the microvasculature is an early and important event in the development of systemic sclerosis; the vascular injury may be immune mediated. An immunologic basis is implied by the presence of mononuclear cell infiltrates in the cutaneous lesions and the presence of antinuclear antibodies in many patients. ICAM-1 is often upregulated on the cell surface of fibroblasts in skin lesions suggesting that T cell interaction with these cells may have a role in the pathogenesis of the disease. Other organs involved include: the gastrointestinal tract: smooth muscle atrophy and fibrosis resulting in abnormal peristalsis/motility; kidney: concentric subendothelial intimal proliferation affecting small arcuate and interlobular arteries with resultant reduced renal cortical blood flow, results in proteinuria, azotemia and hypertension; skeletal muscle: atrophy, interstitial fibrosis; inflammation; lung: interstitial pneumonitis and interstitial fibrosis; and heart: contraction band necrosis, scarring/fibrosis.

Idiopathic inflammatory myopathies including dermatomyositis, polymyositis and others are disorders of chronic muscle inflammation of unknown etiology resulting in muscle weakness. Muscle injury/inflammation is often symmetric and progressive. Autoantibodies are associated with most forms. These myositis-specific autoantibodies are directed against and inhibit the function of components, proteins and RNA's, involved in protein synthesis.

Sjogren's syndrome is due to immune-mediated inflammation and subsequent functional destruction of the tear glands and salivary glands. The disease can be associated with or accompanied by inflammatory connective tissue diseases. The disease is associated with autoantibody production against Ro and La antigens, both of which are small RNA-protein complexes. Lesions result in keratoconjunctivitis sicca, xerostomia, with other manifestations or associations including biliary cirrhosis, peripheral or sensory neuropathy, and palpable purpura.

Systemic vasculitis includes diseases in which the primary lesion is inflammation and subsequent damage to blood vessels which results in ischemia/necrosis/degeneration to tissues supplied by the affected vessels and eventual end-organ dysfunction in some cases. Vasculitides can also occur as a secondary lesion or sequelae to other immune-inflammatory mediated diseases such as rheumatoid arthritis, systemic sclerosis, etc., particularly in diseases also associated with the formation of immune complexes. Diseases in the primary systemic vasculitis group include: systemic necrotizing vasculitis: polyarteritis nodosa, allergic angiitis and granulomatosis, polyangiitis; Wegener's granulomatosis; lymphomatoid granulomatosis; and giant cell arteritis. Miscellaneous vasculitides include: mucocutaneous lymph node syndrome (MLNS or Kawasaki's disease), isolated CNS vasculitis, Behet's disease, thromboangiitis obliterans (Buerger's disease) and cutaneous necrotizing venulitis. The pathogenic mechanism of most of the types of vasculitis listed is believed to be primarily due to the deposition of immunoglobulin complexes in the vessel wall and subsequent induction of an inflammatory response either via ADCC, complement activation, or both.

Sarcoidosis is a condition of unknown etiology which is characterized by the presence of epitheloid granulomas in nearly any tissue in the body; involvement of the lung is most common. The pathogenesis involves the persistence of activated macrophages and lymphoid cells at sites of the disease with subsequent chronic sequelae resultant from the release of locally and systemically active products released by these cell types.

Autoimmune hemolytic anemia including autoimmune hemolytic anemia, immune pancytopenia, and paroxysmal nocturnal hemoglobinuria is a result of production of antibodies that react with antigens expressed on the surface of red blood cells (and in some cases other blood cells including platelets as well) and is a reflection of the removal of those antibody coated cells via complement mediated lysis and/or ADCC/Fc-receptor-mediated mechanisms.

In autoimmune thrombocytopenia including thrombocytopenic purpura, and immune-mediated thrombocytopenia in other clinical settings, platelet destruction/removal occurs as a result of either antibody or complement attaching to platelets and subsequent removal by complement lysis, ADCC or FC-receptor mediated mechanisms.

Thyroiditis including Grave's disease, Hashimoto's thyroiditis, juvenile lymphocytic thyroiditis, and atrophic thyroiditis, are the result of an autoimmune response against thyroid antigens with production of antibodies that react with proteins present in and often specific for the thyroid gland. Experimental models exist including spontaneous models: rats (BUF and BB rats) and chickens (obese chicken strain); inducible models: immunization of animals with either thyroglobulin, thyroid microsomal antigen (thyroid peroxidase).

Type I diabetes mellitus or insulin-dependent diabetes is the autoimmune destruction of pancreatic islet β cells; this destruction is mediated by auto-antibodies and auto-reactive T cells. Antibodies to insulin or the insulin receptor can also produce the phenotype of insulin-non-responsiveness.

Immune mediated renal diseases, including glomerulonephritis and tubulointerstitial nephritis, are the result of antibody or T lymphocyte mediated injury to renal tissue either directly as a result of the production of autoreactive antibodies or T cells against renal antigens or indirectly as a result of the deposition of antibodies and/or immune complexes in the kidney that are reactive against other, non-renal antigens. Thus other immune-mediated diseases that result in the formation of immune-complexes can also induce immune mediated renal disease as an indirect sequelae. Both direct and indirect immune mechanisms result in inflammatory response that produces/induces lesion development in renal tissues with resultant organ function impairment and in some cases progression to renal failure. Both humoral and cellular immune mechanisms can be involved in the pathogenesis of lesions.

Demyelinating diseases of the central and peripheral nervous systems, including Multiple Sclerosis; idiopathic demyelinating polyneuropathy or Guillain-Barr syndrome; and Chronic Inflammatory Demyelinating Polyneuropathy, are believed to have an autoimmune basis and result in nerve demyelination as a result of damage caused to oligodendrocytes or to myelin directly. In MS there is evidence to suggest that disease induction and progression is dependent on T lymphocytes. Multiple Sclerosis is a demyelinating disease that is T lymphocyte-dependent and has either a relapsing-remitting course or a chronic progressive course. The etiology is unknown; however, viral infections, genetic predisposition, environment, and autoimmunity all contribute. Lesions contain infiltrates of predominantly T lymphocyte mediated, microglial cells and infiltrating macrophages; CD4+ T lymphocytes are the predominant cell type at lesions. The mechanism of oligodendrocyte cell death and subsequent demyelination is not known but is likely T lymphocyte driven.

Inflammatory and Fibrotic Lung Disease, including Eosinophilic Pneumonias; Idiopathic Pulmonary Fibrosis, and Hypersensitivity Pneumonitis may involve a disregulated immune-inflammatory response. Inhibition of that response would be of therapeutic benefit.

Autoimmune or Immune-mediated Skin Disease including Bullous Skin Diseases, Erythema Multiforme, and Contact Dermatitis are mediated by auto-antibodies, the genesis of which is T lymphocyte-dependent.

Psoriasis is a T lymphocyte-mediated inflammatory disease. Lesions contain infiltrates of T lymphocytes, macrophages and antigen processing cells, and some neutrophils.

Allergic diseases, including asthma; allergic rhinitis; atopic dermatitis; food hypersensitivity; and urticaria are T lymphocyte dependent. These diseases are predominantly mediated by T lymphocyte induced inflammation, IgE mediated-inflammation or a combination of both.

Transplantation associated diseases, including Graft rejection and Graft-Versus-Host-Disease (GVHD) are T lymphocyte-dependent; inhibition of T lymphocyte function is ameliorative.

Other diseases in which intervention of the immune and/or inflammatory response have benefit are Infectious disease including but not limited to viral infection (including but not limited to AIDS, hepatitis A, B, C, D, E) bacterial infection, fungal infections, and protozoal and parasitic infections (molecules (or derivatives/agonists) which stimulate the MLR can be utilized therapeutically to enhance the immune response to infectious agents), diseases of immunodeficiency (molecules/derivatives/agonists) which stimulate the MLR can be utilized therapeutically to enhance the immune response for conditions of inherited, acquired, infectious induced (as in HIV infection), or iatrogenic (i.e. as from chemotherapy) immunodeficiency), and neoplasia.

The antibody is preferably administered to the mammal in a carrier; preferably a pharmaceutically-acceptable carrier. Suitable carriers and their formulations are described in *Remington's Pharmaceutical Sciences,* 16th ed., 1980, Mack Publishing Co., edited by Oslo et al. Typically, an appropriate amount of a pharmaceutically-acceptable salt is used in the formulation to render the formulation isotonic. Examples of the carrier include saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of antibody being administered.

The antibody can be administered to the mammal by injection (e.g., intravenous, intraperitoneal, subcutaneous, intramuscular, intraportal), or by other methods such as infusion that ensure its delivery to the bloodstream in an effective form. The antibody may also be administered by isolated perfusion techniques, such as isolated tissue perfusion, to exert local therapeutic effects. Local or intravenous injection is preferred.

Effective dosages and schedules for administering the antibody may be determined empirically, and making such determinations is within the skill in the art. Those skilled in the art will understand that the dosage of antibody that must be administered will vary depending on, for example, the mammal which will receive the antibody, the route of administration, the particular type of antibody used and other drugs being administered to the mammal. Guidance in selecting appropriate doses for antibody is found in the literature on therapeutic uses of antibodies, e.g., *Handbook of Monoclonal Antibodies,* Ferrone et al., eds., Noges Publications, Park Ridge, N.J., (1985) ch. 22 and pp. 303-357; Smith et al., *Antibodies in Human Diagnosis and Therapy,* Haber et al., eds., Raven Press, New York (1977) pp. 365-389. A typical daily dosage of the antibody used alone might range from about 1 µg/kg to up to 100 mg/kg of body weight or more per day, depending on the factors mentioned above.

The antibody may also be administered to the mammal in combination with effective amounts of one or more other therapeutic agents. In the treatment of cancer, this is particularly true, since many tumors acquire resistance to chemotherapy or radiotherapy through inactivation of the p53 tumor suppressor gene. Since DR5 stimulates apoptosis independently of p53, it is expected to be clinically useful not only as a single agent but also in combination with other types of cancer treatment, such as, for example, chemotherapy (chemotherapeutic agents), radiation therapy, immunoadjuvants, growth inhibitory agents, cytotoxic agents, and/or cytokines. Other agents known to induce apoptosis in mammalian cells may also be employed, and such agents include TNF-alpha, TNF-beta, CD30 ligand, 4-1 BB ligand and Apo-2 ligand, as well as other antibodies which can induce apoptosis. The one or more other therapies may include therapeutic antibodies (other than the DR5 antibody), and such antibodies may include anti-Her receptor antibodies (such as HERCEPTIN™ (trastuzumab), Genentech, Inc.), anti-VEGF antibodies, anti-CD20 antibodies (such as RITUXAN® (rituximab), Genentech, Inc.) and antibodies against other receptors for Apo-2 ligand, such as anti-DR4 antibodies, or antibodies against other TNF receptor family members such as ENBREL® (etanercept) (Immunex).

Chemotherapies contemplated by the invention include chemical substances or drugs which are known in the art and are commercially available, such as Doxorubicin, 5-Fluorouracil, etoposide, camptothecin, Leucovorin, Cytosine arabinoside, Cyclophosphamide, Thiotepa, Busulfan, Cytoxin, Taxol, Methotrexate, Cisplatin, Melphalan, Vinblastine and Carboplatin. Preparation and dosing schedules for such chemotherapy may be used according to manufacturer's instructions or as determined empirically by the skilled practitioner. Preparation and dosing schedules for such chemotherapy are also described in Chemotherapy Service Ed., M. C. Perry, Williams & Wilkins, Baltimore, Md. (1992).

The chemotherapy is preferably administered in a pharmaceutically-acceptable carrier, such as those described above. The mode of administration of the chemotherapy may be the same as employed for the DR5 antibody or it may be administered to the mammal via a different mode. For example, the DR5 antibody may be injected while the chemotherapy is administered orally to the mammal.

Radiation therapy can be administered to the mammal according to protocols commonly employed in the art and known to the skilled artisan. Such therapy may include cesium, iridium, iodine or cobalt radiation. The radiation therapy may be whole body radiation, or may be directed locally to a specific site or tissue in or on the body. Typically, radiation therapy is administered in pulses over a period of time from about 1 to about 2 weeks. The radiation therapy may, however, be administered over longer periods of time. Optionally, the radiation therapy may be administered as a single dose or as multiple, sequential doses.

The antibody may be administered sequentially or concurrently with the one or more other therapeutic agents. The amounts of antibody and therapeutic agent depend, for example, on what type of drugs are used, the pathological condition being treated, and the scheduling and routes of administration but would generally be less than if each were used individually.

Following administration of antibody to the mammal, the mammal's physiological condition can be monitored in various ways well known to the skilled practitioner.

It is contemplated that the antagonist or blocking DR5 antibodies may also be used in therapy. For example, a DR5 antibody could be administered to a mammal (such as described above) to block DR5 receptor binding to Apo-2L, thus increasing the bioavailability of Apo-2L administered during Apo-2L therapy to induce apoptosis in cancer cells.

The therapeutic effects of the DR5 antibodies of the invention can be examined in in vitro assays and using in vivo animal models. A variety of well known animal models can be used to further understand the role of the DR5 antibodies identified herein in the development and pathogenesis of for instance, cancer or immune-related diseases, and to test the efficacy of the candidate therapeutic agents. The in vivo nature of such models makes them particularly predictive of responses in human patients.

Animal models of immune related diseases include both non-recombinant and recombinant (transgenic) animals. Non-recombinant animal models include, for example, rodent, e.g., murine models. Such models can be generated by introducing cells into syngeneic mice using standard techniques, e.g. subcutaneous injection, tail vein injection, spleen implantation, intraperitoneal implantation, and implantation under the renal capsule.

Animal models, for example, for graft-versus-host disease are known. Graft-versus-host disease occurs when immunocompetent cells are transplanted into immunosuppressed or tolerant patients. The donor cells recognize and respond to host antigens. The response can vary from life threatening severe inflammation to mild cases of diarrhea and weight loss. Graft-versus-host disease models provide a means of assessing T cell reactivity against MHC antigens and minor transplant antigens. A suitable procedure is described in detail in Current Protocols in Immunology, unit 4.3.

An animal model for skin allograft rejection is a means of testing the ability of T cells to mediate in vivo tissue destruction which is indicative of and a measure of their role in anti-viral and tumor immunity. The most common and accepted models use murine tail-skin grafts. Repeated experiments have shown that skin allograft rejection is mediated by T cells, helper T cells and killer-effector T cells, and not antibodies. [Auchincloss, H. Jr. and Sachs, D. H., *Fundamental Immunology*, 2nd ed., W. E. Paul ed., Raven Press, NY, 1989, 889-992]. A suitable procedure is described in detail in Current Protocols in Immunology, unit 4.4. Other transplant rejection models which can be used to test the compositions of the invention are the allogeneic heart transplant models described by Tanabe, M. et al., *Transplantation*, (1994) 58:23 and Tinubu, S. A. et al., *J. Immunol.*, (1994) 4330-4338.

Animal models for delayed type hypersensitivity provides an assay of cell mediated immune function as well. Delayed type hypersensitivity reactions are a T cell mediated in vivo immune response characterized by inflammation which does not reach a peak until after a period of time has elapsed after challenge with an antigen. These reactions also occur in tissue specific autoimmune diseases such as multiple sclerosis (MS) and experimental autoimmune encephalomyelitis (EAE, a model for MS). A suitable procedure is described in detail in Current Protocols in Immunology, unit 4.5.

An animal model for arthritis is collagen-induced arthritis. This model shares clinical, histological and immunological characteristics of human autoimmune rheumatoid arthritis and is an acceptable model for human autoimmune arthritis. Mouse and rat models are characterized by synovitis, erosion of cartilage and subchondral bone. The DR5 antibodies of the invention can be tested for activity against autoimmune arthritis using the protocols described in Current Protocols in Immunology, above, units 15.5. See also the model using a monoclonal antibody to CD18 and VLA4 integrins described in Issekutz, A. C. et al., *Immunology*, (1996) 88:569.

A model of asthma has been described in which antigen-induced airway hyper-reactivity, pulmonary eosinophilia and inflammation are induced by sensitizing an animal with ovalbumin and then challenging the animal with the same protein delivered by aerosol. Several animal models (guinea pig, rat, non-human primate) show symptoms similar to atopic asthma in humans upon challenge with aerosol antigens. Murine models have many of the features of human asthma. Suitable procedures to test the compositions of the invention for activity and effectiveness in the treatment of asthma are described by Wolyniec, W. W. et al., *Am. J. Respir. Cell Mol. Biol.*, (1998) 18:777 and the references cited therein.

Additionally, the DR5 antibodies of the invention can be tested on animal models for psoriasis like diseases. The DR5 antibodies of the invention can be tested in the scid/scid mouse model described by Schon, M. P. et al., *Nat. Med.*, (1997) 3:183, in which the mice demonstrate histopathologic skin lesions resembling psoriasis. Another suitable model is the human skin/scid mouse chimera prepared as described by Nickoloff, B. J. et al., *Am. J. Path.*, (1995) 146:580.

Various animal models are well known for testing the safety and anti-cancer activity of a candidate therapeutic composition. These include human tumor xenografting into athymic nude mice or scid/scid mice, or genetic murine tumor models such as p53 knockout mice.

Recombinant (transgenic) animal models can be engineered by introducing the coding portion of the molecules identified herein into the genome of animals of interest, using standard techniques for producing transgenic animals. Animals that can serve as a target for transgenic manipulation include, without limitation, mice, rats, rabbits, guinea pigs, sheep, goats, pigs, and non-human primates, e.g. baboons, chimpanzees and monkeys, such as cynomolgus monkeys. Techniques known in the art to introduce a transgene into such animals include pronucleic microinjection (Hoppe and Wanger, U.S. Pat. No. 4,873,191); retrovirus-mediated gene transfer into germ lines (e.g., Van der Putten et al., *Proc. Natl. Acad. Sci. USA*, 82, 6148-615 [1985]); gene targeting in embryonic stem cells (Thompson et al., *Cell*, 56, 313-321 [1989]); electroporation of embryos (Lo, *Mol. Cel. Biol.*, 3, 1803-1814 [1983]); sperm-mediated gene transfer (Lavitrano et al., *Cell*, 57, 717-73 [1989]). For review, see, for example, U.S. Pat. No. 4,736,866.

For the purpose of the present invention, transgenic animals include those that carry the transgene only in part of their cells ("mosaic animals"). The transgene can be integrated either as a single transgene, or in concatamers, e.g., head-to-head or head-to-tail tandems. Selective introduction of a transgene into a particular cell type is also possible by following, for example, the technique of Lasko et al., *Proc. Natl. Acad. Sci. USA*. 89, 6232-636 (1992).

The expression of the transgene in transgenic animals can be monitored by standard techniques. For example, Southern blot analysis or PCR amplification can be used to verify the integration of the transgene. The level of mRNA expression can then be analyzed using techniques such as in situ hybridization, Northern blot analysis, PCR, or immunocytochemistry. The animals may be further examined for signs of immune disease pathology, for example by histological examination to determine infiltration of immune cells into specific tissues or for the presence of cancerous or malignant tissue.

Alternatively, "knock out" animals can be constructed which have a defective or altered gene encoding a polypeptide identified herein, as a result of homologous recombination between the endogenous gene encoding the polypeptide and altered genomic DNA encoding the same polypeptide introduced into an embryonic cell of the animal. For example, cDNA encoding a particular polypeptide can be used to clone genomic DNA encoding that polypeptide in accordance with established techniques. A portion of the genomic DNA encoding a particular polypeptide can be deleted or replaced with another gene, such as a gene encoding a selectable marker which can be used to monitor integration. Typically, several kilobases of unaltered flanking DNA (both at the 5' and 3' ends) are included in the vector [see e.g., Thomas and Capecchi, *Cell*, 51:503 (1987) for a description of homologous recombination vectors]. The vector is introduced into an embryonic stem cell line (e.g., by electroporation) and cells in which the introduced DNA has homologously recombined with the endogenous DNA are selected [see e.g., Li et al., *Cell*, 69:915 (1992)]. The selected cells are then injected into a blastocyst of an animal (e.g., a mouse or rat) to form aggregation chimeras [see e.g., Bradley, in *Teratocarcinomas and Embryonic Stem Cells: A Practical Approach*, E. J. Robertson, ed. (IRL, Oxford, 1987), pp. 113-152]. A chimeric embryo can then be implanted into a suitable pseudopregnant female foster animal and the embryo brought to term to create a "knock out" animal. Progeny harboring the homologously recombined DNA in their germ cells can be identified by standard techniques and used to breed animals in which all cells of the animal contain the homologously recombined DNA. Knockout animals can be characterized for instance, for their ability to defend against certain pathological conditions and for their development of pathological conditions due to absence of the polypeptide.

In another embodiment of the invention, methods for employing the antibody in diagnostic assays are provided. For instance, the antibodies may be employed in diagnostic assays to detect expression or overexpression of DR5 in specific cells and tissues. Various diagnostic assay techniques known in the art may be used, such as in vivo imaging assays, in vitro competitive binding assays, direct or indirect sandwich assays and immunoprecipitation assays conducted in either heterogeneous or homogeneous phases [Zola, *Monoclonal Antibodies: A Manual of Techniques*, CRC Press, Inc. (1987) pp. 147-158]. The antibodies used in the diagnostic assays can be labeled with a detectable moiety. The detectable moiety should be capable of producing, either directly or indirectly, a detectable signal. For example, the detectable moiety may be a radioisotope, such as $^3H$, $^{14}C$, $^{32}P$, $^{35}S$, or $^{125}I$, a fluorescent or chemiluminescent compound, such as fluorescein isothiocyanate, rhodamine, or luciferin, or an enzyme, such as alkaline phosphatase, beta-galactosidase or horseradish peroxidase. Any method known in the art for conjugating the antibody to the detectable moiety may be employed, including those methods described by Hunter et al., *Nature*, 144:945 (1962); David et al., *Biochemistry*, 13:1014-1021 (1974); Pain et al., *J. Immunol. Meth.*, 40:219-230 (1981); and Nygren, *J. Histochem. and Cytochem.*, 30:407-412 (1982).

DR5 antibodies also are useful for the affinity purification of DR5 from recombinant cell culture or natural sources. In this process, the antibodies against DR5 are immobilized on a suitable support, such a Sephadex resin or filter paper, using methods well known in the art. The immobilized antibody then is contacted with a sample containing the DR5 to be purified, and thereafter the support is washed with a suitable solvent that will remove substantially all the material in the sample except the DR5, which is bound to the immobilized antibody. Finally, the support is washed with another suitable solvent that will release the DR5 from the antibody.

In a further embodiment of the invention, there are provided articles of manufacture and kits containing materials useful for treating pathological conditions or detecting or purifying DR5. The article of manufacture comprises a container with a label. Suitable containers include, for example, bottles, vials, and test tubes. The containers may be formed from a variety of materials such as glass or plastic. The container holds a composition having an active agent which is effective for treating pathological conditions or for detecting or purifying DR5. The active agent in the composition is a DR5 antibody and preferably, comprises monoclonal antibodies specific for DR5. The label on the container indicates that the composition is used for treating pathological conditions or detecting or purifying DR5, and may also indicate directions for either in vivo or in vitro use, such as those described above.

The kit of the invention comprises the container described above and a second container comprising a buffer. It may further include other materials desirable from a commercial and user standpoint, including other buffers, diluents, filters, needles, syringes, and package inserts with instructions for use.

The following examples are offered for illustrative purposes only, and are not intended to limit the scope of the present invention in any way.

All patent and literature references cited in the present specification are hereby incorporated by reference in their entirety.

EXAMPLES

Commercially available reagents referred to in the examples were used according to manufacturer's instructions unless otherwise indicated. The source of those cells identified in the following examples, and throughout the specification, by ATCC accession numbers is the American Type Culture Collection, Manassas, Va. A number of the reagents and protocols disclosed herein are further discussed in WO 99/37684, WO 00/73349, WO 98/32856, WO 98/51793, and WO 99/64461, the contents of which are hereby incorporated by reference in their entirety.

Example 1

Design and Testing of Anti-DR5 Antibody Variants

Anti-DR5 antibody 16E2 was derived as an scFv from a human antibody phage-display library and has been described in WO 98/51793 published Nov. 19, 1998 (see Example 14). The nucleotide and amino acid sequences of scFv 16E2 are shown in FIG. 5 (SEQ ID NO: 9) and FIG. 6 (SEQ ID NO: 10), respectively. In FIG. 6, the signal sequence and the heavy and light chain CDR regions are identified (CDR1, CDR2, and CDR3 regions are underlined).

Materials and Methods

Construction of Full-Length Anti-DR5 Antibody 16E2

For the experiments described below, full length IgGs were desired. Therefore, the variable domains of 16E2 were cloned into previously described pRK vectors suitable for mammalian cell expression of full length IgG1 antibodies (Gorman et al., *DNA Prot. Eng. Tech.* 2:3-10 (1990)). Comparison of the amino acid sequence of the 16E2 variable domain to the Kabat data base (Kabat et al., Sequences of Proteins of Immunological Interest, U.S. Dept. of Health and Human Services, NIH, 5th edition) indicated that the light chain variable region (VL) of 16E2 is derived from a human lambda light chain gene family. Therefore, the variable domain of 16E2 was first subcloned into a vector containing a lambda constant domain. PCR primers were designed to add restriction enzyme sites SfiI and MscI and then the amplified variable domain was digested with these two enzymes. This fragment was inserted into the similarly digested vector containing the lambda constant domain. Since this vector was designed for expression of Fabs in *E. coli*, for IgG expression the entire light chain coding region was again PCR amplified using primers to add the restriction site AgeI at the 5' end of the coding region, and HindIII at the 3' end. Then, this AgeI to HindIII fragment was inserted into a similarly digested vector, pDR1 (Clontech). The entire sequence of plasmid pDR1 is shown in FIG. 11 (SEQ ID NO: 15).

For the heavy chain of Version 1, the heavy chain variable (VH) domain of the scFv 16E2 was PCR-amplified using primers designed to add a PvuII site at the 5'-end and an ApaI site at the 3'-end of the domain. This fragment was then cloned into the PvuII/ApaI sites of the vector pDR2 (Clontech) for expression of the complete heavy chain (VH-CH1-CH2-CH3 domains). The entire sequence of plasmid pDR2 is shown in FIG. 12 (SEQ ID NO: 16).

The nucleotide and amino acid sequences of full-length antibody 16E2 heavy and light chains are shown in FIGS. 7-10 (SEQ ID NOS: 11-14), respectively. In particular, FIGS. 7 and 8 (SEQ ID NOS: 11 and 12) show the amino acid and nucleotide sequences of full-length 16E2 heavy chain, and FIGS. 9 and 10 (SEQ ID NOS: 13 and 14) show the amino acid and nucleotide sequences of full-length 16E2 light chain. The heavy and light chains of the full-length 16E2 antibody will be hereinafter also referred to as "Version 1."

Construction of IgG variants. Variants were constructed on the light or heavy chain separately using site-directed mutagenesis (Kunkel et al., Proc. Natl. Acad. Sci USA 82:488-492 (1985)). Plasmid pDR1 encoding light chain Version 1, or pDR2 encoding heavy chain Version 1, was transformed into *E. coli* strain CJ236 (BioRad, Joyce and Grindley, J. Bacteriol. 158:636-643 (1984)) for preparation of deoxyuridine-containing single-stranded DNA templates. Aliquots of the mutagenesis reactions were transformed into *E. coli* strain XL-1 Blue (Stratagene, San Diego, Calif.) for purification of double stranded DNA. For each variant, the DNA coding for the light or heavy chain was completely sequenced using ABI377x1, or ABI3730x1 automated DNA sequencer (Perkin-Elmer Corp.).

For each IgG variant, transient transfections were performed by cotransfecting a light-chain expressing plasmid and a heavy-chain expressing plasmid into an adenovirus-transformed human embryonic kidney cell line, 293 (Graham et al., *J. Gen. Virol.*, 36:59-74, (1977)). Briefly, 293 cells were split on the day prior to transfection, and plated in serum-containing medium. On the following day, a calcium phosphate precipitate was prepared from double stranded DNA of the light and heavy chains, along with pAdVantage™ DNA (Promega, Madison, Wis.), and added dropwise to the plates. Cells were incubated overnight at 37° C., then washed with PBS and cultured in serum-free medium for 4 days at which time conditioned medium was harvested. Antibodies were purified from culture supernatants using protein A-Sepharose CL-4B, then buffer exchanged into 10 mM sodium succinate, 140 mM NaCl, pH 6.0, and concentrated using a Centricon-10 (Amicon). Protein concentrations were determined by measuring absorbance at 280 nm or by quantitative amino acid analysis.

Electrochemiluminescent DR5-Binding Assay. The relative binding of the anti-DR5 antibodies was determined in a solution phase, competition-ELISA format. DR5-Fc fusion protein was biotinylated using biotin-X-NHS (Research Organics, Cleveland, Ohio), and the standard antibody (either Version 1 or Apomab 7.3) was labeled with ORI-TAG NHS ester (IGEN International, Gaithersburg, Md.) according to the manufacturer's directions. To perform the binding assay, test antibody samples were serially diluted in assay buffer (PBS, pH 7.4, containing 0.5% BSA and 0.5% Tween-20). Equal volumes (25 µl each) of the antibody sample (concentrations ranging from 50,000-0.85 ng/ml), ORI-TAG standard antibody (150 ng/ml), and biotinylated human DR5-Fc (15 ng/ml) were added to 96 well polypropylene plates and incubated for 1.5 hr at room temperature with gentle agitation. Magnetic streptavidin beads (IGEN International) were then added (25 µl/well), and the plates were incubated as above for an additional 30 min. Assay buffer was added to bring the final volume to 250 µl per well, and the plates were read using an ORIGEN M384 instrument (IGEN International). The IC50 values were calculated using four parameter fits of the sample curves.

Bioassay: tumor cell growth inhibition/killing. The apparent potency of each antibody variant was determined in an in vitro tumor cell-killing assay. Colo205 human colon carcinoma cell line was cultured in RPM medium containing 10% fetal bovine serum. Two-fold serial dilutions of standard (either Version 1 or Apomab 7.3) and samples were performed in 96-well tissue culture plates containing medium with, or without, a cross-linking antibody (anti-human Fc, goat affinity-purified F(ab')$_2$) at 10 micrograms/ml. Cells (20,000/well) were then added to the plates. The plates were incubated at 37° C. for a total of 48 h. AlamarBlue was added to the wells for the last 3 h of incubation. Fluorescence was read using a fluorometer with excitation at 530 nm and emission of 590 nm. The data were analyzed using a four parameter curve-fitting program.

Results

The overall goal of this work has been to develop anti-DR5 antibodies with improved biochemical properties and improved efficacy, without compromising safety.

Several approaches were used to achieve the desired improvements, including amino acid substitutions in the DR5 heavy and light chains in order to improve chemical or thermal stability; folding; alanine scanning of the CDR residues in order to determine which residues might be important for binding or folding, and therefore might be changed for greater affinity; and the use of phage-display libraries of the CDRs to identify clones with improved affinity. Changes in the framework regions were also studied for their possible effects on immunogenicity and biological activity.

Figure 19:
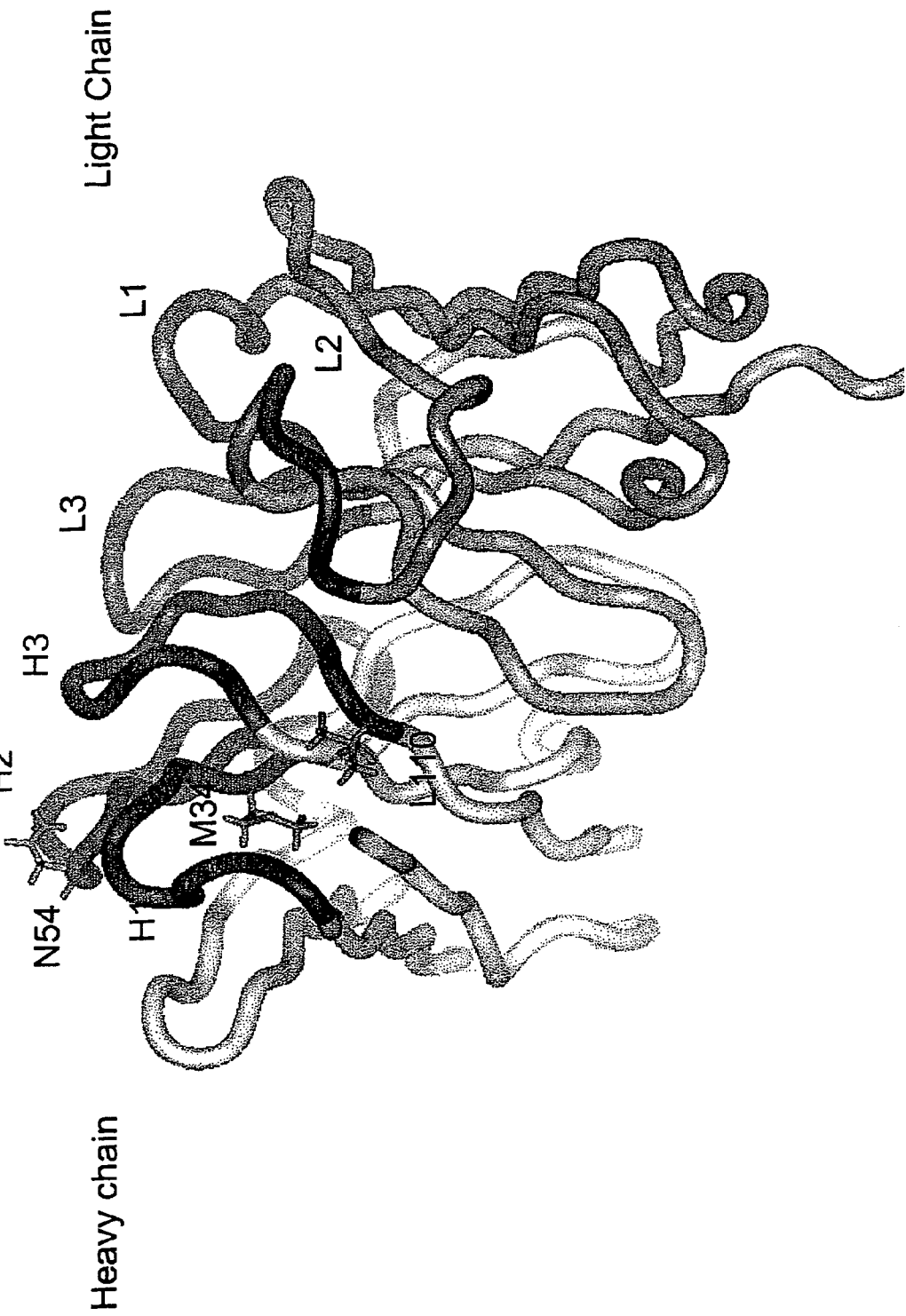
FIG. 19 is a homology model for anti-DR5 antibody heavy chain.
Figure 20:
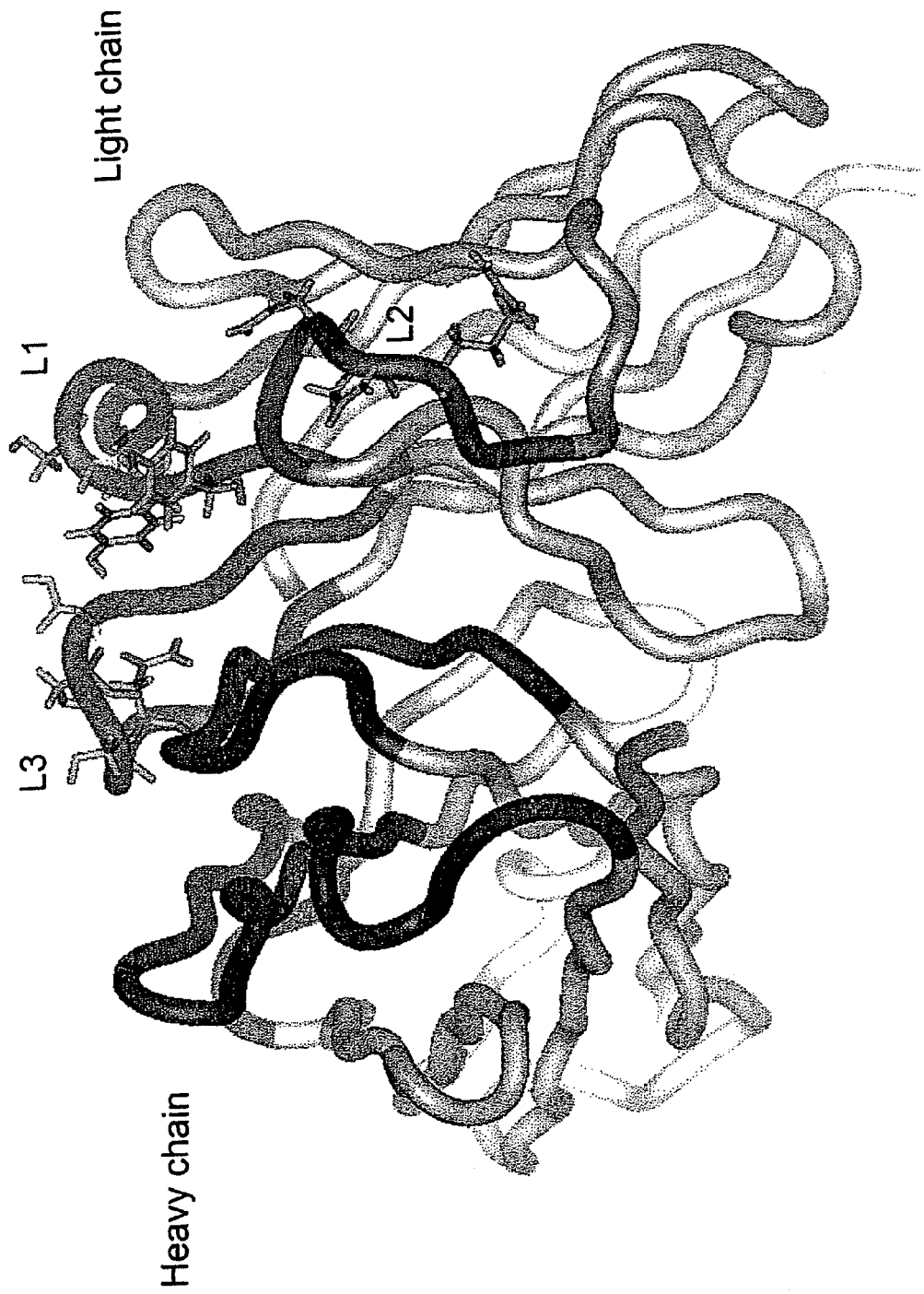
FIG. 20 is a homology model for anti-DR5 antibody light chain.

Homology models (FIGS. 19 and 20) were used as an aid to selection of many of these changes.

Heavy Chain Variants

Series 1

Version 2 of the heavy chain contains 5 changes from Version 1. These changes (Q6E, V11L, E12V, R13Q, and K105Q) are in the framework of the variable domain, and were added in order to bring the framework closer to the human $V_H$III consensus sequence. Shown in Table 1 are the first variants constructed with changes in the heavy chain CDRs. The ssDNA template for these mutants was version 2. The Leu to Tyr change at position 102 was made to improve packing, and thus stability. In combination with this change, Asn53 was changed to Gln or Tyr in order to remove the potential deamidation site. Met34 was changed to Leu to remove a potential oxidation site. These heavy chain variants were expressed with the original light chain to give versions 20-23 (Table 1). The heavy chain containing the three mutations M34L, N53Q, and L102Y, and the framework changes as in version 2, is subsequently referred to as "triple heavy one" or TH1, while the heavy chain with the three mutations M34L, N53Y, and L102Y and the framework of version 2, is similarly termed TH2.

TABLE 1

Heavy Chain CDR Variants

| Version[a] | Substitutions | IC50 VARIANT IC50 v1[b] | Bioassay activity with crosslinking[c] | Bioassay activity without crosslinking[d] |
|---|---|---|---|---|
| 20 | N53Q, L102Y | 0.11 | 0.24 | * |
| 21 | M34L, N53Q, L102Y | 0.42 | 0.54 | <1 |
| 22 | N53Y, L102Y | 0.08 | 1.30 | slight |
| 23 | M34L, N53Y, L102Y | 0.28 | 4.47 | none |

[a]Template: version 2
[b]Origen ® competitive human DR5 binding assay
[c]Tumor cell inhibition assay

[d]Tumor cell inhibition assay

Since there was a loss of binding and in vitro cell-killing activity with the addition of the M34L mutation (i.e., v21 compared to v20, v23 compared to v22, Table 1), a series of additional mutations, substituting either alanine or other residues suggested by scanning the Kabat database, were made in heavy chain CDR1 using heavy chain version 20 as the template. These heavy chains were expressed with light chain Version 1. The amino acids that were mutated, the resultant binding relative to v1, and the bioassay data for these versions are shown in Table 2. Changing Gly33 to Ala gave enhancement of binding as well as improved potency. This heavy chain containing the three mutations, G33A, N53Q, and L102Y is termed TH3. Likewise, TH4 was constructed having G33A, N53Y, and L102Y. Changing Thr28 to Ala also gave enhanced activity compared to v1, and the heavy chain containing T28A, N53Q, L102Y is termed TH9. The CDR changes in TH1, TH2, TH3, TH4, and TH9 are summarized in Table 5. These five heavy chains were further studied after co-expressing them with Light chain combinations (see below)

TABLE 2

Variants in CDR H1

| Version[a] | Mutation | IC50 MUTANT IC50 v1[b] | Bioassay activity with cross-linking[c] | Bioassay activity without cross-linking[d] |
|---|---|---|---|---|
| 111 | G26A | 0.11 | 0.42 | None |
| | F27A | ND | ND | ND |
| 112 | T28A | 0.19 | 0.8 | Same as v1 |
| 127 | F29A | 7.6 | None | |
| 55 | D30A | 2.2 | ND | ND |
| 54 | D30S | 2.1 | ND | ND |
| 57 | D31A | >10 | ND | ND |
| 56 | D31S | 4.3 | ND | ND |
| 113 | Y32A | 1.65 | >100 | None |
| 58 | G33A | 0.1 | 0.097 | Slight |
| 59 | M34A | 0.8 | 3.49 | Slight |
| 49 | M34I | 1.2 | 14.6 | None |
| 50 | M34S | 1.0 | 13.8 | None |
| | S35H | ND | ND | ND |
| 130 | S35A | ND | ND | ND |

[a]Template for all variants is version 20

[b]Origen ® competitive human DR5 binding assay

[c]Tumor cell inhibition assay

[d]Tumor cell inhibition assay

Ala-Scanning CDRH2 and CDRH3. To further elucidate the contribution of each amino acid of heavy chain CDR2 and CDR3, mutants were constructed with alanine substituting for each of these residues. Site directed mutagenesis with synthetic oligonucleotides encoding the alanine substitution was performed using heavy chain Version 1 as template. These heavy chains were expressed using Version 1 light chain. The changes in apparent affinity and potency of the resultant antibodies are shown in Tables 3 and 4. Gly99Ala and Arg100Ala each show improved activity, and therefore, these changes could be used to construct additional combination mutants of the heavy chain.

TABLE 3

Alanine Scanning of CDRH2

| Version[a] | Mutation | Binding ratio to v1[b] | Bioassay activity with crosslinking[c] | Bioassay activity without crosslinking[d] |
|---|---|---|---|---|
| 139 | G50A | 3.55 | 1.91 | none |
| 140 | I51A | ND | ND | ND |
| 141 | N52A | 2.42 | ND | ND |
| | W52aA | ND | ND | ND |
| 142 | N53A | ND | 0.19 | slight |
| 160 | G54A | 1.49 | ND | ND |
| 151 | G55A | 1.0 | 0.86 | >100 × down |
| 143 | S56A | 1.1 | 0.81 | ~ equal to v1 |
| 144 | T57A | 1.2 | 0.54 | >100 × down |
| 152 | G58A | 0.55 | 1.24 | ~5 × down |
| 153 | Y59A | 2.22 | 3.42 | none |
| 154 | A60A | 0.55 | 0.49 | >100 × down |
| 158 | D61A | 0.725 | ND | ND |
| 155 | S62A | 0.65 | 0.73 | >100 × down |
| 156 | V63A | 0.041 | ND | ~3 × down |
| 159 | K64A | ND | ND | ND |
| | G65A | ND | ND | ND |

[a]Template: Version 1

[b]Origen ® competitive human DR5 binding assay

[c]Tumor cell inhibition assay

[d]Tumor cell inhibition assay

TABLE 4

Alanine mutants in CDRH3

| Version[a] | Mutation | Binding ratio to v1[b] | Bioassay activity with crosslinking | Bioassay activity without crosslinking[d] |
|---|---|---|---|---|
| 108 | K102A | 1.82 | >10 | none |
| 109 | I95A | 8.38 | None | none |
| (1040) | L96A | ND | ND | ND |
| 126 | G97A | 8.52 | None | none |
| 110 | Y98A | 24.2 | None | none |
| 128 | G99A | 0.09 | 0.43 | ~8 × up |
| 129 | R100A | 0.47 | 0.128 | ~4 × up |
| 116 | G100aA | 2.84 | None | none |
| 117 | W100bA | Na | None | none |
| 118 | Y100cA | 10.85 | None | none |
| 119 | F100dA | Na | None | none |
| 120 | D101A | 1.83 | ~1 | none |

[a]Template: Version 1
[b]Origen ® competitive human DR5 binding assay
[c]Tumor cell inhibition assay
[d]Tumor cell inhibition assay Series 2

A second series of heavy chains using the same CDRs as versions TH1, TH2, TH3, TH4 were constructed in which the framework residues E6, L11, V12, Q13, and Q105 were reverted to the amino acids found in Version 1, i.e. Q6, V11, E12, R13 and K105. These heavy chains are referred to as TH5, TH6, TH7, and TH8 (see Table 5).

TABLE 5

Heavy chain variants with mutations in all CDR loops

| Heavy chain combination | Mutation in CDR H1 | Mutation in CDR H2 | Mutation in CDR H3 | Framework residues at 6, 11, 12, 13, 105 |
|---|---|---|---|---|
| TH1 | M34L | N53Q | L102Y | E, L, V, Q, Q |
| TH2 | M34L | N53Y | L102Y | E, L, V, Q, Q |
| TH3 | G33A | N53Q | L102Y | E, L, V, Q, Q |
| TH4 | G33A | N53Y | L102Y | E, L, V, Q, Q |
| TH5 | M34L | N53Q | L102Y | Q, V, E, R, K |
| TH6 | M34L | N53Y | L102Y | Q, V, E, R, K |
| TH7 | G33A | N53Q | L102Y | Q, V, E, R, K |
| TH8 | G33A | N53Y | L102Y | Q, V, E, R, K |
| TH9 | T28A | N53Q | L102Y | E, L, V, Q, Q |

Light Chain Variants
Alanine-Scanning of the Light Chain CDRs

To better understand the contribution to binding and biological activity of the CDR residues of the light chain, each amino acid was changed to alanine using site-directed mutagenesis. Each of the light chain variants was combined with heavy chain v1 for transient expression of IgG as described above. Results of the light chain CDR ala scan are summarized in Table 6. Interestingly, in contrast to many other antibodies, CDR L1 appears to play a significant role in antigen binding. This light chain is a lambda chain, and the model shown in FIG. 20 suggests that CDR1 could form an alpha helix. Substitutions to alanine in L2 and L3 are more tolerated with the exception of G50A in CDR2 which abolishes binding. Conversely, some ala substitutions, especially R91A and K51A improved binding and bioactivity.

TABLE 6

| Light chain alanine scanning mutants | | | | | |
|---|---|---|---|---|---|
| Version[a] | Location | Mutation | Binding[b] | Bioassay[c] | Bioassay[d] |
| 89 | CDR L1 | Q24A | 1.22 | 0.87 | * |
| 40 | CDR L1 | G25A | 2.54 | ND | ND |
| 90 | CDR L1 | D26A | 0.76 | 0.88 | None |
| 41 | CDR L1 | S27A | 2.36 | 2.79 | Slight |
| 42 | CDR L1 | L28A | >100 | ND | ND |
| 46 | CDR L1 | R29A | 3.0 | ND | ND |
| 38 | CDR L1 | S30A | 2.35 | 5.51 | N/A |
| 39 | CDR L1 | Y31A | >10 | ND | ND |
| 47 | CDR L1 | A33G | 6.4 | ND | ND |
| 43 | CDR L1 | S34A | 1.54 | 3.23 | Slight |
| 64 | CDR L2 | G50A | >1000 | ND | ND |
| 65 | CDR L2 | K51A | 0.4 | 0.027 | *** |
| 93 | CDR L2 | N52A | 3.12 | ND | ND |
| 94 | CDR L2 | N53A | 7.54 | ND | ND |
| 95 | CDR L2 | R54A | 0.89 | 0.87 | * |
| 107 | CDR L2 | P55A | 0.95 | 1.35 | Slight |
| 163 | CDR L2 | S56A | 1.9 | ND | ND |
| 72 | CDR L3 | N89A | 3.1 | Na | None |
| 73 | CDR L3 | S90A | 0.9 | 0.91 | 1.0 |
| 74 | CDR L3 | R91A | 0.5 | 0.098 | **** |
| 164 | CDR L3 | D92A | 0.22 | ND | ND |
| 137 | CDR L3 | S93A | 2.51 | 0.85 | Slight |
| 138 | CDR L3 | S94A | 0.31 | 0.15 | Slight |
| 165 | CDR L3 | G95A | 0.06 | ND | ND |
| 71 | CDR L3 | N95aA | 1.0 | 1.17 | ND |
| (1024) | CDR L3 | H95bA | ND | ND | ND |
| 166 | CDR L3 | V96A | 1.34 | ND | ND |
| 167 | CDR L3 | V97A | 1.05 | ND | ND |

[a]Template: Version 1
[b]Origen ® competitive human DR5 binding assay
[c]Tumor cell inhibition assay
[d]Tumor cell inhibition assay Gene Family Residue Swaps A second type of directed mutants was used to study the light chain. In this approach, CDR residues which in the model appeared to be at either side of the loops, and thus might play a supporting role rather than being directly involved in antigen binding, were swapped for residues in corresponding locations in other closely related lambda gene families. These mutants were also expressed using v1 heavy chain, and results are summarized in Table 7. In CDR L2, the combination of G50K, K51D gives significant improvement in both binding and bioactivity, and the combination which comprises the four mutations G50K, K51D, N52S, N53E, is also improved over v1. Other more conservative changes in the same region, involving only one residue substitution, were not tolerated.

TABLE 7

| Light chain variants based on related gene family sequences. | | | | | |
|---|---|---|---|---|---|
| Version[a] | Location | Mutation | Binding[b] | Bioassay[c] | Bioassay[d] |
| 25 | CDR L1 | Q24S, D26E, Y31K, S34Y | 11.7 | ND | ND |
| 24 | | D26E, Y31K | >100 | ND | ND |
| 51 | | S34Y | >100 | ND | ND |

TABLE 7-continued Light chain variants based on related gene family sequences.

| Version[a] | Location | Mutation | Binding[b] | Bioassay[c] | Bioassay[d] |
|---|---|---|---|---|---|
| 44 | | Q24S | 0.96 | 1.23 | slight |
| 45 | | Y31K | >1000 | ND | ND |
| 106 | | Y32H | 5.1 | 1.71 | none |
| 26 | CDR L2 | G50K, K51D, N52S, N53E | 0.33 | 0.071 | 1 |
| 27 | | G50S, K51D, N52S | 0.92 | 0.29 | slight |
| 91 | | G50K, K52S, N53E | 14.71 | ND | ND |
| 92 | | G50K, K51D | 0.09 | 0.43 | *** |
| 28 | | N52L | 6.88 | ND | ND |
| 125 | | G50S, K51D, N52S, N53E | 1.99 | 1.0 | ND |
| 32 | | N52Q | 5.28 | ND | ND |
| 33 | | N53Q | 4.48 | ND | ND |
| 61 | | N52S, N53E | >100 | ND | ND |
| 62 | | N52S | 1.1 | 1.1 | none |
| 63 | | N52Q, N53S | >10 | ND | ND |
| 60 | CDR L3 | N89L, R91A, N95aT, H95bY | >100 | ND | ND |
| 52 | | N95aT, H95bY | 2.3 | ND | ND |
| 30 | | N95aQ | 1.65 | 7.3 | slight |
| 31 | | N89Q | >1000 | ND | ND |
| 29 | | H95bY | 1.68 | 2.14 | slight |
| 66 | | H95bR | 0.7 | 0.97 | 1.0 |
| 67 | | N95aK | 1.0 | 0.44 | 1.0 |

[a]Template: Version 1
[b]Origen ® competitive human DR5 binding assay
[c]Tumor cell inhibition assay
[d]Tumor cell inhibition assay Affinity Selection with Antibody-Phage Libraries For each of the CDRs L1, L2, and L3, phage display libraries were constructed separately and selected for clones with increased affinity to DR5-Ig. Inspection of the model (FIG. 20) indicated which residues of the CDRs were likely to be exposed and these residues were chosen for randomization. The entire lambda light chain and the VH domain of Version 1 were cloned into the phage-display vector pS1602, referenced in Vajdos et al., J. Mol. Biol. 320:415-428 (2002), and further described in Sidhu et al., Curr. Opin. Biotechnol. 11:610-616 (2002). Kunkel mutagenesis was used in construction of the libraries. The v1 phagemid was transformed into E. coli strain CJ236 for single stranded DNA preparation and oligonucleotides containing TAA codons at each site chosen for randomization were used to generate the library templates. Oligos using the degenerate codon NNS (where N is an equal mixture of G, A, T, and C, while S is an equal mixture of G and C) were then used to construct the libraries. CDRL1 was mutated using stop template oligo CA945 and library oligo CA946. CDRL1 was mutated using stop template oligo CA947 and library oligo CA948. CDRL3 was mutated using stop template oligo CA949 and library oligo CA950. Library construction is summarized in Table 8.

TABLE 8

| Oligo number | Region | Purpose | Sequence |
|---|---|---|---|
| CA945 | CDRL1 | Stop Template | CAT GCC AAG GAG ACT AAC TCA GAT AAT ATT AAG CTA GCT GGT ACC AGC (SEQ ID NO: 21) |
| CA946 | CDRL1 | randomization | CAT GCC AAG GAG ACN NSC TCA GAN NST ATN NSG CTA GCT GGT ACC AGC (SEQ ID NO: 22) |
| CA947 | CDRL2 | Stop template | GTC ATC TAT GGT AAA TAA TAA CGG CCG TCT GGC ATC CCA GAC CG (SEQ ID NO: 23) |
| CA948 | CDRL2 | randomization | CTT GTC ATC TAT GGT AAA NNS NNS NNS CCG TCT GGC ATC CCA GAC CG (SEQ ID NO: 24) |
| CA949 | CDRL3 | Stop template | GCT GAC TAT TAC TGT AAC TCC CGG TAA TAA TAA GGC TAA CAT GTG GTA TTC GGC GGA GG (SEQ ID NO: 25) |
| CA950 | CDRL3 | randomization | GCT GAC TAT TAC TGT AAC TCC CGG NNS NNS NNS GGC NNS CAT GTG GTA TTC GGC GGA GG (SEQ ID NO: 26) |

The products of random mutagenesis reactions were electroporated into XLI-Blue E. coli cells (Stratagene) and amplified by growing 14-16 hours with M13K07 helper phage. Library size was estimated by serial dilution and plating if the initial transformation was onto carbenicillin plates, and was from $1.9 \times 10^9$ to $2.2 \times 10^9$ clones.

The libraries were panned for 4 rounds in solution using biotinylated DR5-Ig (Genentech). Approximately $10^{11}$ phage were blocked with a one ml solution of 3% nonfat dry milk, 0.2% Tween in PBS (phage block) on a rotating wheel for 1 h at RT. DR4-IG and CD4-IG were each added to the block solution at 1 micromolar to decrease non-specific binding. Biotinylated antigen was then added at 100 nM for the first round and binding was allowed to proceed for 2 h. In subsequent rounds of panning, antigen concentration was lowered to 10, 5 and 1 nanomolar.

For capture of antigen-binding phage, strepavidin-coated magnetic beads (Dynal) were first washed three times with phage block, and then blocked with one ml of phage block for 1 h at RT. Beads were concentrated using a magnet and added to the antigen-phage solution for 15 min. The magnet was then used to pull the bead-antigen-phage complexes out of solution. These particles were then washed 3 times with phage block, 3 times with PBS-Tween (0.02% Tween) and once with PBS. Phage were eluted from the beads with 100 microliters of 0.1 M HCl for 10 min, and neutralized with NaOH. Eluted phage were used to infect XL1Blue E. coli, and propagated as above for subsequent rounds. Stringency of washing was increased at each round.

Clones from each library were sequenced. For the L1 libraries, only wild type sequences were obtained, supporting the idea that this CDR is important for antigen binding or antibody conformation, and few mutations in the potential helix can be tolerated. For the libraries in L2, no consensus sequences were found, suggesting that multiple CDRL2 sequences are acceptable for binding to DR5. For the L3 libraries, several sequences appeared multiple times, and these sequences were grafted onto the full-length light chain vector using oligo-directed mutagenesis. Expression of IgGs was again in 293 cells, using heavy chain Version 1 for co-transfection. Table 9 describes the L3 sequences which were expressed as full length antibodies, and the results of binding and bioassays. Two of the sequences tested, incorporated into versions 69 and 70, gave antibodies with improved binding and bioactivity compared to Version 1.

TABLE 9

Protein sequences of light chain CDR3, derived from phage library

| Version[a] | CDR L3 sequence | Binding ratio to v1[b] | Bioassay activity with crosslinking[c] | Bioassay activity without crosslinking[d] |
|---|---|---|---|---|
| 68 | NSRDSSGSHVV | 1.3 | 0.973 | 1.0 |
| 69 | NSRSYSGNHVV | 0.1 | 0.143 | **** |
| 70 | NSRSSSGSHVV | 0.2 | 0.152 | *** |

[a]Template: Version 1
[b]Origen ® competitive human DR5 binding assay
[c]Tumor cell inhibition assay
[d]Tumor cell inhibition assay Combination Light Chains As described above, mutations were identified in each of the light chain CDRs which individually enhanced binding and tumor cell killing in vitro. These mutations were then combined to make several light chains with improvements in each of the CDRs. These were designated TL1, TL2, and TL3 for "triple light 1" etc., and are described in Table 10. Thus, TL1 contains the L1 mutation identified in version 44 combined with the L2 mutation identified in version 26 and the L3 mutation in version 29. Likewise, TL2 contains the L1 mutation from version 44 with the L2 mutation from v65 and the L3 mutation from v69, while TL3 combines L1 from v44 with L2 from v65 and L3 from v74.

TABLE 10

Mutations in light chain combinations

| Light chain combination | Mutation, CDR L1 | Mutations, CDR L2 | Mutations, CDR L3 |
|---|---|---|---|
| TL1 | Q24S | G50K, K51D, N52S, N53E | H95bY |
| TL2 | Q24S | K51A | D92S, S93Y |
| TL3 | Q24S | K51A | R91A |

TABLE 11

Apomab nomenclature.

| | Light chain: Heavy chain | | |
|---|---|---|---|
| | TL1 | TL2 | TL3 |
| TH1 | Apomab 1.1 | Apomab 1.2 | Apomab 1.3 |
| TH2 | Apomab 2.1 | Apomab 2.2 | Apomab 2.3 |
| TH3 | Apomab 3.1 | Apomab 3.2 | Apomab 3.3 |
| TH4 | Apomab 4.1 | Apomab 4.2 | Apomab 4.3 |
| TH5 | Apomab 5.1 | Apomab 5.2 | Apomab 5.3 |
| TH6 | Apomab 6.1 | Apomab 6.2 | Apomab 6.3 |
| TH7 | Apomab 7.1 | Apomab 7.2 | Apomab 7.3 |
| TH8 | Apomab 8.1 | Apomab 8.2 | Apomab 8.3 |
| TH9 | Apomab 9.1 | Apomab 9.2 | Apomab 9.3 |

Further Apomab antibodies are shown in Table 12.

TABLE 12

| Apomab version | Framework amino acid sequence at positions 6, 11, 12, 13, and 102 | Binding to DR5, relative to Apomab 7.3 | Potency, relative to Apomab 7.3, With crosslinking | Bioassay activity with crosslinking |
|---|---|---|---|---|
| 7.3* | Q VER K | 1.00 | 1 | ND |
| 3.3** | E LVQ Q | 2.50 | 0.53 | None |
| 18.3 | E LVQ K | 0.51 | 0.75 | None |
| 24.3 | E VER Q | 0.80 | 1 | None |
| 25.3 | Q LVQ K | 0.77 | 1 | ~3 × down |
| 26.3 | Q VER Q | 0.53 | 1 | ~6 × down |
| 27.3 | E VER K | 1.90 | 1.2 | none |
| 28.3 | Q LER K | 0.48 | 0.94 | ~5 × down |
| 29.3 | Q LEQ K | 0.52 | 1.2 | ~7 × down |
| 30.3 | Q VVQ K | 0.78 | 0.66 | ~3 × up |
| 36.3 | Q VVR K | 0.66 | ND | ND |
| 37.3 | Q VEN K | 0.84 | ND | ND |
| 38.3 | Q LVR K | 0.47 | ND | ND |
| 18.2 | E LVQ K | 0.11 | 0.16 | None |
| 24.2 | E VER Q | 0.14 | 0.18 | none |
| 25.2 | Q LVQ K | 0.10 | 0.13 | ~32 × up |
| 26.2 | Q VER Q | 0.14 | 0.22 | ~10 × up |
| 27.2 | E VER K | 0.10 | 0.15 | none |

*same framework as Version 1
**same framework as human consensus VH-III

Apomab Expression

After deriving the triple heavy chains, and the triple light chains, a 9×3 grid of combination antibodies was created by co-transfecting each of the three light chains with each of the nine heavy chains in 293 cells and purifying the resultant antibodies as described above. In vitro studies with these Apomabs indicated that several versions were quite potent in the bioassays. Therefore, material was prepared which was suitable for in vivo mouse tumor model studies.

Apomab Recovery and Purification

A method for recovering and purifying Apomab antibodies from a Harvested Cell Culture Fluid (HCCF) is described as follows:

Prosep Protein A Chromatography—Harvested Cell Culture Fluid (HCCF) produced from Chinese Hamster Ovary (CHO) cells is adjusted pH to 7.0 with 1.5 M Tris base and then loaded onto the Prosep Protein A column (Millipore, U.S.A.) that is equilibrated with 25 mM NaCl/25 mM Tris/5 mM EDTA, pH 7.5. The non-binding proteins are flowed through and removed by washing with equilibration buffer followed by a second wash step with 0.5 M TMAC in the equilibration buffer and a third wash with equilibration buffer. Apomab antibody is eluted off the Protein A column using a step elution of 0.1 M Acetic acid. Column eluent is monitored by A280. The Apomab antibody peak is pooled.

SP-Sepharose Fast Flow Chromatography—The pool of Apomab antibody from Prosep Protein A is adjusted pH to 5.5 with 1.5 M Trisbase and then loaded onto a column of SP-Sepharose Fast Flow (Amersham Pharmacia, Sweden) that is equilibrated with 25 mM MOPS pH 7.1. After sample is loaded, the column is washed with equilibration buffer to baseline @A280. The Apomab antibody is eluted out of the column by using a linear, 12 column-volume gradient of 0 to 0.2 M Sodium chloride in the equilibration buffer, pH 8. Column eluent is monitored by A280. Fractions are collected and those which contain properly-folded Apomab antibody, as determined by SEC-HPLC analysis, are pooled.

Q-Sephrose Fast Flow Chromatography—The pool of SP-Sepharose fractions is then loaded onto a column of Q-Sepharose FF (Amersham pharmacia, Sweden) that is equilibrated in 50 mM Sodium chloride/25 mM Tris buffer, pH 8. The column is washed with equilibration buffer, and the Apomab antibody is collected in the column effluent.

UF/DF Formulation—The pool of Q-Sepharose is concentrated by Ultrafiltration on a membrane having a molecular weight cut off about 10,000 daltons. The concentrated Q Sepharose FF pool is then diafiltrated with 10 volumes of 10 mM Histidine/8% Sucrose, pH 6. The diafiltrated Q Sepharose pool is conditioned with 10% Polysorbate 20 to achieve a final concentration of 0.02% Polysorbate 20. The formulated bulk is filtered through a sterile 0.22 μm filter and stored at 2-8° C. or −70° C. The final purity of Apomab antibodies is determined by SDS-PAGE, SEC-HPLC and Amino Acid sequence analysis.

Sequencing is performed on ABI3700 or ABI3730 Applied Biosystems sequencing machines. The sequencing chromatograms are analyzed using Sequencer (GeneCodes, Ann Arbor, Mich.) sequence analysis software.

Testing In Vitro Activity of Apomabs

Before beginning in vivo studies with Apomabs, each lot was tested for in vitro activity as described above. These results are shown in Table 13.

TABLE 13

In vitro activity of Apomabs

| Apomab version | Fold increase in apparent affinity, relative to version 1 (v1) | Fold increase in apparent potency, with crosslinking, relative to version 1 (v1) | Apparent potency, without crosslinking, relative to version 1 (v1) |
|---|---|---|---|
| 1.1 | 11.30 | 24 | None |
| 1.2 | 52.10 | 14 | None |
| 1.3 | 13.10 | 6.5 | None |
| 2.1 | 12.80 | 5.5 | None |
| 2.2 | 9.60 | 3 | None |
| 2.3 | 29.00 | 6.5 | None |
| 3.1 | 15.00 | 14 | None |
| 3.2 | 29.20 | 22 | None |
| 3.3 | 15.00 | 8 | None |
| 4.1 | 25.70 | 11 | None |
| 4.2 | 23.10 | 6 | None |
| 4.3 | 10.30 | 12 | None |
| 5.2 | 26.90 | 22 | ~8 × up |
| 5.3 | 2.80 | 10 | ~2.4 × down |

TABLE 13-continued

In vitro activity of Apomabs

| Apomab version | Fold increase in apparent affinity, relative to version 1 (v1) | Fold increase in apparent potency, with crosslinking, relative to version 1 (v1) | Apparent potency, without crosslinking, relative to version 1 (v1) |
|---|---|---|---|
| 6.2 | 31.60 | 6 | ~2 × up |
| 6.3 | 1.50 | 4 | ~4 × down |
| 7.2 | 31.20 | 22 | ~5 × up |
| 7.3 | 4.30 | 16 | ~2 × down |
| 8.2 | 28.60 | 9 | very slight |
| 8.3 | 8.30 | 11 | ~8 × down |
| 9.1 | 21.90 | 36 | None |
| 9.2 | 29.90 | 48 | None |
| 9.3 | 10.00 | ND | None |

Example 2

Evaluation of Apomab Antitumor Activity in the Colo 205 Human Colon Carcinoma Xenograft Model and Other Xenograft Models of Colorectal Cancer Commonly used abbreviations used in this and in subsequent examples are as follows:

| | |
|---|---|
| CR | complete regression |
| PR | partial regression |
| MTD | maximum tolerated dose |
| MTV | median tumor volume |
| NTR | non-treatment related death |
| LTTFS | long-term tumor-free survivor |
| PBS | phosphate-buffered saline |
| q3d × 4 | once every three days for a total of four doses |
| qd × 1 | one dose given on Day 1 |
| qd × 5 | once daily for five days |
| TFS | tumor-free survivor |
| TR | treatment related death |
| TTE | time to endpoint |
| T – C | difference, in days, between the median TTE values of treated and control animals |
| TGD | tumor growth delay; T – C; increase in median TTE for a treatment group, compared to a control group, usually expressed as % of control. |
| Time to 2 × Vo | doubling time (DT); time during which the volume of a tumor doubles. difference between the logarithm of the actual tumor volume at the time of treatment, $\log_{10}(V_{pre})$, and $\log_{10}(V_{post})$ (Chenevert et al., Clin. Cancer Res. 3: 1457-1466 (1997). |

6-8 week old female athymic nude mice (Charles River Laboratories) were inoculated with 5 million Colo 205 cells per mouse in a 0.2 ml volume/mouse, subcutaneously, in the right dorsal flank area. All mice were ear-tagged for identification. Once the tumor volume was approximately 100-200 mm³, the Colo 205 tumor-bearing mice were randomly grouped and treatment was administered.

Treatment regimen was a single dose intraperitoneally, with doses of vehicle control, or standard and test antibodies, at 3 mg/kg/mouse or 10 mg/kg/mouse. In some instances, 3 or 4 mice were euthanized from the vehicle and 10 mg/kg groups, and serum and tumors were collected at 5 minutes, 24 hours or 48 hours post treatment for serum drug concentration and tumor histology studies. In the remaining mice, tumor measurements were taken twice a week for the first 2 weeks, then once a week for another 4 weeks.

Results obtained in the Colo 205 Xenograft Athymic Nude Mouse Model are shown in FIGS. 21-25.

Figure 21:
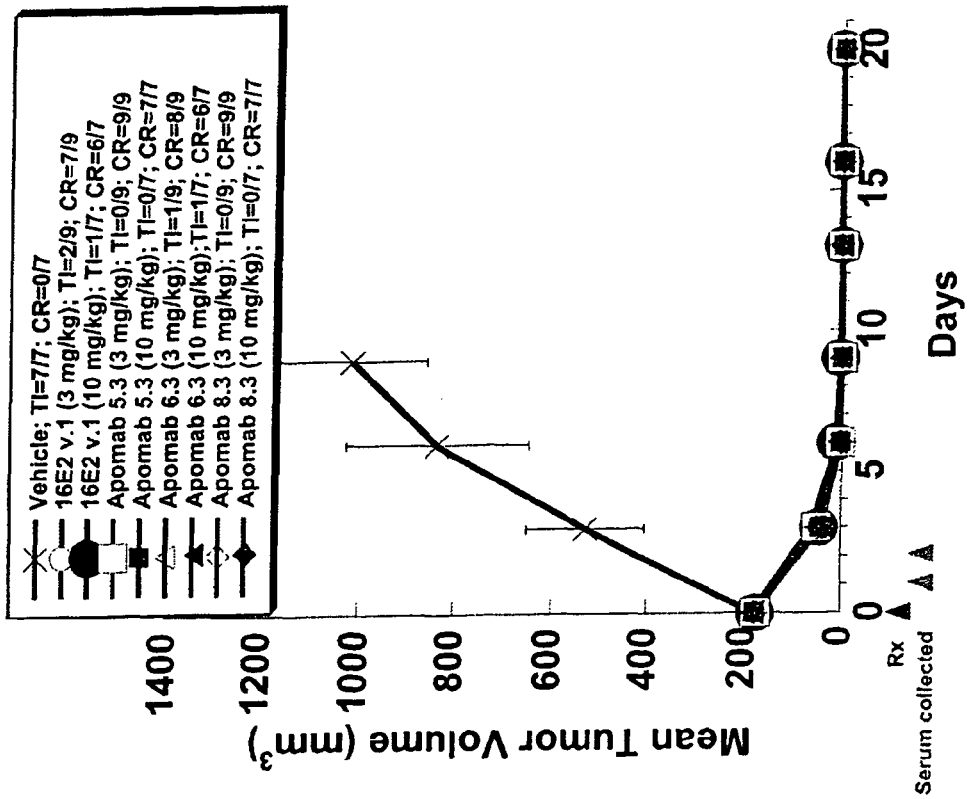
FIG. 21 shows the anticancer activity of a single intraperitoneal (IP) dose of Apomabs 5.3, 6.3 and 8.3 as compared to the full-length 16E2 (Version 1) antibody in the Colo 205 xenograft athymic nude mouse model of human colon cancer.

FIG. 21 shows that each of Apomabs 5.3, 6.3 and 8.3 was highly effective in reducing the mean tumor volume at all dosages tested, and their efficacy was essentially the same as that of antibody 16E2 version 1.

Figure 22:
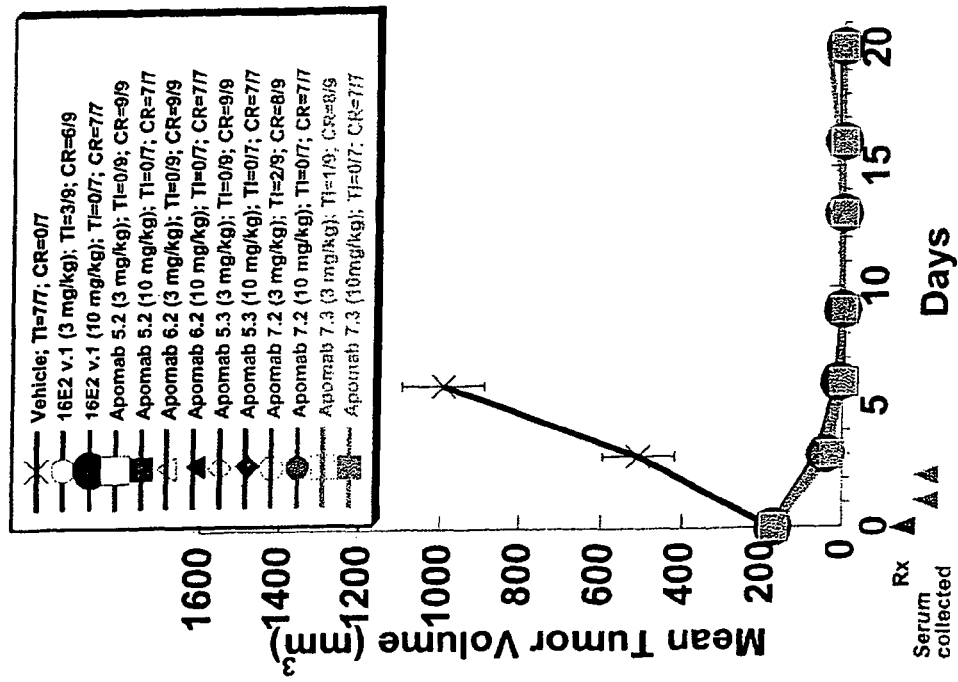
FIG. 22 shows the anticancer activity of a single IP dose of Apomabs 5.2, 6.2, 5.3, 7.2 and 7.3 compared to the full-length 16E2 (Version 1) antibody in the Colo 205 xenograft athymic nude mouse model of human colon cancer.

The efficacy of single intraperitoneal doses of Apomabs 5.2, 6.2, 5.3, 7.2 and 7.3 was tested in the Colo 205 Xenograft Athymic Nude Mouse Model, and the results are shown in FIG. 22. All Apomabs tested were highly efficient in reducing tumor volume, and their efficacy was essentially the same as that of antibody 16E2 version 1.

Figure 23:
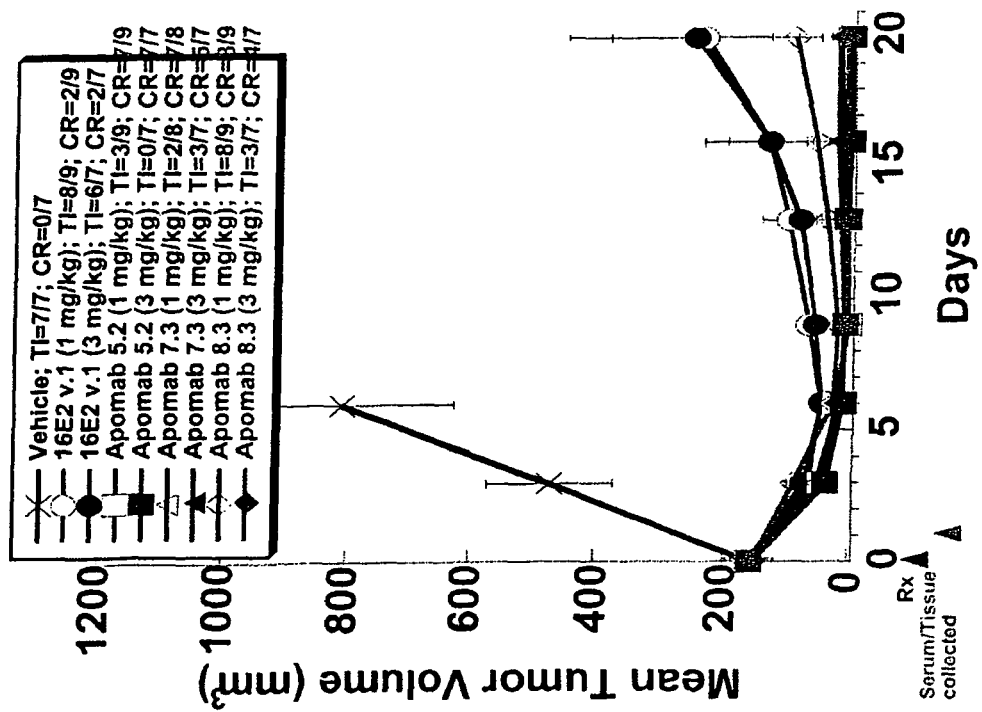
FIG. 23 shows the anticancer activity of a single IP dose of Apomabs 5.2, 7.3 and 8.3 compared to the full-length 16E2

Similarly, the results shown in FIG. 23 show that Apomabs 5.2, 7.3 and 8.3 were effective in reducing tumor volume in this model of colorectal cancer. In this experiment, Apomabs and 16E2 were administered in 1 mg/kg and 3 mg/kg doses, but otherwise treated as described above. The efficacy of Apomabs 7.3 and 8.3 is particularly remarkable, and does not show any reversal during the 20-day test period.

As shown in FIG. 24, the anticancer activity of Apomab 7.3 far exceeded the activity of Apomabs 23.3 and 25.3 in the Colo 205 xenograft model.

FIG. 25 illustrates the results of an assay comparing the antitumor activity of Apomab 7.3 derived from stable and transient cell lines in the Colo 205 mouse xenograft model. In brief, female athymic nude mice, 6-8 weeks of age, were inoculated with 5 million Colo 205 cells/mouse in a 0.2 ml volume/mouse, subcutaneously in the right dorsal flank area, as described above. The dosages are shown in the figure. The data in FIG. 25 shows that Apomab 7.3 derived from stable and transient cell lines, respectively, is equally effective in the Colo 205 mouse xenograft model.

FIG. 26 shows the result of an experiment testing the anti-cancer activity of Apomab 7.3 (10 mg/kg dose) as monotherapy or as combination therapy with 80 mg/kg CPT-11 (irinotecan, a known drug for the treatment of colorectal cancer) in an HCT15 xenograft model of colorectal cancer. As attested by the result shown, while both Apomab 7.3 and CPT-11 were effective when administered alone, the combination of the two showed a superior effect, exceeding the activity of both Apomab 7.3 and CPT-11 administered as monotherapy.

The results of a representative experiment in nude mice bearing sarcoma LS180 xenografts, treated with Apomab 7.3 in combination with CPT-11 (irinotecan) are shown in FIG. 27. Again, combination therapy has been found superior relative to administering either Apomab 7.3 or CPT-11 as a single agent, and the difference was statistically significant (second panel). Tukey-Kramer P<0.05 for all pairs compared.

Example 3

Evaluation of Apomab 7.3 Anticancer Activity in the BJAB Xenograft Model of Non-Hodgkin's Lymphoma The anticancer activity of Apomab 7.3 (10 mg/kg q1 wk) alone and in combination with RITUXAN® (rituximab, Genentech. Inc.) (4 mg/kg, q1 wk) was assessed in a BJAB xenograft model of non-Hodgkin's lymphoma. Since lymphoma cells are known to grow better in SCID mice, 6-8 weeks old SCID mice (Charles River Laboratory) were used in this study. The treatment parameters and results are shown in FIG. 28. Apomab 7.3 and RITUXAN®, when administered as a combination, showed synergistic activity.

Example 4

Evaluation of Apomab 7.3 Anticancer Activity in the BxPC3 Xenograft Model of Human Pancreatic Adenocarcinoma The anticancer activity of Apomab 7.3 (10 mg/kg, i.v.) alone and in combination with gemcitabine (160 mg/kg, ip) in a BxPC3 xenograft model of human pancreatic adenocarcinoma in female athymic nude mice (Charles River Laboratory) was investigated. The treatment parameters and results are shown in FIG. 29. The data show that the anticancer activity of Apomab 7.3 administered as monotherapy was far superior to the efficacy of gemcitabine. Combined administration of Apomab 7.3 and gemcitabine resulted in additional improvement in efficacy.

Example 5

Evaluation of Apomab 7.3 Anticancer Activity Alone and in Combination with Carboplatin and Taxol in the H460 Xenograft Model of Human Lung Cancer The anticancer activity of Apomab 7.3 (10 mg/kg, 1× wk, IP) alone and in combination with carboplatin and taxol was assessed relative to a vehicle control and to the combination of carboplatin and taxol. Sixty female athymic nude mice (Charles River Laboratory) were inoculated with 5 million H460 cells/mouse in a 0.2 volume/mouse subcutaneously in the right dorsal flank area. All mice were ear tagged for identification. Tumors were allowed to reach a mean tumor volume of 100-200 $mm^3$ and treated as shown in FIG. 30. In brief, the mice were divided in four groups. Group 1 was a vehicle-treated control group (10 mM histidine, 8% sucrose and 0.02% Tween 20 (pH 6)). Group 2 was treated with Apomab 7.3 in a 10 mg/kg/mouse dose, IP, 1x/week for 2 weeks. Group 3 was administered carboplatin (100 mg/kg/mouse, IP, a single dose on Day 0)+taxol (6.25 mg/kg/mouse, s.c., daily for 5 consecutive days for 2 weeks). Group 4 received Apomab 7.3 (10 mg/kg/mouse dose, IP, 1×/week for 2 weeks)+carboplatin (100 mg/kg/mouse, IP, a single dose on Day 0)+taxol (6.25 mg/kg/mouse, s.c., daily for 5 consecutive days for 2 weeks). The anticancer activity of Apomab 7.3 administered as monotherapy was comparable to that of the carboplatin+taxol combination. Combined administration of Apomab 7.3+carboplatin+taxol was found to be superior when compared to the other treatment modalities.

Example 6

Evaluation of Apomab 7.3 Anticancer Activity Alone and in Combination with Carboplatin and Taxol in the H2122 Xenograft Model of Human Lung Cancer In this study, female athymic nude mice (Charles River Laboratory, 10 mice/group) were inoculated with 5 million H2122 cells/mouse in a 0.2 ml volume/mouse, subcutaneously, in the right dorsal flank area. All mice were ear tagged for identification. Tumors were allowed to reach a mean tumor volume of 100-200 $mm^3$, randomly grouped in four groups (6 mice/group), and treated as shown in FIG. 31. Group 1 was a vehicle-treated control group (10 mM histidine, 8% sucrose and 0.02% Tween 20 (pH 6)). Group 2 was administered carboplatin (100 mg/kg/mouse, IP, a single dose on Day 0)+taxol (6.25 mg/kg/mouse, s.c., daily for 5 consecutive days for 2 weeks). Group 3 received Apomab 7.3 (10 mg/kg/mouse dose, IP, 1×/week for 2 weeks). Group 4 received Apomab 7.3 (10 mg/kg/mouse dose, IP, 1×/week for 2 weeks)+carboplatin (100 mg/kg/mouse, IP, a single dose on Day 0)+taxol (6.25 mg/kg/mouse, s.c., daily for 5 consecutive days for 2 weeks). As shown in FIG. 31, the combination of carboplatin+taxol did not show significant anticancer activity relative to the vehicle-treated control group. In stark contrast, Apomab 7.3 administered as monotherapy showed remarkable antitumor activity. All six mice treated with Apomab 7.3 showed a complete response (CR) without any reversal during the 70-day treatment period. The same activity was found in the group treated with the Apomab 7.3+carboplatin+taxol combination.

To determine the maximum effective dose of Apomab 7.3 in this model, female athymic nude mice (Charles River Laboratory), 6-8 weeks of age, were inoculated with 5 million H2122 cells/mouse in a 0.2 ml volume/mouse, subcutaneously in the right dorsal flank area. All mice were ear tagged for identification. Tumors were allowed to reach a mean tumor volume of 100-200 $mm^3$ and randomly grouped (13 mice/group) and treated as described below. Any mice excluded from the treatment groups were euthanized.

Group A was a vehicle-treated control group (0.5 M arginine succinate, 20 mM Tris, 0.02% Tween 20, pH 7.2). Vehicle was administered 5×/week, IP for one week. Group B was administered Apomab 7.3 in a 1 mg/kg/mouse single IV dose. Group C was administered Apomab 7.3 in a 3 mg/kg/mouse single IV dose. Group D was administered Apomab 7.3 in a 10 mg/kg/mouse single IV dose. 48 hours following the first treatment, three mice from each of Groups B, C and D were euthanized, and their tumors were collected as follows. One tumor was preserved in 10% formalin for histology study. One tumor was frozen in liquid nitrogen for RNA studies. One tumor was frozen in liquid nitrogen for Western blot. Tumor measurements were taken 2×/week for the first 2 weeks then 1x/week for the next 4 weeks. At the end of 6 weeks or until tumors reached an approximate volume of 800-1000 $mm^3$, all remaining mice were euthanized. The dose-response curves shown in FIG. 32, first panel, indicate that Apomab 7.3 was efficacious in all doses tested, but the 3 mg/kg and 10 mg/kg doses showed a distinct (although not statistically significant) improvement relative to the 1 mg/kg dose. Tukey-Kramer $P<0.05$ for all pairs compared (see, FIG. 32, second panel).

Example 7

Evaluation of Anticancer Activity of Apomabs 23.3, 25.3 and 7.3 in the Colo 205 Xenograft Model of Human Colorectal Cancer In this study, female athymic nude mice (Charles River Laboratory) were inoculated with 5 million Colo 205 cells/mouse in a 0.2 ml volume/mouse, subcutaneously, in the right dorsal flank area. All mice were ear tagged for identification. Tumors were allowed to reach a mean tumor volume of 100-200 $mm^3$, randomly grouped in seven groups (10 mice/group), and treated as shown in FIG. 33. Group 1 was a vehicle-treated control group (10 mM histidine, 8% sucrose and 0.02% Tween 20 (pH 6)). Group 2 was administered a single 3 mg/kg/mouse i.v. dose of Apomab 7.3. Group 3 was administered a single 10 mg/kg/mouse i.v. dose of Apomab 7.3. Group 4 was administered a single 3 mg/kg/mouse i.v. dose of Apomab 23.3. Group 5 was administered a single 10 mg/mg/mouse i.v. dose of Apomab 23.3. Group 6 was administered a single 3 mg/kg/mouse i.v. dose of Apomab 25.3. Group 7 was administered a single 10 mg/kg/mouse i.v. dose of Apomab 25.3. 24 hours post treatment all mice were weighed. Tumors were measured 2×/week for the first 2 weeks and then weekly for the next 4 weeks. After 6 weeks or when the tumors reached a size of >1000 mm³, the mice were sacrificed.

The results are shown in FIG. 33. As illustrated by the 25-day data, both Apomab 7.3 and Apomab 25.3 showed significant anticancer activity in this model.

Example 8

Evaluation of the Anti-Cancer Activity of Monoclonal Antibody Apomab 7.3 Against Colo 205 Human Colon Carcinoma Xenografts in Nude Mice Animals Female athymic nude mice (nu/nu, Harlan) were 11 or 12 weeks old on Day 1 of the study. The animals were fed ad libitum water and NIH 31 Modified and Irradiated Lab Diet® consisting of 18.0% crude protein, 5.0% crude fat, and 5.0% crude fiber. The mice were housed on irradiated ALPHA-Dri® Bed-O'Cobs® Laboratory Animal Bedding in static microisolators on a 12-hour light cycle at 21-22° C. and 40-60% humidity.

Tumor Implantation

Xenografts were initiated from cultured Colo 205 human colon carcinoma cells. The tumor cells were growth to mid-log phase in RPMI-1640 supplemented with 10% heat-inactivated fetal bovine serum, 100 units/mL penicillin G sodium, 100 µg/mL streptomycin sulfate, 0.25 µg/mL amphotericin B, and 25 µg/mL gentamicin, 2 mM glutamine, 1 mM sodium pyruvate, 10 mM HEPES and 0.075% sodium bicarbonate. Cell cultures were maintained in tissue culture flasks in a humidified incubator at 37° C., in an atmosphere of 5% $CO_2$ and 95% air. On the day of tumor cell implant, Colo 205 cells were harvested and resuspended in 50% Matrigel matrix (BD Biosciences) in PBS at a concentration of $5\times10^6$ cells/mL. Each test mouse received $1\times10^6$ Colo 205 cells implanted subcutaneously in the right flank, and tumor growth was monitored as the average size approached 100 to 300 mm³. Thirteen days later, designated as Day 1 of the study, individual tumor volumes ranged from 126 to 288 mm³, and the animals were sorted into six groups each consisting of ten mice with mean tumor volumes of 188 mm³.

Test Materials and Treatment

The test materials were kept on ice during dosing, and dosing solutions were subsequently stored at 4° C. In the vehicle control group (Group 1), mice received vehicle administered intraperitoneally once daily for five days, followed by two day rest, then once daily for an additional five days. In the test groups (Groups 24) animals were treated with Apo2L.0 ligand (60 mg/kg i.p. on a 5/2/5 schedule), Apomab 7.3 (3 mg/kg i.v. Days 1, 8), and an anti-VEGF murine monoclonal antibody B20-4.1 (10 mg/kg i.p. Days 1 and 8). Groups 5 and 6 received the combination of B20-4.1 with Apo2L.0 and B20-4.1 with Apomab 7.3, respectively. Each dose was delivered in a volume of 0.2 mL per 20 g body weight (10 mL/kg), scaled to the body weight of the animal.

Endpoint

Tumors were measured twice weekly using calipers. Each animal was euthanized when its tumor reached a volume of 2000 mm³ or at the conclusion of the study on Day 68, whichever came first. An endpoint tumor volume of 1000 mm³ was selected for analysis of tumor growth delay, due to the number of tumors that did not attain the 2000 mm³ size. The time to endpoint (TTE) for each mouse was calculated from the following equation:

TTE (days)=log 10(endpoint volume, mm³)−$b/M$

Where b is the intercept and m is the slope of the line obtained by linear regression of a log-transformed tumor growth data set. The data set was comprised of the first observation that exceeded the study endpoint volume and the three consecutive observations that immediately preceded the attainment of the endpoint volume. Animals that did not reach the endpoint were assigned a TTE value equal to the last date of the study. Animals suffering treatment-related death or non-treatment related death due to metastasis were assigned a TTE value equal to the day of death. Animals suffering non-treatment related death or death of unknown causes were excluded from the TTE calculations.

Treatment outcome was evaluated by tumor growth delay (TGD), which is defined as the increase in the median time to endpoint (TTE) in the treatment group compared to the control group:

TGD=$T-C$, expressed in days, or as a percentage of the median TTE of the control group $$\% TGD = \frac{T - C}{C} \times 100$$

where:
T=median TTE for the treatment group,
C=median TTE for the control group.

Treatment may cause partial regression (PR) or complete regression (CR) of tumor in an animal. In a PR response, the tumor volume is 50% or less of its Day 1 volume for three consecutive measurements during the course of the study, and equal to or greater than 13.5 mm³ for one or more of these three measurements. In a CR response, the tumor volume is less than 13.5 mm³ for one or more of these three measurements during the course of the study. An animal with a CR response at the termination of the study is additionally classified as a tumor-free survivor (TFS). Regression responses were monitored and recorded.

Sampling

Tumor samples were taken at endpoint from animals in each group. These animals were euthanized by cervical dislocation just prior to sampling. The tumors of three animals per group were harvested, bisected, and preserved in 10% neutral buffered formalin for 12 to 24 hours at room temperature.

Statistical and Graphical Analyses

The Logrank test was use to analyze the significance of the differences between the TTE values of treated and control groups. Two-tailed statistical analyses were conducted at significance level P=0.05, with results deemed significant at $0.01 \leq P \leq 0.05$, and highly significant at P<0.01.

Median tumor growth curves show group median tumor volumes as a function of time. When an animal exited the study due to tumor size, the final tumor volume recorded for the animal was included with the data used to calculate the group median tumor volume at subsequent time points. Kaplan-Meier plots were constructed to show the percentage of animals remaining in the study as a function of time. These plots used the same data set as the Logrank test.

Results

FIG. 34 shows the group median tumor growth curves (upper panel) and the Kaplan-Meier plots (lower panel) for each group in this study. The median TTE of vehicle-treated control mice was 10.0 days, with one tumor (of ten) that did not attain the 1000 mm³ endpoint tumor volume. B20-4.1 administered at 10 mg/kg i.p. on Days 1 and 8 produced a modest 19.9-day (113%) TGD that was not statistically significant. Apo2L.0 and Apomab 7.3 monotherapies were efficacious against Colo 205, producing tumor growth delays of 28.4 days (190%) and 53.0 days (355%), respectively. The addition of B20-4.1 to either Apo2L.0 or Apomab 7.3 did not improve the efficacy of treatment with respect to TGD or regression responses.

Example 9

Evaluation of the Anti-Cancer Activity of Monoclonal Antibody Apomab 7.3 as Monotherapy and in Combination with Carboplatin Plus Paclitaxel Against SKMES-1 Human NSCLC The in vivo antitumor activities of the Apo2L.0 ligand and Apomab 7.3, as monotherapies, and in combination with carboplatin plus paclitaxel against SKMES-1 human NSCLC were tested.

Animals

Female athymic nude mice (nu/nu, Harlan) were 9 to 10 weeks old and had body weights ranging from 17.4 to 25.4 g on Day 1 of the study. The animals were fed ad libitum water and NIH 31 Modified and Irradiated Lab Diet® consisting of 18.0% crude protein, 5.0% crude fat, and 5.0% crude fiber. The mice were housed on irradiated ALPHA-Dri® Bed-O'Cobs® Laboratory Animal Bedding in static microisolators on a 12-hour light cycle at 21-22° C. and 40-60% humidity.

Tumor Implantation

Xenografts were initiated from SKMES-1 lung tumors maintained by serial transplantation at PRC. Each test mouse received a 1 $mm^3$ SKMES-1 tumor fragment implanted subcutaneously in the right flank, and tumor growth was monitored. Thirteen days later, designated as Day 1 of the study, individual tumor volumes ranged from 63 to 144 $mm^3$, and the animals were sorted into four groups each consisting of ten mice and two groups each consisting of nine mice. Mean tumor volumes were 93 to 95

Test Materials and Treatment

All test materials were provided ready to dose at 0.1 mL per 20 g body weight (5 mL/kg), and were stored at −80° C. upon receipt. The test materials were thawed on the first day of dosing, kept on ice during dosing, then subsequently stored at 4° C. Carboplatin (PARAPLATIN® injection, Bristol Myers Squibb) was diluted with 5% dextrose in water (D5W) to yield the desired dose in a volume of 0.2 mL per 10 g body weight (10 mL/kg). Paclitaxel (Natural Pharmaceuticals, Inc.) was diluted with D5W on each day of dosing from a 10× stock solution to yield a vehicle consisting of 5% ethanol and 5% Cremophor EL in 90% D5W (5% EC vehicle), so that the desired dose was delivered in 0.1 mL per 20 g body weight.

Group 1 (vehicle control) mice received vehicle administered intraperitoneally once daily for five days (i.p. qd×5), and served as tumor growth controls. Mice in Groups 2 and 3 received monotherapy with Apo2L.0 (60 mg/kg s.c. qd×5) and Apomab 7.3 (10 mg/kg i.v. qd×1), respectively. Mice in Group 4 received the combination of carboplatin (100 mg/kg i.p. qd×1) plus paclitaxel (6.25 mg/kg s.c. qd×5). Mice in Groups 5 and 6 received carboplatin plus paclitaxel in combination with Apo2L or Apomab 7.3, respectively. Each dose was administered in the volume indicated in the previous section, and was scaled to the body weight of the animal.

Endpoint, Sampling and Statistical Analyses

Endpoint was determined, and sampling and statistical analyses performed as described in previous Example 8.

Results

FIGS. 35 and 36 show the group median tumor growth curves and Kaplan-Meier plots for groups treated with Apo2L.0 and Apomab 7.3, respectively.

The tumors of all vehicle-treated control mice grew to be 1500 $mm^3$ endpoint volume with a median TTE of 18.9 days. Therefore, the maximum TGD achievable in this 45-day study was 26.1 days (138%). The median tumor growth curve and Kaplan-Meier plot for the control group are included in the upper and lower panels of FIGS. 35 and 36.

For the Apo2L.0 treated group (Group 2), the median TTE was 22.9 days, and corresponded to a 4.0-day (21%) TGD and statistically non-significant activity. FIG. 28 (upper panel) indicates that median tumor volumes in Group 2 shrank during the treatment period, then rapid tumor growth returned.

The median TTE of Group 3 was 2.0 days, and corresponding to a 7.1-day (38%) TGD and highly statistically significant activity (P=0.005). No regression responses were documented, and all tumors attained the 1500 $mm^3$ endpoint volume. The Group 3 median tumor growth curve suggests an initial delay in tumor growth relative to controls.

The median TTE of Group 4 mice treated with carboplatin plus paclitaxel was 26.5 days, and corresponded to a 7.6-day (40%) TGF and statistically significant activity (P=0.01). All Group 4 tumors grew to the 1500 $mm^3$ endpoint volume and no regression responses were documented. The median tumor growth curve for Group 4 mice indicates a modest delay in tumor growth relative to control mice (see FIGS. 35 and 36, upper panels).

Treatment with the triple combination of Apo2L.0, carboplatin and paclitaxel produced a median TTE of 32.7 days, corresponding to a 13.9-day (73%) TGD and highly significant activity relative to Group 1 (P=0.002). The 32.7-day median TTE with this triple combination was longer than the 22.9-day median TTE of Apo2L.0 monotherapy group or the 16.5-day median TTE of the chemotherapy control treatment, but the differences did not achieve statistical significance by Logrank analysis. Despite the lack of statistical significance, the median tumor growth curves indicated greater activity with the Group 5 combination compared to either the Apo2L.0 monotherapy or carboplatin plus paclitaxel chemotherapy (see FIG. 28, upper panel).

Treatment with the triple combination of Apomab 7.3 (Group 6), carboplatin and paclitaxel resulted in 3/10 TR death, therefore, this group was not evaluable for TGD. However, the median tumor growth curves indicated greater activity with the Group 6 combination compared to either the Apomab 7.3 monotherapy or the carboplatin plus paclitaxel chemotherapy (see, FIG. 37, upper panel).

Conclusion

Despite the relatively high mortality in this experiment, the data suggest that either of Apo2L.0 and Apomab 7.3 may add antitumor benefit to treatment with carboplatin and paclitaxel.

Example 10

Evaluation of the Anti-Cancer Activity of Monoclonal Antibody Apomab 7.3 as Monotherapy and in Combination with an Anti-VEGF Antibody in the Human Colo 205 Carcinoma Xenograft Model Animals Female athymic nude mice (nu/nu, Harlan) were 7-8 weeks old on Day 1 of the study. The animals were fed ad libitum water and NIH 31 Modified and Irradiated Lab Diets consisting of 18.0% crude protein, 5.0% crude fat, and 5.0% crude fiber. The mice were housed on irradiated ALPHA-Dri® Bed-O'Cobs® Laboratory Animal Bedding in static microisolators on a 12-hour light cycle at 21-22° C. and 40-60% humidity.

Tumor Cell Culture

Human Colo 205 colon carcinoma cells were cultured in RPMI 1640 medium containing 100 units/mL penicillin G sodium, 100 µg/mL streptomycin sulfate, 0.25 µg/mL amphotericin B, and 25 µg/mL gentamicin. The medium was supplemented with 10% heat-inactivated fetal bovine serum, 2 mM glutamine, and 1 mM sodium bicarbonate. The tumor cells were cultured in tissue culture flasks in a humidified incubator at 37° C., in an atmosphere of 5% $CO_2$ and 95% air.

In Vivo Implantation

The human Colo 205 carcinoma cells used for implantation were harvested during log phase growth and resuspended in 50% matrigel at $5 \times 10^6$ cells/mL. Each mouse was injected s.c. in the right flank with $1 \times 10^6$ cells (0.2 mL cell suspension). Tumors were monitored twice weekly and then daily as their volumes approached 100-300 $mm^3$. On Day 1 of the study, animals were sorted into treatment groups with tumor sizes of 108.0-220.5 $mm^3$ and a group mean tumor size of 149.8 $mm^3$. Tumor weight may be estimated with the assumption that 1 mg is equivalent to 1 $mm^3$ of tumor volume.

Test Materials and Treatment

The test materials were provided ready for dosing. The dosing solutions were stored at 4° C.

Mice were sorted into six groups with ten mice per group. All treatments were administered intraperitoneally (i.p.). Apo2L.0 and its vehicle were each administered once daily on Days 1-5 (qd×5). Apomab 7.3 and murine anti-VEGF antibody anti-G6 were each given once on Day 1 (qd×1). Control Group 1 mice were treated with the vehicle for Apo2L.0. Group 2 received Apo2L.0 monotherapy at 60 mg/kg. Group 3 received Apomab 7.3 monotherapy at 3 mg/kg. Group 4 received BY4 monotherapy at 5 mg/kg. Groups 5 and 6 received Apo2L.0 at 60 mg/kg and Apomab 7.3 at 3 mg/kg, respectively, each in combination with anti-G6 at 5 mg/kg. In all groups, the dosing volume of 0.2 ml/20 g mouse was scaled to the body weight of each animal.

Endpoint, Sampling and Statistical Analyses

Endpoint was determined, and sampling and statistical analyses performed as described in previous Example 8.

Results

The results are shown in FIG. 37, where the curves in the upper panel show group median tumor volumes, versus time the Kaplan-Meier plot in the lower panel shows the percentage of evaluable animals remaining in each group, versus time.

Control Group 1 mice received Apo2L.0 vehicle, and served as the control for all treatment groups. Tumors in all ten mice grew to the 1500 $mm^3$ endpoint volume with a median TTE of 20.8 days. Therefore, the maximum possible TGD in this 61-day study was 193%.

Group 2 received Apo2L.0 monotherapy at 60 mg/kg. This treatment produced highly significant anti-tumor activity relative to the vehicle control group ($P<0.001$), and a median TTE of 53.6 days. This median TTE corresponds to a 32.8-day T-C and 158% TGD. The median tumor volume on Day 61 for five mice was 1,210 $mm^3$. One LTTFS was recorded.

Group 3 received Apomab 7.3 monotherapy at 3 mg/kg. This treatment produced highly significant activity ($P<0.001$), with the maximum possible 193% TGD and an MTV(6) of 776 $mm^3$. One LTTFS, one transient CR response, and three FR responses were recorded.

Group 4 received anti-G6 monotherapy at 5 mg/kg. This treatment produced highly significant activity ($P<0.01$), with 86% TGF and an MTV(3) of 1,224 $mm^3$. No regression responses were recorded.

Group 5 received Apo2L.0 at 60 mg/kg, in combination with anti-G6 at 5 mg/kg. The combination treatment produced 138% TGD. Antitumor activity was highly significant relative to the vehicle treatment ($P<0.001$), but insignificant relative to both monotherapies. In Group 5, the MTV(3) was 1,080 $mm^3$, and one PR response was recorded.

Group 6 received combination treatment with Apomab 7.3 at 3 mg/kg and anti-G6 at 5 mg/kg. This treatment produced the maximum possible 193% TGD. Antitumor activity was highly significant relative to the vehicle treatment ($P<0.001$), significant relative to anti-G6 monotherapy, but insignificant relative to Apomab 7.3 monotherapy. In Group 6, the MTV(8) was 208 $mm^3$, and five PR responses were recorded.

Conclusions

Tumors responded strongly to monotherapy with 3 mg/kg qd×1 Apomab 7.3 (Group 3). This treatment produced highly significant activity relative to the vehicle control group, and the maximum possible 193% TGD. Among six mice that survived to Day 61 with an MTV of 776 $mm^3$, five animals experienced tumor regression. This monotherapy yielded one LTTFS, one transient CR response, and three PR responses. The median tumor volume did not increase until after Day 15 (FIG. 37).

Combination therapy with Apomab 7.3 and murine anti-VEGF antibody anti-G6 yielded stronger activity than observed with either Apomab 7.3 or anti-G6 alone. This combination treatment yielded eight 61-day survivors, and generated the study's lowest MTV, 208 $mm^3$. The median tumor growth curve shows tumor reduction or stasis until Day 33, followed by very slow tumor growth (FIG. 37). The combination produced significantly stronger activity than the anti-G6 monotherapy, but did not differ significantly from the results of the Apomab 7.3 monotherapy. In addition, the combination yielded five PR responses, whereas the five regression responses obtained with Apomab 7.3 monotherapy include one transient CR and one LTTFS.

All therapies were well tolerated. No body weight loss or other overt toxicity was observed in the study.

In summary, the Apomab 7.3/anti-G6 combination therapy produced more 61-day survivors and a lower MTV than treatment with either of the corresponding monotherapies. The Apomab 7.3/anti-G6 combination did not, however, produce curative activity, which was observed with Apomab 7.3 monotherapy.

SEQUENCE LISTING

<160> NUMBER OF SEQ ID NOS: 29

<210> SEQ ID NO 1
<211> LENGTH: 281
<212> TYPE: PRT

<213> ORGANISM: Homo sapiens

<400> SEQUENCE: 1

```
Met Ala Met Met Glu Val Gln Gly Gly Pro Ser Leu Gly Gln Thr Cys
1               5                   10                  15
Val Leu Ile Val Ile Phe Thr Val Leu Leu Gln Ser Leu Cys Val Ala
            20                  25                  30
Val Thr Tyr Val Tyr Phe Thr Asn Glu Leu Lys Gln Met Gln Asp Lys
        35                  40                  45
Tyr Ser Lys Ser Gly Ile Ala Cys Phe Leu Lys Glu Asp Asp Ser Tyr
    50                  55                  60
Trp Asp Pro Asn Asp Glu Glu Ser Met Asn Ser Pro Cys Trp Gln Val
65                  70                  75                  80
Lys Trp Gln Leu Arg Gln Leu Val Arg Lys Met Ile Leu Arg Thr Ser
                85                  90                  95
Glu Glu Thr Ile Ser Thr Val Gln Glu Lys Gln Gln Asn Ile Ser Pro
            100                 105                 110
Leu Val Arg Glu Arg Gly Pro Gln Arg Val Ala Ala His Ile Thr Gly
        115                 120                 125
Thr Arg Gly Arg Ser Asn Thr Leu Ser Ser Pro Asn Ser Lys Asn Glu
130                 135                 140
Lys Ala Leu Gly Arg Lys Ile Asn Ser Trp Glu Ser Ser Arg Ser Gly
145                 150                 155                 160
His Ser Phe Leu Ser Asn Leu His Leu Arg Asn Gly Glu Leu Val Ile
                165                 170                 175
His Glu Lys Gly Phe Tyr Tyr Ile Tyr Ser Gln Thr Tyr Phe Arg Phe
            180                 185                 190
Gln Glu Glu Ile Lys Glu Asn Thr Lys Asn Asp Lys Gln Met Val Gln
        195                 200                 205
Tyr Ile Tyr Lys Tyr Thr Ser Tyr Pro Asp Pro Ile Leu Leu Met Lys
    210                 215                 220
Ser Ala Arg Asn Ser Cys Trp Ser Lys Asp Ala Glu Tyr Gly Leu Tyr
225                 230                 235                 240
Ser Ile Tyr Gln Gly Gly Ile Phe Glu Leu Lys Glu Asn Asp Arg Ile
                245                 250                 255
Phe Val Ser Val Thr Asn Glu His Leu Ile Asp Met Asp His Glu Ala
            260                 265                 270
Ser Phe Phe Gly Ala Phe Leu Val Gly
        275                 280
```

<210> SEQ ID NO 2
<211> LENGTH: 1042
<212> TYPE: DNA
<213> ORGANISM: Homo sapiens
<220> FEATURE:
<221> NAME/KEY: misc_feature
<222> LOCATION: 447
<223> OTHER INFORMATION: n = t or g

<400> SEQUENCE: 2

```
tttcctcact gactataaaa gaatagagaa ggaagggctt cagtgaccgg ctgcctggct      60
gacttacagc agtcagactc tgacaggatc atggctatga tggaggtcca gggggggccc     120
agcctgggac agacctgcgt gctgatcgtg atcttcacag tgctcctgca gtctctctgt     180
gtggctgtaa cttacgtgta ctttaccaac gagctgaagc agatgcagga caagtactcc     240
aaaagtggca ttgcttgttt cttaaaagaa gatgacagtt attgggaccc caatgacgaa     300
```

```
gagagtatga acagccctg ctggcaagtc aagtggcaac tccgtcagct cgttagaaag    360
atgattttga gaacctctga ggaaaccatt tctacagttc aagaaaagca acaaaatatt    420
tctccctag tgagagaaag aggtccncag agagtagcag ctcacataac tgggaccaga    480
ggaagaagca acacattgtc ttctccaaac tccaagaatg aaaaggctct gggccgcaaa    540
ataaactcct gggaatcatc aaggagtggg cattcattcc tgagcaactt gcacttgagg    600
aatggtgaac tggtcatcca tgaaaaaggg ttttactaca tctattccca aacatacttt    660
cgatttcagg aggaaataaa agaaaacaca aagaacgaca acaaatggt ccaatatatt    720
tacaaataca caagttatcc tgaccctata ttgttgatga aaagtgctag aaatagttgt    780
tggtctaaag atgcagaata tggactctat tccatctatc aagggggaat atttgagctt    840
aaggaaaatg acagaatttt tgtttctgta acaaatgagc acttgataga catgaccat    900
gaagccagtt ttttcggggc ctttttagtt ggctaactga cctggaaaga aaagcaata    960
acctcaaagt gactattcag ttttcaggat gatacactat gaagatgttt caaaaatct   1020
gaccaaaaca aacaaacaga aa                                            1042

<210> SEQ ID NO 3
<211> LENGTH: 468
<212> TYPE: PRT
<213> ORGANISM: Homo sapiens

<400> SEQUENCE: 3

Met Ala Pro Pro Ala Arg Val His Leu Gly Ala Phe Leu Ala Val
 1               5                  10                  15

Thr Pro Asn Pro Gly Ser Ala Ala Ser Gly Thr Glu Ala Ala Ala
            20                  25                  30

Thr Pro Ser Lys Val Trp Gly Ser Ala Gly Arg Ile Glu Pro Arg
        35                  40                  45

Gly Gly Gly Arg Gly Ala Leu Pro Thr Ser Met Gly Gln His Gly Pro
    50                  55                  60

Ser Ala Arg Ala Arg Ala Gly Arg Ala Pro Gly Pro Arg Pro Ala Arg
65                  70                  75                  80

Glu Ala Ser Pro Arg Leu Arg Val His Lys Thr Phe Lys Phe Val Val
                85                  90                  95

Val Gly Val Leu Leu Gln Val Val Pro Ser Ser Ala Ala Thr Ile Lys
            100                 105                 110

Leu His Asp Gln Ser Ile Gly Thr Gln Gln Trp Glu His Ser Pro Leu
        115                 120                 125

Gly Glu Leu Cys Pro Pro Gly Ser His Arg Ser Glu Arg Pro Gly Ala
    130                 135                 140

Cys Asn Arg Cys Thr Glu Gly Val Gly Tyr Thr Asn Ala Ser Asn Asn
145                 150                 155                 160

Leu Phe Ala Cys Leu Pro Cys Thr Ala Cys Lys Ser Asp Glu Glu
                165                 170                 175

Arg Ser Pro Cys Thr Thr Thr Arg Asn Thr Ala Cys Gln Cys Lys Pro
            180                 185                 190

Gly Thr Phe Arg Asn Asp Asn Ser Ala Glu Met Cys Arg Lys Cys Ser
        195                 200                 205

Thr Gly Cys Pro Arg Gly Met Val Lys Val Lys Asp Cys Thr Pro Trp
    210                 215                 220

Ser Asp Ile Glu Cys Val His Lys Glu Ser Gly Asn Gly His Asn Ile
225                 230                 235                 240

Trp Val Ile Leu Val Val Thr Leu Val Val Pro Leu Leu Leu Val Ala
```

```
                245                 250                 255
Val Leu Ile Val Cys Cys Cys Ile Gly Ser Gly Cys Gly Gly Asp Pro
            260                 265                 270

Lys Cys Met Asp Arg Val Cys Phe Trp Arg Leu Gly Leu Leu Arg Gly
        275                 280                 285

Pro Gly Ala Glu Asp Asn Ala His Asn Glu Ile Leu Ser Asn Ala Asp
    290                 295                 300

Ser Leu Ser Thr Phe Val Ser Glu Gln Gln Met Glu Ser Gln Glu Pro
305                 310                 315                 320

Ala Asp Leu Thr Gly Val Thr Val Gln Ser Pro Gly Glu Ala Gln Cys
                325                 330                 335

Leu Leu Gly Pro Ala Glu Ala Glu Gly Ser Gln Arg Arg Arg Leu Leu
            340                 345                 350

Val Pro Ala Asn Gly Ala Asp Pro Thr Glu Thr Leu Met Leu Phe Phe
        355                 360                 365

Asp Lys Phe Ala Asn Ile Val Pro Phe Asp Ser Trp Asp Gln Leu Met
    370                 375                 380

Arg Gln Leu Asp Leu Thr Lys Asn Glu Ile Asp Val Val Arg Ala Gly
385                 390                 395                 400

Thr Ala Gly Pro Gly Asp Ala Leu Tyr Ala Met Leu Met Lys Trp Val
                405                 410                 415

Asn Lys Thr Gly Arg Asn Ala Ser Ile His Thr Leu Leu Asp Ala Leu
            420                 425                 430

Glu Arg Met Glu Glu Arg His Ala Lys Glu Lys Ile Gln Asp Leu Leu
        435                 440                 445

Val Asp Ser Gly Lys Phe Ile Tyr Leu Glu Asp Gly Thr Phe Ser Ala
    450                 455                 460

Val Ser Leu Glu
465

<210> SEQ ID NO 4
<211> LENGTH: 2152
<212> TYPE: DNA
<213> ORGANISM: Homo sapien

<400> SEQUENCE: 4
ttcgggcacg agggcaggat ggcgccacca ccagctagag tacatctagg tgcgttcctg      60
gcagtgactc cgaatcccgg gagcgcagcg agtgggacag aggcagccgc ggccacaccc     120
agcaaagtgt ggggctcttc cgcggggagg attgaaccac gaggcggggg ccgaggagcg     180
ctccctacct ccatgggaca gcacggaccc agtgcccggg cccgggcagg gcgcgcccca     240
ggacccaggc cggcgcggga agccagccct cggctccggg tccacaagac cttcaagttt     300
gtcgtcgtcg gggtcctgct gcaggtcgta cctagctcag ctgcaaccat caaacttcat     360
gatcaatcaa ttggcacaca gcaatgggaa catagccctt gggagagtt gtgtccacca     420 ggatctcata gatcagaacg tcctggagcc tgtaaccggt gcacagaggg tgtgggttac     480
accaatgctt ccaacaattt gtttgcttgc ctcccatgta cagcttgtaa atcagatgaa     540
gaagagagaa gtccctgcac cacgaccagg aacacagcat gtcagtgcaa accaggaact     600
ttccggaatg acaattctgc tgagatgtgc cggaagtgca gcacagggtg ccccagaggg     660
atggtcaagg tcaaggattg tacgccctgg agtgacatcg agtgtgtcca caagaatca      720 ggcaatggac ataatatatg ggtgattttg ttgtgacttt ggttgttcc gttgctgttg      780 gtggctgtgc tgattgtctg ttgttgcatc ggctcaggtt gtggagggga ccccaagtgc     840
```

-continued

```
atggacaggg tgtgtttctg gcgcttgggt ctcctacgag ggcctggggc tgaggacaat    900
gctcacaacg agattctgag caacgcagac tcgctgtcca ctttcgtctc tgagcagcaa    960
atggaaagcc aggagccggc agatttgaca ggtgtcactg tacagtcccc aggggaggca   1020
cagtgtctgc tgggaccggc agaagctgaa gggtctcaga ggaggaggct gctggttcca   1080
gcaaatggtg ctgaccccac tgagactctg atgctgttct ttgacaagtt tgcaaacatc   1140
gtgccctttg actcctggga ccagctcatg aggcagctgg acctcacgaa aaatgagatc   1200
gatgtggtca gagctggtac agcaggccca ggggatgcct tgtatgcaat gctgatgaaa   1260
tgggtcaaca aaactggacg gaacgcctcg atccacaccc tgctggatgc cttggagagg   1320
atggaagaga gacatgcaaa agagaagatt caggacctct tggtggactc tggaaagttc   1380
atctacttag aagatggcac aggctctgcc gtgtccttgg agtgaaagac tcttttacc    1440
agaggtttcc tcttaggtgt taggagttaa tacatattag gttttttttt ttttttaacat   1500
gtatacaaag taaattctta gccacgtgta ttggctcctg cctgtaatcc catcactttg   1560
ggaggctgac gccggtggat ccacttgagg tccgaagttc aagaccagc cctgaaccaa    1620
catcgtggaa atgcccgtct tttacaaaaa ataccaaaa attcaactgg aatgtgcatg    1680
gtgtgtgcca tcatttcctc ggctaactac gggaggtctg aggccaggag aatccacttg   1740
aaccccacga aggacagtgt agactgcaga ttgcaccact gcactcccag cctgggaaca   1800
cagagcaaga ctctgtctca agataaaata aaataaactt gaaagaatta ttgcccgact   1860
gaggctcaca tgccaaagga aaatctggtt ctcccctgag ctggcctccg tgtgtttcct   1920
tatcatggtg gtcaattgga ggtgttaatt tgaatggatt aaggaacacc tagaacactg   1980
gtaaggcatt atttctggga cattatttct gggcatgtct tcgagggtgt ttccagaggg   2040
gattggcatg cgatcgggtg gactgagtgg aaaagaccta cccttaattt ggggggggcac   2100
cgtccgacag actggggagc aagatagaag aaaacaaaaa aaaaaaaaaa aa           2152
```

<210> SEQ ID NO 5
<211> LENGTH: 411
<212> TYPE: PRT
<213> ORGANISM: Homo sapiens
<220> FEATURE:
<221> NAME/KEY: VARIANT
<222> LOCATION: 410
<223> OTHER INFORMATION: Xaa = Leu or Met

<400> SEQUENCE: 5

```
Met Glu Gln Arg Gly Gln Asn Ala Pro Ala Ala Ser Gly Ala Arg Lys
 1               5                  10                  15

Arg His Gly Pro Gly Pro Arg Glu Ala Arg Gly Ala Arg Pro Gly Leu
                20                  25                  30

Arg Val Pro Lys Thr Leu Val Leu Val Val Ala Ala Val Leu Leu Leu
            35                  40                  45

Val Ser Ala Glu Ser Ala Leu Ile Thr Gln Gln Asp Leu Ala Pro Gln
        50                  55                  60

Gln Arg Ala Ala Pro Gln Gln Lys Arg Ser Ser Pro Ser Glu Gly Leu
    65                  70                  75                  80

Cys Pro Pro Gly His His Ile Ser Glu Asp Gly Arg Asp Cys Ile Ser
                85                  90                  95

Cys Lys Tyr Gly Gln Asp Tyr Ser Thr His Trp Asn Asp Leu Leu Phe
               100                 105                 110

Cys Leu Arg Cys Thr Arg Cys Asp Ser Gly Glu Val Glu Leu Ser Pro
           115                 120                 125
```

```
Cys Thr Thr Thr Arg Asn Thr Val Cys Gln Cys Glu Glu Gly Thr Phe
        130                 135                 140

Arg Glu Glu Asp Ser Pro Glu Met Cys Arg Lys Cys Arg Thr Gly Cys
145                 150                 155                 160

Pro Arg Gly Met Val Lys Val Gly Asp Cys Thr Pro Trp Ser Asp Ile
                165                 170                 175

Glu Cys Val His Lys Glu Ser Gly Ile Ile Ile Gly Val Thr Val Ala
                180                 185                 190

Ala Val Val Leu Ile Val Ala Val Phe Val Cys Lys Ser Leu Leu Trp
                195                 200                 205

Lys Lys Val Leu Pro Tyr Leu Lys Gly Ile Cys Ser Gly Gly Gly Gly
210                 215                 220

Asp Pro Glu Arg Val Asp Arg Ser Ser Gln Arg Pro Gly Ala Glu Asp
225                 230                 235                 240

Asn Val Leu Asn Glu Ile Val Ser Ile Leu Gln Pro Thr Gln Val Pro
                245                 250                 255

Glu Gln Glu Met Glu Val Gln Glu Pro Ala Glu Pro Thr Gly Val Asn
                260                 265                 270

Met Leu Ser Pro Gly Glu Ser Glu His Leu Leu Glu Pro Ala Glu Ala
            275                 280                 285

Glu Arg Ser Gln Arg Arg Arg Leu Leu Val Pro Ala Asn Glu Gly Asp
        290                 295                 300

Pro Thr Glu Thr Leu Arg Gln Cys Phe Asp Asp Phe Ala Asp Leu Val
305                 310                 315                 320

Pro Phe Asp Ser Trp Glu Pro Leu Met Arg Lys Leu Gly Leu Met Asp
                325                 330                 335

Asn Glu Ile Lys Val Ala Lys Ala Glu Ala Ala Gly His Arg Asp Thr
                340                 345                 350

Leu Tyr Thr Met Leu Ile Lys Trp Val Asn Lys Thr Gly Arg Asp Ala
                355                 360                 365

Ser Val His Thr Leu Leu Asp Ala Leu Glu Thr Leu Gly Glu Arg Leu
        370                 375                 380

Ala Lys Gln Lys Ile Glu Asp His Leu Leu Ser Ser Gly Lys Phe Met
385                 390                 395                 400

Tyr Leu Glu Gly Asn Ala Asp Ser Ala Xaa Ser
                405                 410
```

<210> SEQ ID NO 6
<211> LENGTH: 1799
<212> TYPE: DNA
<213> ORGANISM: Homo sapiens

<400> SEQUENCE: 6

```
cccacgcgtc cgcataaatc agcacgcggc cggagaaccc cgcaatctct gcgcccacaa      60
aatacaccga cgatgcccga tctactttaa gggctgaaac ccacgggcct gagagactat     120
aagagcgttc cctaccgcca tggaacaacg ggacagaaac gccccggccg cttcgggggc     180
ccggaaaagg cacggcccag gacccaggga ggcgcgggga ccaggcctg ggctccgggt      240
ccccaagacc cttgtgctcg ttgtcgccgc ggtcctgctg ttggtctcag ctgagtctgc     300
tctgatcacc caacaagacc tagctcccca gcagagagcg gccccacaac aaaagaggtc     360
cagcccctca gagggattgt gtccacctgg acaccatatc tcagaagacg gtagagattg     420
catctcctgc aaatatggac aggactatag cactcactgg aatgaccctc ttttctgctt     480
gcgctgcacc aggtgtgatt caggtgaagt ggagctaagt ccctgcacca cgaccagaaa     540
```

```
cacagtgtgt cagtgcgaag aaggcacctt ccgggaagaa gattctcctg agatgtgccg    600
gaagtgccgc acagggtgtc ccagagggat ggtcaaggtc ggtgattgta cccctggag    660
tgacatcgaa tgtgtccaca agaatcagg catcatcata ggagtcacag ttgcagccgt    720
agtcttgatt gtggctgtgt tgtttgcaa gtcttactg tggaagaaag tccttcctta    780
cctgaaaggc atctgctcag gtggtggtgg ggaccctgag cgtgtggaca aagctcaca    840
acgacctggg gctgaggaca atgtcctcaa tgagatcgtg agtatcttgc agcccaccca    900
ggtccctgag caggaaatgg aagtccagga gccagcagag ccaacaggtg tcaacatgtt    960
gtcccccggg gagtcagagc atctgctgga accggcagaa gctgaaaggt ctcagaggag   1020
gaggctgctg gttccagcaa atgaaggtga tcccactgag actctgagac agtgcttcga   1080
tgactttgca gacttggtgc cctttgactc ctgggagccg ctcatgagga agttgggcct   1140
catggacaat gagataaagg tggctaaagc tgaggcagcg ggccacaggg acaccttgta   1200
cacgatgctg ataaagtggg tcaacaaaac cgggcgagat gcctctgtcc acaccctgct   1260
ggatgccttg gagacgctgg gagagagact tgccaagcag aagattgagg accacttgtt   1320
gagctctgga aagttcatgt atctagaagg taatgcagac tctgccwtgt cctaagtgtg   1380
attctcttca ggaagtgaga ccttccctgg tttacctttt ttctggaaaa agcccaactg   1440
gactccagtc agtaggaaag tgccacaatt gtcacatgac cggtactgga agaaactctc   1500
ccatccaaca tcacccagtg gatggaacat cctgtaactt ttcactgcac ttggcattat   1560
ttttataagc tgaatgtgat aataaggaca ctatggaaat gtctggatca ttccgtttgt   1620
gcgtactttg agatttggtt tgggatgtca ttgttttcac agcactttt tatcctaatg    1680
taaatgcttt atttatttat ttgggctaca ttgtaagatc catctacaaa aaaaaaaaa    1740
aaaaaaaaag ggcggccgcg actctagagt cgacctgcag aagcttggcc gccatggcc   1799
```

<210> SEQ ID NO 7
<211> LENGTH: 440
<212> TYPE: PRT
<213> ORGANISM: Homo sapiens

<400> SEQUENCE: 7

```
Met Glu Gln Arg Gly Gln Asn Ala Pro Ala Ser Gly Ala Arg Lys
 1               5                  10                  15

Arg His Gly Pro Gly Pro Arg Glu Ala Arg Gly Ala Arg Pro Gly Pro
                20                  25                  30

Arg Val Pro Lys Thr Leu Val Leu Val Val Ala Ala Val Leu Leu Leu
            35                  40                  45

Val Ser Ala Glu Ser Ala Leu Ile Thr Gln Gln Asp Leu Ala Pro Gln
        50                  55                  60

Gln Arg Ala Ala Pro Gln Gln Lys Arg Ser Ser Pro Ser Glu Gly Leu
65                  70                  75                  80

Cys Pro Pro Gly His His Ile Ser Glu Asp Gly Arg Asp Cys Ile Ser
                85                  90                  95

Cys Lys Tyr Gly Gln Asp Tyr Ser Thr His Trp Asn Asp Leu Leu Phe
            100                 105                 110

Cys Leu Arg Cys Thr Arg Cys Asp Ser Gly Glu Val Glu Leu Ser Pro
        115                 120                 125

Cys Thr Thr Thr Arg Asn Thr Val Cys Gln Cys Glu Glu Gly Thr Phe
    130                 135                 140

Arg Glu Glu Asp Ser Pro Glu Met Cys Arg Lys Cys Arg Thr Gly Cys
145                 150                 155                 160
```

```
Pro Arg Gly Met Val Lys Val Gly Asp Cys Thr Pro Trp Ser Asp Ile
            165                 170                 175
Glu Cys Val His Lys Glu Ser Gly Thr Lys His Ser Gly Glu Ala Pro
        180                 185                 190
Ala Val Glu Glu Thr Val Thr Ser Ser Pro Gly Thr Pro Ala Ser Pro
    195                 200                 205
Cys Ser Leu Ser Gly Ile Ile Ile Gly Val Thr Val Ala Ala Val Val
210                 215                 220
Leu Ile Val Ala Val Phe Val Cys Lys Ser Leu Leu Trp Lys Lys Val
225                 230                 235                 240
Leu Pro Tyr Leu Lys Gly Ile Cys Ser Gly Gly Gly Gly Asp Pro Glu
            245                 250                 255
Arg Val Asp Arg Ser Ser Gln Arg Pro Gly Ala Glu Asp Asn Val Leu
        260                 265                 270
Asn Glu Ile Val Ser Ile Leu Gln Pro Thr Gln Val Pro Glu Gln Glu
    275                 280                 285
Met Glu Val Gln Glu Pro Ala Glu Pro Thr Gly Val Asn Met Leu Ser
290                 295                 300
Pro Gly Glu Ser Glu His Leu Leu Glu Pro Ala Glu Ala Glu Arg Ser
305                 310                 315                 320
Gln Arg Arg Arg Leu Leu Val Pro Ala Asn Glu Gly Asp Pro Thr Glu
            325                 330                 335
Thr Leu Arg Gln Cys Phe Asp Asp Phe Ala Asp Leu Val Pro Phe Asp
        340                 345                 350
Ser Trp Glu Pro Leu Met Arg Lys Leu Gly Leu Met Asp Asn Glu Ile
    355                 360                 365
Lys Val Ala Lys Ala Glu Ala Ala Gly His Arg Asp Thr Leu Tyr Thr
370                 375                 380
Met Leu Ile Lys Trp Val Asn Lys Thr Gly Arg Asp Ala Ser Val His
385                 390                 395                 400
Thr Leu Leu Asp Ala Leu Glu Thr Leu Gly Glu Arg Leu Ala Lys Gln
            405                 410                 415
Lys Ile Glu Asp His Leu Leu Ser Ser Gly Lys Phe Met Tyr Leu Glu
        420                 425                 430
Gly Asn Ala Asp Ser Ala Met Ser
    435                 440

<210> SEQ ID NO 8
<211> LENGTH: 1323
<212> TYPE: DNA
<213> ORGANISM: Homo sapiens

<400> SEQUENCE: 8
atggaacaac ggggacagaa cgccccggcc gcttcggggg cccggaaaag gcacggccca      60
ggacccaggg aggcgcgggg agccaggcct gggctccggg tccccaagac ccttgtgctc     120
gttgtcgccg cggtcctgct gttggtctca gctgagtctg ctctgatcac ccaacaagac     180
ctagctcccc agcagagagt ggccccacaa caaaagaggt ccagcccctc agagggattg     240
tgtccacctg acaccatat ctcagaagac ggtagagatt gcatctcctg caaatatgga     300
caggactata gcactcactg gaatgacctc cttttctgct tgcgctgcac caggtgtgat     360
tcaggtgaag tggagctaag tccctgcacc acgaccagaa acacagtgtg tcagtgcgaa     420
gaaggcacct tccgggaaga agattctcct gagatgtgcc ggaagtgccg cacagggtgt     480
cccagaggga tggtcaaggt cggtgattgt acaccctgga gtgacatcga atgtgtccac     540
```

```
aaagaatcag gtacaaagca cagtggggaa gccccagctg tggaggagac ggtgacctcc      600
agcccaggga ctcctgcctc tccctgttct ctctcaggca tcatcatagg agtcacagtt      660
gcagccgtag tcttgattgt ggctgtgttt gtttgcaagt ctttactgtg aagaaagtc       720 cttccttacc tgaaaggcat ctgctcaggt ggtggtgggg accctgagcg tgtggacaga      780
agctcacaac gacctggggc tgaggacaat gtcctcaatg agatcgtgag tatcttgcag      840
cccacccagg tccctgagca ggaaatggaa gtccaggagc cagcagagcc aacaggtgtc      900
aacatgttgt cccccgggga gtcagagcat ctgctggaac cggcagaagc tgaaaggtct      960
cagaggagga ggctgctggt tccagcaaat gaaggtgatc ccactgagac tctgagacag     1020
tgcttcgatg actttgcaga cttggtgccc tttgactcct gggagccgct catgaggaag     1080
ttgggcctca tggacaatga gataaaggtg gctaaagctg aggcagcggg ccacagggac     1140
accttgtaca cgatgctgat aaagtgggtc aacaaaaccg ggcgagatgc ctctgtccac     1200
accctgctgg atgccttgga gacgctggga gagagacttg ccaagcagaa gattgaggac     1260
cacttgttga gctctggaaa gttcatgtat ctagaaggta atgcagactc tgccatgtcc     1320
taa                                                                  1323

<210> SEQ ID NO 9
<211> LENGTH: 930
<212> TYPE: DNA
<213> ORGANISM: Homo sapien

<400> SEQUENCE: 9
atgaccatga ttacgccaag cttttggagcc ttttttttgg agattttcaa cgtgaaaaaa       60
ttattattcg caattccttt agttgttcct ttctatgcgg cccagccggc catggccgag      120
gtgcagctgg tgcagtctgg gggaggtgtg aacggccgg ggggtccct gagactctcc       180 tgtgcagcct ctggattcac ctttgatgat tatggcatga gctgggtccg ccaagctcca      240
ggggaggggc tggagtgggt ctctggtatt aattggaatg gtggtagcac aggatatgca      300
gactctgtga agggccgagt caccatctcc agagacaacg ccaagaactc cctgtatctg      360
caaatgaaca gcctgagagc cgaggacacg gccgtatatt actgtgcgaa atcctgggt      420 gccggacggg gctggtactt cgatctctgg gggaagggga ccacggtcac cgtctcgagt      480 ggtgaggcg gttcaggcgg aggtggcagc ggcggtggcg gatcgtctga gctgactcag      540
gaccctgctg tgtctgtggc cttgggacag acagtcagga tcacatgcca aggagacagc      600
ctcagaagct attatgcaag ctggtaccag cagaagccag gacaggcccc tgtacttgtc      660
atctatggta aaaacaaccg gccctcaggg atcccagacc gattctctgg ctccagctca      720
ggaaacacag cttccttgac catcactggg gctcaggcgg aagatgaggc tgactattac      780
tgtaactccc gggacagcag tggtaaccat gtggtattcg gcggagggac caagctgacc      840
gtcctaggtg cggccgcaca tcatcatcac catcacgggg ccgcagaaca aaaactcatc      900
tcagaagagg atctgaatgg ggccgcatag                                     930

<210> SEQ ID NO 10
<211> LENGTH: 309
<212> TYPE: PRT
<213> ORGANISM: Homo sapien

<400> SEQUENCE: 10

Met Thr Met Ile Thr Pro Ser Phe Gly Ala Phe Phe Leu Glu Ile Phe
 1               5                  10                  15

Asn Val Lys Lys Leu Leu Phe Ala Ile Pro Leu Val Val Pro Phe Tyr
```

```
                20                  25                  30
Ala Ala Gln Pro Ala Met Ala Glu Val Gln Leu Val Gln Ser Gly Gly
                35                  40                  45

Gly Val Glu Arg Pro Gly Gly Ser Leu Arg Leu Ser Cys Ala Ala Ser
 50                  55                  60

Gly Phe Thr Phe Asp Asp Tyr Gly Met Ser Trp Val Arg Gln Ala Pro
65                  70                  75                  80

Gly Lys Gly Leu Glu Trp Val Ser Gly Ile Asn Trp Asn Gly Gly Ser
                85                  90                  95

Thr Gly Tyr Ala Asp Ser Val Lys Gly Arg Val Thr Ile Ser Arg Asp
            100                 105                 110

Asn Ala Lys Asn Ser Leu Tyr Leu Gln Met Asn Ser Leu Arg Ala Glu
            115                 120                 125

Asp Thr Ala Val Tyr Tyr Cys Ala Lys Ile Leu Gly Ala Gly Arg Gly
        130                 135                 140

Trp Tyr Phe Asp Leu Trp Gly Lys Gly Thr Thr Val Thr Val Ser Ser
145                 150                 155                 160

Gly Gly Gly Gly Ser Gly Gly Gly Gly Ser Gly Gly Gly Gly Ser Ser
                165                 170                 175

Glu Leu Thr Gln Asp Pro Ala Val Ser Val Ala Leu Gly Gln Thr Val
            180                 185                 190

Arg Ile Thr Cys Gln Gly Asp Ser Leu Arg Ser Tyr Tyr Ala Ser Trp
        195                 200                 205

Tyr Gln Gln Lys Pro Gly Gln Ala Pro Val Leu Val Ile Tyr Gly Lys
            210                 215                 220

Asn Asn Arg Pro Ser Gly Ile Pro Asp Arg Phe Ser Gly Ser Ser Ser
225                 230                 235                 240

Gly Asn Thr Ala Ser Leu Thr Ile Thr Gly Ala Gln Ala Glu Asp Glu
                245                 250                 255

Ala Asp Tyr Tyr Cys Asn Ser Arg Asp Ser Ser Gly Asn His Val Val
            260                 265                 270

Phe Gly Gly Gly Thr Lys Leu Thr Val Leu Gly Ala Ala Ala His His
        275                 280                 285

His His His His Gly Ala Ala Glu Gln Lys Leu Ile Ser Glu Glu Asp
    290                 295                 300

Leu Asn Gly Ala Ala
305

<210> SEQ ID NO 11
<211> LENGTH: 451
<212> TYPE: PRT
<213> ORGANISM: Homo sapiens

<400> SEQUENCE: 11

Glu Val Gln Leu Val Gln Ser Gly Gly Gly Val Glu Arg Pro Gly Gly
1               5                   10                  15

Ser Leu Arg Leu Ser Cys Ala Ala Ser Gly Phe Thr Phe Asp Asp Tyr
                20                  25                  30

Gly Met Ser Trp Val Arg Gln Ala Pro Gly Lys Gly Leu Glu Trp Val
            35                  40                  45

Ser Gly Ile Asn Trp Asn Gly Gly Ser Thr Gly Tyr Ala Asp Ser Val
        50                  55                  60

Lys Gly Arg Val Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
```

```
                    85                  90                  95
Ala Lys Ile Leu Gly Ala Gly Arg Gly Trp Tyr Phe Asp Leu Trp Gly
                100                 105                 110

Lys Gly Thr Thr Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 12
<211> LENGTH: 1353
<212> TYPE: DNA
<213> ORGANISM: Homo sapiens

<400> SEQUENCE: 12
gaagttcagc tggtgcagtc tgggggaggt gtggaacggc cggggggggtc cctgagactc      60
```

```
tcctgtgcag cctctggatt caccttttgat gattatggca tgagctgggt ccgccaagct    120
ccagggaagg ggctggagtg ggtctctggt attaattgga atggtggtag cacaggatat    180
gcagactctg tgaagggccg agtcaccatc tccagagaca acgccaagaa ctccctgtat    240
ctgcaaatga acagcctgag agccgaggac acggccgtat attactgtgc gaaaatcctg    300
ggtgccggac ggggctggta cttcgatctc tggggggaagg ggaccacggt caccgtctcg    360
agtgcctcca ccaagggccc atcggtcttc cccctggcac cctcctccaa gagcacctct    420
gggggcacag cggccctggg ctgcctggtc aaggactact tccccgaacc ggtgacggtg    480
tcgtggaact caggcgccct gaccagcggc gtgcacacct tcccggctgt cctacagtcc    540
tcaggactct actccctcag cagcgtggtg actgtgccct ctagcagctt gggcacccag    600
acctacatct gcaacgtgaa tcacaagccc agcaacacca aggtggacaa gaaagttgag    660
cccaaatctt gtgacaaaac tcacacatgc ccaccgtgcc cagcacctga actcctgggg    720
ggaccgtcag tcttcctctt ccccccaaaa cccaaggaca ccctcatgat ctcccggacc    780
cctgaggtca catgcgtggt ggtggacgtg agccacgaag accctgaggt caagttcaac    840
tggtacgtgg acggcgtgga ggtgcataat gccaagacaa agccgcggga ggagcagtac    900
aacagcacgt accgtgtggt cagcgtcctc accgtcctgc accaggactg gctgaatggc    960
aaggagtaca agtgcaaggt ctccaacaaa gccctcccag cccccatcga gaaaaccatc   1020
tccaaagcca agggcagccc cgagaaccca caggtgtaca ccctgcccc atcccgggaa   1080
gagatgacca agaaccaggt cagcctgacc tgcctggtca aaggcttcta tcccagcgac   1140
atcgccgtgg agtgggagag caatgggcag ccggagaaca actacaagac cacgcctccc   1200
gtgctggact ccgacggctc cttcttcctc tacagcaagc tcaccgtgga caagagcagg   1260
tggcagcagg ggaacgtctt ctcatgctcc gtgatgcatg aggctctgca caaccactac   1320
acgcagaaga gcctctccct gtctccgggt aaa                                 1353

<210> SEQ ID NO 13
<211> LENGTH: 213
<212> TYPE: PRT
<213> ORGANISM: Homo sapiens

<400> SEQUENCE: 13

Ser Glu Leu Thr Gln Asp Pro Ala Val Ser Val Ala Leu Gly Gln Thr
  1               5                  10                  15

Val Arg Ile Thr Cys Gln Gly Asp Ser Leu Arg Ser Tyr Tyr Ala Ser
             20                  25                  30

Trp Tyr Gln Gln Lys Pro Gly Gln Ala Pro Val Leu Val Ile Tyr Gly
         35                  40                  45

Lys Asn Asn Arg Pro Ser Gly Ile Pro Asp Arg Phe Ser Gly Ser Ser
     50                  55                  60

Ser Gly Asn Thr Ala Ser Leu Thr Ile Thr Gly Ala Gln Ala Glu Asp
 65                  70                  75                  80

Glu Ala Asp Tyr Tyr Cys Asn Ser Arg Asp Ser Ser Gly Asn His Val
                 85                  90                  95

Val Phe Gly Gly Gly Thr Lys Leu Thr Val Leu Gly Gln Pro Lys Ala
            100                 105                 110

Ala Pro Ser Val Thr Leu Phe Pro Ser Ser Glu Glu Leu Gln Ala
            115                 120                 125

Asn Lys Ala Thr Leu Val Cys Leu Ile Ser Asp Phe Tyr Pro Gly Ala
        130                 135                 140
```

```
Val Thr Val Ala Trp Lys Ala Asp Ser Ser Pro Val Lys Ala Gly Val
145                 150                 155                 160

Glu Thr Thr Thr Pro Ser Lys Gln Ser Asn Asn Lys Tyr Ala Ala Ser
                165                 170                 175

Ser Tyr Leu Ser Leu Thr Pro Glu Gln Trp Lys Ser His Lys Ser Tyr
            180                 185                 190

Ser Cys Gln Val Thr His Glu Gly Ser Thr Val Glu Lys Thr Val Ala
        195                 200                 205

Pro Thr Glu Cys Ser
    210
```

```
<210> SEQ ID NO 14
<211> LENGTH: 639
<212> TYPE: DNA
<213> ORGANISM: Homo sapiens

<400> SEQUENCE: 14
tctgagctga ctcaggaccc tgctgtgtct gtggccttgg gacagacagt caggatcaca     60
tgccaaggag acagcctcag aagctattat gcaagctggt accagcagaa gccaggacag    120
gcccctgtac ttgtcatcta tggtaaaaac aaccggccct cagggatccc agaccgattc    180
tctggctcca gctcaggaaa cacagcttcc ttgaccatca ctgggctca ggcggaagat     240 gaggctgact attactgtaa ctcccgggac agcagtggta ccatgtggt attcggcgga    300 gggaccaagc tgaccgtcct ggccaacct aaggctgcac catctgtcac cctcttcccg    360
ccatcttctg aggagttgca agctaacaaa gccactcttg tgtgcctgat cagtgacttc    420
tatcccggag cggtcacagt agcgtggaag gcggatagct cccccgtaaa ggctggcgtc    480
gagacgacta ccccttcgaa gcagagcaac aacaaatacg ccgccagcag ctacctgtcg    540
ctgaccccag aacagtggaa gagccacaaa gctactcct gccaagtcac ccatgagggc     600
tcgaccgtcg aaaagaccgt cgccccgaca gagtgttct                            639
```

```
<210> SEQ ID NO 15
<211> LENGTH: 5391
<212> TYPE: DNA
<213> ORGANISM: Homo sapiens

<400> SEQUENCE: 15
ttcgagctcg cccgacattg attattgact agttattaat agtaatcaat tacggggtca     60
ttagttcata gcccatatat ggagttccgc gttacataac ttacggtaaa tggcccgcct    120
ggctgaccgc ccaacgaccc ccgcccattg acgtcaataa tgacgtatgt tcccatagta    180
acgccaatag ggactttcca ttgacgtcaa tgggtggagt atttacgta aactgcccac     240 ttggcagtac atcaagtgta tcatatgcca agtacgcccc ctattgacgt caatgacggt    300
aaatggcccg cctggcatta tgcccagtac atgaccttat gggactttcc tacttggcag    360
tacatctacg tattagtcat cgctattacc atggtgatgc ggttttggca gtacatcaat    420
gggcgtggat agcggtttga ctcacgggga tttccaagtc tccacccccat tgacgtcaat    480 gggagtttgt tttggcacca aaatcaacgg gactttccaa aatgtcgtaa caactccgcc    540
ccattgacgc aaatgggcgg taggcgtgta cggtgggagg tctatataag cagagctcgt    600
ttagtgaacc gtcagatcgc ctggagacgc catccacgct gttttgacct ccatagaaga    660
caccgggacc gatccagcct ccgcggccgg gaacggtgca ttggaacgcg gattccccgt    720
gccaagagtg acgtaagtac cgcctataga gtctataggc ccacccccctt ggcttcgtta    780 gaacgcggct acaattaata cataacctta tgtatcatac acatacgatt taggtgacac    840
```

```
tatagaataa catccacttt gcctttctct ccacaggtgt ccactcccag gtccaactgc    900
acctcggttc tatcgattga attccaccat gggatggtca tgtatcatcc ttttctagt   960 agcaactgca actggagtac attcagatat ccagatgacc cagtcccga gctccctgtc   1020 cgcctctgtg ggcgataggg tcaccatcac ctgccgtgcc agtcaggaca tccgtaatta  1080
tttgaactgg tatcaacaga accaggaaa agctccgaaa ctactgattt actataccte   1140 ccgcctggag tctggagtcc cttctcgctt ctctggttct ggttctggga cggattacac  1200
tctgaccatc agtagtctgc aaccggagga cttcgcaact tattactgtc agcaaggtaa  1260
tactctgccg tggacgttcg gacagggcac caaggtggag atcaaacgaa ctgtggctgc  1320
accatctgtc ttcatcttcc cgccatctga tgagcagttg aaatctggaa ctgcctctgt  1380
tgtgtgcctg ctgaataact tctatcccag agaggccaaa gtacagtgga aggtggataa  1440
cgccctccaa tcgggtaact cccaggagag tgtcacagag caggacagca aggacagcac  1500
ctacagcctc agcagcaccc tgacgctgag caaagcagac tacgagaaac acaaagtcta  1560
cgcctgcgaa gtcacccatc agggcctgag ctcgcccgtc acaaagagct caacaggggg  1620
agagtgttaa gcttggccgc catggcccaa cttgtttatt gcagcttata atggttacaa  1680
ataaagcaat agcatcacaa atttcacaaa taaagcattt tttcactgc attctagttg  1740 tggtttgtcc aaactcatca atgtatctta tcatgtctgg atcgatcggg aattaattcg  1800
gcgcagcacc atggcctgaa ataacctctg aaagaggaac ttggttaggt accttctgag  1860
gcggaaagaa ccagctgtgg aatgtgtgtc agttagggtg tggaaagtcc ccaggctccc  1920
cagcaggcag aagtatgcaa agcatgcatc tcaattagtc agcaaccagg tgtggaaagt  1980
ccccaggctc cccagcaggc agaagtatgc aaagcatgca tctcaattag tcagcaacca  2040
tagtcccgcc cctaactccg cccatcccgc cctaactcc gcccagttcc gcccattctc    2100
cgccccatgg ctgactaatt ttttttattt atgcagaggc cgaggccgcc tcggcctctg  2160
agctattcca gaagtagtga ggaggctttt ttggaggcct aggcttttgc aaaaagctgt  2220
taacagcttg gcactggccg tcgttttaca acgtcgtgac tgggaaaacc ctggcgttac  2280
ccaacttaat cgccttgcag cacatccccc cttcgccagc tggcgtaata gcgaagaggc  2340
ccgcaccgat cgcccttccc aacagttgcg tagcctgaat ggcgaatggc gcctgatgcg  2400
gtattttctc cttacgcatc tgtgcggtat ttcacaccgc atacgtcaaa gcaaccatag  2460
tacgcgccct gtagcggcgc attaagcgcg gcgggtgtgg tggttacgcg cagcgtgacc  2520
gctacacttg ccagcgccct agcgcccgct cctttcgctt tcttcccttc ctttctcgcc  2580
acgttcgccg gctttccccg tcaagctcta aatcggggc tcccttttagg gttccgattt  2640 agtgctttac ggcacctcga ccccaaaaaa cttgatttgg gtgatggttc acgtagtggg  2700
ccatcgccct gatagacggt ttttcgccct ttgacgttgg agtccacgtt ctttaatagt  2760
ggactcttgt tccaaactgg aacaacactc aaccctatct cgggctattc ttttgattta  2820
taagggattt tgccgatttc ggcctattgg ttaaaaaatg agctgattta acaaaaattt  2880
aacgcgaatt ttaacaaaat attaacgttt acaattttat ggtgcactct cagtacaatc  2940
tgctctgatg ccgcatagtt aagccaactc cgctatcgct acgtgactgg gtcatggctg  3000
cgccccgaca cccgccaaca cccgctgacg cgccctgacg gcttgtctg ctcccggcat   3060 ccgcttacag acaagctgtg accgtctccg ggagctgcat gtgtcagagg ttttcaccgt  3120
catcaccgaa acgcgcgagg cagtattctt gaagacgaaa gggcctcgtg atacgcctat  3180
ttttataggt taatgtcatg ataataatgg tttcttagac gtcaggtggc acttttcggg  3240
```

| | | | | |
|---|---|---|---|---|
| gaaatgtgcg | cggaacccct | atttgtttat | ttttctaaat | acattcaaat atgtatccgc | 3300 |
| tcatgagaca | ataaccctga | taaatgcttc | aataatattg | aaaaaggaag agtatgagta | 3360 |
| ttcaacattt | ccgtgtcgcc | cttattccct | tttttgcggc | attttgcctt cctgttttg | 3420 |
| ctcacccaga | aacgctggtg | aaagtaaaag | atgctgaaga | tcagttgggt gcacgagtgg | 3480 |
| gttacatcga | actggatctc | aacagcggta | agatccttga | gagttttcgc ccgaagaac | 3540 |
| gttttccaat | gatgagcact | tttaaagttc | tgctatgtgg | cgcggtatta tcccgtgatg | 3600 |
| acgccgggca | agagcaactc | ggtcgccgca | tacactattc | tcagaatgac ttggttgagt | 3660 |
| actcaccagt | cacagaaaag | catcttacgg | atggcatgac | agtaagagaa ttatgcagtg | 3720 |
| ctgccataac | catgagtgat | aacactgcgg | ccaacttact | tctgacaacg atcggaggac | 3780 |
| cgaaggagct | aaccgctttt | ttgcacaaca | tgggggatca | tgtaactcgc cttgatcgtt | 3840 |
| gggaaccgga | gctgaatgaa | gccataccaa | acgacgagcg | tgacaccacg atgccagcag | 3900 |
| caatggcaac | aacgttgcgc | aaactattaa | ctggcgaact | acttactcta gcttcccggc | 3960 |
| aacaattaat | agactggatg | gaggcggata | aagttgcagg | accacttctg cgctcggccc | 4020 |
| ttccggctgg | ctggtttatt | gctgataaat | ctggagccgg | tgagcgtggg tctcgcggta | 4080 |
| tcattgcagc | actggggcca | gatggtaagc | cctcccgtat | cgtagttatc tacacgacgg | 4140 |
| ggagtcaggc | aactatggat | gaacgaaata | gacagatcgc | tgagataggt gcctcactga | 4200 |
| ttaagcattg | gtaactgtca | gaccaagttt | actcatatat | actttagatt gatttaaaac | 4260 |
| ttcattttta | atttaaaagg | atctaggtga | agatcctttt | tgataatctc atgaccaaaa | 4320 |
| tcccttaacg | tgagttttcg | ttccactgag | cgtcagaccc | cgtagaaaag atcaaaggat | 4380 |
| cttcttgaga | tcctttttt | ctgcgcgtaa | tctgctgctt | gcaaacaaaa aaaccaccgc | 4440 |
| taccagcggt | ggtttgtttg | ccggatcaag | agctaccaac | tcttttccg aaggtaactg | 4500 |
| gcttcagcag | agcgcagata | ccaaatactg | tccttctagt | gtagccgtag ttaggccacc | 4560 |
| acttcaagaa | ctctgtagca | ccgcctacat | acctcgctct | gctaatcctg ttaccagtgg | 4620 |
| ctgctgccag | tggcgataag | tcgtgtctta | ccgggttgga | ctcaagacga tagttaccgg | 4680 |
| ataaggcgca | gcggtcgggc | tgaacggggg | gttcgtgcac | acagcccagc ttggagcgaa | 4740 |
| cgacctacac | cgaactgaga | tacctacagc | gtgagcattg | agaaagcgcc acgcttcccg | 4800 |
| aagggagaaa | ggcggacagg | tatccggtaa | gcggcagggt | cggaacagga gagcgcacga | 4860 |
| gggagcttcc | agggggaaac | gcctggtatc | tttatagtcc | tgtcgggttt cgccacctct | 4920 |
| gacttgagcg | tcgatttttg | tgatgctcgt | caggggggcg | gagcctatgg aaaaacgcca | 4980 |
| gcaacgcggc | cttttacgg | ttcctggcct | tttgctggcc | ttttgctcac atgttctttc | 5040 |
| ctgcgttatc | ccctgattct | gtggataacc | gtattaccgc | ctttgagtga gctgataccg | 5100 |
| ctcgccgcag | ccgaacgacc | gagcgcagcg | agtcagtgag | cgaggaagcg gaagagcgcc | 5160 |
| caatacgcaa | accgcctctc | cccgcgcgtt | ggccgattca | ttaatccagc tggcacgaca | 5220 |
| ggtttcccga | ctggaaagcg | ggcagtgagc | gcaacgcaat | taatgtgagt tacctcactc | 5280 |
| attaggcacc | ccaggcttta | cactttatgc | ttccggctcg | tatgttgtgt ggaattgtga | 5340 |
| gcggataaca | atttcacaca | ggaaacagct | atgaccatga | ttacgaatta a | 5391 |

<210> SEQ ID NO 16
<211> LENGTH: 6135
<212> TYPE: DNA
<213> ORGANISM: Homo sapiens

<400> SEQUENCE: 16

```
attcgagctc gcccgacatt gattattgac tagttattaa tagtaatcaa ttacggggtc    60
attagttcat agcccatata tggagttccg cgttacataa cttacggtaa atggcccgcc   120
tggctgaccg cccaacgacc cccgcccatt gacgtcaata atgacgtatg ttcccatagt   180
aacgccaata gggactttcc attgacgtca atgggtggag tatttacggt aaactgccca   240
cttggcagta catcaagtgt atcatatgcc aagtacgccc cctattgacg tcaatgacgg   300
taaatggccc gcctggcatt atgcccagta catgacctta tgggactttc ctacttggca   360
gtacatctac gtattagtca tcgctattac catggtgatg cggttttggc agtacatcaa   420
tgggcgtgga tagcggtttg actcacgggg atttccaagt ctccacccca ttgacgtcaa   480
tgggagtttg ttttggcacc aaaatcaacg ggactttcca aaatgtcgta acaactccgc   540
cccattgacg caaatgggcg gtaggcgtgt acggtgggag gtctatataa gcagagctcg   600
tttagtgaac cgtcagatcg cctgagacg ccatccacgc tgttttgacc tccatagaag   660
acaccgggac cgatccagcc tccgcggccg ggaacggtgc attggaacgc ggattccccg   720
tgccaagagt gacgtaagta ccgcctatag agtctatagg cccacccct tggcttcgtt    780
agaacgcggc tacaattaat acataacctt atgtatcata cacatacgat ttaggtgaca   840
ctatagaata catccactt tgcctttctc tccacaggtg tccactccca ggtccaactg    900
cacctcggtt ctatcgattg aattccacca tgggatggtc atgtatcatc cttttctag    960
tagcaactgc aactggagta cattcagaag ttcagctggt ggagtctggc ggtggcctgg  1020
tgcagccagg gggctcactc cgtttgtcct gtgcagcttc tggctactcc tttaccggct  1080
acactatgaa ctgggtgcgt caggccccag gtaagggcct ggaatgggtt gcactgatta  1140
atccttataa aggtgttact acctatgccg atagcgtcaa gggccgtttc actataagcg  1200
tagataaatc caaaaacaca gcctacctgc aaatgaacag cctgcgtgct gaggacactg  1260
ccgtctatta ttgtgctaga agcggatact acggcgatag cgactggtat tttgacgtct  1320
ggggtcaagg aaccctggtc accgtctcct cggcctccac caagggccca tcggtcttcc  1380
ccctggcacc ctcctccaag agcacctctg ggggcacagc ggccctgggc tgcctggtca  1440
aggactactt ccccgaaccg gtgacggtgt cgtggaactc aggcgccctg accagcggcg  1500
tgcacacctt cccggctgtc ctacagtcct caggactcta ctccctcagc agcgtggtga  1560
ctgtgccctc tagcagcttg ggcacccaga cctacatctg caacgtgaat cacaagccca  1620
gcaacaccaa ggtggacaag aaagttgagc ccaaatcttg tgacaaaact cacacatgcc  1680
caccgtgccc agcacctgaa ctcctggggg gaccgtcagt cttcctcttc cccccaaaac  1740
ccaaggacac cctcatgatc tcccggaccc ctgaggtcac atgcgtggtg gtggacgtga  1800
gccacgaaga ccctgaggtc aagttcaact ggtacgtgga cggcgtggag gtgcataatg  1860
ccaagacaaa gccgcgggag gagcagtaca acagcacgta ccgtgtggtc agcgtcctca  1920
ccgtcctgca ccaggactgg ctgaatggca aggagtacaa gtgcaaggtc tccaacaaag  1980
ccctcccagc ccccatcgag aaaaccatct ccaaagccaa agggcagccc cgagaaccac  2040
aggtgtacac cctgccccca tcccgggaag agatgaccaa gaaccaggtc agcctgacct  2100
gcctggtcaa aggcttctat cccagcgaca tcgccgtgga gtgggagagc aatgggcagc  2160
cggagaacaa ctacaagacc acgcctcccg tgctggactc cgacggctcc ttcttcctct  2220
acagcaagct caccgtggac aagagcaggt ggcagcaggg gaacgtcttc tcatgctccg  2280
tgatgcatga ggctctgcac aaccactaca cgcagaagag cctctccctg tctccgggta  2340
aatgagtgcg acggccctag agtcgacctg cagaagcttg gccgccatgg cccaacttgt  2400
```

```
ttattgcagc ttataatggt tacaaataaa gcaatagcat cacaaatttc acaaataaag    2460
catttttttc actgcattct agttgtggtt tgtccaaact catcaatgta tcttatcatg    2520
tctggatcga tcgggaatta attcggcgca gcaccatggc ctgaaataac ctctgaaaga    2580
ggaacttggt taggtacctt ctgaggcgga aagaaccatc tgtggaatgt gtgtcagtta    2640
gggtgtggaa agtccccagg ctccccagca ggcagaagta tgcaaagcat gcatctcaat    2700
tagtcagcaa ccaggtgtgg aaagtcccca ggctcccag  caggcagaag tatgcaaagc    2760
atgcatctca attagtcagc aaccatagtc ccgcccctaa ctccgcccat cccgcccta     2820 actccgccca gttccgccca ttctccgccc catggctgac taattttttt tatttatgca    2880
gaggccgagg ccgcctcggc ctctgagcta ttccagaagt agtgaggagg cttttttgga    2940
ggcctaggct tttgcaaaaa gctgttaaca gcttggcact ggccgtcgtt ttacaacgtc    3000
gtgactggga aaaccctggc gttacccaac ttaatcgcct tgcagcacat ccccccttcg    3060
ccagttggcg taatagcgaa gaggcccgca ccgatcgccc ttcccaacag ttgcgtagcc    3120
tgaatggcga atggcgcctg atgcggtatt ttctccttac gcatctgtgc ggtatttcac    3180
accgcatacg tcaaagcaac catagtacgc gccctgtagc ggcgcattaa gcgcggcggg    3240
tgtggtggtt acgcgcagcg tgaccgctac acttgccagc gccctagcgc ccgctccttt    3300
cgctttcttc ccttcctttc tcgccacgtt cgccggcttt cccgtcaag  ctctaaatcg    3360 ggggctccct ttagggttcc gatttagtgc tttacggcac ctcgacccca aaaaacttga    3420
tttgggtgat ggttcacgta gtgggccatc gccctgatag acggttttc  gcccttgac    3480 gttggagtcc acgttcttta atagtggact cttgttccaa actggaacaa cactcaaccc    3540
tatctcgggc tattcttttg atttataagg gattttgccg atttcggcct attggttaaa    3600
aaatgagctg atttaacaaa aatttaacgc gaattttaac aaaatattaa cgtttacaat    3660
tttatggtgc actctcagta caatctgctc tgatgccgca tagttaagcc aactccgcta    3720
tcgctacgtg actgggtcat ggctgcgccc cgacacccgc caacacccgc tgacgcgccc    3780
tgacgggctt gtctgctccc ggcatccgct tacagacaag ctgtgaccgt ctccgggagc    3840
tgcatgtgtc agaggttttc accgtcatca ccgaaacgcg cgaggcagta ttcttgaaga    3900
cgaaagggcc tcgtgatacg cctatttttta taggttaatg tcatgataat aatggtttct    3960
tagacgtcag gtggcacttt tcggggaaat gtgcgcggaa cccctatttg tttatttttc    4020
taaatacatt caaatatgta tccgctcatg agacaataac cctgataaat gcttcaataa    4080
tattgaaaaa ggaagagtat gagtattcaa catttccgtg tcgcccttat tccctttttt    4140
gcggcatttt gccttcctgt ttttgctcac ccagaaacgc tggtgaaagt aaaagatgct    4200
gaagatcagt tgggtgcacg agtgggttac atcgaactgg atctcaacag cggtaagatc    4260
cttgagagtt ttcgccccga agaacgtttt ccaatgatga gcacttttaa agttctgcta    4320
tgtggcgcgg tattatcccg tgatgacgcc gggcaagagc aactcggtcg ccgcatacac    4380
tattctcaga atgacttggt tgagtactca ccagtcacag aaaagcatct tacgatggc     4440 atgacagtaa gagaattatg cagtgctgcc ataaccatga gtgataacac tgcggccaac    4500
ttacttctga caacgatcgg aggaccgaag gagctaaccg cttttttgca caacatgggg    4560
gatcatgtaa ctcgccttga tcgttgggaa ccggagctga tgaagccat  accaaacgac    4620 gagcgtgaca ccacgatgcc agcagcaatg gcaacaacgt tgcgcaaact attaactggc    4680
gaactactta ctctagcttc ccggcaacaa ttaatagact ggatggaggc ggataaagtt    4740
gcaggaccac ttctgcgctc ggcccttccg gctggctggt ttattgctga taaatctgga    4800
```

```
gccggtgagc gtgggtctcg cggtatcatt gcagcactgg ggccagatgg taagccctcc    4860
cgtatcgtag ttatctacac gacggggagt caggcaacta tggatgaacg aaatagacag    4920
atcgctgaga taggtgcctc actgattaag cattggtaac tgtcagacca agtttactca    4980
tatatacttt agattgattt aaaacttcat ttttaattta aaaggatcta ggtgaagatc    5040 cttttttgata atctcatgac caaaatccct taacgtgagt tttcgttcca ctgagcgtca    5100
gaccccgtag aaaagatcaa aggatcttct tgagatcctt ttttctgcg cgtaatctgc    5160 tgcttgcaaa caaaaaaacc accgctacca gcggtggttt gtttgccgga tcaagagcta    5220
ccaactcttt ttccgaaggt aactggcttc agcagagcgc agataccaaa tactgtcctt    5280
ctagtgtagc cgtagttagg ccaccacttc aagaactctg tagcaccgcc tacatacctc    5340
gctctgctaa tcctgttacc agtggctgct gccagtggcg ataagtcgtg tcttaccggg    5400
ttggactcaa gacgatagtt accggataag gcgcagcggt cgggctgaac ggggggttcg    5460
tgcacacagc ccagcttgga gcgaacgacc tacaccgaac tgagatacct acagcgtgag    5520
cattgagaaa gcgccacgct tcccgaaggg agaaaggcgg acaggtatcc ggtaagcggc    5580
agggtcggaa caggagagcg cacgagggag cttccagggg gaaacgcctg gtatctttat    5640
agtcctgtcg ggtttcgcca cctctgactt gagcgtcgat ttttgtgatg ctcgtcaggg    5700
gggcggagcc tatggaaaaa cgccagcaac gcggcctttt tacggttcct ggccttttgc    5760
tggccttttg ctcacatgtt ctttcctgcg ttatcccctg attctgtgga taaccgtatt    5820
accgcctttg agtgagctga taccgctcgc cgcagccgaa cgaccgagcg cagcgagtca    5880
gtgagcgagg aagcggaaga gcgcccaata cgcaaaccgc ctctccccgc gcgttggccg    5940
attcattaat ccaactggca cgacaggttt cccgactgga agcgggcag tgagcgcaac    6000 gcaattaatg tgagttacct cactcattag gcaccccagg ctttacactt tatgcttccg    6060
gctcgtatgt tgtgtggaat tgtgagcgga taacaatttc acacaggaaa cagctatgac    6120
catgattacg aatta                                                    6135

<210> SEQ ID NO 17
<211> LENGTH: 1353
<212> TYPE: DNA
<213> ORGANISM: Homo sapiens

<400> SEQUENCE: 17
gaagttcagc tggtgcagtc tgggggaggt gtggaacggc cggggggggtc cctgagactc      60 tcctgtgcag cctctggatt cacctttgat gattatgcca tgagctgggt ccgccaagct     120
ccagggaagg ggctggagtg ggtctctggt atcaattggc agggtggtag cacaggatat     180
gcagactctg tgaagggccg agtcaccatc tccagagaca acgccaagaa ctccctgtat     240
ctgcaaatga acagcctgag agccgaggac acggccgtat attactgtgc gaaaatcctg     300
ggtgccggac ggggctggta cttcgattac tggggaagg ggaccacggt caccgtctcg     360
agtgcctcca ccaagggccc atcggtcttc cccctggcac cctcctccaa gagcacctct     420
gggggcacag cggccctggg ctgcctggtc aaggactact ccccgaacc ggtgacggtg     480 tcgtggaact caggcgccct gaccagcggc gtgcacacct tcccggctgt cctacagtcc     540
tcaggactct actccctcag cagcgtggtg actgtgccct ctagcagctt gggcacccag     600
acctacatct gcaacgtgaa tcacaagccc agcaacacca aggtggacaa gaaagttgag     660
cccaaatctt gtgacaaaac tcacacatgc ccaccgtgcc cagcacctga actcctgggg     720
ggaccgtcag tcttcctctt ccccccaaaa cccaaggaca cctcatgat ctcccggacc     780
```

```
cctgaggtca catgcgtggt ggtggacgtg agccacgaag accctgaggt caagttcaac    840
tggtacgtgg acggcgtgga ggtgcataat gccaagacaa agccgcggga ggagcagtac    900
aacagcacgt accgtgtggt cagcgtcctc accgtcctgc accaggactg gctgaatggc    960
aaggagtaca agtgcaaggt ctccaacaaa gccctcccag cccccatcga gaaaaccatc   1020
tccaaagcca aagggcagcc ccgagaacca caggtgtaca ccctgccccc atcccgggaa   1080
gagatgacca agaaccaggt cagcctgacc tgcctggtca aaggcttcta tcccagcgac   1140
atcgccgtgg agtgggagag caatgggcag ccggagaaca actacaagac cacgcctccc   1200
gtgctggact ccgacggctc cttcttcctc tacagcaagc tcaccgtgga caagagcagg   1260
tggcagcagg ggaacgtctt ctcatgctcc gtgatgcatg aggctctgca caaccactac   1320
acgcagaaga gcctctccct gtctccgggt aaa                                1353

<210> SEQ ID NO 18
<211> LENGTH: 451
<212> TYPE: PRT
<213> ORGANISM: Artificial Sequence
<220> FEATURE:
<223> OTHER INFORMATION: Synthesized sequence

<400> SEQUENCE: 18

Glu Val Gln Leu Val Gln Ser Gly Gly Gly Val Glu Arg Pro Gly Gly
  1               5                  10                  15

Ser Leu Arg Leu Ser Cys Ala Ala Ser Gly Phe Thr Phe Asp Asp Tyr
             20                  25                  30

Ala Met Ser Trp Val Arg Gln Ala Pro Gly Lys Gly Leu Glu Trp Val
         35                  40                  45

Ser Gly Ile Asn Trp Gln Gly Ser Thr Gly Tyr Ala Asp Ser Val
     50                  55                  60

Lys Gly Arg Val Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Lys Ile Leu Gly Ala Gly Arg Gly Trp Tyr Phe Asp Tyr Trp Gly
            100                 105                 110

Lys Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
```

```
                260             265              270
Glu Asp Pro Glu Val Lys Phe Asn Trp Tyr Val Asp Gly Val Glu Val
            275                 280                 285
His Asn Ala Lys Thr Lys Pro Arg Glu Glu Gln Tyr Asn Ser Thr Tyr
        290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Ala Leu Pro Ala Pro Ile
                325                 330                 335
Glu Lys Thr Ile Ser Lys Ala Lys Gly Gln Pro Arg Glu Pro Gln Val
            340                 345                 350
Tyr Thr Leu Pro Pro Ser Arg Glu Glu Met Thr Lys Asn Gln Val Ser
        355                 360                 365
Leu Thr Cys Leu Val Lys Gly Phe Tyr Pro Ser Asp Ile Ala Val Glu
    370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
                405                 410                 415
Asp Lys Ser Arg Trp Gln Gln Gly Asn Val Phe Ser Cys Ser Val Met
            420                 425                 430
His Glu Ala Leu His Asn His Tyr Thr Gln Lys Ser Leu Ser Leu Ser
        435                 440                 445
Pro Gly Lys
    450

<210> SEQ ID NO 19
<211> LENGTH: 639
<212> TYPE: DNA
<213> ORGANISM: Artificial Sequence
<220> FEATURE:
<223> OTHER INFORMATION: Synthesized sequence

<400> SEQUENCE: 19
tctgagctga ctcaggaccc tgctgtgtct gtggccttgg gacagacagt caggatcaca      60
tgctcaggag acagcctcag aagctattat gcaagctggt accagcagaa gccaggacag     120
gcccctgtac ttgtcatcta tggtgcaaac aacaggcctt cagggatccc agaccgattc     180
tctggctcca gctcaggaaa cacagcttcc ttgaccatca ctggggctca ggcggaagat     240
gaggctgact attactgtaa ctccgcggac agcagtggta accatgtggt attcggcgga     300
gggaccaagc tgaccgtcct tggccaacct aaggctgcac catctgtcac cctcttcccg     360
ccatcttctg aggagttgca agctaacaaa gccactcttg tgtgcctgat cagtgacttc     420
tatcccggag cggtcacagt agcgtggaag gcggatagct cccccgtaaa ggctggcgtc     480
gagacgacta ccccttcgaa gcagagcaac aacaaatacg ccgccagcag ctacctgtcg     540
ctgaccccag aacagtggaa gagccacaaa agctactcct gccaagtcac ccatgagggc     600
tcgaccgtcg aaaagaccgt cgccccgaca gagtgttct                            639

<210> SEQ ID NO 20
<211> LENGTH: 213
<212> TYPE: PRT
<213> ORGANISM: Artificial Sequence
<220> FEATURE:
<223> OTHER INFORMATION: Synthesized sequence

<400> SEQUENCE: 20
```

```
Ser Glu Leu Thr Gln Asp Pro Ala Val Ser Val Ala Leu Gly Gln Thr
 1               5                  10                  15

Val Arg Ile Thr Cys Ser Gly Asp Ser Leu Arg Ser Tyr Tyr Ala Ser
            20                  25                  30

Trp Tyr Gln Gln Lys Pro Gly Gln Ala Pro Val Leu Val Ile Tyr Gly
        35                  40                  45

Ala Asn Asn Arg Pro Ser Gly Ile Pro Asp Arg Phe Ser Gly Ser Ser
    50                  55                  60

Ser Gly Asn Thr Ala Ser Leu Thr Ile Thr Gly Ala Gln Ala Glu Asp
65                  70                  75                  80

Glu Ala Asp Tyr Tyr Cys Asn Ser Ala Asp Ser Ser Gly Asn His Val
                85                  90                  95

Val Phe Gly Gly Gly Thr Lys Leu Thr Val Leu Gly Gln Pro Lys Ala
            100                 105                 110

Ala Pro Ser Val Thr Leu Phe Pro Pro Ser Ser Glu Glu Leu Gln Ala
        115                 120                 125

Asn Lys Ala Thr Leu Val Cys Leu Ile Ser Asp Phe Tyr Pro Gly Ala
    130                 135                 140

Val Thr Val Ala Trp Lys Ala Asp Ser Ser Pro Val Lys Ala Gly Val
145                 150                 155                 160

Glu Thr Thr Thr Pro Ser Lys Gln Ser Asn Asn Lys Tyr Ala Ala Ser
                165                 170                 175

Ser Tyr Leu Ser Leu Thr Pro Glu Gln Trp Lys Ser His Lys Ser Tyr
            180                 185                 190

Ser Cys Gln Val Thr His Glu Gly Ser Thr Val Glu Lys Thr Val Ala
        195                 200                 205

Pro Thr Glu Cys Ser
    210
```

<210> SEQ ID NO 21
<211> LENGTH: 48
<212> TYPE: DNA
<213> ORGANISM: Artificial Sequence
<220> FEATURE:
<223> OTHER INFORMATION: Synthesized sequence

<400> SEQUENCE: 21
catgccaagg agactaactc agataatatt aagctagctg gtaccagc         48

<210> SEQ ID NO 22
<211> LENGTH: 48
<212> TYPE: DNA
<213> ORGANISM: Artificial Sequence
<220> FEATURE:
<223> OTHER INFORMATION: Synthesized sequence
<220> FEATURE:
<221> NAME/KEY: misc_feature
<222> LOCATION: 15, 16, 24, 25, 30, 31
<223> OTHER INFORMATION: n = A,T,C and G
<220> FEATURE:
<221> NAME/KEY: misc_feature
<222> LOCATION: 17, 26, 32
<223> OTHER INFORMATION: s = G and C

<400> SEQUENCE: 22
catgccaagg agacnnsctc agannstatn nsgctagctg gtaccagc         48

<210> SEQ ID NO 23
<211> LENGTH: 44
<212> TYPE: DNA
<213> ORGANISM: Artificial Sequence
<220> FEATURE:

<223> OTHER INFORMATION: Synthesized sequence

<400> SEQUENCE: 23
gtcatctatg gtaaataata acggccgtct ggcatcccag accg         44

<210> SEQ ID NO 24
<211> LENGTH: 47
<212> TYPE: DNA
<213> ORGANISM: Artificial Sequence
<220> FEATURE:
<223> OTHER INFORMATION: Synthesized sequence
<220> FEATURE:
<221> NAME/KEY: misc_feature
<222> LOCATION: 19, 20, 22, 23, 25, 26
<223> OTHER INFORMATION: n = A,T,C or G
<220> FEATURE:
<221> NAME/KEY: misc_feature
<222> LOCATION: 21, 24, 27
<223> OTHER INFORMATION: s = G and C

<400> SEQUENCE: 24
cttgtcatct atggtaaann snnsnnsccg tctggcatcc cagaccg       47

<210> SEQ ID NO 25
<211> LENGTH: 59
<212> TYPE: DNA
<213> ORGANISM: Artificial Sequence
<220> FEATURE:
<223> OTHER INFORMATION: Synthesized sequence

<400> SEQUENCE: 25
gctgactatt actgtaactc ccggtaataa taaggctaac atgtggtatt cggcggagg       59

<210> SEQ ID NO 26
<211> LENGTH: 59
<212> TYPE: DNA
<213> ORGANISM: Artificial Sequence
<220> FEATURE:
<223> OTHER INFORMATION: Synthesized sequence
<220> FEATURE:
<221> NAME/KEY: misc_feature
<222> LOCATION: 25, 26, 28, 29, 31, 32, 37, 38
<223> OTHER INFORMATION: n = A,T,C or G
<220> FEATURE:
<221> NAME/KEY: misc_feature
<222> LOCATION: 27, 30, 33, 39
<223> OTHER INFORMATION: s = G and C

<400> SEQUENCE: 26
gctgactatt actgtaactc ccggnnsnns nnsggcnnsc atgtggtatt cggcggagg       59

<210> SEQ ID NO 27
<211> LENGTH: 11
<212> TYPE: PRT
<213> ORGANISM: Artificial Sequence
<220> FEATURE:
<223> OTHER INFORMATION: Synthesized sequence

<400> SEQUENCE: 27

Asn Ser Arg Asp Ser Ser Gly Ser His Val Val
 1               5                  10

<210> SEQ ID NO 28
<211> LENGTH: 11
<212> TYPE: PRT
<213> ORGANISM: Artificial Sequence
<220> FEATURE:
<223> OTHER INFORMATION: Synthesized sequence

<400> SEQUENCE: 28

```
Asn Ser Arg Ser Tyr Ser Gly Asn His Val Val
 1               5                   10

<210> SEQ ID NO 29
<211> LENGTH: 11
<212> TYPE: PRT
<213> ORGANISM: Artificial Sequence
<220> FEATURE:
<223> OTHER INFORMATION: Synthesized sequence

<400> SEQUENCE: 29

Asn Ser Arg Ser Ser Ser Gly Ser His Val Val
 1               5                   10
```

What is claimed is:

1. Isolated nucleic acid encoding the heavy or light chain of an anti-DR5 antibody or a functional fragment thereof, wherein:
   (a) said heavy chain comprises the variable domain sequence of 16E2 antibody heavy chain of SEQ ID NO: 11, wherein G at position 33 of CDRH1 is substituted by A, N at position 53 of CDRH2 is substituted by Q, and L at position 102 of CDRH3 is substituted by Y, and
   (b) said light chain comprises the variable domain sequence of 16E2 antibody light chain of SEQ ID NO: 13, wherein Q at position 24 of CDRL1 is substituted by S, K at position 51 of CDRL2 is substituted by A, and R at position 91 of CDRL3 is substituted by A.

2. The isolated nucleic acid of claim 1 wherein said heavy chain further comprises the substitution of Q, V, E, R, K at framework residues 6, 11, 12, 13, and 105 of SEQ ID NO: 11.

3. A vector comprising the nucleic acid of claim 1 or claim 2.

4. An isolated recombinant host cell comprising the nucleic acid of claim 1 or claim 2.

5. A method of producing an anti-DR5 antibody comprising culturing the recombinant host cell of claim 4 under conditions wherein the nucleic acid is expressed.

6. The isolated nucleic acid of claim 1 wherein said anti-DR5 antibody heavy chain further comprises one or more substitutions in the framework of the full length 16E2 antibody heavy chain (SEQ ID NO: 11) variable domain.

7. The isolated nucleic acid of claim 6 wherein said anti-DR5 antibody heavy chain comprises a set of substitutions selected from the group consisting of (i) N53Q, L102Y; (ii) M34L, N53Q, L102Y; (iii) N53Y, L102Y; (iv) M34L, L102Y; (v) G33A, N53Q, L102Y; (vi) M34L, N53Y, L102Y; (vii) G33A, N53Q, L102Y; (viii) G33A, N53Y, L102Y; (ix) T28A, N53Q, L102Y; and (x) T28A, N53Y, L102Y in the amino acid sequence of SEQ ID NO: 11.

8. An isolated nucleic acid encoding the anti-DR5 antibody heavy chain amino acid sequence of SEQ ID NO: 18 or light chain amino acid sequence of SEQ ID NO: 20, or a fragment thereof.

* * * * *